US008809027B1

(12) United States Patent
Lynch et al.

(10) Patent No.: US 8,809,027 B1
(45) Date of Patent: Aug. 19, 2014

(54) GENETICALLY MODIFIED ORGANISMS FOR INCREASED MICROBIAL PRODUCTION OF 3-HYDROXYPROPIONIC ACID INVOLVING AN OXALOACETATE ALPHA-DECARBOXYLASE

(75) Inventors: Michael D Lynch, Boulder, CO (US); Christopher P. Mercogliano, Superior, CO (US)

(73) Assignee: OPX Biotechnologies, Inc., Boulder, CO (US)

( * ) Notice: Subject to any disclaimer, the term of this patent is extended or adjusted under 35 U.S.C. 154(b) by 348 days.

(21) Appl. No.: 12/891,760

(22) Filed: Sep. 27, 2010

Related U.S. Application Data

(60) Provisional application No. 61/246,140, filed on Sep. 27, 2009.

(51) Int. Cl.
*C12P 7/40* (2006.01)

(52) U.S. Cl.
USPC ............. 435/136; 435/6; 435/320.1; 435/7.1; 435/252

(58) Field of Classification Search
None
See application file for complete search history.

(56) References Cited

U.S. PATENT DOCUMENTS

| | | | |
|---|---|---|---|
| 2,408,889 A | 10/1946 | Short | |
| 2,464,768 A | 3/1949 | Redmon et al. | |
| 2,469,701 A | 5/1949 | Redmon | |
| 2,798,053 A | 7/1957 | Brown et al. | |
| 3,904,685 A | 9/1975 | Shahidi et al. | |
| 3,915,921 A | 10/1975 | Schlatzer, Jr. | |
| 4,029,577 A | 6/1977 | Godlewski et al. | |
| 4,268,641 A | 5/1981 | Koenig et al. | |
| 4,301,266 A | 11/1981 | Muenster et al. | |
| 4,431,547 A | 2/1984 | Dubin | |
| 4,666,983 A | 5/1987 | Tsubakimoto et al. | |
| 4,685,915 A | 8/1987 | Hasse et al. | |
| 4,708,997 A | 11/1987 | Stanley, Jr. et al. | |
| 4,734,478 A | 3/1988 | Tsubakimoto et al. | |
| 4,857,610 A | 8/1989 | Chmelir et al. | |
| 4,952,505 A | 8/1990 | Cho | |
| 4,985,518 A | 1/1991 | Alexander et al. | |
| 5,009,653 A | 4/1991 | Osborn, III | |
| 5,093,472 A | 3/1992 | Bresciani | |
| 5,135,677 A | 8/1992 | Yamaguchi et al. | |
| 5,145,906 A | 9/1992 | Chambers et al. | |
| 5,180,798 A | 1/1993 | Nakamura et al. | |
| 5,331,059 A | 7/1994 | Engelhardt et al. | |
| 5,342,899 A | 8/1994 | Graham et al. | |
| 5,350,799 A | 9/1994 | Woodrum et al. | |
| 5,426,199 A | 6/1995 | Lundquist | |
| 5,432,071 A * | 7/1995 | Ichikawa et al. | ............. 435/190 |
| 5,470,928 A | 11/1995 | Harwood et al. | |
| 5,510,307 A | 4/1996 | Narayanan et al. | |
| 5,510,526 A | 4/1996 | Baniel et al. | |
| 5,558,656 A | 9/1996 | Bergman | |
| 5,723,639 A | 3/1998 | Datta et al. | |
| 5,817,870 A | 10/1998 | Haas et al. | |
| 5,827,255 A | 10/1998 | Crainic | |
| 5,876,983 A | 3/1999 | Sugimoto et al. | |
| 6,004,773 A | 12/1999 | Araki et al. | |
| 6,087,140 A | 7/2000 | Cameron et al. | |
| 6,284,495 B1 | 9/2001 | Sato et al. | |
| 6,297,319 B1 | 10/2001 | Nagasuna et al. | |
| 6,472,188 B1 | 10/2002 | Lee et al. | |
| 6,534,679 B2 | 3/2003 | Eyal et al. | |
| 6,610,836 B1 * | 8/2003 | Breton et al. | ................. 536/23.1 |
| 6,623,944 B2 | 9/2003 | Rieping | |
| 6,709,919 B2 | 3/2004 | Tu | |
| 6,723,799 B2 | 4/2004 | Sun et al. | |
| 6,852,517 B1 | 2/2005 | Suthers et al. | |
| 6,960,455 B2 | 11/2005 | Livshits et al. | |
| 7,041,814 B1 * | 5/2006 | Weinstock et al. | .......... 536/24.1 |
| 7,090,008 B2 | 8/2006 | Ishikawa et al. | |
| 7,141,154 B2 | 11/2006 | Lin et al. | |
| 7,153,663 B2 | 12/2006 | Payne et al. | |
| 7,166,743 B2 | 1/2007 | Zhong et al. | |
| 7,186,541 B2 | 3/2007 | Gokarn et al. | |
| 7,186,856 B2 | 3/2007 | Meng et al. | |
| 7,223,567 B2 | 5/2007 | Ka-Yiu et al. | |
| 7,279,598 B2 | 10/2007 | Meng et al. | |

(Continued)

FOREIGN PATENT DOCUMENTS

| | | |
|---|---|---|
| EP | 1124789 B1 | 9/2004 |
| EP | 1036190 B1 | 5/2005 |
| EP | 1305439 B1 | 6/2006 |
| EP | 1124979 B1 | 8/2006 |
| EP | 1731604 A1 | 12/2006 |
| EP | 1105514 B1 | 2/2008 |
| EP | 1778840 B1 | 6/2008 |
| EP | 1975236 A2 | 10/2008 |
| EP | 1654212 B1 | 7/2009 |
| EP | 1975236 A3 | 9/2009 |

(Continued)

OTHER PUBLICATIONS

Strauss et al. (Eur. J. Biochem., vol. 215, pp. 633-643, 1993).*
U.S. Appl. No. 13/575,581, filed Jul. 26, 2012, Lynch et al.
Broun, et al. Catalytic plasticity of fatty acid modification enzymes underlying chemical diversity of plant lipids. Science. Nov. 13, 1998;282(5392):1315-7.
Chica, et al. Semi-rational approaches to engineering enzyme activity: combining the benefits of directed evolution and rational design. Curr Opin Biotechnol. Aug. 2005;16(4):378-84.

(Continued)

*Primary Examiner* — Hope Robinson
(74) *Attorney, Agent, or Firm* — Wilson Sonsini Goodrich & Rosati

(57) ABSTRACT

Microorganism compositions are described that comprise combinations of genetic modifications that include a genetic modification to increase oxaloacetate alpha-decarboxylase enzymatic activity. By such genetic modification a 3-hydroxypropionic acid ("3-HP") production pathway is provided or improved. In various embodiments, comprising other genetic modifications, including selected gene disruptions, 3-HP production is greater than in a control microorganism lacking such combinations of genetic modifications.

26 Claims, 9 Drawing Sheets

(56) References Cited

U.S. PATENT DOCUMENTS

| | | | |
|---|---|---|---|
| 7,285,406 B2 | 10/2007 | Payne et al. | |
| 7,309,597 B2 | 12/2007 | Liao et al. | |
| 7,326,557 B2 | 2/2008 | San et al. | |
| 7,358,071 B2 | 4/2008 | Payne et al. | |
| 7,393,676 B2 | 7/2008 | Gokarn et al. | |
| 7,538,247 B2 | 5/2009 | Craciun et al. | |
| 7,638,316 B2 | 12/2009 | Gokarn et al. | |
| 7,678,869 B2 | 3/2010 | Matyjaszewski et al. | |
| 7,687,661 B2 | 3/2010 | Lilga et al. | |
| 7,700,319 B2 * | 4/2010 | Liao et al. | 435/69.1 |
| 7,785,837 B2 * | 8/2010 | Liao et al. | 435/69.1 |
| 7,833,761 B2 * | 11/2010 | Terashita et al. | 435/106 |
| 7,943,362 B2 | 5/2011 | Frost | |
| 8,030,045 B2 * | 10/2011 | Jessen et al. | 435/193 |
| 8,076,111 B2 | 12/2011 | Fukui et al. | |
| 8,124,388 B2 * | 2/2012 | Liao et al. | 435/183 |
| 2002/0164729 A1 | 11/2002 | Skraly et al. | |
| 2003/0101486 A1 | 5/2003 | Facciotti et al. | |
| 2003/0191146 A1 | 10/2003 | Kabbash et al. | |
| 2003/0211131 A1 | 11/2003 | Martin et al. | |
| 2003/0233675 A1 | 12/2003 | Cao et al. | |
| 2003/0235892 A1 | 12/2003 | Katz et al. | |
| 2004/0076982 A1 | 4/2004 | Gokarn et al. | |
| 2004/0152159 A1 | 8/2004 | Causey et al. | |
| 2004/0152174 A1 | 8/2004 | Cervin et al. | |
| 2004/0209337 A1 | 10/2004 | Frost et al. | |
| 2004/0210087 A1 | 10/2004 | Meng et al. | |
| 2004/0214294 A1 | 10/2004 | Rieping | |
| 2005/0054060 A1 | 3/2005 | Chateau et al. | |
| 2005/0196758 A1 | 9/2005 | Rock et al. | |
| 2005/0222458 A1 | 10/2005 | Craciun et al. | |
| 2005/0239179 A1 | 10/2005 | Skraly et al. | |
| 2005/0283029 A1 | 12/2005 | Meng et al. | |
| 2006/0014977 A1 | 1/2006 | Miller et al. | |
| 2006/0084098 A1 | 4/2006 | Gill et al. | |
| 2007/0010708 A1 | 1/2007 | Ness | |
| 2007/0087403 A1 | 4/2007 | Bestel-Corre et al. | |
| 2007/0107080 A1 | 5/2007 | Liao et al. | |
| 2007/0148749 A1 | 6/2007 | Yasuda et al. | |
| 2007/0184524 A1 | 8/2007 | Gokarn et al. | |
| 2007/0219390 A1 | 9/2007 | Zacher et al. | |
| 2007/0245431 A1 | 10/2007 | Metz et al. | |
| 2008/0076167 A1 | 3/2008 | Gokarn et al. | |
| 2008/0124785 A1 | 5/2008 | Liao et al. | |
| 2008/0193989 A1 | 8/2008 | Verser et al. | |
| 2008/0199926 A1 | 8/2008 | Burgard et al. | |
| 2009/0017514 A1 | 1/2009 | Datta et al. | |
| 2009/0023006 A1 | 1/2009 | Bub et al. | |
| 2009/0031453 A1 | 1/2009 | Jessen et al. | |
| 2009/0053783 A1 | 2/2009 | Gokarn et al. | |
| 2009/0076297 A1 | 3/2009 | Bogan, Jr. et al. | |
| 2009/0082286 A1 | 3/2009 | Huang et al. | |
| 2009/0111151 A1 | 4/2009 | Julien et al. | |
| 2009/0234146 A1 | 9/2009 | Cooney et al. | |
| 2009/0291480 A1 | 11/2009 | Jessen et al. | |
| 2009/0298144 A1 | 12/2009 | Tsobanakis et al. | |
| 2009/0305369 A1 | 12/2009 | Donaldson et al. | |
| 2009/0325248 A1 | 12/2009 | Marx et al. | |
| 2010/0151536 A1 | 6/2010 | Baynes et al. | |
| 2010/0210017 A1 | 8/2010 | Gill et al. | |
| 2011/0125118 A1 | 5/2011 | Lynch | |
| 2011/0183391 A1 | 7/2011 | Frost | |
| 2011/0244575 A1 | 10/2011 | Lipscomb et al. | |
| 2011/0275851 A1 | 11/2011 | Orjuela et al. | |
| 2012/0041232 A1 | 2/2012 | Lynch | |
| 2012/0244586 A1 | 9/2012 | Gokarn et al. | |

FOREIGN PATENT DOCUMENTS

| | | |
|---|---|---|
| EP | 1706457 B1 | 2/2012 |
| JP | H 09-505463 | 6/1997 |
| WO | WO 98/21339 A1 | 5/1998 |
| WO | WO 98/55442 A1 | 12/1998 |
| WO | WO 00/56693 A1 | 9/2000 |
| WO | WO 01/16346 A1 | 3/2001 |
| WO | WO 01/38284 A1 | 5/2001 |
| WO | WO 02/42418 A2 | 5/2002 |
| WO | WO 03/040690 A2 | 5/2003 |
| WO | WO 02/42418 A3 | 6/2003 |
| WO | WO 03/062173 A2 | 7/2003 |
| WO | WO 2004/018621 A2 | 3/2004 |
| WO | WO 2004/033646 A2 | 4/2004 |
| WO | WO 2004/018621 A3 | 9/2004 |
| WO | WO 03/040690 A3 | 10/2004 |
| WO | WO 2005/003074 A1 | 1/2005 |
| WO | WO 2005/047498 A1 | 5/2005 |
| WO | WO 03/062173 A3 | 11/2005 |
| WO | WO 2005/105770 A2 | 11/2005 |
| WO | WO 2005/118719 A2 | 12/2005 |
| WO | WO 2005/105770 A3 | 3/2006 |
| WO | WO 2004/033646 A3 | 5/2006 |
| WO | WO 2005/118719 A3 | 9/2006 |
| WO | WO 2006/121755 A2 | 11/2006 |
| WO | WO 2007/012078 A1 | 1/2007 |
| WO | WO 2007/030830 A2 | 3/2007 |
| WO | WO 2007/042494 A2 | 4/2007 |
| WO | WO 2007/047680 A2 | 4/2007 |
| WO | WO 2006/121755 A3 | 6/2007 |
| WO | WO 2007/030830 A3 | 10/2007 |
| WO | WO 2007/042494 A3 | 11/2007 |
| WO | WO 2007/047680 A3 | 11/2007 |
| WO | WO 2008/027742 A1 | 3/2008 |
| WO | WO 2008/028002 A1 | 3/2008 |
| WO | WO 2008/089102 A2 | 7/2008 |
| WO | WO 2008/091627 A2 | 7/2008 |
| WO | WO 2008/089102 A3 | 1/2009 |
| WO | WO 2009/031737 A1 | 3/2009 |
| WO | WO 2008/091627 A3 | 5/2009 |
| WO | WO 2009/062190 A2 | 5/2009 |
| WO | WO 2009/094485 A1 | 7/2009 |
| WO | WO 2009/062190 A3 | 9/2009 |
| WO | WO 2011/038364 A1 | 3/2011 |
| WO | WO 2011/063363 A2 | 5/2011 |
| WO | WO 2011/063304 A1 | 6/2011 |
| WO | WO 2011/063363 A3 | 8/2011 |
| WO | WO 2011/094457 A1 | 8/2011 |

OTHER PUBLICATIONS

Cho, et al. Simultaneous synthesis of enantiomerically pure (S)-amino acids and (R)-amines using coupled transaminase reactions. Biotechnol Bioeng. Mar. 30, 2003;81(7):783-9.

Devos, et al. Practical limits of function prediction. Proteins. Oct. 1, 2000;41(1):98-107.

Ivanova, et al. Genome sequence of *Bacillus cereus* and comparative analysis with *Bacillus anthracis*. Nature. May 1, 2003;423(6935):87-91.

Kimchi-Sarfarty, et al. A "silent" polymorphism in the MDR1 gene changes substrate specificity. Science. Jan. 26, 2007;315(5811):525-8. Epub Dec. 21, 2006.

Kisselev. Polypeptide release factors in prokaryotes and eukaryotes: same function, different structure. Structure. Jan. 2002;10(1):8-9.

Nackley, et al. Human catechol-O-methyltransferase haplotypes modulate protein expression by altering mRNA secondary structure. Science. Dec. 22, 2006;314(5807):1930-3.

Office action dated Jul. 11, 2012 for U.S. Appl. No. 13/055,138.

Office action dated Aug. 29, 2012 for Chinese Application No. 200980137400.4 (in Chinese with English translation).

Office action dated Sep. 18, 2012 for U.S. Appl. No. 12/891,790.

Office action dated Sep. 19, 2012 for JP Application No. 2012-531103 (in Japanese with English translation).

Sauna, et al. Silent polymorphisms speak: how they affect pharmacogenomics and the treatment of cancer. Cancer Res. Oct. 15, 2007;67(20):9609-12.

Seffernick, et al. Melamine deaminase and atrazine chlorohydrolase: 98 percent identical but functionally different. J Bacteriol. Apr. 2001;183(8):2405-10.

Sen, et al. Developments in directed evolution for improving enzyme functions. Appl Biochem Biotechnol. Dec. 2007;143(3):212-23.

(56) References Cited

OTHER PUBLICATIONS

Sousa, et al. The ARO4 gene of Candida albicans encodes a tyrosine-sensitive DAHP synthase: evolution, functional conservation and phenotype of Aro3p-, Aro4p-deficient mutants. Microbiology. May 2002;148(Pt 5):1291-303.
Takamura, et al. Changes in the intracellular concentration of acetyl-CoA and malonyl-CoA in relation to the carbon and energy metabolism of *Escherichia coli* K12. J Gen Microbiol. Aug. 1988;134(8):2249-53.
Third party submission under 37 C.F.R Section 1.290 dated Sep. 17, 2012 against U.S. Appl. No. 13/284,337.
Whisstock, et al. Prediction of protein function from protein sequence and structure. Q Rev Biophys. Aug. 2003;36(3):307-40.
Wishart, et al. A single mutation converts a novel phosphotyrosine binding domain into a dual-specificity phosphatase. J Biol Chem. Nov. 10, 1995;270(45):26782-5.
Witkowski, et al. Conversion of a beta-ketoacyl synthase to a malonyl decarboxylase by replacement of the active-site cysteine with glutamine. Biochemistry. Sep. 7, 1999;38(36):11643-50.
U.S. Appl. No. 12/891,790, filed Sep. 27, 2010, Lynch.
U.S. Appl. No. 13/062,917, filed Mar. 8, 2011, Lynch.
Alber, et al. Malonyl-coenzyme A reductase in the modified 3-hydroxypropionate cycle for autotrophic carbon fixation in archaeal *Metallosphaera* and *Sulfolobus* spp. J Bacteriol. Dec. 2006;188(24):8551-9.
Barbin, et al. Induction of specific base-pair substitutions in *E. coli* trpA mutants by chloroethylene oxide, a carcinogenic vinyl chloride metabolite. Mutat Res. Nov.-Dec. 1985;152(2-3):147-56.
Bastian, et al. Engineered ketol-acid reductoisomerase and alcohol dehydrogenase enable anaerobic 2-methylpropan-1-ol production at theoretical yield in *Escherichia coli*. Metab Eng. May 2011;13(3):345-52.
Bergler et al. Sequences of the envM gene and of two mutated alleles in *Escherichia coli*. J Gen Microbiol. Oct. 1992;138(10):2093-100.
Brock, et al. Naturally occurring adenines within mRNA coding sequences affect ribosome binding and expression in *Escherichia coli*. J Bacteriol. Jan. 2007;189(2):501-10. Epub Nov. 3, 2006.
Bunch, et al. The ldhA gene encoding the fermentative lactate dehydrogenase of *Escherichia coli*. Microbiology. Jan. 1997;143 ( Pt 1):187-95.
Canada, et al. Directed evolution of toluene ortho-monooxygenase for enhanced 1-naphthol synthesis and chlorinated ethene degradation. J Bacteriol. Jan. 2002;184(2):344-9.
Chang, et al. Acetate metabolism in a pta mutant of *Escherichia coli* W3110: importance of maintaining acetyl coenzyme A flux for growth and survival. J Bacteriol. Nov. 1999;181(21):6656-63.
Cleusix, et al. Inhibitory activity spectrum of reuterin produced by *Lactobacillus reuteri* against intestinal bacteria. BMC Microbiol. Nov. 12, 2007;7:101.
Cowan, et al. Characterization of the major promoter for the plasmid-encoded sucrose genes scrY, scrA, and scrB. J Bacteriol. Dec. 1991;173(23):7464-70.
Cronan, et al. Genetic and biochemical analyses of pantothenate biosynthesis in *Escherichia coli* and *Salmonella typhimurium*.J Bacteriol. Mar. 1982;149(3):916-22.
Cronan, J.E., Beta-Alanine Synthesis in *Escherichia coli* J Bacteriol. Mar. 1980;141(3):1291-7.
Den, et al. Enzymatic Conversion of β-Hydroxypropionate to Malonic Semialdehyde. J Biol Chem Jul. 1959;234(7):1666-1671.
Dohr, et al. Engineering of a functional human NADH-dependent cytochrome P450 system. Proc Natl Acad Sci U S A. Jan. 2, 2001;98(1):81-6.
Drake, et al. Structure of the EntB multidomain nonribosomal peptide synthetase and functional analysis of its interaction with the EntE adenylation domain. Chem Biol. Apr. 2006;13(4):409-19.
European search report dated Jul. 2, 2010 for Application No. 08727619.2.
Funa, et al. A novel quinone-forming monooxygenase family involved in modification of aromatic polyketides. J Biol Chem. Apr. 15, 2005;280(15):14514-23. Epub Feb. 8, 2005.

GenBank Accession No. X81461 AF473544 (Sep. 7, 1994).
GenBank Accession No. AAS20429.1 (Jan. 19, 2004).
Gill, et al. Genome-wide screening for trait conferring genes using DNA microarrays. Proc Natl Acad Sci U S A. May 14, 2002;99(10):7033-8. Epub May 7, 2002.
Gokarn, et al. Metabolic analysis of *Escherichia coli* in the presence and absence of the carboxylating enzymes phosphoenolpyruvate carboxylase and pyruvate carboxylase. Appl Environ Microbiol. May 2000;66(5):1844-50.
Goodwin, et al. Purification and characterization of methylmalonate-semialdehyde dehydrogenase from rat liver. Identity to malonate-semialdehyde dehydrogenase. J Biol Chem. Sep. 5, 1989;264(25):14965-71.
Gulmezian, et al. Genetic evidence for an interaction of the UbiG O-methyltransferase with UbiX in *Escherichia coli* coenzyme Q biosynthesis. J Bacteriol. Sep. 2006;188(17):6435-9.
Hall, et al. Structure-function analysis of NADPH:nitrate reductase from *Aspergillus nidulans*: analysis of altered pyridine nucleotide specificity in vivo. Microbiology. Jun. 2000;146 ( Pt 6):1399-406.
Hatzimanikatis, et al. Exploring the diversity of complex metabolic networks. Bioinformatics. Apr. 15, 2005;21(8):1603-9. Epub Dec. 21, 2004.
He, et al. A T42M substitution in bacterial 5-enolpyruvylshikimate-3-phosphate synthase (EPSPS) generates enzymes with increased resistance to glyphosate. Biosci Biotechnol Biochem. Jun. 2003;67(6):1405-9.
Heath, et al. Enoyl-acyl carrier protein reductase (fabI) plays a determinant role in completing cycles of fatty acid elongation in *Escherichia coli*. J Biol Chem. Nov. 3, 1995;270(44):26538-42.
Henry, et al. Discovery of novel routes for the biosynthesis of industrial chemicals: 3-Hydroxypropanoate. Slides. AICHE Annual Meeting. Nov. 8, 2007. Salt Lake City, UT.
Herter, et al. Autotrophic $CO_2$ Fixation by *Chloroflexus aurantiacus*: Study of Glyoxylate Formation and Assimilation via the 3-Hydroxypropionate Cycle. J Bacteriol Jul. 2001;183(14):4305-4316.
Hondorp et al. Oxidation of cysteine 645 of cobalamin-independent methionine synthase causes a methionine limitation in *Escherichia coli*. J Bacteriol. May 2009;191(10):3407-10. Epub Mar. 13, 2009.
Hügler, et al. Malonyl-Coenzyme A Reductase from *Chloroflexus aurantiacus*, a Key Enzyme of the 3-Hydroxypropionate Cycle for Autotrophic $CO_2$ Fixation. J Bacteriol May 2002;184(9):2404-2410.
International search report and written report dated Jun. 3, 2011 for PCT Application No. US2010/057690.
International search report dated Feb. 3, 2011 for PCT Application No. US2010/050436.
International search report dated Jun. 4, 2010 for PCT Application No. US2009/51607.
International search report dated Jun. 16, 2011 for PCT Application No. US2011/022790.
International search report dated Dec. 5, 2008 for PCT Application No. US08/50921.
International search report dated Apr. 29, 2010 for PCT Application No. US2009/57058.
Joike, et al. Amino acid substitutions affecting catalytic activity and subunit interactions of aminodeoxychorismate synthase in *E. coli*. Abstracts of the General Meeting of the American Society for Microbiology. 2002; 102:275-276, and 102nd General Meeting of the American Society for Microbiology; Salt Lake, UT, USA; May 19-23, 2002.
Kapol, et al. Purification and characterization of 2-oxoglutarate decarboxylase of *Leuconostoc oenos*. Journal of General Microbiology 136 (1990), 1497-1499.
Kern, et al. Engineering primary metabolic pathways of industrial micro-organisms. J Biotechnol. Mar. 30, 2007;129(1):6-29. Epub Dec. 2, 2006.
Kim et al. Extractive Recovery of Products from Fermentation Broths. Biotechnol. Bioprocess Eng., 1999; 4:1-11.
Kim, et al. The Rut pathway for pyrimidine degradation: novel chemistry and toxicity problems. J Bacteriol. Aug. 2010;192(16):4089-102. Epub Apr. 16, 2010.

(56) References Cited

OTHER PUBLICATIONS

Kim, et al. Dihydrolipoamide dehydrogenase mutation alters the NADH sensitivity of pyruvate dehydrogenase complex of *Escherichia coli* K-12. J Bacteriol. Jun. 2008;190(11):3851-8. Epub Mar. 28, 2008.

Kim, et al. Effect of overexpression of *Actinobacillus succinogenes* phosphoenolpyruvate carboxykinase on succinate production in *Escherichia coli*. Appl Environ Microbiol. Feb. 2004;70(2):1238-41.

Kwon, et al. A physiology study of *Escherichia coli* overexpressing phosphoenolpyruvate carboxykinase. Biosci Biotechnol Biochem. Apr. 2008;72(4):1138-41.

Kwon, et al. Influence of Gluconeogenic Phosphoenolpyruvate Carboxykinase (PCK) Expression on Succinic Acid Fermentation in *Escherichia coli* Under High Bicarbonate Condition. Journal of Microbiology and Biotechnology. 2006; 16(9):1448-1452.

Lennen, et al. A process for microbial hydrocarbon synthesis: Overproduction of fatty acids in *Escherichia coli* and catalytic conversion to alkanes. Biotechnol Bioeng. Jun. 1, 2010;106(2):193-202.

Lipscomb, et al. Poster—Understanding production of 3-Hydroxypropionic Acid (3-HP) in a genomic context. OPX Biotechnologies. Metabolic Engineering. Sep. 17, 2008.

Lutke-Eversloh, et al. Feedback inhibition of chorismate mutase/prephenate dehydrogenase (TyrA) of *Escherichia coli*: generation and characterization of tyrosine-insensitive mutants. Appl Environ Microbiol. Nov. 2005;71(11):7224-8.

Lynch, et al. SCALEs: multiscale analysis of library enrichment. Nat Methods. Jan. 2007;4(1):87-93.

Lynch, M. Rapid optimization of microorganisms for the cost superior production of chemicals & fuels. OPX Biotechnologies. Sep. 15, 2008.

Magnuson et al. Regulation of fatty acid biosynthesis in *Escherichia coli*. Microbiol Rev. Sep. 1993;57(3):522-42.

Mehta, et al. Aminotransferases: demonstration of homology and division into evolutionary subgroups. Eur J Biochem. Jun. 1, 1993;214(2):549-61.

Mohan, et al. Effect of process parameters on 3-hydroxypropionic acid production from glycerol using a recombinant *Escherichia coli*. Appl Microbiol Biotechnol. Sep. 2009;84(4):649-57. Abstract only.

Moreau. Diversion of the metabolic flux from pyruvate dehydrogenase to pyruvate oxidase decreases oxidative stress during glucose metabolism in nongrowing *Escherichia coli* cells incubated under aerobic, phosphate starvation conditions. J Bacteriol. Nov. 2004;186(21):7364-8.

NCBI Reference Sequence: NP_414657.1 (Jan. 16, 1997).
NCBI Reference Sequence: NP_415792.1 (Jan. 16, 1997).
NCBI Reference Sequence: NP_416366.1 (Jan. 16, 1997).
NCBI Reference Sequence: NP_418812.1 (Jan. 16, 1997).
NCBI Reference Sequence: YP_001277512.1 (Jun. 6, 2007).
NCBI Reference Sequence: YP_001433009.1 (Sep. 4, 2007).
NCBI Reference Sequence: YP_001636209.1 (Dec. 21, 2007).
NCBI Reference Sequence: YP_002462600.1 (Dec, 29, 2008).
NCBI Reference Sequence: ZP_01039179.1 (Jan. 16, 2006).
NCBI Reference Sequence: ZP_01626393.1 (Dec. 15, 2006).
NCBI Reference Sequence: ZP_04957196.1 (Sep. 15, 2008).
NCBI Reference Sequence: ZP_05125944.1 (Sep. 15, 2008).

Nexant, Inc. Chemsystems Perp Program, Acrylic Acid, 08/09-3, Jul. 2010.

Office action dated Apr. 29, 2011 for US Appl. No. 12/328,588.
Office action dated Jul. 4, 2011 for EP Applilcation No. 08727619.2.
Office action dated Sep. 17, 2010 for US Appl. No. 12/328,588.

Okamura et al. Unprecedented acetoacetyl-coenzyme A synthesizing enzyme of the thiolase superfamily involved in the mevalonate pathway. Proc Natl Acad Sci U S A. Jun. 22, 2010;107(25):11265-70. Epub Jun. 7, 2010.

Ozcelik et al. Metabolic engineering of aromatic group amino acid pathway in *Bacillus subtilis* for L-phenylalanine production. Chemical Engineering Science. 2004;59(22-23):5019-5026.

Parikh, et al. Directed evolution of RuBisCO hypermorphs through genetic selection in engineered *E.coli*. Protein Eng Des Sel. Mar. 2006;19(3):113-9. Epub Jan. 19, 2006.

Ponce, et al. Cloning of the Two Pyruvate Kinase Isoenzyme StructuralGenes from *Escherichia coli*: the Relative Roles of These Enzymes in Pyruvate Biosynthesis. J Bacteriol. Oct. 1995;177(19):5719-22.

Raj, et al. Effect of process parameters on 3-hydroxypropionic acid production from glycerol using a recombinant *Escherichia coli*. Appl Microbiol Biotechnol. Sep. 2009;84(4):649-57. Epub Apr. 8, 2009.

Ramey, et al. Poster—Translation of genomics data into useful metabolic engineering strategies: construction of a 3-hydroxypropionic acid tolerant *E. coli*. Date unknown.

Ray et al. Mutational analysis of the catalytic and feedback sites of the tryptophan-sensitive 3-deoxy-D-arabino-heptulosonate-7-phosphate synthase of *Escherichia coli*. J Bacteriol. Dec. 1988;170(12):5500-6.

Saier, et al. The catabolite repressor/activator (Cra) protein of enteric bacteria. J Bacteriol. Jun. 1996;178(12):3411-7.

Singh, et al. Genes restoring redox balance in fermentation-deficient *E. coli* NZN111. Metab Eng. Nov. 2009; 11(6):347-54. Epub Jul. 21, 2009.

Straathoff, et al. Feasibility of acrylic acid production by fermentation. Appl Microbiol Biotechnol. Jun. 2005;67(6):727-34.

Strauss, et al. Enzymes of a novel autotrophic CO2 fixation pathway in the phototrophic bacterium *Chloroflexus aurantiacus*, the 3-hydroxypropionate cycle. Eur J Biochem. Aug. 1, 1993;215(3):633-43.

Tian, et al. Mycobacterium tuberculosis appears to lack an alpha-ketoglutarate dehydrogenase and encodes pyruvate dehydrogenase in widely separated genes. Mol Microbiol. Aug. 2005;57(3):859-68.

Tian, et al. Variant tricarboxylic acid cycle in Mycobacterium tuberculosis: Identification of alpha-ketoglutarate decarboxylase. Proc Natl Acad Sci U S A. Jul. 26, 2005;102(30):10670-5. Epub Jul. 18, 2005.

Vedantam, et al. Characterization of mutations contributing to sulfathiazole resistance in *Escherichia coli*. Antimicrob Agents Chemother. Jan. 1998;42(1):88-93.

Warnecke, et al. A genomics approach to improve the analysis and design of strain selections. Metab Eng. May-Jul. 2008;10(3-4):154-65.

Warnecke, et al. Organic acid toxicity, tolerance, and production in *Escherichia coli* biorefining applications. Microbial Cell Factories. 2005;4(25):1-8.

Warnecke, et al. Rapid dissection of a complex phenotype through genomic-scale mapping of fitness altering genes. Metab Eng. May 2010;12(3):241-50.

Wasewar, et al. Fermentation of Glucose to Lactic Acid Coupled with Reactive Extraction: A Review. Ind. Eng. Chem. Res. 2004; 43:5969-5982.

Werpy, et al. Pacific Northwest National Laboratory. Top Value Added Chemicals From Biomass, vol. 1—Results of Screening for Potential candidates From Sugars and Synthesis Gas, U.S. Department of Energy, Aug. 2004.

Yee, et al. On the role of helix 0 of the tryptophan synthetase alpha chain of *Escherichia coli*. J Biol Chem. Jun. 21, 1996;271(25):14754-63.

Yoshida, et al. Identification of PhoB binding sites of the yibD and ytfK promoter regions in *Escherichia coli*. J Microbiol. Apr. 2011;49(2):285-9. Epub May 3, 2011.

Zha, et al. Improving cellular malonyl-CoA level in *Escherichia coli* via metabolic engineering. Metab Eng. May 2009;11(3):192-8. Epub Feb. 5, 2009.

Zhao et al. Binding of two flaviolin substrate molecules, oxidative coupling, and crystal structure of Streptomyces coelicolor A3(2) cytochrome P450 158A2. J Biol Chem. Mar. 25, 2005;280(12):11599-607. Epub Jan. 19, 2005.

Zhou, et al. Interdomain communication between the thiolation and thioesterase domains of EntF explored by combinatorial mutagenesis and selection. Chem Biol. Aug. 2006;13(8):869-79.

Asano, et al. A new enzymatic method of acrylamide production. Agricultural and Biological Chemistry. 1982; 46(5):1183-1190.

Brown, et al. Synthesis of labeled acrylamide and N-methylolacrylamide (NMA) : 15N-acrylamide, 13C-NMA, 15N-NMA, and 13C,15N-NMA. Journal of labelled compounds & radiopharmaceuticals. 2005; 48(14):1031-1039.

(56) References Cited

OTHER PUBLICATIONS

Kurcok, et al. Reactions of β-lactones with potassium alkoxides and their complexes with 18-crown-6 in aprotic solvents. Journal of Organic Chemistry. 1993; 58(16):4219-4220.

Langlois, et al. A new preparation of trifluoromethanesulfinate salts. Journal of Fluorine Chemistry. 2007; 128(7):851-856.

Liang, et al. Fe2(SO4)3·4H2O/concentrated H2SO4: an efficient catalyst for esterification. Journal of Chemical Research, Synopses. 2004; 3:226-227.

Orjuela, et al. Presentation: Recovery of succinic acid from fermentative broth through esterification with ethanol. Department of Chemical Engineering and Materials Science. Michigan State University. East Lansing, Michigan 48824. Jun. 29, 2010.

Ramalinga, et al. A mild and efficient method for esterification and transesterification catalyzed by iodine. Tetrahedron Letters. 2002; 43(5):879-882.

Ren, et al. Molecular Iodine in Ionic Liquid: A Green Catalytic System for Esterification and Transesterification. Synthetic Communications. 2010; 40(11):1670-1676.

Rodriguez, et al. Structure-cytoprotective activity relationship of simple molecules containing an alpha,beta-unsaturated carbonyl system. J Med Chem. Jun. 6, 1997;40(12):1827-34.

Sun, et al. ZrOC12 × 8H20: an efficient, cheap and reusable catalyst for the esterification of acrylic acid and other carboxylic acids with equimolar amounts of alcohols. Molecules. Apr. 10, 2006;11(4):263-71.

U.S. Appl. No. 13/527,799, filed Jun. 20, 2012, Tengler et al.

Dell'Aquila, et al. Acid-base balance in peritoneal dialysis. J Nephrol. Mar.-Apr. 2006;19 Suppl 9:S104-7.

Duncan, et al. Lactate-utilizing bacteria, isolated from human feces, that produce butyrate as a major fermentation product. Appl Environ Microbiol. Oct. 2004;70(10):5810-7.

Kozliak, et al. Expression of proteins encoded by the *Escherichia coli* cyn operon: carbon dioxide-enhanced degradation of carbonic anhydrase. J Bacteriol. Sep. 1994;176(18):5711-7.

Kozliak, et al. Role of bicarbonate/CO2 in the inhibition of *Escherichia coli* growth by cyanate. J Bacteriol. Jun. 1995;177(11):3213-9.

Meng, et al. Nucleotide sequence of the *Escherichia coli* cad operon: a system for neutralization of low extracellular pH. J Bacteriol. Apr. 1992;174(8):2659-69.

Moreau. The lysine decarboxylase CadA protects *Escherichia coli* starved of phosphate against fermentation acids. J Bacteriol. Mar. 2007;189(6):2249-61. Epub Jan. 5, 2007.

Stim, et al. Nucleotide sequence of the adi gene, which encodes the biodegradative acid-induced arginine decarboxylase of *Escherichia coli*. J Bacteriol. Mar. 1993;175(5):1221-34.

Turlin, et al. 3-phenylpropionate catabolism and the *Escherichia coli* oxidative stress response. Res Microbiol. Apr. 2005;156(3):312-21. Epub Jan. 27, 2005.

Warnecke, et al. Identification of a 21 amino acid peptide conferring 3-hydroxypropionic acid stress-tolerance to *Escherichia coli*. Biotechnol Bioeng. May 2012;109(5):1347-52. doi: 10.1002/bit. 24398. Epub Jan. 2, 2012.

U.S. Appl. No. 13/416,103, filed Mar. 9, 2012, Lipscomb et al.

U.S. Appl. No. 13/498,468, filed Mar. 27, 2012, Lynch.

Agriculture Project Fact Sheet. U.S. Department of Energy, Office of Industrial Technologies. 2001. Chemicals From Lignocellulose, http://www.oit.doe.gov/agriculture/factsheets/lignocellulose.pdf (Apr. 21, 2004).

Bailey, et al. Inverse metabolic engineering: A strategy for directed genetic engineering of useful phenotypes. BBiotechnol Bioeng. Sep. 5, 2002;79(5):568-79.

Bailey. Toward a science of metabolic engineering. Science. Jun. 21, 1991;252(5013):1668-75.

Beguin et al. The biological degradation of cellulose. FEMS Microbiol Rev. Jan. 1994;13(1):25-58.

Chotani, et al. The commercial production of chemicals using pathway engineering. Biochim Biophys Acta. Dec. 29, 2000;1543(2):434-455. . . .

Crameri, et al. DNA shuffling of a family of genes from diverse species accelerates directed evolution . Nature. Jan. 15, 1998;391(6664):288-91.

De Mendoza, et al Thermal regulation of membrane lipid fluidity in bacteria. Trends Biochem. Sci. 1983; 8:49-52.

Energetics Incorporated. 2003. Industrial Bioproducts: Today and Tomorrow. U.S. Department of Energy, Office of Energy Efficiency and Renewable Energy, Office of the Biomass Program, Washington, D.C.

Eppink, et al. Switch of coenzyme specificity of p-hydroxybenzoate hydroxylase. J Mol Biol. Sep. 10, 1999;292(1):87-96.

Epstein, et al. Oil: A Life Cycle Analysis of its Health and Environmental Impacts. The Center for Health and the Global Environment, Harvard Medical School. Mar. 2002. www.med.harvard.edu/chge/oil.html.

Farmer, et al. Improving lycopene production in *Escherichia coli* by engineering metabolic control. Nat Biotechnol. May 2000;18(5):533-7.

Fodor, et al. Light-Directed, Spatially Addressable Parallel Chemical Synthesis. Science. Feb. 15, 1991;251(4995):767-73.

Gronenborn. Overproduction of phage lambda repressor under control of the lac promotor of *Escherichia coli*. Mol Gen Genet. Nov. 17, 1976;148(3):243-50.

Li, et al. Effect of poxB gene knockout on metabolism in *Escherichia coli* based on growth characteristics and enzyme activities. World Journal of Microbiology and Biotechnology V 23(4). Apr. 2007. p. 573-580.

Martin, et al. Engineering a mevalonate pathway in *Escherichia coli* for production of terpenoids. Nat Biotechnol. Jul. 2003;21(7):796-802. Epub Jun. 1, 2003.

Ohmiya, et al. Structure of cellulases and their applications. Biotechnol Genet Eng Rev. 1997;14:365-414.

Ohnishi, et al. A novel methodology employing Corynebacterium glutamicum genome information to generate a new L-lysine-producing mutant. Appl Microbiol Biotechnol. Feb. 2002;58(2):217-23. . . .

Patnaik, et al. Genome shuffling of *Lactobacillus* for improved acid tolerance. Nat Biotechnol. Jul. 2002; 20(7):707-12.

Pohl et al. A new perspective on thiamine catalysis. Curr Opin Biotechnol. Aug. 2004;15(4):335-42.

Schmidt-Dannert, et al. Molecular breeding of carotenoid biosynthetic pathways. Nat Biotechnol. Jul. 2000; 18(7):750-3.

Service. Sugary Recipe Boosts Grow-Your-Own Plastics. Science. Jun. 30, 2006;312(5782):1861.

Stephanopoulos, et al. Network Rigidity and Metabolic Engineering in Metabolite Overproduction. Science. Jun. 21, 1991;252(5013):1675-81.

Stephanopoulos. Challenges in engineering microbes for biofuels production. Science. Feb. 9, 2007;315(5813):801-4.

Tunnicliff, et al. The inhibition by substrate analogues of gamma-aminobutyrate aminotransferase from mitochondria of different subcellular fractions of rat brain. Can J Biochem. Apr. 1977;55(4):479-84.

U.S. Appl. No. 13/916,534, filed Jun. 12, 2013, Lynch.

Anton, et al. Sequencing and overexpression of the *Escherichia coli* aroE gene encoding shikimate dehydrogenase. Biochem J. Jan. 15, 1988;249(2):319-26.

Dewick, P. Chapter 4. The Shikimate Pathway: Aromatic Amino Acids and Phenylpropanoids. Medicinal Natural Products: A Biosynthetic Approach, Second Edition (2002): 121-166.

Duncan, et al. The overexpression and complete amino acid sequence of *Escherichia coli* 3-dehydroquinase. Biochem J. Sep. 1, 1986;238(2):475-83.

European search report dated Jan. 3, 2013 for Application No. 09813810.0.

Ginkel, et al. Identification and cloning of the Mycobacterium avium folA gene, required for dihydrofolate reductase activity. FEMS Microbiol Lett. Nov. 1, 1997;156(1):69-78.

Gray, et al. Monofunctional chorismate mutase from *Bacillus subtilis*: purification of the protein, molecular cloning of the gene, and overexpression of the gene product in *Escherichia coli*. Biochemistry. Jan. 16, 1990; 29(2):376-83.

(56) References Cited

OTHER PUBLICATIONS

Jiang, et al. Cloning and Expression of aroG Gene of *E. coli* and Its Co-expression with pheA and tyrB Genes. Sheng Wu Hua Xue Yu Sheng Wu Wu Li Xue Bao (Shanghai). 1998;30(6):593-596. (In Chinese with English abstract).
Office action dated Feb. 13, 2013 for U.S. Appl. No. 12/523,047.
Office action dated Jun. 3, 2013 for U.S. Appl. No. 13/416,103.
Office action dated Jun. 5, 2013 for U.S. Appl. No. 13/284,337.
Office action dated Jun. 19, 2013 for U.S. Appl. No. 12/891,790.
Oliveira, et al. Cloning and overexpression in soluble form of functional shikimate kinase and 5-enolpyruvylshikimate 3-phosphate synthase enzymes from Mycobacterium tuberculosis. Protein Expr Purif.Aug. 2001;22(3):430-5.
Roe, et al. Inhibition of *Escherichia coli* growth by acetic acid: a problem with methionine biosynthesis and homocysteine toxicity. Microbiology. Jul. 2002;148(Pt 7):2215-22.
Welch, et al. Extensive mosaic structure revealed by the complete genome sequence of uropathogenic *Escherichia coli*. Proc Natl Acad Sci U S A. Dec. 24, 2002;99(26):17020-4. Epub Dec. 5, 2002.
White, et al. The overexpression, purification and complete amino acid sequence of chorismate synthase from *Escherichia coli* K12 and its comparison with the enzyme from *Neurospora crassa*. Biochem J. Apr. 15, 1988;251(2):313-22.
Zhang, et al. Inhibiting bacterial fatty acid synthesis. J Biol Chem. Jun. 30, 2006;281(26):17541-4. Epub Apr. 28, 2006.
European search report and opinion dated Sep. 23, 2013 for EP Application No. 10832342.9.
U.S. Appl. No. 14/067,838, filed Oct. 30, 2013, Lynch.
European search report and opinion dated Jul. 18, 2013 for EP Application No. 09801031.7.
Office Action dated Sep. 19, 2013, for U.S. Appl. No. 13/055,138.
Tomar, A. Master Thesis. Production of Pyruvate by *Escherichia coli* Using Metabolic Engineering. The University of Georgia, May 2002, pp. 1-171.
Office Action dated Oct. 23, 2013 for U.S. Appl. No. 12/523,047.
Cronk, et al. Cloning, crystallization and preliminary characterization of a beta-carbonic anhydrase from *Escherichia coli*. Acta Crystallogr D Biol Crystallogr. Sep. 2000;56(Pt 9):1176-9.
Diaz, et al. Characterization of the hca cluster encoding the dioxygenolytic pathway for initial catabolism of 3-phenylpropionic acid in *Escherichia coli* K-12. J Bacteriol. Jun. 1998;180(11):2915-23.
Fernando, et al. Biorefineries: current status, challenges and future direction Energ. Fuel. 2006; 20:1727-1737.
Figge, et al. Methionine biosynthesis is *Escherichia coli* and *Corynebacterium glutamicum*. Microbiol Monogro. 2007; 5:163-193.
Muday, et al. The tyrosine repressor negatively regulates aroH expression in *Escherichia coli*. Bacteriol. Jun. 1991;173(12):3930-2.
Office action dated Nov. 2, 2012 for U.S. Appl. No. 13/416,103.
Office action dated Nov. 27, 2012 for U.S. Appl. No. 13/284,337.
Price-Carter, et al. Polyphosphate kinase protects *Salmonella enterica* from weak organic acid stress. Journal of Bacteriology. 2005; 187:3088-3099.
Warnecke, et al. Engineering of Organic Acid Tolerance Genes in *E. coli* for Biorefinery Applications. 2006 AIChE Annual Meeting in San Francisco, California, Nov. 12-17, 2006, https://aiche.confex.comlaiche/2006/techprogram/P67122.HTM.

\* cited by examiner

Figure 1: CLUSTAL 2.0.12 multiple sequence alignment of Carbonic Anhydrase Polypeptides

|  |  | SEQ ID NO: |
|---|---|---|
| gi\|70728869\|ref\|YP_258618.1\| | MQNIIDGFLKFQREAFPQRSELFKQLASTQNPGTLFVTCSDSRVVPELLT 50 | 59 |
| gi\|238754662\|ref\|ZP_04616015.1 | MQDIIDGFLKFQREVFPQRSELFKRLADTQHPGALFVTCSDSRVVPELLT 50 | 59 |
| gi\|83646817\|ref\|YP_435252.1\| | MKDIIEGFLKFQREAFPERKELFKDLANQQQPRTLFISCSDSRLVPELVT 50 | 60 |
| gi\|206562261\|ref\|YP_002233024. | MKDIIEGFLKFQRDAYPARAALFRDLARSQNPRALFISCSDSRLVPELVT 50 | 61 |
| gi\|15800068\|ref\|NP_286080.1\| | MKEIIDGFLKFQREAFPKREALFKQLATQQSPRTLFISCSDSRLVPELVT 50 | 57 |
| gi\|238790503\|ref\|ZP_04634271.1 | MKEIIDGFLKFQRDAFPERAELFRSLATQQSPKTLFISCSDSRMVPELVT 50 | 62 |
| gi\|104782623\|ref\|YP_609121.1\| | MQDIIDGFLKFQRDAFPERVKLFKDLATQQSPRALFISCSDSRLVPELVT 50 | 63 |
| gi\|170722264\|ref\|YP_001749952. | MKAIIDGFLKFQKNAFPERVKLFKDLANQQAPKALFISCSDSRLVPELVT 50 | 64 |
| gi\|157369777\|ref\|YP_001477766. | MKEVIEGFLKFQREAFVERTALFQRLATQQSPRTLFISCSDSRLVPELIT 50 | 65 |
| gi\|188533851\|ref\|YP_001907648. | MQHIVEGFLNFQKDIFPEQKELFRSLASSQNPKALFISCSDSRLVPELVT 50 | 66 |
| gi\|152985230\|ref\|YP_001348595. | MRDIIDGFLRFQRDAYPARSQLFKSLATRQAPKALFIACSDSRVVPELLT 50 | 67 |
| gi\|271966225\|ref\|YP_003340421. | MQDLEEGVARFQRDVFPAKTELFTRLATAHQPATLFISCSDARVVPELIT 50 | 68 |
|  | *: :.* .:: .  ** ;* :::*:*:****:* |  |

| gi\|70728869\|ref\|YP_258618.1\| | QQEPGDLFVIRNAGNIVPSYGP-EPGGVSATVEYAVAVLGVSDIVCGHS 99 |
|---|---|
| gi\|238754662\|ref\|ZP_04616015.1 | QREPGELFVIRNAGNIVPSYGP-EPGGVSATVEYAVAVLGVTDVVICGHS 99 |
| gi\|83646817\|ref\|YP_435252.1\| | QREPGDLFVIRNAGNIVPPYGP-EPGGVSASVEYAVAALRVADIVVCGHS 99 |
| gi\|206562261\|ref\|YP_002233024. | QREPGDLFVIRNAGNIVPSYGP-EPGGVSASVEYAVAALRVTDVVICGHS 99 |
| gi\|15800068\|ref\|NP_286080.1\| | QREPGDLFVIRNAGNIVPSYGP-EPGGVSASVEYAVAALRVSDIVCGHS 99 |
| gi\|238790503\|ref\|ZP_04634271.1 | QREPGDLFVIRNAGNIVPSYGP-EPGGISASVEYAVTALKVTDIVICGHS 99 |
| gi\|104782623\|ref\|YP_609121.1\| | QREPGDLFVIRNAGNIVPSYGP-EPGGVSASVEYAVAALQVADIVICGHS 99 |
| gi\|170722264\|ref\|YP_001749952. | QREPGDLFVIRNAGNIVPSYGP-EPGGVSASVEYAVAGLNVADIVCGHS 99 |
| gi\|157369777\|ref\|YP_001477766. | QREPGDLFVIRNAGNIVPSFGP-EPGGVSASVEYAVSALGVEDIVCGHS 99 |
| gi\|188533851\|ref\|YP_001907648. | QQDPGQLFVIRNAGNIVPSFGP-EPGGVSATIEYAVVALGVSDIVCGHS 99 |
| gi\|152985230\|ref\|YP_001348595. | QREPGELFVIRNAGNIVPGYGP-QPGGVSASVEYAVAVLGVADIVVCGHS 99 |
| gi\|271966225\|ref\|YP_003340421. | QSEPGELFVIRTAGNLVPAYAPGSADGVAAGIEYAVAVLGVSDIVVCGHS 100 |
|  | *: *:*:*** *:** .* ..*; ** * *: * *** |

| gi\|70728869\|ref\|YP_258618.1\| | DCGAMTAISTCKCLDHLPAVANWLRHAESAKVINAARQHASPAEHLDALV 149 |
|---|---|
| gi\|238754662\|ref\|ZP_04616015.1 | NCGAMSAIAECQCLDHLPAVAAWLRHADSAKLVNAALPHASPKDRLNSLV 149 |
| gi\|83646817\|ref\|YP_435252.1\| | NCGAMTAVATCQCIDHMPAVAHWLRYADSAKVVNQARKHASERAKIEDMV 149 |
| gi\|206562261\|ref\|YP_002233024. | DCGAMTAIATCQCMDHMPAVGHWLRYADSARVVNEARTHRSERERIDSMV 149 |
| gi\|15800068\|ref\|NP_286080.1\| | NCGAMTAIASCQCMDHMPAVSHWLRYADSARVVNEARPHSDLPSKAAAMV 149 |
| gi\|238790503\|ref\|ZP_04634271.1 | DCGAMTAIAKCHCLDHMPAVKHWLQYADSAKVVNESREYKNIHDKTISMV 149 |
| gi\|104782623\|ref\|YP_609121.1\| | DCGAMTAIATCKCLDHMPAVAGWLRYADSARVVNEARQHQSPHAKVEAMV 149 |
| gi\|170722264\|ref\|YP_001749952. | DCGAMTAIATCKCLDHMPAVAGWLRHADSAKVVNEARHHVDKPSKVASMV 149 |
| gi\|157369777\|ref\|YP_001477766. | DCGAMTAIATCQCLQHMPTVANWLRYADSAKVVNQAYQHASENEKVSSMV 149 |
| gi\|188533851\|ref\|YP_001907648. | NCGAMKAIATCQCLAPMPAVEHWLRYADAAKAVVEKKNYDTEEDKVNAMV 149 |
| gi\|152985230\|ref\|YP_001348595. | DCGAMGAIASCACLDHLPAVAGWLRHAEAARAMNSAHEHSSDAARLDALV 149 |
| gi\|271966225\|ref\|YP_003340421. | GCGAMTAVADGLDPAALPAVAGWLRHADASRARVTTTETGTG--EVAALV 148 |
|  | .**** *:. :*.* **:: *:... . :* |

| gi\|70728869\|ref\|YP_258618.1\| | RDNVIAQLANLKTHPSVALALEQGRLNLHGWVYDIESGAIVALDGNTQRF 199 |
|---|---|
| gi\|238754662\|ref\|ZP_04616015.1 | RENVIAQLANIKTHPSVALACAQGRLRLHGWVYDIETGSIDVLDELTRTF 199 |
| gi\|83646817\|ref\|YP_435252.1\| | RENVIAQLANLQTHPSVRLALQEGRLTMHGWFYDIESGGIDAYDGSRHAF 199 |
| gi\|206562261\|ref\|YP_002233024. | RENVIAQLANLKTHPAVRLALEEGRLALHGWVYDIESGCIDAYDGATGRF 199 |
| gi\|15800068\|ref\|NP_286080.1\| | RENVIAQLANLQTHPSVRLALEEGRIALHGWVYDIESGSIAAFDGATRQF 199 |
| gi\|238790503\|ref\|ZP_04634271.1 | HENVVAQLANIQTHPSVRLALEEGRLTIHGWVYDIESGLISAFDRASRQF 199 |
| gi\|104782623\|ref\|YP_609121.1\| | RENVIAQLANIQTHPSVRLALEEGRVALHGWIYDIESGRIDAFDGRTGQF 199 |
| gi\|170722264\|ref\|YP_001749952. | RENVIAQLANIQTHPSVRLALEEGRVTLHGWIYDIETGGIDAFDGSTGTF 199 |
| gi\|157369777\|ref\|YP_001477766. | RENVIAQLNNIKTHPSVALALEQGRLKLHGWVYDIASGGIEALDGETRRF 199 |
| gi\|188533851\|ref\|YP_001907648. | QENVIAQLNNIKTHPSVGLRNNALRLHGWVYDIESGAIRALDKDSKKF 199 |
| gi\|152985230\|ref\|YP_001348595. | RHNVIAQLANLRTHPSVARALEQGRLNLHGWVYDIESGRIDALDGASRRF 199 |
| gi\|271966225\|ref\|YP_003340421. | RQNVLTQLANLATHPSVAHALAGKTVTLHGWIYDIGTGTVAELD-ATGRP 197 |
|  | :.:. ***. : .:*.*** ;* * |

| gi\|70728869\|ref\|YP_258618.1\| | VSLAEYPHTCALASQASSAA- 219 |
|---|---|
| gi\|238754662\|ref\|ZP_04616015.1 | SPLSAY----SVVSKPTE--- 213 |
| gi\|83646817\|ref\|YP_435252.1\| | VPLAEHPEARAIPGKLSHAV- 219 |
| gi\|206562261\|ref\|YP_002233024. | VSLADHPGVRATPATLPVAA- 219 |
| gi\|15800068\|ref\|NP_286080.1\| | VPLAANPRVCAIPLRQPTAA- 219 |
| gi\|238790503\|ref\|ZP_04634271.1 | VSLAANPNVRAVPAHN----- 215 |
| gi\|104782623\|ref\|YP_609121.1\| | VSLADNPEVRAVSHASRHVA- 219 |
| gi\|170722264\|ref\|YP_001749952. | VSLAENPEVHAVSQQARHVA- 219 |
| gi\|157369777\|ref\|YP_001477766. | IPLATNPEVTATPAVSRF--- 217 |
| gi\|188533851\|ref\|YP_001907648. | VLLSDNPQVHFE--------- 211 |
| gi\|152985230\|ref\|YP_001348595. | VSLAEHPGVRAVGGEPGQAVA 220 |
| gi\|271966225\|ref\|YP_003340421. | SALAV---------------- 202 |
|  | *: |

Figure 3
A. Natural mixed acid fermentation in *E coli*
B. Proposed 3-HP fermentation
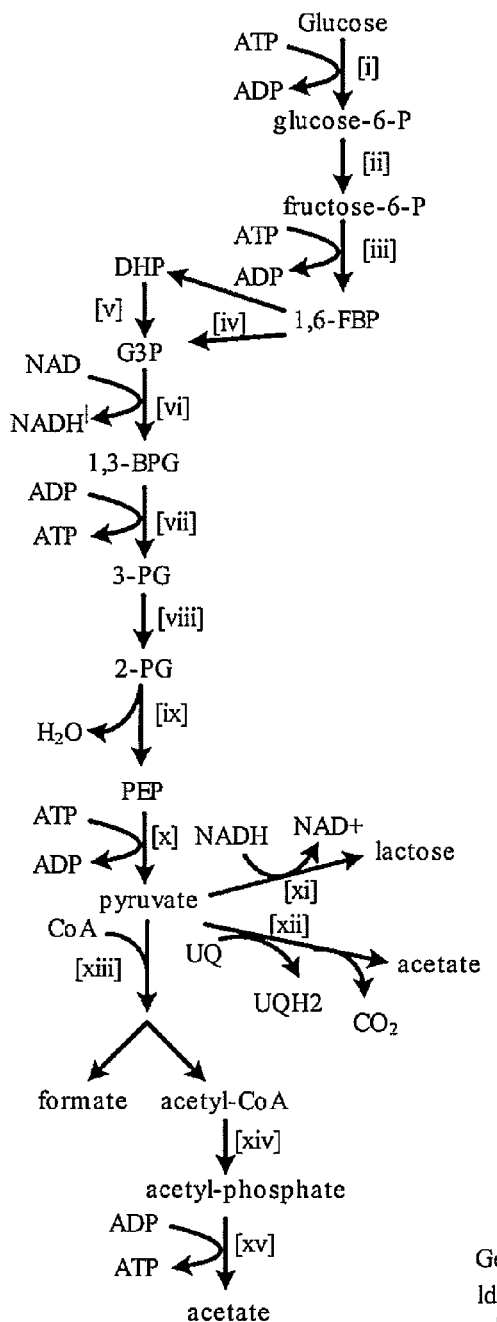
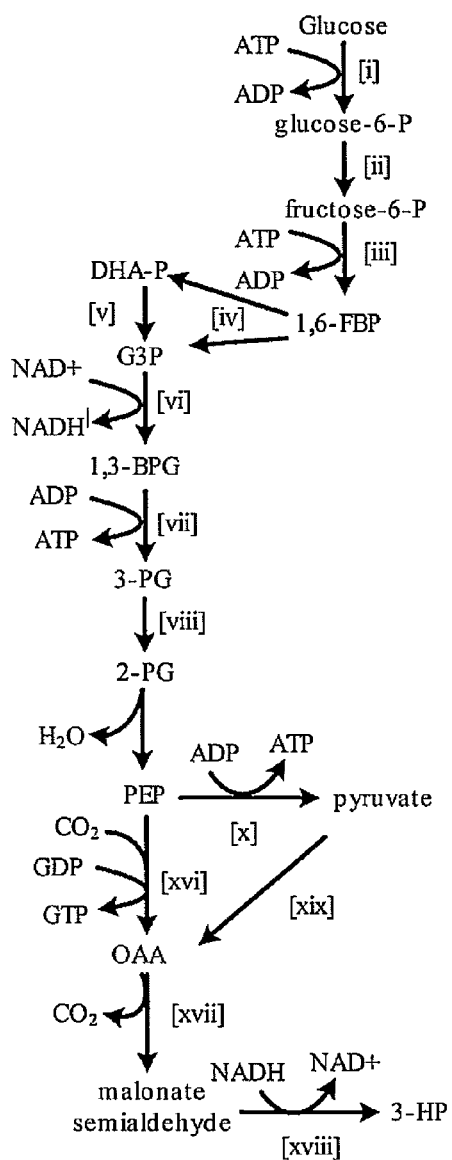
Gene Deletions:
ldhA: pyruvate ⇸ lactate
pflB: pyruvate ⇸ formate + acetyl coA
poxB: pyruvate ⇸ acetate
pta: acetyl-coA ⇸ acetate Figure 5: YdfG reaction with 3-HP
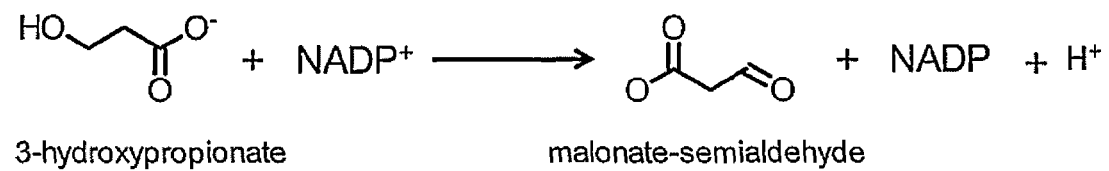

Figure 7
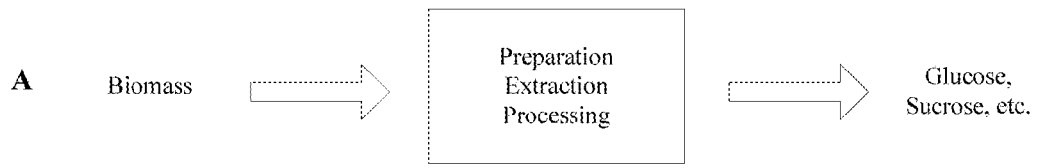
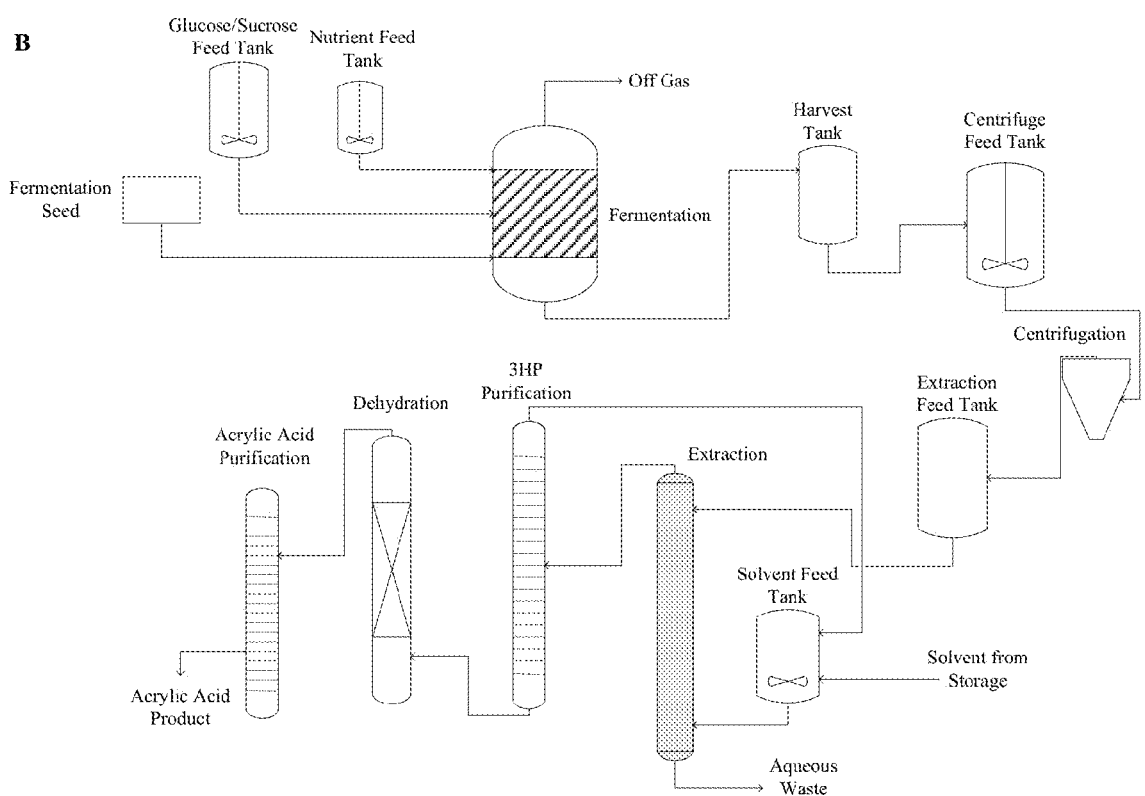
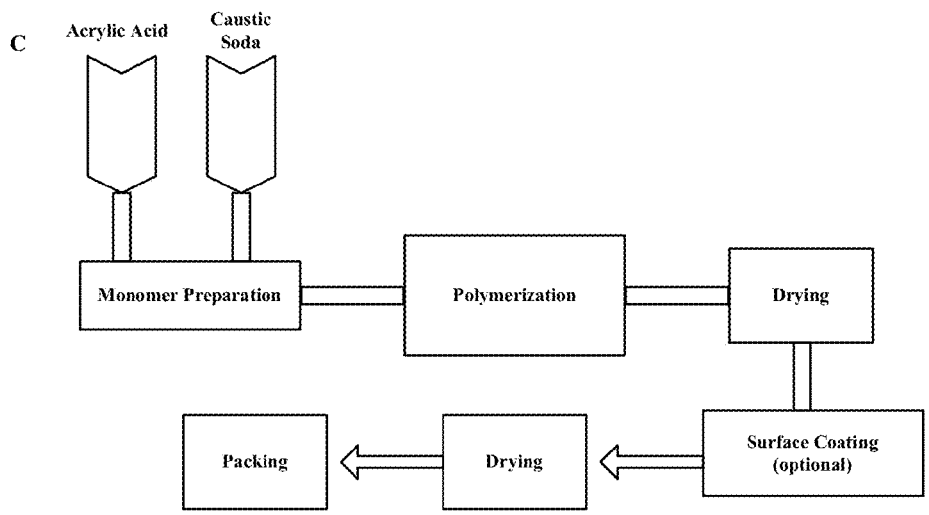

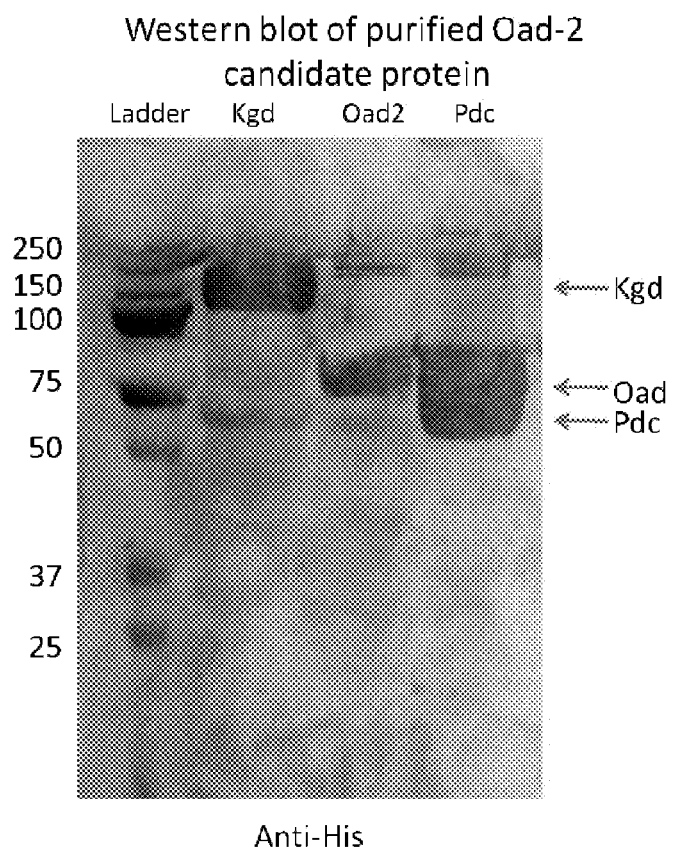
Figure 8: Western blot of purified proteins probed with anti-6xHis antibody

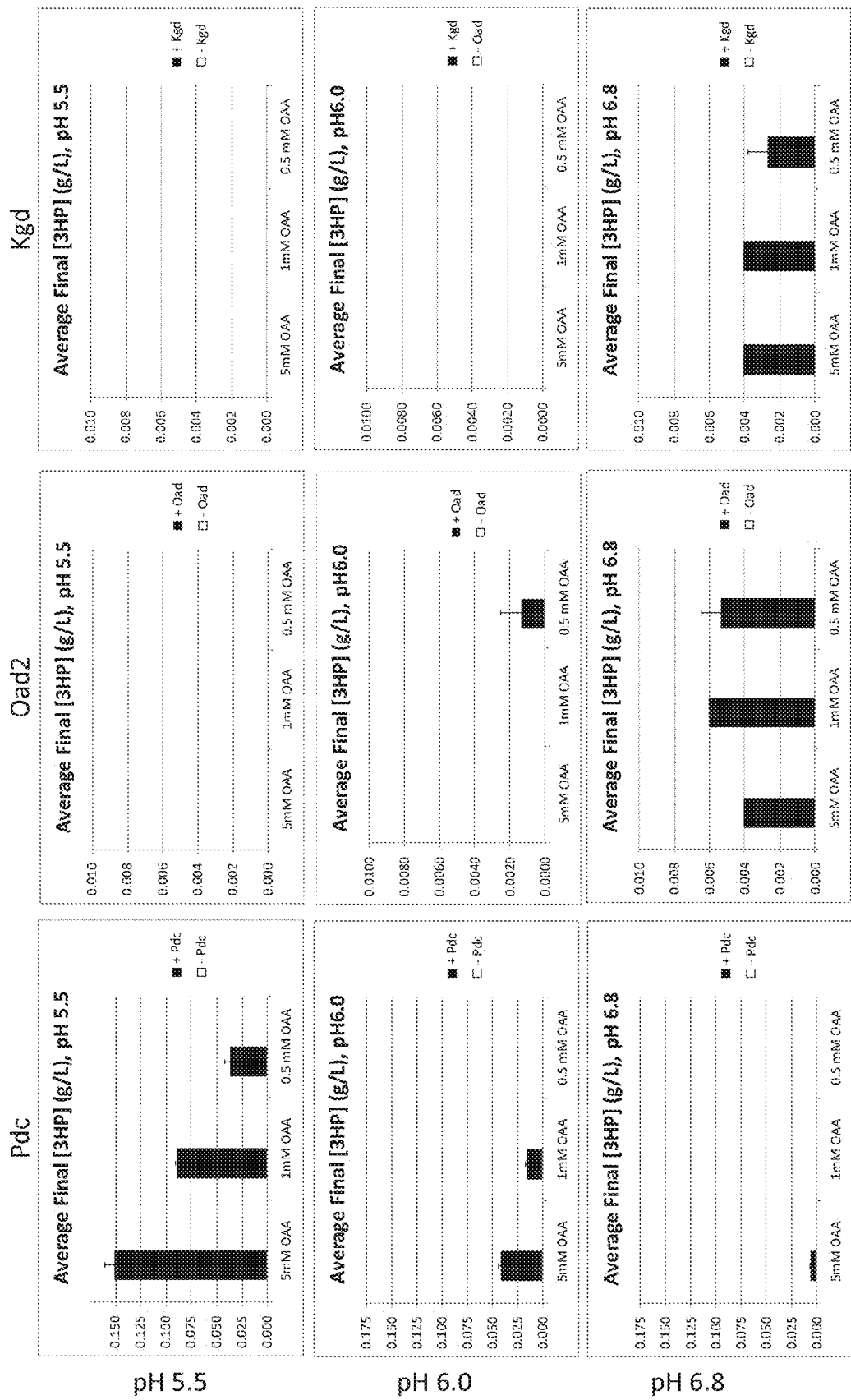
Figure 9: GC-MS results at various pH with and without addition of Oad-2 candidate enzymes

GENETICALLY MODIFIED ORGANISMS FOR INCREASED MICROBIAL PRODUCTION OF 3-HYDROXYPROPIONIC ACID INVOLVING AN OXALOACETATE ALPHA-DECARBOXYLASE

CROSS-REFERENCE TO RELATED APPLICATIONS

This application claims priority from U.S. Provisional Application 61/246,140, filed Sep. 27, 2009. The entire contents of this application are hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Feb. 10, 2011, is named OPXX2005.txt and is 234,626 bytes in size.

FIELD OF THE INVENTION

This invention relates to metabolically engineered microorganisms, such as bacterial strains, in which an identified functional variant of oxaloacetate alpha-decarboxylase is provided for production of a chemical product, 3-hydroxypropionic acid (3-HP) and products made from 3-HP. The metabolically engineered microorganisms may be adapted to exhibit increased tolerance to 3-HP. Production of products made from 3-HP so produced also is disclosed.

SEQUENCE LISTING

This provisional patent application provides a paper copy of sequence listings that are to be provided on compact disk in appropriate format in a later filing or submission.

BACKGROUND OF THE INVENTION

There are various approaches to increasing a genetically modified microorganism's productivity of 3-hydroxypropionic acid ("3-HP"). These approaches may be applied to a microorganism intended to be used in a production strain having the purpose of 3-HP production in an industrial microbial production system, whether or not 3-HP is the intended final product.

For example, without being limiting, various 3-HP production pathways are described in U.S. Pat. No. 6,852,517, WO2002/042418 (PCT/US01/43607), and U.S. Patent Publication No. US2008/0199926.

Nonetheless, notwithstanding these and other various microbial 3-HP production pathways, there remains a need in the art for alternative 3-HP production pathways.

SUMMARY OF THE INVENTION

According to one embodiment, the invention is directed to a method for producing an acrylic acid-based consumer product, said method comprising i) combining a carbon source and a microorganism cell culture to produce 3-hydroxypropionic acid, a) wherein said microorganism is genetically modified for increased enzymatic activity in the organism by introduction of a heterologous nucleic acid sequence coding for a polypeptide having oxaloacetate alpha-decarboxylase enzymatic activity, the heterologous nucleic acid sequence expressing a mutated oxaloacetate alpha-decarboxylaseoxaloacetate alpha-decarboxylase.

The carbon source according to the invention may be predominantly glucose, sucrose, fructose, dextrose, lactose, or a combination thereof. Alternatively, the carbon source is glycerol.

Included within the invention are embodiments where the cell culture comprises a genetically modified microorganism. The genetically modified microorganism may be modified for increased activity and specificity to convert oxaloacetate to malonate semialdehyde, increased tolerance to 3-hydroxypropionic acid, increased enzymatic activity in the organism's NADPH-dependent transhydrogenase pathway, increased intracellular bicarbonate levels, and combinations thereof.

In various embodiments, the genetically modified microorganism is modified for increased tolerance to 3-hydroxypropionic acid. The increase in tolerance to 3-hydroxypropionic acid may occur in one or more components of the 3-HP toleragenic complex (3HPTGC) complex.

The genetically modified bacteria may be further modified to decrease activity of, lactate dehydrogenase, phosphate acetyltransferase, pyruvate oxidase, or pyruvate-formate lyase, alcohol dehydrogenase, and combinations thereof.

The method according to the invention may further comprise separating and/or purifying 3-hydroxypropionic acid from said cell culture by extraction of 3-hydroxypropionic acid from said culture in the presence of a tertiary amine.

The method of the invention may include production of a consumer product, such as diapers, carpet, paint, adhesives, and acrylic glass. The invention includes biologically-produced 3-hydroxypropionic acid, where the 3-hydroxypropionic acid is produced according to the method of the invention. Such 3-hydroxypropionic acid may be essentially free of chemical catalyst, including a molybdenum and/or vanadium based catalyst. The 3-hydroxypropionic acid is produced according to the method of the invention may have a ratio of carbon-14 to carbon-12 of about $1.0 \times 10^{-14}$ or greater. In various aspects, the 3-hydroxypropionic acid contains less than about 10% carbon derived from petroleum. In addition, 3-hydroxypropionic acid according to the invention may contain a residual amount of organic material related to its method of production. In various embodiments, the 3-hydroxypropionic acid contains a residual amount of organic material in an amount between 1 and 1,000 parts per million of the 3-hydroxypropionic acid.

Acrylic acid and a polymer produced from acrylic acid, where such are produced according to the method of the invention, are also included within the invention. Products, including commercial and consumer products, obtained from the polymers are also encompassed. For example, diapers, carpet, paint, adhesives, and acrylic glass are encompassed.

In addition, the invention encompasses a system for bioproduction of acrylic acid, said system comprising: a tank for saccharification of biomass; a line for passing the product of saccharification to a fermentation tank optionally via a pre-fermentation tank; a fermentation tank suitable for microorganism cell culture; a line for discharging contents from the fermentation tank to an extraction and/or separation vessel; an extraction and/or separation vessel suitable for removal of 3-hydroxypropionic acid from cell culture waste; a line for transferring 3-hydroxypropionic acid to a dehydration vessel; and a dehydration vessel suitable for conversion of 3-hydroxypropionic acid to acrylic acid. In various embodiments, the system further comprises one or more pre-fermentation tanks, distillation columns, centrifuge vessels, back extraction columns, mixing vessels, or combinations thereof. In various embodiments, the system has a minimum production capacity of at least 1 ton acrylic acid per year.

In various embodiments, a further genetic modification has been made that increases NADH/NADPH transhydrogenase activity. For example, the transhydrogenase activity may be soluble, may be membrane bound, may have a further genetic modification that has been made that increases cyanase activity, may include a further genetic modification that increases carbonic anhydrase activity, and/or may include a further genetic modification that increases pyruvate dehydrogenase activity.

In various embodiments, the invention includes a culture system comprising a carbon source in an aqueous medium and a genetically modified microorganism according to any one of claims, wherein said genetically modified microorganism is present in an amount selected from greater than 0.05 gDCW/L, 0.1 gDCW/L, greater than 1 gDCW/L, greater than 5 gDCW/L, greater than 10 gDCW/L, greater than 15 gDCW/L or greater than 20 gDCW/L, such as when the volume of the aqueous medium is selected from greater than 5 mL, greater than 100 mL, greater than 0.5 L, greater than 1 L, greater than 2 L, greater than 10 L, greater than 250 L, greater than 1000 L, greater than 10,000 L, greater than 50,000 L, greater than 100,000 L or greater than 200,000 L, and such as when the volume of the aqueous medium is greater than 250 L and contained within a steel vessel.

Variously, the carbon source for such culture systems is selected from dextrose, sucrose, a pentose, a polyol, a hexose, both a hexose and a pentose, and combinations thereof.

In various embodiments, the invention is an aqueous broth obtained from a culture system according to any one of claims, wherein said aqueous broth comprises i) a concentration of 3-hydroxypropionate selected from greater than 5 g/L, greater than 10 g/L, greater than 15 g/L, greater than 20 g/L, greater than 25 g/L, greater than 30 g/L, greater than 35 g/L, greater than 40 g/L, greater than 50 g/L, greater than 60 g/L, greater than 70 g/L, greater than 80 g/L, greater than 90 g/L, or greater than 100 g/L 3-hydroxypropionate; and ii) a concentration of 1,3-propanediol selected from less than 30 g/L; less than 20 g/L; less than 10 g/L; less than 5 g/L; less than 1 g/L; or less than 0.5 g/L. In some aspects, the aqueous broth comprises an amount of biomass selected from less than 20 gDCW/L biomass, less than 15 gDCW/L biomass, less than 10 gDCW/L biomass, less than 5 gDCW/L biomass or less than 1 gDCW/L biomass. Alternatively, the aqueous broth according to the invention is such that the 3-HP/succinate ratio (g3-HP/g succinate) is greater than 3, greater than 10 greater than 30, greater than 60, greater than 100, greater than 150 or greater than 200. In various aspects, the 3-HP/fumarate ratio (g3-HP/g fumarate) is greater than 3, greater than 10 greater than 30, greater than 60, greater than 100, greater than 150 or greater than 200, or the 3-HP/glycerol ratio (g3-HP/g glycerol) is greater than 3, greater than 10, greater than 30, greater than 60, greater than 100, greater than 150 or greater than 200, or the 3-HP/acetate ratio (g3-HP/g acetate) is greater than 1.5, greater than 3, greater than 10, greater than 30, greater than 60, greater than 100, greater than 150 or greater than 200, or the 3-HP/alanine ratio (g3-HP/g alanine) is greater than 3, greater than 10, greater than 30, greater than 60, greater than 100, greater than 150 or greater than 200, or the 3-HP/beta-alanine ratio (g3-HP/g beta-alanine) is greater than 1.5, greater than 3, greater than 10, greater than 30, greater than 60, greater than 100, greater than 150 or greater than 200, or the 3-HP/glutamate ratio (g3-HP/g glutamate) is greater than 3, greater than 10, greater than 30, greater than 60, greater than 100, greater than 150 or greater than 200, or the 3-HP/glutamine ratio (g3-HP/g glutamine) is greater than 3, greater than 10, greater than 30, greater than 60, greater than 100, greater than 150 or greater than 200, or the 3-HP/3-hydroxypropionaldehyde ratio (g3-HP/g 3-hydroxypropionaldehyde) is greater than 1.5, greater than 3, greater than 10, greater than 30, greater than 60, greater than 100, greater than 150 or greater than 200, or the 3-HP/1,3-propanediol ratio (g3-HP/g 1,3-propanediol) is greater than 1.5, greater than 3, greater than 10, greater than 30, greater than 60, greater than 100, greater than 150 or greater than 200, and/or the 3-HP/lactate ratio (g3-HP/g lactate) is greater than 3, greater than 10, greater than 30, greater than 60, greater than 100, greater than 150 or greater than 200.

BRIEF DESCRIPTION OF THE DRAWINGS

The novel features of the invention are set forth with particularity in the claims. A better understanding of the features and advantages of the present invention will be obtained by reference to the following detailed description that sets forth illustrative embodiments, in which the principles of the invention are utilized, and the accompanying drawings of which:

FIG. 1 depicts a CLUSTAL 2.0.12 multiple sequence alignment of Carbonic Anhydrase Polypeptides.

FIG. 3A depicts the natural mixed acid fermentation routes in *E. coli*

FIG. 3B depicts the proposed 3-HP fermentation pathway of the present invention

FIG. 5 depicts the reaction catalyzed by the YdfG enzyme.

FIG. 7 provides a schematic of processing from biomass to polymerized acrylic acid.

FIG. 8 is a Western blot of purified Kgd, Oad, and Pdc proteins

FIG. 9 are the results of GC-MS analysis of 3-HP production by various Oad-2 candidate enzymes Tables also are provided herein and are part of the specification.

DETAILED DESCRIPTION OF THE INVENTION

Figure 2:
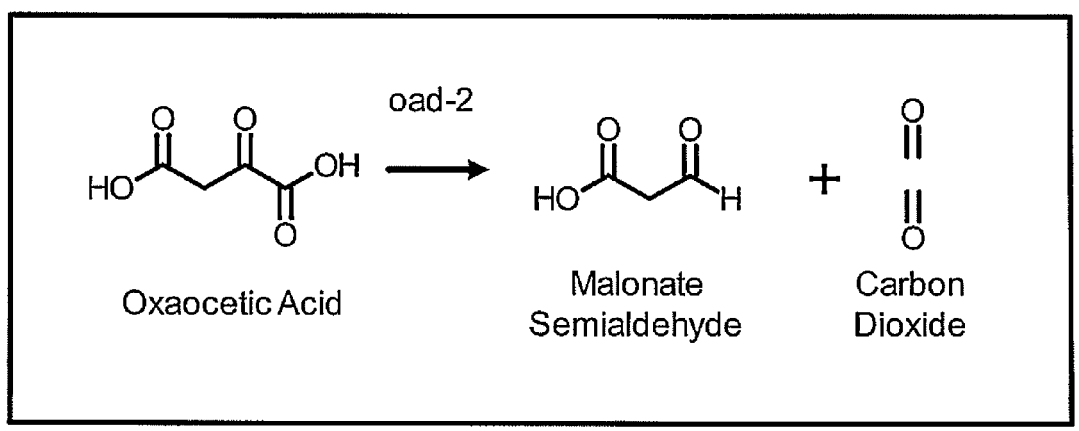
FIG. 2 depicts the reaction catalyzed by an oxaloacetate alpha-decarboxylase enzyme.

The present invention is related to various production methods and/or genetically modified microorganisms that have utility for fermentative production of 3-hydroxypropionic acid ("3-HP", CAS No. 503-66-2), which may be converted to a number of basic building blocks for polymers used in a wide range of industrial and consumer products. The present invention also is directed to methods of making 3-HP that utilize populations of these microorganisms in vessels, and to systems for chemical production that employ these microorganisms and methods. As noted herein, various aspects of the present invention are directed to a microorganism cell comprises a metabolic pathway from oxaloacetate to malonate semialdehyde, and also in various embodiments the capability to convert malonate semialdehyde to 3-HP, whether native and/or provided by a heterologous nucleic acid sequence encoding a protein having such activity.

Functional variants of an oxaloacetate alpha-decarboxylaseoxaloacetate alpha-decarboxylase are provided herein, with a demonstration of improved enzymatic conversion using these variant forms. In particular, three identified functional variant forms of an oxaloacetate alpha-decarboxylase from *Leuconostoc mesenteroides* are shown to have increased enzymatic activity. These may be provided in microorganisms that may also be provided with other genetic modifications described herein, resulting in improved capacity to produce 3-HP, which thereafter is converted to other chemicals, including acrylic acid, which is utilized for a number of industrial and consumer products.

Further as to the microorganisms of the present invention, in various embodiments additional genetic modifications may be made, such as to 1) increase intracellular bicarbonate levels, such as by increasing carbonic anhydrase, 2) increase enzymatic activity of NADPH-dependent transhydrogenase.

Additionally, genetic modifications for increasing tolerance may be combined with the present invention. Moreover, genetic modifications to increase expression and/or enzymatic activity of carbonic anhydrase and/or cyanase may provide dual-functions to advantageously improve both 3-HP production and 3-HP tolerance.

Other additional genetic modifications are disclosed herein for various embodiments.

DEFINITIONS

As used in the specification and the claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

As used herein, dry cell weight (DCW) for *E. coli* strains is calculated as 0.33 times the measured $OD_{600}$ value, based on baseline DCW to $OD_{600}$ determinations.

As used herein, "reduced enzymatic activity," "reducing enzymatic activity," and the like is meant to indicate that a microorganism cell's, or an isolated enzyme, exhibits a lower level of activity than that measured in a comparable cell of the same species or its native enzyme. That is, enzymatic conversion of the indicated substrate(s) to indicated product(s) under known standard conditions for that enzyme is at least 10, at least 20, at least 30, at least 40, at least 50, at least 60, at least 70, at least 80, or at least 90 percent less than the enzymatic activity for the same biochemical conversion by a native (non-modified) enzyme under a standard specified condition. This term also can include elimination of that enzymatic activity. A cell having reduced enzymatic activity of an enzyme can be identified using any method known in the art. For example, enzyme activity assays can be used to identify cells having reduced enzyme activity. See, for example, Enzyme Nomenclature, Academic Press, Inc., New York 2007.

The term "heterologous DNA," "heterologous nucleic acid sequence," and the like as used herein refers to a nucleic acid sequence wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid.

The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome).

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

In various contexts, a gene disruption is taken to mean any genetic modification to the DNA, mRNA encoded from the DNA, and the corresponding amino acid sequence that results in reduced polypeptide activity. Many different methods can be used to make a cell having reduced polypeptide activity. For example, a cell can be engineered to have a disrupted regulatory sequence or polypeptide-encoding sequence using common mutagenesis or knock-out technology. See, e.g., *Methods in Yeast Genetics* (1997 edition), Adams et al., Cold Spring Harbor Press (1998). One particularly useful method of gene disruption is complete gene deletion because it reduces or eliminates the occurrence of genetic reversions in the genetically modified microorganisms of the invention. Accordingly, a disruption of a gene whose product is an enzyme thereby disrupts enzymatic function. Alternatively, antisense technology can be used to reduce the activity of a particular polypeptide. For example, a cell can be engineered to contain a cDNA that encodes an antisense molecule that prevents a polypeptide from being translated. Further, gene silencing can be used to reduce the activity of a particular polypeptide.

The term "antisense molecule" as used herein encompasses any nucleic acid molecule or nucleic acid analog (e.g., peptide nucleic acids) that contains a sequence that corresponds to the coding strand of an endogenous polypeptide. An antisense molecule also can have flanking sequences (e.g., regulatory sequences). Thus, antisense molecules can be ribozymes or antisense oligonucleotides.

As used herein, a ribozyme can have any general structure including, without limitation, hairpin, hammerhead, or axhead structures, provided the molecule cleaves RNA.

The term "reduction" or "to reduce" when used in such phrase and its grammatical equivalents are intended to encompass a complete elimination of such conversion(s).

Bio-production, as used herein, may be aerobic, microaerobic, or anaerobic. Also as used herein, the terms "production" and "bio-production" are used interchangeably when referring to microbial synthesis of 3-HP.

As used herein, the language "sufficiently homologous" refers to proteins or portions thereof that have amino acid sequences that include a minimum number of identical or equivalent amino acid residues when compared to an amino acid sequence of the amino acid sequences provided in this application (including the SEQ ID Nos./sequence listings) such that the protein or portion thereof is able to achieve the respective enzymatic reaction and/or other function. To determine whether a particular protein or portion thereof is sufficiently homologous may be determined by an assay of enzymatic activity, such as those commonly known in the art.

Descriptions and methods for sequence identity and homology are intended to be exemplary and it is recognized that these concepts are well-understood in the art. Further, it is appreciated that nucleic acid sequences may be varied and still encode an enzyme or other polypeptide exhibiting a desired functionality, and such variations are within the scope of the present invention.

Further to nucleic acid sequences, "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1M, more usually less than about 500 mM and less than about 200 mM. Hybridization temperatures can be as low as 5° C., but are typically greater than 22° C., more typically greater than about 30° C., and often are in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook and Russell and Anderson "Nucleic Acid Hybridization" 1$^{st}$ Ed., BIOS Scientific Publishers Limited (1999), which are hereby incorporated by reference for hybridization protocols. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

The term "identified enzymatic functional variant" means a polypeptide that is determined to possess an enzymatic activity and specificity of an enzyme of interest but which has an amino acid sequence different from such enzyme of interest. A corresponding "variant nucleic acid sequence" may be constructed that is determined to encode such an identified enzymatic functional variant. For a particular purpose, such as increased tolerance to 3-HP via genetic modification to increase enzymatic conversion at one or more of the enzymatic conversion steps of the 3HPTGC in a microorganism, one or more genetic modifications may be made to provide one or more heterologous nucleic acid sequence(s) that encode one or more identified 3HPTGC enzymatic functional variant(s). That is, each such nucleic acid sequence encodes a polypeptide that is not exactly the known polypeptide of an enzyme of the 3HPTGC, but which nonetheless is shown to exhibit enzymatic activity of such enzyme. Such nucleic acid sequence, and the polypeptide it encodes, may not fall within a specified limit of homology or identity yet by its provision in a cell nonetheless provide for a desired enzymatic activity and specificity. The ability to obtain such variant nucleic acid sequences and identified enzymatic functional variants is supported by recent advances in the states of the art in bioinformatics and protein engineering and design, including advances in computational, predictive and high-throughput methodologies. Functional variants more generally include enzymatic functional variants, and the nucleic acids sequences that encode them, as well as variants of non-enzymatic polypeptides, wherein the variant exhibits the function of the original (target) sequence.

The use of the phrase "segment of interest" is meant to include both a gene and any other nucleic acid sequence segment of interest. One example of a method used to obtain a segment of interest is to acquire a culture of a microorganism, where that microorganism's genome includes the gene or nucleic acid sequence segment of interest.

When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

In some embodiments a truncated respective polypeptide has at least about 90% of the full length of a polypeptide encoded by a nucleic acid sequence encoding the respective native enzyme, and more particularly at least 95% of the full length of a polypeptide encoded by a nucleic acid sequence encoding the respective native enzyme. By a polypeptide having an amino acid sequence at least, for example, 95% "identical" to a reference amino acid sequence of a polypeptide is intended that the amino acid sequence of the claimed polypeptide is identical to the reference sequence except that the claimed polypeptide sequence can include up to five amino acid alterations per each 100 amino acids of the reference amino acid of the polypeptide. In other words, to obtain a polypeptide having an amino acid sequence at least 95% identical to a reference amino acid sequence, up to 5% of the amino acid residues in the reference sequence can be deleted or substituted with another amino acid, or a number of amino acids up to 5% of the total amino acid residues in the reference sequence can be inserted into the reference sequence. These alterations of the reference sequence can occur at the amino or carboxy terminal positions of the reference amino acid sequence or anywhere between those terminal positions, interspersed either individually among residues in the reference sequence or in one or more contiguous groups within the reference sequence. In other embodiments truncation may be more substantial, as described elsewhere herein.

Species and other phylogenic identifications are according to the classification known to a person skilled in the art of microbiology.

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

Prophetic examples provided herein are meant to be broadly exemplary and not limiting in any way. This applies to the examples regarding separation and purification of 3-HP, and conversions of 3-HP to downstream compounds, since there are numerous possible approaches to such steps and conversions, including those disclosed in references recited and incorporated herein.

The meaning of abbreviations is as follows: "C" means Celsius or degrees Celsius, as is clear from its usage, DCW means dry cell weight, "s" means second(s), "min" means minute(s), "h," "hr," or "hrs" means hour(s), "psi" means pounds per square inch, "nm" means nanometers, "d" means day(s), "µL" or "uL" or "ul" means microliter(s), "mL" means milliliter(s), "L" means liter(s), "mm" means millimeter(s), "nm" means nanometers, "mM" means millimolar, "µM" or "uM" means micromolar, "M" means molar, "mmol" means millimole(s), "µmol" or "uMol" means micromole(s)", "g" means gram(s), "µg" or "ug" means microgram(s) and "ng" means nanogram(s), "PCR" means polymerase chain reaction, "OD" means optical density, "$OD_{600}$" means the optical density measured at a photon wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "IPTG" means isopropyl-µ-D-thiogalactopyranoiside, "RBS" means ribosome binding site, "rpm" means revolutions per minute, "HPLC" means high performance liquid chromatography, and "GC" means gas chromatography. As disclosed herein, "3-HP" means 3-hydroxypropionic acid and "3HPTGC" means the 3-HP toleragenic complex. Also, 10^5 and the like are taken to mean $10^5$ and the like.

I. Carbon Sources

Bio-production media, which is used in the present invention with recombinant microorganisms having a biosynthetic pathway for 3-HP, must contain suitable carbon sources or substrates for the intended metabolic pathways. Suitable substrates may include, but are not limited to, monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, carbon monoxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity.

Although it is contemplated that all of the above mentioned carbon substrates and mixtures thereof are suitable in the present invention as a carbon source, common carbon substrates used as carbon sources are glucose, fructose, and sucrose, as well as mixtures of any of these sugars. Other suitable substrates include xylose, arabinose, other cellulose-based C-5 sugars, high-fructose corn syrup, and various other sugars and sugar mixtures as are available commercially. Sucrose may be obtained from feedstocks such as sugar cane, sugar beets, cassava, bananas or other fruit, and sweet sorghum. Glucose and dextrose may be obtained through saccharification of starch based feedstocks including grains such as corn, wheat, rye, barley, and oats. Also, in some embodiments all or a portion of the carbon source may be glycerol. Alternatively, glycerol may be excluded as an added carbon source.

In one embodiment, the carbon source is selected from glucose, fructose, sucrose, dextrose, lactose, glycerol, and mixtures thereof. Variously, the amount of these components in the carbon source may be greater than about 50%, greater than about 60%, greater than about 70%, greater than about 80%, greater than about 90%, or more, up to 100% or essentially 100% of the carbon source.

In addition, methylotrophic organisms are known to utilize a number of other carbon containing compounds such as methylamine, glucosamine and a variety of amino acids for metabolic activity. For example, methylotrophic yeast are known to utilize the carbon from methylamine to form trehalose or glycerol (Hellion et al., Microb. Growth C1 Compd. (Int. Symp.), 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., Arch. Microbiol. 153:485-489 (1990)). Hence it is contemplated that the source of carbon utilized in embodiments of the present invention may encompass a wide variety of carbon-containing substrates.

In addition, fermentable sugars may be obtained from cellulosic and lignocellulosic biomass through processes of pretreatment and saccharification, as described, for example, in U.S. Patent Publication No. 2007/0031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure. Any such biomass may be used in a bio-production method or system to provide a carbon source. Various approaches to breaking down cellulosic biomass to mixtures of more available and utilizable carbon molecules, including sugars, include: heating in the presence of concentrated or dilute acid (e.g., <1% sulfuric acid); treating with ammonia; treatment with ionic salts; enzymatic degradation; and combinations of these. These methods normally follow mechanical separation and milling, and are followed by appropriate separation processes.

In various embodiments, any of a wide range of sugars, including, but not limited to sucrose, glucose, xylose, cellulose or hemicellulose, are provided to a microorganism, such as in an industrial system comprising a reactor vessel in which a defined media (such as a minimal salts media including but not limited to M9 minimal media, potassium sulfate minimal media, yeast synthetic minimal media and many others or variations of these), an inoculum of a microorganism providing one or more of the 3-HP biosynthetic pathway alternatives, and the a carbon source may be combined. The carbon source enters the cell and is cataboliized by well-known and common metabolic pathways to yield common metabolic intermediates, including phosphoenolpyruvate (PEP). (See Molecular Biology of the Cell, 3rd Ed., B. Alberts et al. Garland Publishing, New York, 1994, pp. 42-45, 66-74, incorporated by reference for the teachings of basic metabolic catabolic pathways for sugars; Principles of Biochemistry, 3rd Ed., D. L. Nelson & M. M. Cox, Worth Publishers, New York, 2000, pp 527-658, incorporated by reference for the teachings of major metabolic pathways; and Biochemistry, 4th Ed., L. Stryer, W.H. Freeman and Co., New York, 1995, pp. 463-650, also incorporated by reference for the teachings of major metabolic pathways.)

Bio-based carbon can be distinguished from petroleum-based carbon according to a variety of methods, including without limitation ASTM D6866, or various other techniques. For example, carbon-14 and carbon-12 ratios differ in bio-based carbon sources versus petroleum-based sources, where higher carbon-14 ratios are found in bio-based carbon sources. In various embodiments, the carbon source is not petroleum-based, or is not predominantly petroleum based. In various embodiments, the carbon source is greater than about 50% non-petroleum based, greater than about 60% non-petroleum based, greater than about 70% non-petroleum based, greater than about 80% non-petroleum based, greater than about 90% non-petroleum based, or more. In various embodiments, the carbon source has a carbon-14 to carbon-12 ratio of about $1.0 \times 10^{-14}$ or greater.

Various components may be excluded from the carbon source. For example, in some embodiments, acrylic acid, 1,4-butanediol, and/or glycerol are excluded or essentially excluded from the carbon source. As such, the carbon source according to some embodiments of the invention may be less than about 50% glycerol, less than about 40% glycerol, less than about 30% glycerol, less than about 20% glycerol, less than about 10% glycerol, less than about 5% glycerol, less than about 1% glycerol, or less. For example, the carbon source may be essentially glycerol-free. By essentially glycerol-free is meant that any glycerol that may be present in a residual amount does not contribute substantially to the production of the target chemical compound.

II. Microorganisms

Features as described and claimed herein may be provided in a microorganism selected from the listing herein, or another suitable microorganism, that also comprises one or more natural, introduced, or enhanced 3-HP bio-production pathways. Thus, in some embodiments the microorganism comprises an endogenous 3-HP production pathway (which may, in some such embodiments, be enhanced), whereas in other embodiments the microorganism does not comprise an endogenous 3-HP production pathway.

Varieties of these genetically modified microorganisms may comprise genetic modifications and/or other system alterations as may be described in other patent applications of one or more of the present inventor(s) and/or subject to assignment to the owner of the present patent application.

The examples describe specific modifications and evaluations to certain bacterial and yeast microorganisms. The scope of the invention is not meant to be limited to such species, but to be generally applicable to a wide range of suitable microorganisms. Generally, a microorganism used for the present invention may be selected from bacteria, cyanobacteria, filamentous fungi and yeasts.

For some embodiments, microbial hosts initially selected for 3-HP toleragenic bio-production should also utilize sugars including glucose at a high rate. Most microbes are capable of utilizing carbohydrates. However, certain environmental microbes cannot utilize carbohydrates to high efficiency, and therefore would not be suitable hosts for such embodiments that are intended for glucose or other carbohydrates as the principal added carbon source.

As the genomes of various species become known, the present invention easily may be applied to an ever-increasing range of suitable microorganisms. Further, given the relatively low cost of genetic sequencing, the genetic sequence of a species of interest may readily be determined to make application of aspects of the present invention more readily obtainable (based on the ease of application of genetic modifications to an organism having a known genomic sequence).

More particularly, based on the various criteria described herein, suitable microbial hosts for the bio-production of 3-HP that comprise tolerance aspects provided herein generally may include, but are not limited to, any gram negative organisms, more particularly a member of the family Enterobacteriaceae, such as *E. coli*, or *Oligotropha carboxidovorans*, or *Pseudomononas* sp.; any gram positive microorganism, for example *Bacillus subtilis*, *Lactobaccilus* sp. or *Lactococcus* sp.; a yeast, for example *Saccharomyces cerevisiae*, *Pichia pastoris* or *Pichia stipitis*; and other groups or microbial species. More particularly, suitable microbial hosts for the bio-production of 3-HP generally include, but are not limited to, members of the genera *Clostridium*, *Zymomonas*, *Escherichia*, *Salmonella*, *Rhodococcus*, *Pseudomonas*, *Bacillus*, *Lactobacillus*, *Enterococcus*, *Alcaligenes*, *Klebsiella*, *Paenibacillus*, *Arthrobacter*, *Corynebacterium*, *Brevibacterium*, *Pichia*, *Candida*, *Hansenula* and *Saccharomyces*. Hosts that may be particularly of interest include: *Oligotropha carboxidovorans* (such as strain OM5), *Escherichia coli*, *Alcaligenes eutrophus* (*Cupriavidus necator*), *Bacillus licheniformis*, *Paenibacillus macerans*, *Rhodococcus erythropolis*, *Pseudomonas putida*, *Lactobacillus plantarum*, *Enterococcus faecium*, *Enterococcus gallinarium*, *Enterococcus faecalis*, *Bacillus subtilis* and *Saccharomyces cerevisiae*.

More particularly, suitable microbial hosts for the bio-production of 3-HP generally include, but are not limited to, members of the genera *Clostridium*, *Zymomonas*, *Escherichia*, *Salmonella*, *Rhodococcus*, *Pseudomonas*, *Bacillus*, *Lactobacillus*, *Enterococcus*, *Alcaligenes*, *Klebsiella*, *Paenibacillus*, *Arthrobacter*, *Corynebacterium*, *Brevibacterium*, *Pichia*, *Candida*, *Hansenula* and *Saccharomyces*.

Hosts that may be particularly of interest include: *Oligotropha carboxidovorans* (such as strain $OM5^T$), *Escherichia coli*, *Alcaligenes eutrophus* (*Cupriavidus necator*), *Bacillus licheniformis*, *Paenibacillus macerans*, *Rhodococcus erythropolis*, *Pseudomonas putida*, *Lactobacillus plantarum*, *Enterococcus faecium*, *Enterococcus gallinarium*, *Enterococcus faecalis*, *Bacillus subtilis* and *Saccharomyces cerevisiae*. Also, any of the known strains of these species may be utilized as a starting microorganism, as may any of the following species including respective strains thereof—*Cupriavidus basilensis*, *Cupriavidus campinensis*, *Cupriavidus gilardi*, *Cupriavidus laharsis*, *Cupriavidus metallidurans*, *Cupriavidus oxalaticus*, *Cupriavidus pauculus*, *Cupriavidus pinatubonensis*, *Cupriavidus respiraculi*, and *Cupriavidus taiwanensis*.

In some embodiments, the recombinant microorganism is a gram-negative bacterium. In some embodiments, the recombinant microorganism is selected from the genera *Zymomonas*, *Escherichia*, *Pseudomonas*, *Alcaligenes*, and *Klebsiella*. In some embodiments, the recombinant microorganism is selected from the species *Escherichia coli*, *Cupriavidus neca-*

*tor, Oligotropha carboxidovorans*, and *Pseudomonas putida*. In some embodiments, the recombinant microorganism is an *E. coli* strain.

In some embodiments, the recombinant microorganism is a gram-positive bacterium. In some embodiments, the recombinant microorganism is selected from the genera *Clostridium, Salmonella, Rhodococcus, Bacillus, Lactobacillus, Enterococcus, Paenibacillus, Arthrobacter, Corynebacterium*, and *Brevibacterium*. In some embodiments, the recombinant microorganism is selected from the species *Bacillus licheniformis, Paenibacillus macerans, Rhodococcus erythropolis, Lactobacillus plantarum, Enterococcus faecium, Enterococcus gallinarium, Enterococcus faecalis*, and *Bacillus subtilis*. In particular embodiments, the recombinant microorganism is a *B. subtilis* strain.

In some embodiments, the recombinant microorganism is a yeast. In some embodiments, the recombinant microorganism is selected from the genera *Pichia, Candida, Hansenula* and *Saccharomyces*. In particular embodiments, the recombinant microorganism is *Saccharomyces cerevisiae*.

III. Media and Culture Conditions

In addition to an appropriate carbon source, such as selected from one of the herein-disclosed types, bio-production media must contain suitable minerals, salts, cofactors, buffers and other components, known to those skilled in the art, suitable for the growth of the cultures and promotion of the enzymatic pathway necessary for 3-HP production, or other products made under the present invention.

Another aspect of the invention regards media and culture conditions that comprise genetically modified microorganisms of the invention and optionally supplements.

Typically cells are grown at a temperature in the range of about 25° C. to about 40° C. in an appropriate medium, as well as up to 70° C. for thermophilic microorganisms. Suitable growth media in the present invention are common commercially prepared media such as Luria Bertani (LB) broth, M9 minimal media, Sabouraud Dextrose (SD) broth, Yeast medium (YM) broth, (Ymin) yeast synthetic minimal media, and minimal media as described herein, such as M9 minimal media. Other defined or synthetic growth media may also be used, and the appropriate medium for growth of the particular microorganism will be known by one skilled in the art of microbiology or bio-production science. In various embodiments a minimal media may be developed and used that does not comprise, or that has a low level of addition of various components, for example less than 10, 5, 2 or 1 g/L of a complex nitrogen source including but not limited to yeast extract, peptone, tryptone, soy flour, corn steep liquor, or casein. These minimal medias may also have limited supplementation of vitamin mixtures including biotin, vitamin B12 and derivatives of vitamin B12, thiamin, pantothenate and other vitamins. Minimal medias may also have limited simple inorganic nutrient sources containing less than 28, 17, or 2.5 mM phosphate, less than 25 or 4 mM sulfate, and less than 130 or 50 mM total nitrogen.

Bio-production media, which is used in embodiments of the present invention with genetically modified microorganisms, must contain suitable carbon substrates for the intended metabolic pathways. As described hereinbefore, suitable carbon substrates include carbon monoxide, carbon dioxide, and various monomeric and oligomeric sugars.

Suitable pH ranges for the bio-production are between pH 3.0 to pH 10.0, where pH 6.0 to pH 8.0 is a typical pH range for the initial condition. However, the actual culture conditions for a particular embodiment are not meant to be limited by these pH ranges.

Bio-productions may be performed under aerobic, microaerobic, or anaerobic conditions, with or without agitation.

The amount of 3-HP or other product(s) produced in a bio-production media generally can be determined using a number of methods known in the art, for example, high performance liquid chromatography (HPLC), gas chromatography (GC), or GC/Mass Spectroscopy (MS). Specific HPLC methods for the specific examples are provided herein.

IV. Bio-Production Reactors and Systems

Fermentation systems utilizing methods and/or compositions according to the invention are also within the scope of the invention.

Any of the recombinant microorganisms as described and/or referred to herein may be introduced into an industrial bio-production system where the microorganisms convert a carbon source into 3-HP in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to 3-HP. Industrial bio-production systems and their operation are well-known to those skilled in the arts of chemical engineering and bioprocess engineering.

Bio-productions may be performed under aerobic, microaerobic, or anaerobic conditions, with or without agitation. The operation of cultures and populations of microorganisms to achieve aerobic, microaerobic and anaerobic conditions are known in the art, and dissolved oxygen levels of a liquid culture comprising a nutrient media and such microorganism populations may be monitored to maintain or confirm a desired aerobic, microaerobic or anaerobic condition. When syngas is used as a feedstock, aerobic, microaerobic, or anaerobic conditions may be utilized. When sugars are used, anaerobic, aerobic or microaerobic conditions can be implemented in various embodiments.

Any of the recombinant microorganisms as described and/or referred to herein may be introduced into an industrial bio-production system where the microorganisms convert a carbon source into 3-HP, and optionally in various embodiments also to one or more downstream compounds of 3-HP in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to 3-HP.

In various embodiments, syngas components or sugars are provided to a microorganism, such as in an industrial system comprising a reactor vessel in which a defined media (such as a minimal salts media including but not limited to M9 minimal media, potassium sulfate minimal media, yeast synthetic minimal media and many others or variations of these), an inoculum of a microorganism providing an embodiment of the biosynthetic pathway(s) taught herein, and the carbon source may be combined. The carbon source enters the cell and is catabolized by well-known and common metabolic pathways to yield common metabolic intermediates, including phosphoenolpyruvate (PEP). (See *Molecular Biology of the Cell*, $3^{rd}$ Ed., B. Alberts et al. Garland Publishing, New York, 1994, pp. 42-45, 66-74, incorporated by reference for the teachings of basic metabolic catabolic pathways for sugars; *Principles of Biochemistry*, $3^{rd}$ Ed., D. L. Nelson & M. M. Cox, Worth Publishers, New York, 2000, pp. 527-658, incorporated by reference for the teachings of major metabolic pathways; and *Biochemistry*, $4^{th}$ Ed., L. Stryer, W.H. Freeman and Co., New York, 1995, pp. 463-650, also incorporated by reference for the teachings of major metabolic pathways.).

Further to types of industrial bio-production, various embodiments of the present invention may employ a batch type of industrial bioreactor. A classical batch bioreactor system is considered "closed" meaning that the composition of the medium is established at the beginning of a respective bio-production event and not subject to artificial alterations and additions during the time period ending substantially with the end of the bio-production event. Thus, at the beginning of the bio-production event the medium is inoculated with the desired organism or organisms, and bio-production is permitted to occur without adding anything to the system. Typically, however, a "batch" type of bio-production event is batch with respect to the addition of carbon source and attempts are often made at controlling factors such as pH and oxygen concentration. In batch systems the metabolite and biomass compositions of the system change constantly up to the time the bio-production event is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of a desired end product or intermediate.

A variation on the standard batch system is the fed-batch system. Fed-batch bio-production processes are also suitable in the present invention and comprise a typical batch system with the exception that the nutrients, including the substrate, are added in increments as the bio-production progresses. Fed-Batch systems are useful when catabolite repression is apt to inhibit the metabolism of the cells and where it is desirable to have limited amounts of substrate in the media. Measurement of the actual nutrient concentration in Fed-Batch systems may be measured directly, such as by sample analysis at different times, or estimated on the basis of the changes of measurable factors such as pH, dissolved oxygen and the partial pressure of waste gases such as $CO_2$. Batch and fed-batch approaches are common and well known in the art and examples may be found in Thomas D. Brock in *Biotechnology: A Textbook of Industrial Microbiology*, Second Edition (1989) Sinauer Associates, Inc., Sunderland, Mass., Deshpande, Mukund V., Appl. Biochem. Biotechnol., 36:227, (1992), and *Biochemical Engineering Fundamentals*, $2^{nd}$ Ed. J. E. Bailey and D. F. Ollis, McGraw Hill, New York, 1986, herein incorporated by reference for general instruction on bio-production.

Although embodiments of the present invention may be performed in batch mode, or in fed-batch mode, it is contemplated that the invention would be adaptable to continuous bio-production methods. Continuous bio-production is considered an "open" system where a defined bio-production medium is added continuously to a bioreactor and an equal amount of conditioned media is removed simultaneously for processing. Continuous bio-production generally maintains the cultures within a controlled density range where cells are primarily in log phase growth. Two types of continuous bioreactor operation include a chemostat, wherein fresh media is fed to the vessel while simultaneously removing an equal rate of the vessel contents. The limitation of this approach is that cells are lost and high cell density generally is not achievable.

In fact, typically one can obtain much higher cell density with a fed-batch process. Another continuous bioreactor utilizes perfusion culture, which is similar to the chemostat approach except that the stream that is removed from the vessel is subjected to a separation technique which recycles viable cells back to the vessel. This type of continuous bioreactor operation has been shown to yield significantly higher cell densities than fed-batch and can be operated continuously. Continuous bio-production is particularly advantageous for industrial operations because it has less down time associated with draining, cleaning and preparing the equipment for the next bio-production event. Furthermore, it is typically more economical to continuously operate downstream unit operations, such as distillation, than to run them in batch mode.

Continuous bio-production allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Methods of modulating nutrients and growth factors for continuous bio-production processes as well as techniques for maximizing the rate of product formation are well known in the art of industrial microbiology and a variety of methods are detailed by Brock, supra.

It is contemplated that embodiments of the present invention may be practiced using either batch, fed-batch or continuous processes and that any known mode of bio-production would be suitable. It is contemplated that cells may be immobilized on an inert scaffold as whole cell catalysts and subjected to suitable bio-production conditions for 3-HP production, or be cultured in liquid media in a vessel, such as a culture vessel. Thus, embodiments used in such processes, and in bio-production systems using these processes, include a population of genetically modified microorganisms of the present invention, a culture system comprising such population in a media comprising nutrients for the population, and methods of making 3-HP and thereafter, a downstream product of 3-HP.

Embodiments of the invention include methods of making 3-HP in a bio-production system, some of which methods may include obtaining 3-HP after such bio-production event. For example, a method of making 3-HP may comprise: providing to a culture vessel a media comprising suitable nutrients; providing to the culture vessel an inoculum of a genetically modified microorganism comprising genetic modifications described herein such that the microorganism produces 3-HP from syngas and/or a sugar molecule; and maintaining the culture vessel under suitable conditions for the genetically modified microorganism to produce 3-HP.

It is within the scope of the present invention to produce, and to utilize in bio-production methods and systems, including industrial bio-production systems for production of 3-HP, a recombinant microorganism genetically engineered to modify one or more aspects effective to increase tolerance to 3-HP (and, in some embodiments, also 3-HP bio-production) by at least 20 percent over control microorganism lacking the one or more modifications.

In various embodiments, the invention is directed to a system for bioproduction of acrylic acid as described herein, said system comprising: a tank for saccharification of biomass; a line for passing the product of saccharification to a fermentation tank optionally via a pre-fermentation tank; a fermentation tank suitable for microorganism cell culture; a line for discharging contents from the fermentation tank to an extraction and/or separation vessel; an extraction and/or separation vessel suitable for removal of 3-hydroxypropionic acid from cell culture waste; a line for transferring 3-hydroxypropionic acid to a dehydration vessel; and a dehydration vessel suitable for conversion of 3-hydroxypropionic acid to acrylic acid. In various embodiments, the system includes one or more pre-fermentation tanks, distillation columns, centrifuge vessels, back extraction columns, mixing vessels, or combinations thereof.

The following published resources are incorporated by reference herein for their respective teachings to indicate the level of skill in these relevant arts, and as needed to support a disclosure that teaches how to make and use methods of industrial bio-production of 3-HP, or other product(s) produced under the invention, from sugar sources, and also industrial systems that may be used to achieve such conversion with any of the recombinant microorganisms of the present invention (Biochemical Engineering Fundamentals, $2^{nd}$ Ed. J. E. Bailey and D. F. Ollis, McGraw Hill, New York, 1986, entire book for purposes indicated and Chapter 9, pages 533-657 in particular for biological reactor design; Unit Operations of Chemical Engineering, $5^{th}$ Ed., W. L. McCabe et al., McGraw Hill, New York 1993, entire book for purposes indicated, and particularly for process and separation technologies analyses; Equilibrium Staged Separations, P. C. Wankat, Prentice Hall, Englewood Cliffs, N.J. USA, 1988, entire book for separation technologies teachings).

V. Genetic Modifications, Nucleotide Sequences, and Amino Acid Sequences

Embodiments of the present invention may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host organisms based on the nature of antibiotic resistance markers that can function in that host. Also, as disclosed herein, a genetically modified (recombinant) microorganism may comprise modifications other than via plasmid introduction, including modifications to its genomic DNA.

It has long been recognized in the art that some amino acids in amino acid sequences can be varied without significant effect on the structure or function of proteins. Variants included can constitute deletions, insertions, inversions, repeats, and type substitutions so long as the indicated enzyme activity is not significantly adversely affected. Guidance concerning which amino acid changes are likely to be phenotypically silent can be found, inter alia, in Bowie, J. U., et al., "Deciphering the Message in Protein Sequences: Tolerance to Amino Acid Substitutions," Science 247:1306-1310 (1990). This reference is incorporated by reference for such teachings, which are, however, also generally known to those skilled in the art.

In various embodiments polypeptides obtained by the expression of the polynucleotide molecules of the present invention may have at least approximately 50%, 60%, 70%, 80%, 90%, 95%, 96%, 97%, 98%, 99% or 100% identity to one or more amino acid sequences encoded by the genes and/or nucleic acid sequences described herein for the 3-HP tolerance-related and biosynthesis pathways.

As a practical matter, whether any particular polypeptide is at least 50%, 60%, 70%, 80%, 85%, 90%, 92%, 95%, 96%, 97%, 98% or 99% identical to any reference amino acid sequence of any polypeptide described herein (which may correspond with a particular nucleic acid sequence described herein), such particular polypeptide sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set such that the percentage of identity is calculated over the full length of the reference amino acid sequence and that gaps in homology of up to 5% of the total number of amino acid residues in the reference sequence are allowed.

For example, in a specific embodiment the identity between a reference sequence (query sequence, i.e., a sequence of the present invention) and a subject sequence, also referred to as a global sequence alignment, may be determined using the FASTDB computer program based on the algorithm of Brutlag et al. (Comp. App. Biosci. 6:237-245 (1990)). Preferred parameters for a particular embodiment in which identity is narrowly construed, used in a FASTDB amino acid alignment, are: Scoring Scheme=PAM (Percent Accepted Mutations) 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are lateral to the N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence are considered for this manual correction. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for.

More generally, nucleic acid constructs can be prepared comprising an isolated polynucleotide encoding a polypeptide having enzyme activity operably linked to one or more (several) control sequences that direct the expression of the coding sequence in a microorganism, such as E. coli, under conditions compatible with the control sequences. The isolated polynucleotide may be manipulated to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. Examples of suitable promoters for directing transcription of the nucleic acid constructs, especially in an E. coli host cell, are the lac promoter (Gronenborn, 1976, Mol. Gen. Genet. 148: 243-250), tac promoter (DeBoer et al., 1983, Proceedings of the National Academy of Sciences USA 80: 21-25), trc promoter (Brosius et al, 1985, J. Biol. Chem. 260: 3539-3541), T7 RNA polymerase promoter (Studier and Moffatt, 1986, J. Mol. Biol. 189: 113-130), phage promoter $p_L$ (Elvin et al., 1990, Gene 87: 123-126), tetA promoter (Skerra, 1994, Gene 151: 131-135), araBAD promoter (Guzman et al., 1995, J. Bacteriol. 177: 4121-4130), and rhaP$_{BAD}$ promoter (Haldimann et al., 1998, J. Bacteriol. 180: 1277-1286). Other promoters are described in "Useful proteins from recombinant bacteria" in Scientific American, 1980, 242: 74-94; and in Sambrook and Russell, "Molecular Cloning: A Laboratory Manual," Third Edition 2001 (volumes 1-3), Cold Spring Harbor Laboratory Press, Cold Spring Harbor, N.Y.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in an E. coli cell may be used in the present invention. It may also be desirable to add regulatory sequences that allow regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems.

For various embodiments of the invention the genetic manipulations may be described to include various genetic manipulations, including those directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected and/or identified culture conditions and/or to provision of additional nucleic acid sequences such as to increase copy number and/or mutants of an enzyme related to 3-HP production. Specific methodologies and approaches to achieve such genetic modification are well known to one skilled in the art, and include, but are not limited to: increasing expression of an endogenous genetic element; decreasing functionality of a repressor gene; introducing a heterologous genetic element; increasing copy number of a nucleic acid sequence encoding a polypeptide catalyzing an enzymatic conversion step to produce 3-HP; mutating a genetic element to provide a mutated protein to increase specific enzymatic activity; over-expressing; under-expressing; over-expressing a chaperone; knocking out a protease; altering or modifying feedback inhibition; providing an enzyme variant comprising one or more of an impaired binding site for a repressor and/or competitive inhibitor; knocking out a repressor gene; evolution, selection and/or other approaches to improve mRNA stability as well as use of plasmids having an effective copy number and promoters to achieve an effective level of improvement. Random mutagenesis may be practiced to provide genetic modifications that may fall into any of these or other stated approaches. The genetic modifications further broadly fall into additions (including insertions), deletions (such as by a mutation) and substitutions of one or more nucleic acids in a nucleic acid of interest. In various embodiments a genetic modification results in improved enzymatic specific activity and/or turnover number of an enzyme. Without being limited, changes may be measured by one or more of the following: $K_M$; $k_{cat}$; and $K_{avidity}$.

In various embodiments, to function more efficiently, a microorganism may comprise one or more gene deletions. For example, in E. coli, the genes encoding the lactate dehydrogenase (ldhA), phosphate acetyltransferase (pta), pyruvate oxidase (poxB), and pyruvate-formate lyase (pflB) may be disrupted, including deleted. Such gene disruptions, including deletions, are not meant to be limiting, and may be implemented in various combinations in various embodiments. Gene deletions may be accomplished by mutational gene deletion approaches, and/or starting with a mutant strain having reduced or no expression of one or more of these enzymes, and/or other methods known to those skilled in the art. Gene deletions may be effectuated by any of a number of known specific methodologies, including but not limited to the RED/ET methods using kits and other reagents sold by Gene Bridges (Gene Bridges GmbH, Dresden, Germany, <<www.genebridges.com>>).

More particularly as to the latter method, use of Red/ET recombination, is known to those of ordinary skill in the art and described in U.S. Pat. Nos. 6,355,412 and 6,509,156, issued to Stewart et al. and incorporated by reference herein for its teachings of this method. Material and kits for such method are available from Gene Bridges (Gene Bridges GmbH, Dresden, Germany, <<www.genebridges.com>>), and the method may proceed by following the manufacturer's instructions. The method involves replacement of the target gene by a selectable marker via homologous recombination performed by the recombinase from λ-phage. The host organism expressing λ-red recombinase is transformed with a linear DNA product coding for a selectable marker flanked by the terminal regions (generally ~50 bp, and alternatively up to about ~300 bp) homologous with the target gene. The marker could then be removed by another recombination step performed by a plasmid vector carrying the FLP-recombinase, or another recombinase, such as Cre.

Targeted deletion of parts of microbial chromosomal DNA or the addition of foreign genetic material to microbial chromomes may be practiced to alter a host cell's metabolism so as to reduce or eliminate production of undesired metabolic products. This may be used in combination with other genetic modifications such as described herein in this general example. In this detailed description, reference has been made to multiple embodiments and to the accompanying drawings in which is shown by way of illustration specific exemplary embodiments in which the invention may be practiced. These embodiments are described in sufficient detail to enable those skilled in the art to practice the invention, and it is to be understood that modifications to the various disclosed embodiments may be made by a skilled artisan.

Further, for 3-HP production, such genetic modifications may be chosen and/or selected for to achieve a higher flux rate through certain enzymatic conversion steps within the respective 3-HP production pathway and so may affect general cellular metabolism in fundamental and/or major ways.

It will be appreciated that amino acid "homology" includes conservative substitutions, i.e. those that substitute a given amino acid in a polypeptide by another amino acid of similar characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue.

For all nucleic acid and amino acid sequences provided herein, it is appreciated that conservatively modified variants of these sequences are included, and are within the scope of the invention in its various embodiments. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various embodiments of the invention, as are methods and systems comprising such sequences and/or microorganisms. In various embodiments, nucleic acid sequences encoding sufficiently homologous proteins or portions thereof are within the scope of the invention. More generally, nucleic acids sequences that encode a particular amino acid sequence employed in the invention may vary due to the degeneracy of the genetic code, and nonetheless fall within the scope of the invention. The following table provides a summary of similarities among amino acids, upon which conservative and less conservative substitutions may be based, and also various codon redundancies that reflect this degeneracy.

Degeneracy of the amino acid code

| Amino Acid | Relationships | DNA codons |
|---|---|---|
| Alanine | N, Ali | GCT, GCC, GCA, GCG |
| Proline | N | CCT, CCC, CCA, CCG |
| Valine | N, Ali | GTT, GTC, GTA, GTG |
| Leucine | N, Ali | CTT, CTC, CTA, CTG, TTA, TTG |
| Isoleucine | N, Ali | ATT, ATC, ATA |
| Methionine | N | ATG |
| Phenylalanine | N, Aro | TTT, TTC |
| Tryptophan | N | TGG |
| Glycine | PU | GGT, GGC, GGA, GGG |
| Serine | PU | TCT, TCC, TCA, TCG, AGT, AGC |
| Threonine | PU | ACT, ACC, ACA, ACG |
| Asparagine | PU, Ami | AAT, AAC |
| Glutamine | PU, Ami | CAA, CAG |
| Cysteine | PU | TGT, TGC |
| Aspartic acid | NEG, A | GAT, GAC |
| Glutamic acid | NEG, A | GAA, GAG |
| Arginine | POS, B | CGT, CGC, CGA, CGG, AGA, AGG |
| Lysine | POS, B | AAA, AAG |
| Histidine | POS | CAT, CAC |
| Tyrosine | Aro | TAT, TAC |
| Stop Codons |  | TAA, TAG, TGA |

Legend: side groups and other related properties: A = acidic; B = basic; Ali = aliphatic; Ami = amine; Aro = aromatic; N = nonpolar; PU = polar uncharged; NEG = negatively charged; POS = positively charged.

Also, variants and portions of particular nucleic acid sequences, and respective encoded amino acid sequences recited herein may be exhibit a desired functionality, e.g., enzymatic activity at a selected level, when such nucleic acid sequence variant and/or portion contains a 15 nucleotide sequence identical to any 15 nucleotide sequence set forth in the nucleic acid sequences recited herein including, without limitation, the sequence starting at nucleotide number 1 and ending at nucleotide number 15, the sequence starting at nucleotide number 2 and ending at nucleotide number 16, the sequence starting at nucleotide number 3 and ending at nucleotide number 17, and so forth. It will be appreciated that the invention also provides isolated nucleic acid that contains a nucleotide sequence that is greater than 15 nucleotides (e.g., 16, 17, 18, 19, 20, 21, 22, 23, 24, 25, 26, 27, 28, 29, 30 or more nucleotides) in length and identical to any portion of the sequence set forth in nucleic acid sequences recited herein. For example, the invention provides isolated nucleic acid that contains a 25 nucleotide sequence identical to any 25 nucleotide sequence set forth in any one or more (including any grouping of) nucleic acid sequences recited herein including, without limitation, the sequence starting at nucleotide number 1 and ending at nucleotide number 25, the sequence starting at nucleotide number 2 and ending at nucleotide number 26, the sequence starting at nucleotide number 3 and ending at nucleotide number 27, and so forth. Additional examples include, without limitation, isolated nucleic acids that contain a nucleotide sequence that is 50 or more nucleotides (e.g., 100, 150, 200, 250, 300, or more nucleotides) in length and identical to any portion of any of the sequences disclosed herein. Such isolated nucleic acids can include, without limitation, those isolated nucleic acids containing a nucleic acid sequence represented in any one section of discussion and/or examples, such as regarding 3-HP production pathways, nucleic acid sequences encoding enzymes of the fatty acid synthase system, or 3-HP tolerance. For example, the invention provides an isolated nucleic acid containing a nucleic acid sequence listed herein that contains a single insertion, a single deletion, a single substitution, multiple insertions, multiple deletions, multiple substitutions, or any combination thereof (e.g., single deletion together with multiple insertions). Such isolated nucleic acid molecules can share at least 60, 65, 70, 75, 80, 85, 90, 95, 97, 98, or 99 percent sequence identity with a nucleic acid sequence listed herein (i.e., in the sequence listing).

Additional examples include, without limitation, isolated nucleic acids that contain a nucleic acid sequence that encodes an amino acid sequence that is 50 or more amino acid residues (e.g., 100, 150, 200, 250, 300, or more amino acid residues) in length and identical to any portion of an amino acid sequence listed or otherwise disclosed herein.

In addition, the invention provides isolated nucleic acid that contains a nucleic acid sequence that encodes an amino acid sequence having a variation of an amino acid sequence listed or otherwise disclosed herein. For example, the invention provides isolated nucleic acid containing a nucleic acid sequence encoding an amino acid sequence listed or otherwise disclosed herein that contains a single insertion, a single deletion, a single substitution, multiple insertions, multiple deletions, multiple substitutions, or any combination thereof (e.g., single deletion together with multiple insertions). Such isolated nucleic acid molecules can contain a nucleic acid sequence encoding an amino acid sequence that shares at least 60, 65, 70, 75, 80, 85, 90, 95, 97, 98, or 99 percent sequence identity with an amino acid sequence listed or otherwise disclosed herein.

Examples of properties that provide the bases for conservative and other amino acid substitutions are exemplified in Table 1. Accordingly, one skilled in the art may make numerous substitutions to obtain an amino acid sequence variant that exhibits a desired functionality. BLASTP, CLUSTALP, and other alignment and comparison tools may be used to assess highly conserved regions, to which fewer substitutions may be made (unless directed to alter activity to a selected level, which may require multiple substitutions). More substitutions may be made in regions recognized or believed to not be involved with an active site or other binding or structural motif. In accordance with Table 1, for example, substitutions may be made of one polar uncharged (PU) amino acid for a polar uncharged amino acid of a listed sequence, optionally considering size/molecular weight (i.e., substituting a serine for a threonine). Guidance concerning which amino acid changes are likely to be phenotypically silent can be found, inter alia, in Bowie, J. U., et Al., "Deciphering the Message in Protein Sequences: Tolerance to Amino Acid Substitutions," Science 247:1306-1310 (1990). This reference is incorporated by reference for such teachings, which are, however, also generally known to those skilled in the art. Recognized conservative amino acid substitutions comprise (substitutable amino acids following each colon of a set): ala:ser; arg:lys; asn:gln or his; asp:glu; cys:ser; gln:asn; glu: asp; gly:pro; his:asn or gln; ile:leu or val; leu:ile or val; lys: arg or gln or glu; met:leu or ile; phe:met or leu or tyr; ser:thr; thr:ser; trp:tyr; tyr:trp or phe; val:ile or leu.

It is noted that codon preferences and codon usage tables for a particular species can be used to engineer isolated nucleic acid molecules that take advantage of the codon usage preferences of that particular species. For example, the isolated nucleic acid provided herein can be designed to have codons that are preferentially used by a particular organism of interest. Numerous software and sequencing services are available for such codon-optimizing of sequences.

The invention provides polypeptides that contain the entire amino acid sequence of an amino acid sequence listed or otherwise disclosed herein. In addition, the invention provides polypeptides that contain a portion of an amino acid sequence listed or otherwise disclosed herein. For example, the invention provides polypeptides that contain a 15 amino acid sequence identical to any 15 amino acid sequence of an amino acid sequence listed or otherwise disclosed herein including, without limitation, the sequence starting at amino acid residue number 1 and ending at amino acid residue number 15, the sequence starting at amino acid residue number 2 and ending at amino acid residue number 16, the sequence starting at amino acid residue number 3 and ending at amino acid residue number 17, and so forth. It will be appreciated that the invention also provides polypeptides that contain an amino acid sequence that is greater than 15 amino acid residues (e.g., 16, 17, 18, 19, 20, 21, 22, 23, 24, 25, 26, 27, 28, 29, 30 or more amino acid residues) in length and identical to any portion of an amino acid sequence listed or otherwise disclosed herein For example, the invention provides polypeptides that contain a 25 amino acid sequence identical to any 25 amino acid sequence of an amino acid sequence listed or otherwise disclosed herein including, without limitation, the sequence starting at amino acid residue number 1 and ending at amino acid residue number 25, the sequence starting at amino acid residue number 2 and ending at amino acid residue number 26, the sequence starting at amino acid residue number 3 and ending at amino acid residue number 27, and so forth. Additional examples include, without limitation, polypeptides that contain an amino acid sequence that is 50 or more amino acid residues (e.g., 100, 150, 200, 250, 300 or more amino acid residues) in length and identical to any portion of an amino acid sequence listed or otherwise disclosed herein. Further, it is appreciated that, per above, a 15 nucleotide sequence will provide a 5 amino acid sequence, so that the latter, and higher-length amino acid sequences, may be defined by the above-described nucleotide sequence lengths having identity with a sequence provided herein.

In addition, the invention provides polypeptides that an amino acid sequence having a variation of the amino acid sequence set forth in an amino acid sequence listed or otherwise disclosed herein. For example, the invention provides polypeptides containing an amino acid sequence listed or otherwise disclosed herein that contains a single insertion, a single deletion, a single substitution, multiple insertions, multiple deletions, multiple substitutions, or any combination thereof (e.g., single deletion together with multiple insertions). Such polypeptides can contain an amino acid sequence that shares at least 60, 65, 70, 75, 80, 85, 90, 95, 97, 98 or 99 percent sequence identity with an amino acid sequence listed or otherwise disclosed herein. A particular variant amino acid sequence may comprise any number of variations as well as any combination of types of variations.

The invention includes, in various embodiments, an amino acid sequence having a variation of any of the polynucleotide and polypeptide sequences disclosed herein. As one example, variations are exemplified for the carbonic anhydrase (E. coli cynT) amino acid sequence set forth in SEQ ID NO:57. FIG. 1 provides a CLUSTAL multiple sequence alignment of the E. coli carbonic anhydrase aligned with carbonic anhydrases of eleven other species that had relatively high homology, based on low E values, in a BLASTP comparison. SEQ ID NO:57 is the fifth sequence shown. Multiple conservative and less conservative substitutions are shown (i.e., by the ":" and "." designations, respectively), which can lead to additional modifications by one skilled in the art. Thus, examples of variations of the sequence set forth in SEQ ID NO:57 include, without limitation, any variation of the sequences as set forth in FIG. 1. Such variations are provided in FIG. 1 in that a comparison of the amino acid residue (or lack thereof) at a particular position of the sequence set forth in SEQ ID NO:57 with the amino acid residue (or lack thereof) at the same aligned position of any of the other eleven amino acid sequences of FIG. 1 provides a list of specific changes for the sequence set forth in SEQ ID NO:57. For example, the "E" glutamic acid at position 14 of SEQ ID NO:57 can be substituted with a "D" aspartic acid or "N" asparagine as indicated in FIG. 1. It will be appreciated that the sequence set forth in SEQ ID NO:57 can contain any number of variations as well as any combination of types of variations. It is noted that the amino acid sequences provided in FIG. 1 can be polypeptides having carbonic anhydrase activity.

As indicated herein, polypeptides having a variant amino acid sequence can retain enzymatic activity. Such polypeptides can be produced by manipulating the nucleotide sequence encoding a polypeptide using standard procedures such as site-directed mutagenesis or various PCR techniques. As noted herein, one type of modification includes the substitution of one or more amino acid residues for amino acid residues having a similar chemical and/or biochemical property. For example, a polypeptide can have an amino acid sequence set forth in an amino acid sequence listed or otherwise disclosed herein comprising one or more conservative substitutions.

More substantial changes can be obtained by selecting substitutions that are less conservative, and/or in areas of the sequence that may be more critical, for example selecting residues that differ more significantly in their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, e.g., serine or threonine, is substituted for (or by) a hydrophobic residue, e.g., leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine. The effects of these amino acid substitutions (or other deletions or additions) can be assessed for polypeptides having enzymatic activity by analyzing the ability of the polypeptide to catalyze the conversion of the same substrate as the related native polypeptide to the same product as the related native polypeptide. Accordingly, polypeptides having 5, 10, 20, 30, 40, 50 or less conservative substitutions are provided by the invention.

Polypeptides and nucleic acids encoding polypeptides can be produced by standard DNA mutagenesis techniques, for example, M13 primer mutagenesis. Details of these techniques are provided in Sambrook and Russell, 2001. Nucleic acid molecules can contain changes of a coding region to fit the codon usage bias of the particular organism into which the molecule is to be introduced.

Alternatively, the coding region can be altered by taking advantage of the degeneracy of the genetic code to alter the coding sequence in such a way that, while the nucleic acid sequence is substantially altered, it nevertheless encodes a polypeptide having an amino acid sequence identical or substantially similar to the native amino acid sequence. For example, alanine is encoded in the open reading frame by the nucleotide codon triplet GCT. Because of the degeneracy of the genetic code, three other nucleotide codon triplets—GCA, GCC, and GCG—also code for alanine. Thus, the nucleic acid sequence of the open reading frame can be changed at this position to any of these three codons without affecting the amino acid sequence of the encoded polypeptide or the characteristics of the polypeptide. Based upon the degeneracy of the genetic code, nucleic acid variants can be derived from a nucleic acid sequence disclosed herein using standard DNA mutagenesis techniques as described herein, or by synthesis of nucleic acid sequences. Thus, for various embodiments the invention encompasses nucleic acid molecules that encode the same polypeptide but vary in nucleic acid sequence by virtue of the degeneracy of the genetic code. The invention also provides an isolated nucleic acid that is at least about 12 bases in length (e.g., at least about 13, 14, 15, 16, 17, 18, 19, 20, 25, 30, 40, 50, 60, 100, 250, 500, 750, 1000, 1500, 2000, 3000, 4000, or 5000 bases in length) and hybridizes, under hybridization conditions, to the sense or antisense strand of a nucleic acid having a sequence listed or otherwise disclosed herein. The hybridization conditions can be moderately or highly stringent hybridization conditions. Also, in some embodiments the microorganism comprises an endogenous 3-HP production pathway (which may, in some such embodiments, be enhanced), whereas in other embodiments the microorganism does not comprise a 3-HP production pathway, but is provided with one or more nucleic acid sequences encoding polypeptides having enzymatic activity or activities to complete a pathway, described herein, resulting in production of 3-HP. In some embodiments, the particular sequences disclosed herein, or conservatively modified variants thereof, are provided to a selected microorganism, such as selected from one or more of the species and groups of species or other taxonomic groups listed herein.

VI. Specific Mutations, Genetic Modifications, and Combinations Thereof

The present invention, in its various embodiments, is directed to making one, or a combination of, genetic modifications in a microorganism to increase production therein of the commercially important compound 3-hydroxypropionic acid ("3-HP," CAS No. 503-66-2). More generally the present invention relates to methods, systems and compositions, including genetically modified microorganisms, e.g., recombinant microorganisms, comprising one or more genetic modifications directed to increased production of 3-HP based on introduction of a polynucleotide encoding identified functional variant polypeptides exhibiting increased oxaloacetate alpha-decarboxylaseoxaloacetate alpha-decarboxylase activity, and methods of making various products from 3-HP made by cultures of such microorganisms.

Choice of Candidate Oxaloacetate Alpha-Decarboxylase Enzymes:

The desired oxaloacetate alpha-decarboxylase activity catalyzes the conversion of oxaloacetate to malonate semialdehyde (see FIG. 2), and may be referred to more explicitly as an oxaloacetate alpha-decarboxylase. Candidate enzymes were identified and chosen according to their reported activities as decarboxylases of alpha-ketoacids and by their reported substrate preference for shorter chain molecules. The genes for pyruvate decarboxylase from *Zymomonas mobilis* (pdc), 2-oxoglutarate decarboxylase (SEQ ID NO:035), (oad) from *Leuconostoc mesenteroides* (SEQ ID NO:036) and alpha-ketoglutarate decarboxylase (kgd) from *Mycobacterium tuberculosis* (SEQ ID NO:037) were chosen for further evaluation.

Through such evaluation, three functional variants were identified from the 2-oxoglutarate decarboxylase (oad) of *Leuconostoc mesenteroides* (SEQ ID NO:036) These, respectively, have the following mutations of that sequence: N45T, R249L, D302G, V418A and L476Q (SEQ ID NO:054), T479N (SEQ ID NO:055), and R394C, D434G and T511A (SEQ ID NO:056). These respectively showed a 1.6, 2.2 and 2.8 fold improvement in enzymatic conversion of oxaloacetate to malonate semialdehyde compared with a control native enzyme lacking mutations in an in vitro system (see Examples).

In various embodiments additional genetic modifications may be made to increase metabolic flux at one or more specified enzymatic conversion steps, and/or to reduce or eliminate an enzymatic conversion along certain metabolic pathways. In some embodiments, a genetic modification is provided to a selected microorganism cell to increase an oxaloacetate alpha-decarboxylaseoxaloacetate alpha-decarboxylase enzyme activity. Such genetic modification may supplement an existing enzymatic activity, or may provide such activity in a selected microorganism that previously lacked such enzymatic activity (whether inherently or due or other genetic modifications).

As disclosed in U.S. Provisional Patent Application No. 61/246,140, filed Sep. 27, 2009 and to which priority is claimed, SEQ ID NO:001 provides one non-limiting example of an amino acid sequence of an oxaloacetate alpha-decarboxylaseoxaloacetate alpha-decarboxylase enzyme, obtained from *Leuconostoc mesenteroides*. This sequence is observed to have lacked a small portion of the N-terminal, and SEQ ID NO:036 is provided herein as the entire sequence.

FIG. 2 graphically depicts a reaction catalyzed by a oxaloacetate alpha-decarboxylase. A polynucleotide encoding such polypeptide sequence, or variants, including conservative variants thereof, exhibiting such enzymatic activity (hereinafter referred to as "oad-2"), may be provided into a selected microorganism to increase 3-HP production. This is described in more detail below. In various embodiments, such provision, by genetic modification, is practiced in combination with other genetic modifications so as to further increase 3-HP production.

Such sequence may be encoded by a polynucleotide that may be provided to a selected microorganism by a genetic modification, so as to provide or increase such enzymatic activity in the selected microorganism. For example, in some embodiments such genetic modification may comprise providing a plasmid, or other vector (e.g., cosmids, bacteria artificial chromosome ("BAC"), viruses (e.g., bacteriophage, animal viruses, plant viruses), and artificial chromosomes (e.g., yeast artificial chromosomes (YAC)), that comprises a polynucleotide that encodes a sequence as described herein and further comprises appropriate promoter(s), binding site(s), and stop codon, such that the amino acid sequence is expressed to a desirable level in the selected microorganism.

FIG. 3A depicts the natural metabolic pathways utilize by *E. coli* during bio-production which results in the natural products lactate, formate and acetate. By disruptions of appropriate genes, the production of these natural products are reduced or eliminated.

FIG. 3B depicts a proposed metabolic pathway to produce 3-HP as a bio-production product. Arrows represent enzymatic activities. Enzyme activities for FIGS. 3A and 3B are as follows: [i] glucokinase, [ii] phosphoglucose isomerase, [iii] 6-phosphofructose kinase, [iv] fructose bisphosphate aldolase, [v] triose-phosphate isomerase, [vi] glyceraldehyde 3-phosphate dehydrogenase, [vii] phosphoglycerate kinase, [viii] phosphoglycerate mutase, [ix] enolase, [α]pyruvate dehydrogenase, -, [xi] lactate dehydrogenase, [xii]pyruvate oxidase, [xiii]pyruvate-formate lyase, [xiv] phosphate acetyltransferase, [xv]acetate kinase, [xvi] phosphoenolpyruvate carboxykinase, [xvii] the proposed oxaloacetate alpha-decarboxylase (oad-2), [xviii] 3-hydroxypropionate dehydrogenase, [xix]pyruvate carboxylase.

Figure 4:
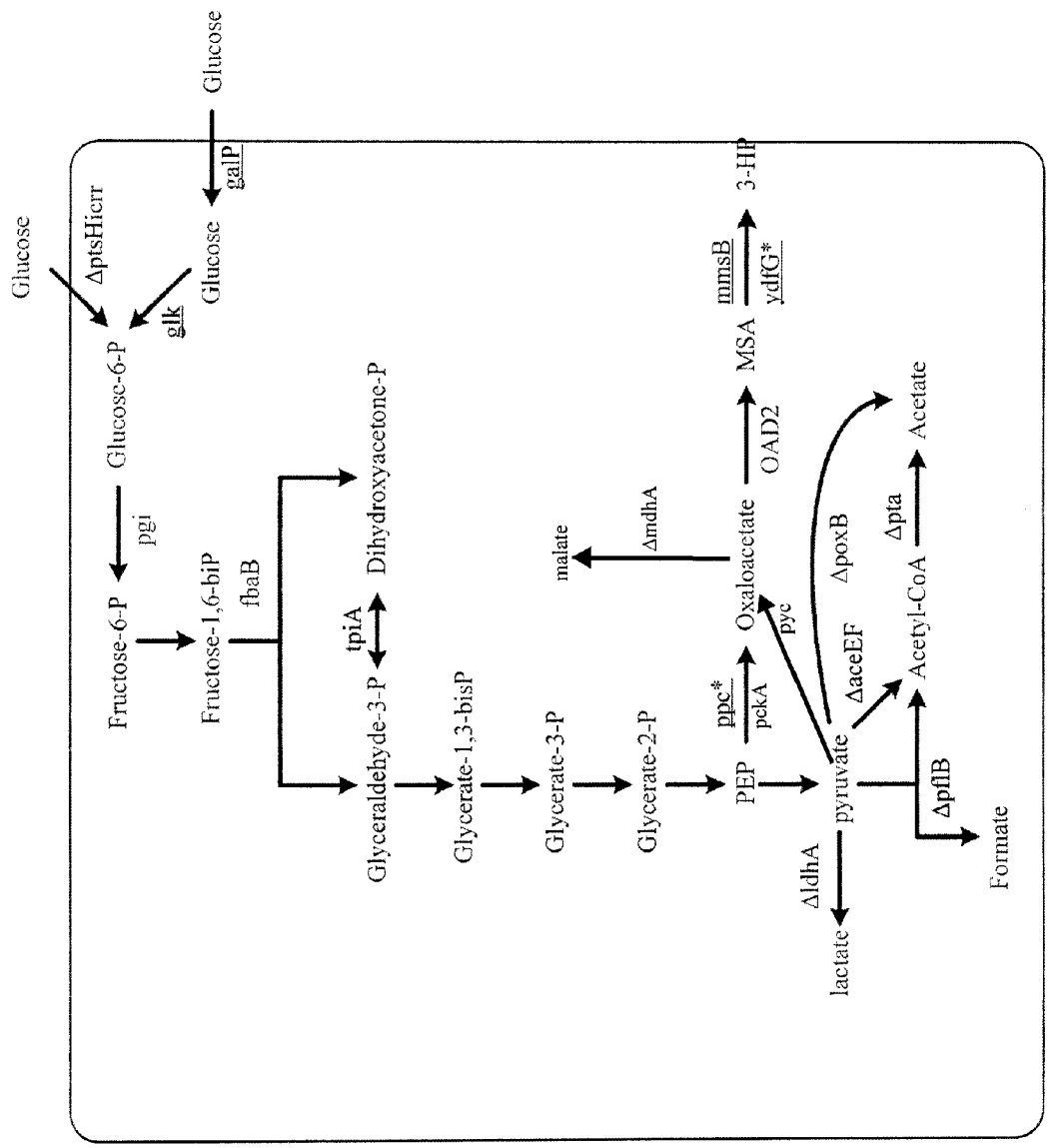
FIG. 4 depicts metabolic pathways of a microorganism related to aspects of the present invention, more particularly related to 3-HP production, with gene names of *E. coli* shown at certain enzymatic steps, the latter for example and not meant to be limiting.

FIG. 4 depicts a generalized embodiment comprising various metabolic modifications, some of which are optional for various embodiments of a genetically modified microorganism of the present invention. For various embodiments, an underlined gene name indicates that genetic modification is made to increase expression and/or enzymatic activity of the respective gene product (i.e., enzyme), a "Δ" before a gene name signifies that this gene is disrupted to decrease or eliminate expression and/or enzymatic activity of the respective gene product, and an asterisk indicates that this gene may be mutated to obtain a mutated form of the encoded gene product that exhibits increased enzymatic activity and/or specificity. Not all such genetic modifications need be made in a particular embodiment, and this full set of genetic modifications would be made for culture under anaerobic conditions.

As noted, the oxaloacetate alpha-decarboxylase is identified as "oad-2" or a grammatically equivalent identification. As shown in FIG. 2, oad-2 converts an oxaloacetate molecule to form malonate semialdehyde ("MSA"). The MSA is converted to 3-HP by a suitable enzyme (native, supplemented, or added), such as mmsB from *Pseudomonas aeruginosa* (SEQ ID NO:002) noting that the predominant reported reaction for this enzyme is conversion of 3-hydroxyisobutyrate to methylmalonate semialdehyde, and that in some embodiments mutant forms of mmsB may be produced, evaluated and identified that have greater, or more specific, activity for the conversion of MSA to 3-HP, such as by use of mutation and selection approaches described herein and/or known to those skilled in the art. Other enzymes for this latter conversion may be selected from enzymes capable of reductive conversions from MSA to 3-HP, such as a native or mutated form of ydfG or its functional equivalent in other species. This reaction is depicted in FIG.

The types of additional genetic modifications are generally divided into two groups—those that are made to increase enzymatic activity and/or specificity, generally so as to increase flux through a particular pathway and/or enzymatic conversion step, and those that are made to decrease or eliminate enzymatic activity at particular enzymatic conversion steps, thereby decreasing or eliminating conversion to particular metabolic intermediates or products. Various embodiments may include combinations of such genetic modifications from these two groups, in combination with the above-described genetic modification of a decarboxylase able to convert oxaloacetate to MSA.

Accordingly, in some embodiments, one or more of the genetic modifications in Table 1 may be provided to the selected microorganism that also is provided with the oxaloacetate alpha-decarboxylase enzymatic activity. Genetic modifications to the microorganism of these enzymes are made to increase enzymatic activity and/or specificity. One or more of these enzymatic functions may be native, and/or genetic modifications may be provided to supplement such native activity, or to provide such activity to a microorganism not previously demonstrating such activity. As described in a section below, there are various approaches to obtaining homologies that may be determined to exhibit a desired functional equivalence.

In some embodiments, one of the enzymatic activities of Table 1, the conversion of phosphoenolpyruvate ("PEP") to OAA, is provided via providing a mutated enzyme exhibiting such activity to a great level than a non-mutated enzyme. For example, the Ppc enzyme of *E. coli*, phosphoenolpyruvate carboxylase, may be mutated, such as by constructing a mutant library of ppc by use of an error-inducing PCR site-directed mutagenesis method. For example, use of the XL1-Red mutator strain, which is deficient in several repair mechanisms necessary for accurate DNA replication and generates mutations in plasmids at a rate 5,000 times that of the wild-type mutation rate, may be employed using appropriate materials following a manufacturer's instructions (see Stratagene QuikChange Mutagenesis Kit, Stratagene, La Jolla, Calif. USA). This technique or other techniques known to those skilled in the art, may be employed and then a population of such mutants, e.g., in a library, is evaluated, such as by a screening or selection method, to identify clones having a suitable or favorable mutation.

In other cases, such as for galP and pckA, genetic modifications can be made to increase overall expression of these protein functions in a microorganism cell. Various methods are known in the art for such types of genetic modifications, and are described in a section below.

In some embodiments a genetic modification provides increased enzymatic activity of pyruvate carboxylase (e.g., pyc from *Corynebacterium glutamicum* or *Rhizobium etli*).

Table 2 lists a number of protein functions, also providing enzyme classes and specific examples (with corresponding SEQ ID NOs.) in the group for which genetic modifications are made to reduce or eliminate the respective enzymatic activity. Once these protein functions are reduced or eliminated, more carbon and energy may flow to production of 3-HP (and also to biomass formation, to an extent, in some embodiments) rather than to the formation of metabolic products such as lactate, acetate, and formate.

Also, as gleaned from Tables 1 and 2, in various embodiments genetic modifications are made to increase enzymatic expression of galP and to decrease or eliminate enzymatic expression of all or part of the ptsHIcrr operon, or their equivalents in a selected species.

Deletions of the polynucleotides encoding the polypeptides exhibiting enzymatic activities or other protein functions in Table 2 may be made in a selected *E. coli* strain using a RED/ET homologous recombination method, such as with kits supplied by Gene Bridges (Gene Bridges GmbH, Heidelberg, Germany, www.genebridges.com) according to manufacturer's instructions. The successful deletion of these genes, as confirmed by standard methodologies, such as PCR, or DNA sequencing, results in a genetically modified microorganism having reduced or eliminated respective enzymatic activities or other protein functions. Methods for gene disruption in other species are known to those skilled in the art.

In view of Tables 1 and 2, it will be recognized that there are many possible combinations of increases in one or more protein functions, optionally with reductions in one or more protein functions. Protein functions can be independently varied, and any combination (i.e., a full factorial) of protein functions in Table 1 and Table 2 herein can be adjusted in various embodiments. In various embodiments of the present invention, these various combinations are provided in combination with one or more genetic modifications to provide, or to increase existing levels of, oxaloacetate alpha-decarboxylase enzymatic activity.

In various independent groupings of such embodiments, one or more protein functions selected from Table 1 may be added or increased, however excluding any substantial addition or change to any one of galP and its homologues, Ppc and its homologues, pckA and its homologues, or excluding two, three, four, or more, of such protein functions and their homologues from such smaller list or sub-list. In other independent groupings of embodiments, the various sub-lists developed from the list of Table 1 exclude one or more of the above-indicated protein functions but not their homologues.

In various independent groupings of such embodiments, one or more protein functions selected from Table 2 may be deleted or disrupted, however excluding any substantial reduction or change to any one of aceE and its homologues, aceF and its homologues, lpd and its homologues, ldhA and its homologues, pflB and its homologues, poxB and its homologues, Pta and its homologues, ptsH and its homologues, ptsI and its homologues, Crr and its homologues, pykA and its homologues, pykF and its homologues, or excluding two, three, four, five, six, seven, eight, nine, ten, eleven twelve, or more, of such protein functions and their homologues from such smaller list or sub-list. In other independent groupings of embodiments, the various sub-lists developed from the list of Table 2 exclude one or more of the above-indicated protein functions but not their homologues.

In addition to the above-described genetic modifications, in various embodiments genetic modifications also are provided to increase the pool and availability of the cofactor NADPH, and/or, consequently, the NADPH/NADP$^+$ ratio. For example, in various embodiments for *E. coli*, this may be done by increasing activity, such as by genetic modification, of one or more of the following genes: pgi (in a mutated form), pntAB, overexpressed, gapA:gapN substitution/replacement, and disrupting or modifying a soluble transhydrogenase such as sthA, and/or genetic modifications of one or more of zwf, gnd, and edd.

Specific nucleic acid and amino acid sequences corresponding to the enzyme names and activities provided herein (e.g., for 3-HP production, and in Tables 1 and 2), including the claims, are readily found at widely used databases including www.metacyc.org, www.brenda-enzymes.org, and www.ncbi.gov. Also, the particular enzymatic activities by enzymes, and other protein functions (and the nucleic acid sequences encoding them) that are disclosed herein are not meant to be limiting particularly in view of the various known approaches, standard in the art, to achieve desired metabolic conversions and to identify functionally analogous enzymes in different species. Different enzymes for different species may also be found on these web sites. The enzyme functions disclosed herein may be related to the stated E.C. numbers provided herein, including Table 1 and 2, which are incorporated into this section. However, it is noted that some protein functions disclosed herein, including in the Tables 1 and 2, are not enzyme functions, and those functions are only stated in the "Protein Function" columns, and in various embodiments may be further limited by the function of the stated *E. coli* gene (which may be applied, in various embodiments, to functionally equivalent homologues in other species). Also, all information of Tables 1 and 2 are incorporated into the claims referring to these tables. Also, based on the teachings provided herein, it is appreciated that the members of a respective table are functionally related as to their overall metabolic effects on production of 3-HP through the 3-HP production pathway that includes oxaloacetate alpha-decarboxylase.

Thus, in various embodiments a genetically modified microorganism comprises a first set of genetic modification(s) to introduce and/or increase enzymatic activity of an oxaloacetate alpha-decarboxylase (such as SEQ ID NO:001 or SEQ ID NO:036), and optionally one or more enzymes capable of converting MSA to 3-HP (such as mmsB and a native or mutated ydfG). In some embodiments, a genetically modified microorganism demonstrates increased production of 3-HP compared to a control microorganism lacking such genetic modification(s). In some embodiments, a genetically modified microorganism comprises one or more genetic modifications to increase enzymatic activities or other protein functions identified in Table 1, and/or comprising one or more genetic modifications to reduce or eliminate enzymatic activities or other protein functions identified in Table 2, and optionally also comprising genetic modifications disclosed herein to increase microorganism NADPH pools and/or availability. Using approaches described herein, genes encoding enzymes having the enzyme activities described herein may be identified in other species, and evaluated as may be appropriate to the circumstance, toward obtaining a genetically modified microorganism of that species that comprises the genetic modifications taught herein to obtain a microorganism that exhibits higher production of 3-HP compared to a relevant control microorganism lacking the genetic modifications.

In some particular embodiments, a combination of genetic modifications are made to an *E. coli* strain, the combination comprising providing a polynucleotide encoding oad-2 and the combination also comprising other genetic modifications shown in FIGS. 3B and 4, as well as described for Tables 1 and 2. In some of these embodiments, at least one of additions of mmsB or a native or mutated ydfG are provided to increase enzymatic conversion of MSA to 3-HP.

Other aspects of the scope of the invention are described in the following paragraphs.

In various embodiments, to function more efficiently, a microorganism may comprise one or more gene deletions. These are summarized in Table 2, described above. For example, in *E. coli*, the genes encoding lactate dehydrogenase (ldhA), phosphate acetyltransferase (pta), pyruvate oxidase (poxB) and pyruvate-formate lyase (pflB), may be disrupted, including deleted. Such gene disruptions, including deletions, are not meant to be limiting, and may be implemented in various combinations in various embodiments. Gene deletions may be accomplished by mutational gene deletion approaches, and/or starting with a mutant strain having reduced or no expression of one or more of these enzymes, and/or other methods known to those skilled in the art. Gene deletions may be effectuated by any of a number of known specific methodologies, including but not limited to the RED/ET methods using kits and other reagents sold by Gene Bridges (Gene Bridges GmbH, Heidelberg, Germany, www.genebridges.com). Further, for 3-HP production, such genetic modifications may be chosen and/or selected for to achieve a higher flux rate through certain basic pathways within the respective 3-HP production pathway and so may affect general cellular metabolism in fundamental and/or major ways.

In some embodiments, the genetically modified microorganism that so possesses oxaloacetate alpha-decarboxylase genetic modification(s) additionally comprises at least one genetic modification to increase, in the genetically modified microorganism, a protein function selected from the protein functions of Table 1 (Glucose transporter function (such as by galP), phosphoenolpyruvate carboxylase, and phosphoenolpyruvate carboxykinase). In certain embodiments, the genetically modified microorganism comprises at least one genetic modification to increase two or three protein functions selected from the protein functions of Table 1.

In some embodiments, such genetically modified microorganism additionally comprises at least one genetic modification to decrease protein functions selected from the protein functions of Table 2 (pyruvate dehydrogenase E1p, dihydrolipoamide acetyltransferase, pyruvate dehydrogenase E3, lactate dehydrogenase, pyruvate formate lyase, pyruvate oxidase, phosphate acetyltransferase, histidyl phosphorylatable protein (of PTS), phosphoryl transfer protein (of PTS), polypeptide chain (of PTS), pyruvate kinase I, and pyruvate kinase II).

In various embodiments, such genetically modified microorganism comprises at least one genetic modification to decrease enzymatic activity of two, three, four, five, six, seven, eight, nine, ten, eleven, or twelve protein functions selected from the protein functions of Table 2.

It will be appreciated that, in various embodiments, there can be many possible combinations of increases in one or more protein functions of Table 1, with reductions in one or more protein functions of Table 2 in the genetically modified microorganism comprising at least one genetic modification to provide or increase oxaloacetate alpha-decarboxylase protein function (i.e, enzymatic activity). Protein functions can be independently varied, and any combination (i.e., a full factorial) of genetic modifications of protein functions in Table 1 and Table 2 herein can be adjusted by the methods taught and provided into the genetically modified microorganism.

In some embodiments, at least one genetic modification to decrease enzymatic activity is a gene disruption. In some embodiments, at least one genetic modification to decrease enzymatic activity is a gene deletion.

In various embodiments, to obtain 3-hydroxypropionic acid (3-HP) as a desired product, the genetically modified microorganism comprises a protein function effective for converting malonate semialdehyde to 3-HP. The protein function effective for converting malonate semialdehyde to 3-HP can be native to the microorganism, but that is by no means necessary.

In some embodiments, the protein function effective for converting malonate semialdehyde to 3-HP is a native or mutated form of mmsB from *Pseudomonas aeruginosa*, or a functional equivalent thereof. Alternatively, or additionally, this protein function can be a native or mutated form of ydfG, or a functional equivalent thereof.

Certain embodiments of the invention additionally comprise a genetic modification to increase the availability of the cofactor NADPH, which can increase the NADPH/NADP+ ratio as may be desired. Non-limiting examples for such genetic modification are pgi (E.C. 5,3.1.9, in a mutated form), pntAB (E.C. 1.6.1.2), overexpressed, gapA (E.C. 1.2.1.12): gapN (E.C. 1.2.1.9, from *Streptococcus mutans*) substitution/replacement, and disrupting or modifying a soluble transhydrogenase such as sthA (E.C. 1.6.1.2), and/or genetic modifications of one or more of zwf (E.C. 1.1.1.49), gnd (E.C. 1.1.1.44), and edd (E.C. 4.2.1.12). Sequences of these genes are available at www.metacyc.org.

In some embodiments, the genetic modification increases microbial synthesis of 3-HP above a rate or titer of a control microorganism lacking said at least one genetic modification to produce 3-HP. In some embodiments, the genetic modification is effective to increase enzymatic conversions to 3-HP by at least about 5 percent, at least about 10 percent, at least about 20 percent, at least about 30 percent, or at least about 50 percent above the enzymatic conversion of a control microorganism lacking the genetic modification.

Variations of the present invention also provide a culture system comprising a population of a genetically modified microorganism as described herein, and a media comprising nutrients for the population.

Variations of this invention additionally include methods. In some variations, the invention provides a method of making a genetically modified microorganism comprising providing to a selected microorganism at least one genetic modification to introduce oxaloacetate alpha-decarboxylase enzymatic activity.

In some embodiments, the method additionally comprises introducing at least one genetic modification to increase enzymatic activity of a protein function selected from the protein functions of Table 1. In various embodiments, the method comprises introducing at least one genetic modification to increase two or three protein functions selected from the protein functions of Table 1 (Glucose transporter function (such as by galP), phosphoenolpyruvate carboxylase, and phosphoenolpyruvate carboxykinase).

In some embodiments, the method additionally comprises introducing at least one genetic modification to decrease a protein function selected from the protein functions of Table 2. In various embodiments, the method comprises introducing at least one genetic modification to decrease two, three, four, five, six, seven, eight, nine, ten, eleven, or twelve protein functions selected from the protein functions of Table 2 (pyruvate dehydrogenase E1p, dihydrolipoamide acetyltransferase, pyruvate dehydrogenase E3, lactate dehydrogenase, pyruvate formate lyase, pyruvate oxidase, phosphate acetyltransferase, histidyl phosphorylatable protein (of PTS), phosphoryl transfer protein (of PTS), polypeptide chain (of PTS), pyruvate kinase I, and pyruvate kinase II).

Again, there are many possible combinations of increases in one or more protein functions, optionally with reductions in one or more protein functions, that may be provided in combination with at least one genetic modification to provide or increase oxaloacetate alpha-decarboxylase enzymatic function, so as to increase 3-HP production in a genetically modified microorganism. Protein functions can be independently varied, and any combination (i.e., a full factorial) of protein functions in Table 1 and Table 2 herein can be adjusted in various methods of the invention. Enzyme-activity and other protein function reductions can be accomplished by gene disruptions, such as gene deletions, or other modifications.

Additionally, genetic modifications and/or media supplements directed to improving tolerance to 3-HP may be provided, such as are taught in PCT Patent Publication No. US/2010/052748, published Jan. 28, 2010, and incorporated by reference for its teachings of tolerance-related genetic modifications and media supplements.

In some embodiments, the invention contemplates a culture system comprising: a) a population of a genetically modified microorganism as described herein; and b) a media comprising nutrients for the population. In some such embodiments the media additionally comprises at least 1 gram/liter of 3-HP.

As described in U.S. Provisional Patent Application No. 61/246,140, filed Sep. 27, 2009, incorporated by reference and to which priority is claimed, various combinations of genetic modifications may be implemented in various embodiments of the invention. These are described in the following paragraphs and also in Tables 1 and 2.

In some embodiments, the genetically modified microorganism that so possesses oxaloacetate alpha-decarboxylase genetic modification(s) additionally comprises at least one genetic modification to increase, in the genetically modified microorganism, a protein function selected from the protein functions of Table 1 (Glucose transporter function (such as by galP in *E. coli*), phosphoenolpyruvate carboxykinase (such as by pckA in *E. coli*), and phosphoenolpyruvate carboxlase (such as by ppc in *E. coli*). In certain embodiments, the genetically modified microorganism comprises at least one genetic modification to increase two, three, or four protein functions selected from the protein functions of Table 2.

In some embodiments, such genetically modified microorganism additionally comprises at least one genetic modification to decrease protein functions selected from the protein functions of Table 2, pyruvate dehydrogenase E1p, lipoate acetyltransferase/dihydrolipoamide acetyltransferase, pyruvate dehydrogenase E3 (lipoamide dehydrogenase), lactate dehydrogenase, pyruvate formate lyase, pyruvate oxidase, phosphate acetyltransferase, histidyl phosphorylatable protein (of PTS), phosphoryl transfer protein (of PTS), the polypeptide chain (of PTS), pyruvate kinase I, and pyruvate kinase II.

In various embodiments, such genetically modified microorganism comprises at least one genetic modification to decrease enzymatic activity of two, three, four, five, six, or seven protein functions selected from the protein functions of Table 2.

It will be appreciated that, in various embodiments, there can be many possible combinations of increases in one or more protein functions of Table 1, with reductions in one or more protein functions of Table 2 in the genetically modified microorganism comprising at least one genetic modification to provide or increase oxaloacetate alpha-decarboxylase protein function (i.e, enzymatic activity). Protein functions can be independently varied, and any combination (i.e., a full factorial) of genetic modifications of protein functions in Tables 1 and 2 herein can be adjusted by the methods taught and provided into said genetically modified microorganism.

In some embodiments, at least one genetic modification to decrease enzymatic activity is a gene disruption. In some embodiments, at least one genetic modification to decrease enzymatic activity is a gene deletion.

In various embodiments, to obtain 3-hydroxypropionic acid (3-HP) as a desired product, the genetically modified microorganism comprises a protein function effective for converting oxaloacetate to malonate semialdehyde, i.e., an oxaloacetate alpha-decarboxylase, and also a protein function effective for converting malonate semialdehyde to 3-HP. The latter can be native to the microorganism, but that is by no means necessary.

In some embodiments, the protein function effective for converting malonate semialdehyde to 3-HP is a native or mutated form of mmsB from *Pseudomonas aeruginosa*, or a functional equivalent thereof. Alternatively, or additionally, this protein function can be a native or mutated form of ydfG, or a functional equivalent thereof.

Certain embodiments of the invention additionally comprise a genetic modification to increase the availability of the cofactor NADPH, which can increase the NADPH/NADP+ ratio as may be desired. Non-limiting examples for such genetic modification are pgi (E.C. 5,3.1.9, in a mutated form), pntAB (E.C. 1.6.1.2), overexpressed, gapA (E.C. 1.2.1.12): gapN (E.C. 1.2.1.9, from *Streptococcus mutans*) substitution/replacement, and disrupting or modifying a soluble transhydrogenase such as sthA (E.C. 1.6.1.2), and/or genetic modifications of one or more of zwf (E.C. 1.1.1.49), gnd (E.C. 1.1.1.44), and edd (E.C. 4.2.1.12). Sequences of these genes are available at www.metacyc.org, and also are available at www.ncbi.gov.

It is appreciated that any combination of genetic modifications described herein may be used in embodiments of the present invention. Also included within the scope of the invention are isolated nucleic acid and amino acid sequences encoding or comprising the mutations to the polypeptide sequences described herein.

Additional genetic modifications may be provided in a microorganism strain of the present invention. Many such modifications may be provided to impart a particular phenotype.

As one example, a deletion, of multifunctional 2-keto-3-deoxygluconate 6-phosphate aldolase and 2-keto-4-hydroxyglutarate aldolase and oxaloacetate alpha-decarboxylase (eda in *E. coli*), may be provided to various strains.

For example, the ability to utilize sucrose may be provided, and this would expand the range of feed stocks that can be utilized to produce 3-HP. Common laboratory and industrial strains of *E. coli*, such as the strains described herein, are not capable of utilizing sucrose as the sole carbon source. Since sucrose, and sucrose-containing feed stocks such as molasses, are abundant and often used as feed stocks for the production by microbial fermentation, adding appropriate genetic modifications to permit uptake and use of sucrose may be practiced in strains having other features as provided herein. Various sucrose uptake and metabolism systems are known in the art (for example, U.S. Pat. No. 6,960,455), incorporated by reference for such teachings. These and other approaches may be provided in strains of the present invention. The examples provide at least two approaches.

Also, genetic modifications may be provided to add functionality for breakdown of more complex carbon sources, such as cellulosic biomass or products thereof, for uptake, and/or for utilization of such carbon sources. For example, numerous cellulases and cellulase-based cellulose degradation systems have been studied and characterized (see, for example, and incorporated by reference herein for such teachings, Beguin, P and Aubert, J-P (1994) FEMS Microbial. Rev. 13: 25-58; Ohima, K. et al. (1997) Biotechnol. Genet. Eng. Rev. 14: 365414).

In addition to the above-described genetic modifications, in various embodiments genetic modifications also are provided to increase the pool and availability of the cofactor NADPH, and/or, consequently, the NADPH/NADP$^+$ ratio. For example, in various embodiments for *E. coli*, this may be done by increasing activity, such as by genetic modification, of one or more of the following genes—pgi (in a mutated form), pntAB, overexpressed, gapA:gapN substitution/replacement, and disrupting or modifying a soluble transhydrogenase such as sthA, and/or genetic modifications of one or more of zwf, gnd, and edd, Any such genetic modifications may be provided to species not having such functionality, or having a less than desired level of such functionality.

More generally, and depending on the particular metabolic pathways of a microorganism selected for genetic modification, any subgroup of genetic modifications may be made to decrease cellular production of fermentation product(s) selected from the group consisting of acetate, acetoin, acetone, acrylic, malate, fatty acid ethyl esters, isoprenoids, glycerol, ethylene glycol, ethylene, propylene, butylene, isobutylene, ethyl acetate, vinyl acetate, other acetates, 1,4-butanediol, 2,3-butanediol, butanol, isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fusel alcohols, and 1,2-propanediol, 1,3-propanediol, formate, fumaric acid, propionic acid, succinic acid, valeric acid, and maleic acid. Gene deletions may be made as disclosed generally herein, and other approaches may also be used to achieve a desired decreased cellular production of selected fermentation products.

VII. Separation and Purification of the Chemical Product 3-HP

When 3-HP is the chemical product, the 3-HP may be separated and purified by the approaches described in the following paragraphs, taking into account that many methods of separation and purification are known in the art and the following disclosure is not meant to be limiting. Osmotic shock, sonication, homogenization, and/or a repeated freeze-thaw cycle followed by filtration and/or centrifugation, among other methods, such as pH adjustment and heat treatment, may be used to produce a cell-free extract from intact cells. Any one or more of these methods also may be employed to release 3-HP from cells as an extraction step.

Further as to general processing of a bio-production broth comprising 3-HP, various methods may be practiced to remove biomass and/or separate 3-HP from the culture broth and its components. Methods to separate and/or concentrate the 3-HP include centrifugation, filtration, extraction, chemical conversion such as esterification, distillation (which may result in chemical conversion, such as dehydration to acrylic acid, under some reactive-distillation conditions), crystallization, chromatography, and ion-exchange, in various forms. Additionally, cell rupture may be conducted as needed to release 3-HP from the cell mass, such as by sonication, homogenization, pH adjustment or heating. 3-HP may be further separated and/or purified by methods known in the art, including any combination of one or more of centrifugation, liquid-liquid separations, including extractions such as solvent extraction, reactive extraction, two-phase aqueous extraction and two-phase solvent extraction, membrane separation technologies, distillation, evaporation, ion-exchange chromatography, adsorption chromatography, reverse phase chromatography and crystallization. Any of the above methods may be applied to a portion of a bio-production broth (i.e., a fermentation broth, whether made under aerobic, anaerobic, or microaerobic conditions), such as may be removed from a bio-production event gradually or periodically, or to the broth at termination of a bio-production event. Conversion of 3-HP to downstream products, such as described herein, may proceed after separation and purification, or, such as with distillation, thin-film evaporation, or wiped-film evaporation optionally also in part as a separation means.

For various of these approaches, one may apply a counter-current strategy, or a sequential or iterative strategy, such as multi-pass extractions. For example, a given aqueous solution comprising 3-HP may be repeatedly extracted with a non-polar phase comprising an amine to achieve multiple reactive extractions.

When a culture event (fermentation event) is at a point of completion, the spent broth may transferred to a separate tank, or remain in the culture vessel, and in either case the temperature may be elevated to at least 60° C. for a minimum of one hour in order to kill the microorganisms. (Alternatively, other approaches to killing the microorganisms may be practiced.) By spent broth is meant the final liquid volume comprising the initial nutrient media, cells grown from the microorganism inoculum (and possibly including some original cells of the inoculum), 3-HP, and optionally liquid additions made after providing the initial nutrient media, such as periodic additions to provide additional carbon source, etc. It is noted that the spent broth may comprise organic acids other than 3-HP, such as for example acetic acid and/or lactic acid.

A centrifugation step may then be practiced to filter out the biomass solids (e.g., dead microorganism cells). This may be achieved in a continuous or batch centrifuge, and solids removal may be at least about 80%, 85%, 90%, or 95% in a single pass, or cumulatively after two or more serial centrifugations.

An optional step is to polish the centrifuged liquid through a filter, such as microfiltration or ultrafiltration, or may comprise a filter press or other filter device to which is added a filter aid such as diatomaceous earth. Alternative or supplemental approaches to this and the centrifugation may include removal of cells by a flocculent, where the cells floc and are allowed to settle, and the liquid is drawn off or otherwise removed. A flocculent may be added to a fermentation broth after which settling of material is allowed for a time, and then separations may be applied, including but not limited to centrifugation.

After such steps, a spent broth comprising 3-HP and substantially free of solids is obtained for further processing. By "substantially free of solids" is meant that greater than 98%, 99%, or 99.5% of the solids have been removed.

In various embodiments this spent broth comprises various ions of salts, such as Na, $C_1$, $SO_4$, and $PO_4$. In some embodiments these ions may be removed by passing this spent broth through ion exchange columns, or otherwise contacting the spent broth with appropriate ion exchange material. Here and elsewhere in this document, "contacting" is taken to mean a contacting for the stated purpose by any way known to persons skilled in the art, such as, for example, in a column, under appropriate conditions that are well within the ability of persons of ordinary skill in the relevant art to determine. As but one example, these may comprise sequential contacting with anion and cation exchange materials (in any order), or with a mixed anion/cation material. This demineralization step should remove most such inorganic ions without removing the 3-HP. This may be achieved, for example, by lowering the pH sufficiently to protonate 3-HP and similar organic acids so that these acids are not bound to the anion exchange material, whereas anions, such as Cl and $SO_4$, that remain charged at such pH are removed from the solution by binding to the resin. Likewise, positively charged ions are removed by contacting with cation exchange material. Such removal of ions may be assessed by a decrease in conductivity of the solution. Such ion exchange materials may be regenerated by methods known to those skilled in the art.

In some embodiments, the spent broth (such as but not necessarily after the previous demineralization step) is subjected to a pH elevation, after which it is passed through an ion exchange column, or otherwise contacted with an ion exchange resin, that comprises anionic groups, such as amines, to which organic acids, ionic at this pH, associate. Other organics that do not so associate with amines at this pH (which may be over 6.5, over 7.5, over 8.5, over 9.5, over 10.5, or higher pH) may be separated from the organic acids at this stage, such as by flushing with an elevated pH rinse. Thereafter elution with a lower pH and/or elevated salt content rinse may remove the organic acids. Eluting with a gradient of decreasing pH and/or increasing salt content rinses may allow more distinct separation of 3-HP from other organic acids, thereafter simplifying further processing.

This latter step of anion-exchange resin retention of organic acids may be practiced before or after the demineralization step. However, the following two approaches are alternatives to the anion-exchange resin step.

A first alternative approach comprises reactive extraction (a form of liquid-liquid extraction) as exemplified in this and the following paragraphs. The spent broth, which may be at a stage before or after the demineralization step above, is combined with a quantity of a tertiary amine such as Alamine-336® (Cognis Corp., Cincinnati, Ohio USA) at low pH. Co-solvents for the Alamine-336 or other tertiary amine may be added and include, but are not limited to benzene, carbon tetrachloride, chloroform, cyclohexane, disobutyl ketone, ethanol, #2 fuel oil, isopropanol, kerosene, n-butanol, isobutanol, octanol, and n-decanol that increase the partition coefficient when combined with the amine. After appropriate mixing a period of time for phase separation transpires, after which the non-polar phase, which comprises 3-HP associated with the Alamine-336 or other tertiary amine, is separated from the aqueous phase.

When a co-solvent is used that has a lower boiling point than the 3-HP/tertiary amine, a distilling step may be used to remove the co-solvent, thereby leaving the 3-HP-tertiary amine complex in the non-polar phase.

Whether or not there is such a distillation step, a stripping or recovery step may be used to separate the 3-HP from the tertiary amine. An inorganic salt, such as ammonium sulfate, sodium chloride, or sodium carbonate, or a base such as sodium hydroxide or ammonium hydroxide, is added to the 3-HP/tertiary amine to reverse the amine protonation reaction, and a second phase is provided by addition of an aqueous solution (which may be the vehicle for provision of the inorganic salt). After suitable mixing, two phases result and this allows for tertiary amine regeneration and re-use, and provides the 3-HP in an aqueous solution. Alternatively, hot water may also be used without a salt or base to recover the 3HP from the amine.

In the above approach the phase separation and extraction of 3-HP to the aqueous phase can serve to concentrate the 3-HP. It is noted that chromatographic separation of respective organic acids also can serve to concentrate such acids, such as 3-HP. In similar approaches other suitable, non-polar amines, which may include primary, secondary and quaternary amines, may be used instead of and/or in combination with a tertiary amine.

A second alternative approach is crystallization. For example, the spent broth (such as free of biomass solids) may be contacted with a strong base such as ammonium hydroxide, which results in formation of an ammonium salt of 3-HP. This may be concentrated, and then ammonium-3-HP crystals are formed and may be separated, such as by filtration, from the aqueous phase. Once collected, ammonium-3-HP crystals may be treated with an acid, such as sulfuric acid, so that ammonium sulfate is regenerated, so that 3-HP and ammonium sulfate result.

Also, various aqueous two-phase extraction methods may be utilized to separate and/or concentrate a desired chemical product from a fermentation broth or later-obtained solution. It is known that the addition of polymers, such as dextran and glycol polymers, such as polyethylene glycol (PEG) and polypropylene glycol (PPG) to an aqueous solution may result in formation of two aqueous phases. In such systems a desired chemical product may segregate to one phase while cells and other chemicals partition to the other phase, thus providing for a separation without use of organic solvents. This approach has been demonstrated for some chemical products, but challenges associated with chemical product recovery from a polymer solution and low selectivities are recognized (See "Extractive Recovery of Products from Fermentation Broths," Joong Kyun Kim et al., Biotechnol. Bioprocess Eng., 1999(4)1-11, incorporated by reference for all of its teachings of extractive recovery methods).

Various substitutions and combinations of the above steps and processes may be made to obtain a relatively purified 3-HP solution. Also, methods of separation and purification disclosed in U.S. Pat. No. 6,534,679, issued Mar. 18, 2003, and incorporated by reference herein for such methods disclosures, may be considered based on a particular processing scheme. Also, in some culture events periodic removal of a portion of the liquid volume may be made, and processing of such portion(s) may be made to recover the 3-HP, including by any combination of the approaches disclosed above.

As noted, solvent extraction is another alternative. This may use any of a number of and/or combinations of solvents, including alcohols, esters, ketones, and various organic solvents. Without being limiting, after phase separation a distillation step or a secondary extraction may be employed to separate 3-HP from the organic phase.

The following published resources are incorporated by reference herein for their respective teachings to indicate the level of skill in these relevant arts, and as needed to support a disclosure that teaches how to make and use methods of industrial bio-production of 3-HP, and also industrial systems that may be used to achieve such conversion with any of the recombinant microorganisms of the present invention (*Biochemical Engineering Fundamentals*, $2^{nd}$ Ed. J. E. Bailey and D. F. 011 is, McGraw Hill, New York, 1986, entire book for purposes indicated and Chapter 9, pp. 533-657 in particular for biological reactor design; *Unit Operations of Chemical Engineering*, $5^{th}$ Ed., W. L. McCabe et al., McGraw Hill, New York 1993, entire book for purposes indicated, and particularly for process and separation technologies analyses; *Equilibrium Staged Separations*, P. C. Wankat, Prentice Hall, Englewood Cliffs, N.J. USA, 1988, entire book for separation technologies teachings).

VII. Conversion of 3-HP to Acrylic Acid and Downstream Products

As discussed herein, various embodiments described herein are related to production of a particular chemical product, 3-hydroxypropionic acid (3-HP). This organic acid, 3-HP, may be converted to various other products having industrial uses, such as but not limited to acrylic acid, esters of acrylic acid, and other chemicals obtained from 3-HP, referred to as "downstream products." Under some approaches the 3-HP may be converted to acrylic acid, acrylamide, and/or other downstream chemical products, in some instances the conversion being associated with the separation and/or purification steps. Many conversions to such downstream products are described herein. The methods of the invention include steps to produce downstream products of 3-HP.

As a $C_3$ building block, 3-HP offers much potential in a variety of chemical conversions to commercially important intermediates, industrial end products, and consumer products. For example, 3-HP may be converted to acrylic acid, acrylates (e.g., acrylic acid salts and esters), 1,3-propanediol, malonic acid, ethyl-3-hydroxypropionate, ethyl ethoxy propionate, propiolactone, acrylamide, or acrylonitrile.

For example, methyl acrylate may be made from 3-HP via dehydration and esterification, the latter to add a methyl group (such as using methanol); acrylamide may be made from 3-HP via dehydration and amidation reactions; acrylonitrile may be made via a dehydration reaction and forming a nitrile moiety; propriolactone may be made from 3-HP via a ring-forming internal esterification reaction (eliminating a water molecule); ethyl-3-HP may be made from 3-HP via esterification with ethanol; malonic acid may be made from 3-HP via an oxidation reaction; and 1,3-propanediol may be made from 3-HP via a reduction reaction. Also, acrylic acid, first converted from 3-HP by dehydration, may be esterified with appropriate compounds to form a number of commercially important acrylate-based esters, including but not limited to methyl acrylate, ethyl acrylate, methyl acrylate, 2-ethylhexyl acrylate, butyl acrylate, and lauryl acrylate. Alternatively, 3HP may be esterified to form an ester of 3HP and then dehydrated to form the acrylate ester.

Additionally, 3-HP may be oligomerized or polymerized to form poly(3-hydroxypropionate) homopolymers, or co-polymerized with one or more other monomers to form various co-polymers. Because 3-HP has only a single stereoisomer, polymerization of 3-HP is not complicated by the stereospecificity of monomers during chain growth. This is in contrast to (S)-2-Hydroxypropanoic acid (also known as lactic acid), which has two (D, L) stereoisomers that must be considered during its polymerizations.

As will be further described, 3-HP can be converted into derivatives starting (i) substantially as the protonated form of 3-hydroxypropionic acid; (ii) substantially as the deprotonated form, 3-hydroxypropionate; or (iii) as mixtures of the protonated and deprotonated forms. Generally, the fraction of 3-HP present as the acid versus the salt will depend on the pH, the presence of other ionic species in solution, temperature (which changes the equilibrium constant relating the acid and salt forms), and to some extent pressure. Many chemical conversions may be carried out from either of the 3-HP forms, and overall process economics will typically dictate the form of 3-HP for downstream conversion.

Also, as an example of a conversion during separation, 3-HP in an amine salt form, such as in the extraction step herein disclosed using Alamine 336 as the amine, may be converted to acrylic acid by contacting a solution comprising the 3-HP amine salt with a dehydration catalyst, such as aluminum oxide, at an elevated temperature, such as 170 to 180 C, or 180 to 190 C, or 190 to 200 C, and passing the collected vapor phase over a low temperature condenser. Operating conditions, including 3-HP concentration, organic amine, co-solvent (if any), temperature, flow rates, dehydration catalyst, and condenser temperature, are evaluated and improved for commercial purposes. Conversion of 3-HP to acrylic acid is expected to exceed at least 80 percent, or at least 90 percent, in a single conversion event. The amine may be re-used, optionally after clean-up. Other dehydration catalysts, as provided herein, may be evaluated. It is noted that U.S. Pat. No. 7,186,856 discloses data regarding this conversion approach, albeit as part of an extractive salt-splitting conversion that differs from the teachings herein. However, U.S. Pat. No. 7,186,856 is incorporated by reference for its methods, including extractive salt-splitting, the latter to further indicate the various ways 3-HP may be extracted from a microbial fermentation broth.

Further as to embodiments in which the chemical product being synthesized by the microorganism host cell is 3-HP, made as provided herein and optionally purified to a selected purity prior to conversion, the methods of the present invention can also be used to produce "downstream" compounds derived from 3-HP, such as polymerized-3-HP (poly-3-HP), acrylic acid, polyacrylic acid (polymerized acrylic acid, in various forms), methyl acrylate, acrylamide, acrylonitrile, propiolactone, ethyl 3-HP, malonic acid, and 1,3-propanediol. Numerous approaches may be employed for such downstream conversions, generally falling into enzymatic, catalytic (chemical conversion process using a catalyst), thermal, and combinations thereof (including some wherein a desired pressure is applied to accelerate a reaction).

As noted, an important industrial chemical product that may be produced from 3-HP is acrylic acid. Chemically, one of the carbon-carbon single bonds in 3-HP must undergo a dehydration reaction, converting to a carbon-carbon double bond and rejecting a water molecule. Dehydration of 3-HP in principle can be carried out in the liquid phase or in the gas phase. In some embodiments, the dehydration takes place in the presence of a suitable homogeneous or heterogeneous catalyst. Suitable dehydration catalysts are both acid and alkaline catalysts. Following dehydration, an acrylic acid-containing phase is obtained and can be purified where appropriate by further purification steps, such as by distillation methods, extraction methods, or crystallization methods, or combinations thereof.

Making acrylic acid from 3-HP via a dehydration reaction may be achieved by a number of commercial methodologies including via a distillation process, which may be part of the separation regime and which may include an acid and/or a metal ion as catalyst. More broadly, incorporated herein for its teachings of conversion of 3-HP, and other β-hydroxy carbonyl compounds, to acrylic acid and other related downstream compounds, is U.S. Patent Publication No. 2007/0219390 A1, published Sep. 20, 2007, now abandoned. This publication lists numerous catalysts and provides examples of conversions, which are specifically incorporated herein. Also among the various specific methods to dehydrate 3-HP to produce acrylic acid is an older method, described in U.S. Pat. No. 2,469,701 (Redmon). This reference teaches a method for the preparation of acrylic acid by heating 3-HP to a temperature between 130 and 190° C., in the presence of a dehydration catalyst, such as sulfuric acid or phosphoric acid, under reduced pressure. U.S. Patent Publication No. 2005/0222458 A1 (Craciun et al.) also provides a process for the preparation of acrylic acid by heating 3-HP or its derivatives. Vapor-phase dehydration of 3-HP occurs in the presence of dehydration catalysts, such as packed beds of silica, alumina, or titania. These patent publications are incorporated by reference for their methods relating to converting 3-HP to acrylic acid.

The dehydration catalyst may comprise one or more metal oxides, such as $Al_2O_3$, $SiO_2$, or $TiO_2$. In some embodiments, the dehydration catalyst is a high surface area $Al_2O_3$ or a high surface area silica wherein the silica is substantially $SiO_2$. High surface area for the purposes of the invention means a surface area of at least about 50, 75, 100 $m^2/g$, or more. In some embodiments, the dehydration catalyst may comprise an aluminosilicate, such as a zeolite.

For example, including as exemplified from such incorporated references, 3-HP may be dehydrated to acrylic acid via various specific methods, each often involving one or more dehydration catalysts. One catalyst of particular apparent value is titanium, such as in the form of titanium oxide, TiO(2). A titanium dioxide catalyst may be provided in a dehydration system that distills an aqueous solution comprising 3-HP, wherein the 3-HP dehydrates, such as upon volatilization, converting to acrylic acid, and the acrylic acid is collected by condensation from the vapor phase.

As but one specific method, an aqueous solution of 3-HP is passed through a reactor column packed with a titanium oxide catalyst maintained at a temperature between 170 and 190 C and at ambient atmospheric pressure. Vapors leaving the reactor column are passed over a low temperature condenser, where acrylic acid is collected. The low temperature condenser may be cooled to 30 C or less, 2 C or less, or at any suitable temperature for efficient condensation based on the flow rate and design of the system. Also, the reactor column temperatures may be lower, for instance when operating at a pressure lower than ambient atmospheric pressure. It is noted that Example 1 of U.S. Patent Publication No. 2007/0219390, published Sep. 20, 2007, now abandoned, provides specific parameters that employs the approach of this method. As noted, this publication is incorporated by reference for this teaching and also for its listing of catalysts that may be used in a 3-HP to acrylic acid dehydration reaction.

Further as to dehydration catalysts, the following table summarizes a number of catalysts (including chemical classes) that may be used in a dehydration reaction from 3-HP (or its esters) to acrylic acid (or acrylate esters). Such catalysts, some of which may be used in any of solid, liquid or gaseous forms, may be used individually or in any combination. This listing of catalysts is not intended to be limiting, and many specific catalysts not listed may be used for specific dehydration reactions. Further without being limiting, catalyst selection may depend on the solution pH and/or the form of 3-HP in a particular conversion, so that an acidic catalyst may be used when 3-HP is in acidic form, and a basic catalyst may be used when the ammonium salt of 3-HP is being converted to acrylic acid. Also, some catalysts may be in the form of ion exchange resins.

TABLE 4

Dehydration Catalysts

| Catalyst by Chemical Class | Non-limiting Examples |
|---|---|
| Acids (including weak and strong) | $H_2SO_4$, HCl, titanic acids, metal oxide hydrates, metal sulfates ($MSO_4$, where M = Zn, Sn, Ca, Ba, Ni, Co, or other transition metals), metal oxide sulfates, metal phosphates (e.g., $M_3$, $(PO_4)_2$, where M = Ca, Ba), metal phosphates, metal oxide phosphates, carbon (e.g., transition metals on a carbon support), mineral acids, carboxylic acids, salts thereof, acidic resins, acidic zeolites, clays, $SiO_2/H_3PO_4$, fluorinated $Al_2O_3$, $Nb_2O_3/PO_5^{-3}$, $Nb_2O_3/SO_4^{-2}$, $Nb_2O_5H_2O$, phosphotungstic acids, phosphomolybdc acids, silicomolybdic acids, silicotungstic acids, carbon dioxide |
| Bases (including weak and strong) | NaOH, ammonia, polyvinylpyridine, metal hydroxides, $Zr(OH)_4$, and substituted amines |
| Oxides (generally metal oxides) | $TiO_2$, ZrO2, $Al_2O_3$, $SiO_2$, $ZnO_2$, $SnO_2$, $WO_3$, $MnO_2$, $Fe_2O_3$, $V_2O_5$ |

As to another specific method using one of these catalysts, concentrated sulfuric acid and an aqueous solution comprising 3-HP are separately flowed into a reactor maintained at 150 to 165° C. at a reduced pressure of 100 mm Hg. Flowing from the reactor is a solution comprising acrylic acid. A specific embodiment of this method, disclosed in Example 1 of US2009/0076297, incorporated by reference herein, indicates a yield of acrylic acid exceeding 95 percent.

Based on the wide range of possible catalysts and knowledge in the art of dehydration reactions of this type, numerous other specific dehydration methods may be evaluated and implemented for commercial production.

The dehydration of 3-HP may also take place in the absence of a dehydration catalyst. For example, the reaction may be run in the vapor phase in the presence of a nominally inert packing such as glass, ceramic, a resin, porcelain, plastic, metallic or brick dust packing and still form acrylic acid in reasonable yields and purity. The catalyst particles can be sized and configured such that the chemistry is, in some embodiments, mass-transfer-limited or kinetically limited. The catalyst can take the form of powder, pellets, granules, beads, extrudates, and so on. When a catalyst support is optionally employed, the support may assume any physical form such as pellets, spheres, monolithic channels, etc. The supports may be co-precipitated with active metal species; or the support may be treated with the catalytic metal species and then used as is or formed into the aforementioned shapes; or the support may be formed into the aforementioned shapes and then treated with the catalytic species.

A reactor for dehydration of 3-HP may be engineered and operated in a wide variety of ways. The reactor operation can be continuous, semi-continuous, or batch. It is perceived that an operation that is substantially continuous and at steady state is advantageous from operations and economics perspectives. The flow pattern can be substantially plug flow, substantially well-mixed, or a flow pattern between these extremes. A "reactor" can actually be a series or network of several reactors in various arrangements.

For example, without being limiting, acrylic acid may be made from 3-HP via a dehydration reaction, which may be achieved by a number of commercial methodologies including via a distillation process, which may be part of the separation regime and which may include an acid and/or a metal ion as catalyst. More broadly, incorporated herein for its teachings of conversion of 3-HP, and other O-hydroxy carbonyl compounds, to acrylic acid and other related downstream compounds, is U.S. Patent Publication No. 2007/0219390 A1, published Sep. 20, 2007, now abandoned. This publication lists numerous catalysts and provides examples of conversions, which are specifically incorporated herein.

For example, including as exemplified from such incorporated references, 3-HP may be dehydrated to acrylic acid via various specific methods, each often involving one or more dehydration catalysts. One catalyst of particular apparent value is titanium, such as in the form of titanium oxide, $TiO_2$. A titanium dioxide catalyst may be provided in a dehydration system that distills an aqueous solution comprising 3-HP, wherein the 3-HP dehydrates, such as upon volatilization, converting to acrylic acid, and the acrylic acid is collected by condensation from the vapor phase.

As but one specific method, an aqueous solution of 3-HP is passed through a reactor column packed with a titanium oxide catalyst maintained at a temperature between 170 and 190° C. and at ambient atmospheric pressure. Vapors leaving the reactor column are passed over a low temperature condenser, where acrylic acid is collected. The low temperature condenser may be cooled to 30° C. or less, 20° C. or less, 2° C. or less, or at any suitable temperature for efficient condensation based on the flow rate and design of the system. Also, the reactor column temperatures may be lower, for instance when operating at a pressure lower than ambient atmospheric pressure. It is noted that Example 1 of U.S. Patent Publication No. 2007/0219390, published Sep. 20, 2007, now abandoned, provides specific parameters that employs the approach of this method. As noted, this publication is incorporated by reference for this teaching and also for its listing of catalysts that may be used in a 3-HP to acrylic acid dehydration reaction.

Crystallization of the acrylic acid obtained by dehydration of 3-HP may be used as one of the final separation/purification steps. Various approaches to crystallization are known in the art, including crystallization of esters.

As noted above, in some embodiments, a salt of 3-HP is converted to acrylic acid or an ester or salt thereof. For example, U.S. Pat. No. 7,186,856 (Meng et al.) teaches a process for producing acrylic acid from the ammonium salt of 3-HP, which involves a first step of heating the ammonium salt of 3-HP in the presence of an organic amine or solvent that is immiscible with water, to form a two-phase solution and split the 3-HP salt into its respective ionic constituents under conditions which transfer 3-HP from the aqueous phase to the organic phase of the solution, leaving ammonia and ammonium cations in the aqueous phase. The organic phase is then back-extracted to separate the 3-HP, followed by a second step of heating the 3-HP-containing solution in the presence of a dehydration catalyst to produce acrylic acid. U.S. Pat. No. 7,186,856 is incorporated by reference for its methods for producing acrylic acid from salts of 3-HP. Various alternatives to the particular approach disclosed in this patent may be developed for suitable extraction and conversion processes.

Methyl acrylate may be made from 3-HP via dehydration and esterification, the latter to add a methyl group (such as using methanol), acrylamide may be made from 3-HP via dehydration and amidation reactions, acrylonitrile may be made via a dehydration reaction and forming a nitrile moiety, propriolactone may be made from 3-HP via a ring-forming internal esterification reaction (eliminating a water molecule), ethyl-3-HP may be made from 3-HP via esterification with ethanol, malonic acid may be made from 3-HP via an oxidation reaction, and 1,3-propanediol may be made from 3-HP via a reduction reaction.

Malonic acid may be produced from oxidation of 3-HP as produced herein. U.S. Pat. No. 5,817,870 (Haas et al.) discloses catalytic oxidation of 3-HP by a precious metal selected from Ru, Rh, Pd, Os, Ir or Pt. These can be pure metal catalysts or supported catalysts. The catalytic oxidation can be carried out using a suspension catalyst in a suspension reactor or using a fixed-bed catalyst in a fixed-bed reactor. If the catalyst, preferably a supported catalyst, is disposed in a fixed-bed reactor, the latter can be operated in a trickle-bed procedure as well as also in a liquid-phase procedure. In the trickle-bed procedure the aqueous phase comprising the 3-HP starting material, as well as the oxidation products of the same and means for the adjustment of pH, and oxygen or an oxygen-containing gas can be conducted in parallel flow or counter-flow. In the liquid-phase procedure the liquid phase and the gas phase are conveniently conducted in parallel flow.

In order to achieve a sufficiently short reaction time, the conversion is carried out at a pH equal or greater than 6, preferably at least 7, and in particular between 7.5 and 9. According to a preferred embodiment, during the oxidation reaction the pH is kept constant, preferably at a pH in the range between 7.5 and 9, by adding a base, such as an alkaline or alkaline earth hydroxide solution. The oxidation is usefully carried out at a temperature of at least 10° C. and maximally 70° C. The flow of oxygen is not limited. In the suspension method it is important that the liquid and the gaseous phase are brought into contact by stirring vigorously. Malonic acid can be obtained in nearly quantitative yields. U.S. Pat. No. 5,817,870 is incorporated by reference herein for its methods to oxidize 3-HP to malonic acid.

1,3-Propanediol may be produced from hydrogenation of 3-HP as produced herein. U.S. Patent Publication No. 2005/0283029 (Meng et al.) is incorporated by reference herein for its methods to hydrogenation of 3-HP, or esters of the acid or mixtures, in the presence of a specific catalyst, in a liquid phase, to prepare 1,3-propanediol. Possible catalysts include ruthenium metal, or compounds of ruthenium, supported or unsupported, alone or in combination with at least one or more additional metal(s) selected from molybdenum, tungsten, titanium, zirconium, niobium, vanadium or chromium. The ruthenium metal or compound thereof, and/or the additional metal(s), or compound thereof, may be utilized in supported or unsupported form. If utilized in supported form, the method of preparing the supported catalyst is not critical and can be any technique such as impregnation of the support or deposition on the support. Any suitable support may be utilized. Supports that may be used include, but are not limited to, alumina, titania, silica, zirconia, carbons, carbon blacks, graphites, silicates, zeolites, aluminosilicate zeolites, aluminosilicate clays, and the like.

The hydrogenation process may be carried out in liquid phase. The liquid phase includes water, organic solvents that are not hydrogenatable, such as any aliphatic or aromatic hydrocarbon, alcohols, ethers, toluene, decalin, dioxane, diglyme, n-heptane, hexane, xylene, benzene, tetrahydrofuran, cyclohexane, methylcyclohexane, and the like, and mixtures of water and organic solvent(s). The hydrogenation process may be carried out batchwise, semi-continuously, or continuously. The hydrogenation process may be carried out in any suitable apparatus. Exemplary of such apparatus are stirred tank reactors, trickle-bed reactors, high pressure hydrogenation reactors, and the like.

The hydrogenation process is generally carried out at a temperature ranging from about 20 to about 250° C., more particularly from about 100 to about 200° C. Further, the hydrogenation process is generally carried out in a pressure range of from about 20 psi to about 4000 psi. The hydrogen containing gas utilized in the hydrogenation process is, optionally, commercially pure hydrogen. The hydrogen containing gas is usable if nitrogen, gaseous hydrocarbons, or oxides of carbon, and similar materials, are present in the hydrogen containing gas. For example, hydrogen from synthesis gas (hydrogen and carbon monoxide) may be employed, such synthesis gas potentially further including carbon dioxide, water, and various impurities.

As is known in the art, it is also possible to convert 3-HP to 1,3-propanediol using biological methods. For example, 1,3-propanediol can be created from either 3-HP-CoA or 3-HP via the use of polypeptides having enzymatic activity. These polypeptides can be used either in vitro or in vivo. When converting 3-HP-CoA to 1,3-propanediol, polypeptides having oxidoreductase activity or reductase activity (e.g., enzymes from the 1.1.1.-class of enzymes) can be used. Alternatively, when creating 1,3-propanediol from 3-HP, a combination of a polypeptide having aldyhyde dehydrogenase activity (e.g., an enzyme from the 1.1.1.34 class) and a polypeptide having alcohol dehydrogenase activity (e.g., an enzyme from the 1.1.1.32 class) can be used.

Another downstream production of 3-HP, acrylonitrile, may be converted from acrylic acid by various organic syntheses, including by not limited to the Sohio acrylonitrile process, a single-step method of production known in the chemical manufacturing industry Also, addition reactions may yield acrylic acid or acrylate derivatives having alkyl or aryl groups at the carbonyl hydroxyl group. Such additions may be catalyzed chemically, such as by hydrogen, hydrogen halides, hydrogen cyanide, or Michael additions under alkaline conditions optionally in the presence of basic catalysts. Alcohols, phenols, hydrogen sulfide, and thiols are known to add under basic conditions. Aromatic amines or amides, and aromatic hydrocarbons, may be added under acidic conditions. These and other reactions are described in Ulmann's Encyclopedia of Industrial Chemistry, Acrylic Acid and Derivatives, WileyVCH Verlag GmbH, Wienham (2005), incorporated by reference for its teachings of conversion reactions for acrylic acid and its derivatives.

Acrylic acid obtained from 3-HP made by the present invention may be further converted to various chemicals, including polymers, which are also considered downstream products in some embodiments. Acrylic acid esters may be formed from acrylic acid (or directly from 3-HP) such as by condensation esterification reactions with an alcohol, releasing water. This chemistry described in Monomeric Acrylic Esters, E. H. Riddle, Reinhold, N.Y. (1954), incorporated by reference for its esterification teachings. Among esters that are formed are methyl acrylate, ethyl acrylate, n-butyl acrylate, hydroxypropyl acrylate, hydroxyethyl acrylate, isobutyl acrylate, and 2-ethylhexyl acrylate, and these and/or other acrylic acid and/or other acrylate esters may be combined, including with other compounds, to form various known acrylic acid-based polymers. Although acrylamide is produced in chemical syntheses by hydration of acrylonitrile, herein a conversion may convert acrylic acid to acrylamide by amidation.

Acrylic acid obtained from 3-HP made by the present invention may be further converted to various chemicals, including polymers, which are also considered downstream products in some embodiments. Acrylic acid esters may be formed from acrylic acid (or directly from 3-HP) such as by condensation esterification reactions with an alcohol, releasing water. This chemistry is described in Monomeric Acrylic Esters, E. H. Riddle, Reinhold, N.Y. (1954), incorporated by reference for its esterification teachings. Among esters that are formed are methyl acrylate, ethyl acrylate, n-butyl acrylate, hydroxypropyl acrylate, hydroxyethyl acrylate, isobutyl acrylate, and 2-ethylhexyl acrylate, and these and/or other acrylic acid and/or other acrylate esters may be combined, including with other compounds, to form various known acrylic acid-based polymers. Although acrylamide is produced in chemical syntheses by hydration of acrylonitrile, herein a conversion may convert acrylic acid to acrylamide by amidation.

Direct esterification of acrylic acid can take place by esterification methods known to the person skilled in the art, by contacting the acrylic acid obtained from 3-HP dehydration with one or more alcohols, such as methanol, ethanol, 1-propanol, 2-propanol, n-butanol, tert-butanol or isobutanol, and heating to a temperature of at least 50, 75, 100, 125, or 150° C. The water formed during esterification may be removed from the reaction mixture, such as by azeotropic distillation through the addition of suitable separation aids, or by another means of separation. Conversions up to 95%, or more, may be realized, as is known in the art.

Several suitable esterification catalysts are commercially available, such as from Dow Chemical (Midland, Mich. US). For example, Amberlyst™ 131 Wet Monodisperse gel catalyst confers enhanced hydraulic and reactivity properties and is suitable for fixed bed reactors. Amberlyst™ 39 Wet is a macroreticular catalyst suitable particularly for stirred and slurry loop reactors. Amberlyst™ 46 is a macroporous catalyst producing less ether byproducts than conventional catalyst (as described in U.S. Pat. No. 5,426,199 to Rohm and Haas, which patent is incorporated by reference for its teachings of esterification catalyst compositions and selection considerations).

Acrylic acid, and any of its esters, may be further converted into various polymers. Polymerization may proceed by any of heat, light, other radiation of sufficient energy, and free radical generating compounds, such as azo compounds or peroxides, to produce a desired polymer of acrylic acid or acrylic acid esters. As one example, an aqueous acrylic acid solution's temperature raised to a temperature known to start polymerization (in part based on the initial acrylic acid concentration), and the reaction proceeds, the process frequently involving heat removal given the high exothermicity of the reaction. Many other methods of polymerization are known in the art. Some are described in Ulmann's Encyclopedia of Industrial Chemistry, Polyacrylamides and Poly(Acrylic Acids), WileyVCH Verlag GmbH, Wienham (2005), incorporated by reference for its teachings of polymerization reactions.

For example, the free-radical polymerization of acrylic acid takes place by polymerization methods known to the skilled worker and can be carried out either in an emulsion or suspension in aqueous solution or another solvent. Initiators, such as but not limited to organic peroxides, often are added to aid in the polymerization. Among the classes of organic peroxides that may be used as initiators are diacyls, peroxydicarbonates, monoperoxycarbonates, peroxyketals, peroxyesters, dialkyls, and hydroperoxides. Another class of initiators is azo initiators, which may be used for acrylate polyermization as well as co-polymerization with other monomers. U.S. Pat. Nos. 5,470,928; 5,510,307; 6,709,919; and 7,678,869 teach various approaches to polymerization using a number of initiators, including organic peroxides, azo compounds, and other chemical types, and are incorporated by reference for such teachings as applicable to the polymers described herein.

Accordingly, it is further possible for co-monomers, such as crosslinkers, to be present during the polymerization. The free-radical polymerization of the acrylic acid obtained from dehydration of 3-HP, as produced herein, in at least partly neutralized form and in the presence of crosslinkers is practiced in certain embodiments. This polymerization may result in hydrogels which can then be comminuted, ground and, where appropriate, surface-modified, by known techniques.

An important commercial use of polyacrylic acid is for superabsorbent polymers. This specification hereby incorporates by reference Modern Superabsorbent Polymer Technology, Buchholz and Graham (Editors), Wiley-VCH, 1997, in its entirety for its teachings regarding superabsorbent polymers components, manufacture, properties and uses. Superabsorbent polymers are primarily used as absorbents for water and aqueous solutions for diapers, adult incontinence products, feminine hygiene products, and similar consumer products. In such consumer products, superabsorbent materials can replace traditional absorbent materials such as cloth, cotton, paper wadding, and cellulose fiber. Superabsorbent polymers absorb, and retain under a slight mechanical pressure, up to 25 times or their weight in liquid. The swollen gel holds the liquid in a solid, rubbery state and prevents the liquid from leaking. Superabsorbent polymer particles can be surface-modified to produce a shell structure with the shell being more highly crosslinked. This technique improves the balance of absorption, absorption under load, and resistance to gel-blocking. It is recognized that superabsorbent polymers have uses in fields other than consumer products, including agriculture, horticulture, and medicine.

Superabsorbent polymers are prepared from acrylic acid (such as acrylic acid derived from 3-HP provided herein) and a crosslinker, by solution or suspension polymerization. Exemplary methods include U.S. Pat. Nos. 5,145,906; 5,350,799; 5,342,899; 4,857,610; 4,985,518; 4,708,997; 5,180,798; 4,666,983; 4,734,478; and 5,331,059, each incorporated by reference for their teachings relating to superabsorbent polymers.

Among consumer products, a diaper, a feminine hygiene product, and an adult incontinence product are made with superabsorbent polymer that itself is made substantially from acrylic acid converted from 3-HP made in accordance with the present invention.

Diapers and other personal hygiene products may be produced that incorporate superabsorbent polymer made from acrylic acid made from 3-HP which is bio-produced by the teachings of the present application. The following provides general guidance for making a diaper that incorporates such superabsorbent polymer. The superabsorbent polymer first is prepared into an absorbent pad that may be vacuum formed, and in which other materials, such as a fibrous material (e.g., wood pulp) are added. The absorbent pad then is assembled with sheet(s) of fabric, generally a nonwoven fabric (e.g., made from one or more of nylon, polyester, polyethylene, and polypropylene plastics) to form diapers.

Figure 6A:
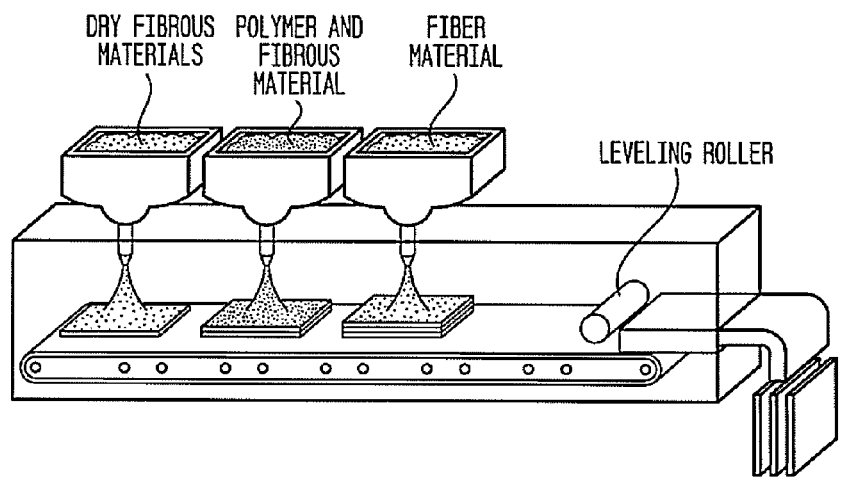
FIG. 6 depicts diaper manufacture.
Figure 6B:
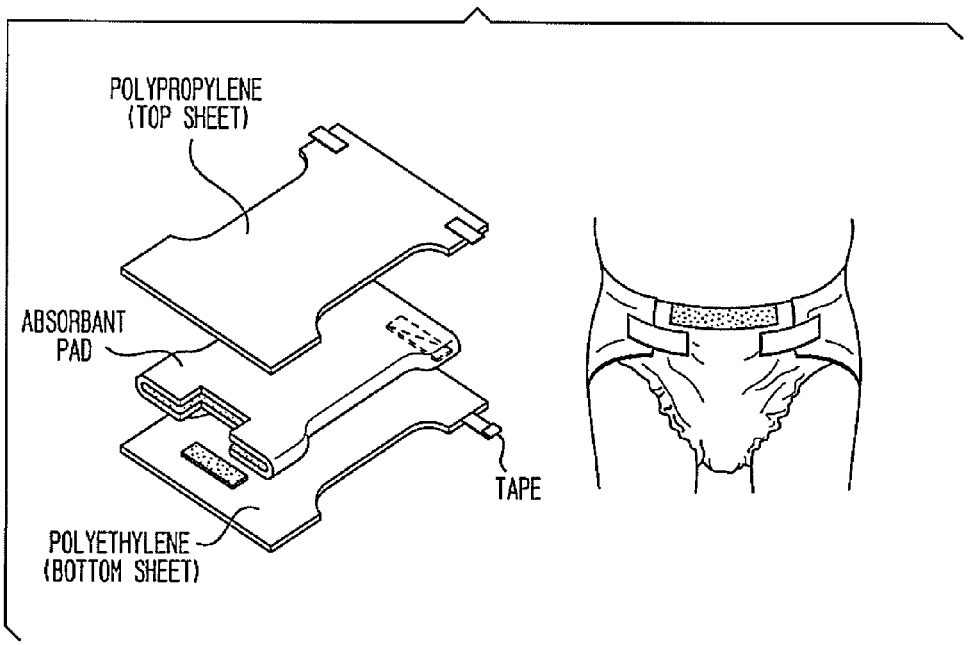

More particularly, in one non-limiting process, above a conveyer belt multiple pressurized nozzles spray superabsorbent polymer particles (such as about 400 micron size or larger), fibrous material, and/or a combination of these onto the conveyer belt at designated spaces/intervals. The conveyor belt is perforated and under vacuum from below, so that the sprayed on materials are pulled toward the belt surface to form a flat pad. In various embodiments, fibrous material is applied first on the belt, followed by a mixture of fibrous material and the superabsorbent polymer particles, followed by fibrous material, so that the superabsorbent polymer is concentrated in the middle of the pad. A leveling roller may be used toward the end of the belt path to yield pads of uniform thickness. Each pad thereafter may be further processed, such as to cut it to a proper shape for the diaper, or the pad may be in the form of a long roll sufficient for multiple diapers. Thereafter, the pad is sandwiched between a top sheet and a bottom sheet of fabric (one generally being liquid pervious, the other liquid impervious), such as on a conveyor belt, and these are attached together such as by gluing, heating or ultrasonic welding, and cut into diaper-sized units (if not previously so cut). Additional features may be provided, such as elastic components, strips of tape, etc., for fit and ease of wearing by a person. FIG. 6 depicts aspects of diaper manufacture and wear. FIG. 7 provides a general, non-limiting depiction of the overall processes leading from biomass to a polymerized acrylic acid-based polymer such as may be used in diapers in accordance with embodiments of the present invention.

The ratio of the fibrous material to polymer particles is known to effect performance characteristics. In some embodiments, this ratio is between 75:25 and 90:10 (see U.S. Pat. No. 4,685,915, incorporated by reference for its teachings of diaper manufacture). Other disposable absorbent articles may be constructed in a similar fashion, such as for adult incontinence, feminine hygiene (sanitary napkins), tampons, etc. (see, for example, U.S. Pat. Nos. 5,009,653, 5,558,656, and 5,827,255 incorporated by reference for their teachings of sanitary napkin manufacture).

Low molecular-weight polyacrylic acid has uses for water treatment, flocculants, and thickeners for various applications including cosmetics and pharmaceutical preparations. For these applications, the polymer may be uncrosslinked or lightly crosslinked, depending on the specific application. The molecular weights are typically from about 200 to about 1,000,000 g/mol. Preparation of these low molecular-weight polyacrylic acid polymers is described in U.S. Pat. Nos. 3,904,685; 4,301,266; 2,798,053; and 5,093,472, each of which is incorporated by reference for its teachings relating to methods to produce these polymers.

Acrylic acid may be co-polymerized with one or more other monomers selected from acrylamide, 2-acrylamido-2-methylpropanesulfonic acid, N,N-dimethylacrylamide, N-isopropylacrylamide, methacrylic acid, and methacrylamide, to name a few. The relative reactivities of the monomers affect the microstructure and thus the physical properties of the polymer. Co-monomers may be derived from 3-HP, or otherwise provided, to produce co-polymers. Ulmann's Encyclopedia of Industrial Chemistry, Polyacrylamides and Poly(Acrylic Acids), WileyVCH Verlag GmbH, Wienham (2005), is incorporated by reference herein for its teachings of polymer and co-polymer processing.

Acrylic acid can in principle be copolymerized with almost any free-radically polymerizable monomers including styrene, butadiene, acrylonitrile, acrylic esters, maleic acid, maleic anhydride, vinyl chloride, acrylamide, itaconic acid, and so on. End-use applications typically dictate the co-polymer composition, which influences properties. Acrylic acid also may have a number of optional substitutions on it, and after such substitutions be used as a monomer for polymerization, or co-polymerization reactions. As a general rule, acrylic acid (or one of its co-polymerization monomers) may be substituted by any substituent that does not interfere with the polymerization process, such as alkyl, alkoxy, aryl, heteroaryl, benzyl, vinyl, allyl, hydroxy, epoxy, amide, ethers, esters, ketones, maleimides, succinimides, sulfoxides, glycidyl and silyl (see U.S. Pat. No. 7,678,869, incorporated by reference above, for further discussion). The following paragraphs provide a few non-limiting examples of copolymerization applications.

Paints that comprise polymers and copolymers of acrylic acid and its esters are in wide use as industrial and consumer products. Aspects of the technology for making such paints can be found in U.S. Pat. Nos. 3,687,885 and 3,891,591, incorporated by reference for its teachings of such paint manufacture. Generally, acrylic acid and its esters may form homopolymers or copolymers among themselves or with other monomers, such as amides, methacrylates, acrylonitrile, vinyl, styrene and butadiene. A desired mixture of homopolymers and/or copolymers, referred to in the paint industry as 'vehicle' (or 'binder') are added to an aqueous solution and agitated sufficiently to form an aqueous dispersion that includes sub-micrometer sized polymer particles. The paint cures by coalescence of these 'vehicle' particles as the water and any other solvent evaporate. Other additives to the aqueous dispersion may include pigment, filler (e.g., calcium carbonate, aluminum silicate), solvent (e.g., acetone, benzol, alcohols, etc., although these are not found in certain no VOC paints), thickener, and additional additives depending on the conditions, applications, intended surfaces, etc. In many paints, the weight percent of the vehicle portion may range from about nine to about 26 percent, but for other paints the weight percent may vary beyond this range.

Acrylic-based polymers are used for many coatings in addition to paints. For example, for paper coating latexes, acrylic acid is used from 0.1-5.0%, along with styrene and butadiene, to enhance binding to the paper and modify rheology, freeze-thaw stability and shear stability. In this context, U.S. Pat. Nos. 3,875,101 and 3,872,037 are incorporated by reference for their teachings regarding such latexes. Acrylate-based polymers also are used in many inks, particularly UV curable printing inks. For water treatment, acrylamide and/or hydroxy ethyl acrylate are commonly co-polymerized with acrylic acid to produce low molecular-weight linear polymers. In this context, U.S. Pat. Nos. 4,431,547 and 4,029,577 are incorporated by reference for their teachings of such polymers. Co-polymers of acrylic acid with maleic acid or itaconic acid are also produced for water-treatment applications, as described in U.S. Pat. No. 5,135,677, incorporated by reference for that teaching. Sodium acrylate (the sodium salt of glacial acrylic acid) can be co-polymerized with acrylamide (which may be derived from acrylic acid via amidation chemistry) to make an anionic co-polymer that is used as a flocculant in water treatment.

For thickening agents, a variety of co-monomers can be used, such as described in U.S. Pat. Nos. 4,268,641 and 3,915,921, incorporated by reference for description of these co-monomers. U.S. Pat. No. 5,135,677 describes a number of co-monomers that can be used with acrylic acid to produce water-soluble polymers, and is incorporated by reference for such description.

Also as noted, some conversions to downstream products may be made enzymatically. For example, 3-HP may be converted to 3-HP-CoA, which then may be converted into polymerized 3-HP with an enzyme having polyhydroxyacid synthase activity (EC 2.3.1.-). Also, 1,3-propanediol can be made using polypeptides having oxidoreductase activity or reductase activity (e.g., enzymes in the EC 1.1.1.-class of enzymes). Alternatively, when creating 1,3-propanediol from 3HP, a combination of (1) a polypeptide having aldehyde dehydrogenase activity (e.g., an enzyme from the 1.1.1.34 class) and (2) a polypeptide having alcohol dehydrogenase activity (e.g., an enzyme from the 1.1.1.32 class) can be used. Polypeptides having lipase activity may be used to form esters. Enzymatic reactions such as these may be conducted in vitro, such as using cell-free extracts, or in vivo.

Thus, various embodiments of the present invention, such as methods of making a chemical, include conversion steps to any such noted downstream products of microbially produced 3-HP, including but not limited to those chemicals described herein and in the incorporated references (the latter for jurisdictions allowing this). For example, one embodiment is making 3-HP molecules by the teachings herein and further converting the 3-HP molecules to polymerized-3-HP (poly-3-HP) or acrylic acid, and such as from acrylic acid then producing from the 3-HP molecules any one of polyacrylic acid (polymerized acrylic acid, in various forms), methyl acrylate, acrylamide, acrylonitrile, propiolactone, ethyl 3-HP, malonic acid, 1,3-propanediol, ethyl acrylate, n-butyl acrylate, hydroxypropyl acrylate, hydroxyethyl acrylate, isobutyl acrylate, 2-ethylhexyl acrylate, and acrylic acid or an acrylic acid ester to which an alkyl or aryl addition is made, and/or to which halogens, aromatic amines or amides, and aromatic hydrocarbons are added.

Also as noted, some conversions to downstream products may be made enzymatically. For example, 3-HP may be converted to 3-HP-CoA, which then may be converted into polymerized 3-HP with an enzyme having polyhydroxyacid synthase activity (EC 2.3.1.-). Also, 1,3-propanediol can be made using polypeptides having oxidoreductase activity or reductase activity (e.g., enzymes in the EC 1.1.1.-class of enzymes). Alternatively, when creating 1,3-propanediol from 3HP, a combination of (1) a polypeptide having aldehyde dehydrogenase activity (e.g., an enzyme from the 1.1.1.34 class) and (2) a polypeptide having alcohol dehydrogenase activity (e.g., an enzyme from the 1.1.1.32 class) can be used. Polypeptides having lipase activity may be used to form esters. Enzymatic reactions such as these may be conducted in vitro, such as using cell-free extracts, or in vivo.

Thus, various embodiments of the present invention, such as methods of making a chemical, include conversion steps to any such noted downstream products of microbially produced 3-HP, including but not limited to those chemicals described herein and in the incorporated references (the latter for jurisdictions allowing this). For example, one embodiment is making 3-HP molecules by the teachings herein and further converting the 3-HP molecules to polymerized-3-HP (poly-3-HP) or acrylic acid, and such as from acrylic acid then producing from the 3-HP molecules any one of polyacrylic acid (polymerized acrylic acid, in various forms), methyl acrylate, acrylamide, acrylonitrile, propiolactone, ethyl 3-HP, malonic acid, 1,3-propanediol, ethyl acrylate, n-butyl acrylate, hydroxypropyl acrylate, hydroxyethyl acrylate, isobutyl acrylate, 2-ethylhexyl acrylate, and acrylic acid or an acrylic acid ester to which an alkyl or aryl addition is made, and/or to which halogens, aromatic amines or amides, and aromatic hydrocarbons are added.

Reactions that form downstream compounds such as acrylates or acrylamides can be conducted in conjunction with use of suitable stabilizing agents or inhibiting agents reducing likelihood of polymer formation. See, for example, U.S. Patent Publication No. 2007/0219390 A1. Stabilizing agents and/or inhibiting agents include, but are not limited to, e.g., phenolic compounds (e.g., dimethoxyphenol (DMP) or alkylated phenolic compounds such as di-tert-butyl phenol), quinones (e.g., t-butyl hydroquinone or the monomethyl ether of hydroquinone (MEHQ)), and/or metallic copper or copper salts (e.g., copper sulfate, copper chloride, or copper acetate). Inhibitors and/or stabilizers can be used individually or in combinations as will be known by those of skill in the art. Also, in various embodiments, the one or more downstream compounds is/are recovered at a molar yield of up to about 100 percent, or a molar yield in the range from about 70 percent to about 90 percent, or a molar yield in the range from about 80 percent to about 100 percent, or a molar yield in the range from about 90 percent to about 100 percent. Such yields may be the result of single-pass (batch or continuous) or iterative separation and purification steps in a particular process.

Acrylic acid and other downstream products are useful as commodities in manufacturing, such as in the manufacture of consumer goods, including diapers, textiles, carpets, paint, adhesives, and acrylic glass.

In some embodiments, the invention contemplates a culture system comprising: a) a population of a genetically modified microorganism as described herein; and b) a media comprising nutrients for the population. In some such embodiments the media additionally comprises at least 1 gram/liter of 3-HP.

The teachings and results of the Examples that follow are hereby incorporated into this section for all applicable purposes.

Also, and more generally, in accordance with disclosures, discussions, examples and embodiments herein, there may be employed conventional molecular biology, cellular biology, microbiology, and recombinant DNA techniques within the skill of the art. Such techniques are explained fully in the literature. (See, e.g., Sambrook and Russell, Molecular Cloning: A Laboratory Manual, Third Edition 2001 (volumes 1-3), Cold Spring Harbor Laboratory Press, Cold Spring Harbor, N.Y.; Animal Cell Culture, R. I. Freshney, ed., 1986). These published resources are incorporated by reference herein for their respective teachings of standard laboratory methods found therein. Further, all patents, patent applications, patent publications, and other publications referenced herein (collectively, "published resource(s)") are hereby incorporated by reference in this application. Such incorporation, at a minimum, is for the specific teaching and/or other purpose that may be noted when citing the reference herein. If a specific teaching and/or other purpose is not so noted, then the published resource is specifically incorporated for the teaching(s) indicated by one or more of the title, abstract, and/or summary of the reference. If no such specifically identified teaching and/or other purpose may be so relevant, then the published resource is incorporated in order to more fully describe the state of the art to which the present invention pertains, and/or to provide such teachings as are generally known to those skilled in the art, as may be applicable. However, it is specifically stated that a citation of a published resource herein shall not be construed as an admission that such is prior art to the present invention. Also, in the event that one or more of the incorporated published resources differs from or contradicts this application, including but not limited to defined terms, term usage, described techniques, or the like, this application controls.

While various embodiments of the present invention have been shown and described herein, it is emphasized that such embodiments are provided by way of example only. Numerous variations, changes and substitutions may be made without departing from the invention herein in its various embodiments. Specifically, and for whatever reason, for any grouping of compounds, nucleic acid sequences, polypeptides including specific proteins including functional enzymes, metabolic pathway enzymes or intermediates, elements, or other compositions, or concentrations stated or otherwise presented herein in a list, table, or other grouping (such as metabolic pathway enzymes shown in a figure), unless clearly stated otherwise, it is intended that each such grouping provides the basis for and serves to identify various subset embodiments, the subset embodiments in their broadest scope comprising every subset of such grouping by exclusion of one or more members (or subsets) of the respective stated grouping. Moreover, when any range is described herein, unless clearly stated otherwise, that range includes all values therein and all sub-ranges therein. Accordingly, it is intended that the invention be limited only by the spirit and scope of appended claims, and of later claims, and of either such claims as they may be amended during prosecution of this or a later application claiming priority hereto.

EXAMPLES

Example 1

Preparing a Genetically Modified *E. coli* Host Cell Comprising an Oxaloacetate Alpha-Decarboxylase (oad-2) in Combination with Other Genetic Modifications to Increase 3-HP Production Relative to a Control *E. coli* Cell (Prophetic)

Referring to FIG. 4 and Tables 1 and 2, genetic modifications are made to introduce a polypeptide that encodes SEQ ID NO:001 or SEQ ID NO:036, or its functional equivalents, and also to introduce a vector that encodes mmsB (SEQ ID NO:002). Vectors comprising galP and a native or mutated Ppc also may be introduced by methods known to those skilled in the art (see, e.g., Sambrook and Russell, Molecular Cloning: A Laboratory Manual, Third Edition 2001 (volumes 1-3), Cold Spring Harbor Laboratory Press, Cold Spring Harbor, N.Y., "Sambrook and Russell, 2001"), additionally recognizing that mutations may be made by a method using the XL1-Red mutator strain, using appropriate materials following a manufacturer's instructions (Stratagene QuikChange Mutagenesis Kit, Stratagene, La Jolla, Calif. USA) and selected for or screened under standard protocols.

Also, genetic modifications are made to reduce or eliminate the enzymatic activities of the *E. coli* genes listed in Table 2. These genetic modifications are achieved by using the RED/ET homologous recombination method with kits supplied by Gene Bridges (Gene Bridges GmbH, Dresden, Germany, www.genebridges.com) according to manufacturer's instructions.

The so-genetically modified microorganism is evaluated and found to exhibit higher productivity of 3-HP compared with a control *E. coli* lacking said genetic modifications. Productivity is measured by standard metrics, such as volumetric productivity (grams of 3-HP/hour) under similar culture conditions.

Example 2

General Example of Genetic Modification to a Host Cell (Prophetic and Non-Specific)

This example is meant to describe a non-limiting approach to genetic modification of a selected microorganism to introduce a nucleic acid sequence of interest. Alternatives and variations are provided within this general example. The methods of this Example are conducted to achieve a combination of desired genetic modifications in a selected microorganism species, such as a combination of genetic modifications selected from those shown in FIG. 4, and their equivalents in species other than *E. coli*.

A gene or other nucleic acid sequence segment of interest is identified in a particular species (such as *E. coli* as described above) and a nucleic acid sequence comprising that gene or segment is obtained. For clarity below the use of the term "segment of interest" below is meant to include both a gene and any other nucleic acid sequence segment of interest. One example of a method used to obtain a segment of interest is to acquire a culture of a microorganism, where that microorganism's genome includes the gene or nucleic acid sequence segment of interest.

Based on the nucleic acid sequences at the ends of or adjacent the ends of the segment of interest, 5' and 3' nucleic acid primers are prepared. Each primer is designed to have a sufficient overlap section that hybridizes with such ends or adjacent regions. Such primers may include enzyme recognition sites for restriction digest of transposase insertion that could be used for subsequent vector incorporation or genomic insertion. These sites are typically designed to be outward of the hybridizing overlap sections. Numerous contract services are known that prepare primer sequences to order (e.g., Integrated DNA Technologies, Coralville, Iowa USA).

Once primers are designed and prepared, polymerase chain reaction (PCR) is conducted to specifically amplify the desired segment of interest. This method results in multiple copies of the region of interest separated from the microorganism's genome. The microorganism's DNA, the primers, and a thermophilic polymerase are combined in a buffer solution with potassium and divalent cations (e.g., Mg or Mn) and with sufficient quantities of deoxynucleoside triphosphate molecules. This mixture is exposed to a standard regimen of temperature increases and decreases. However, temperatures, components, concentrations, and cycle times may vary according to the reaction according to length of the sequence to be copied, annealing temperature approximations and other factors known or readily learned through routine experimentation by one skilled in the art.

In an alternative embodiment the segment of interest may be synthesized, such as by a commercial vendor, and prepared via PCR per above, rather than obtaining from a microorganism or other natural source of DNA.

The nucleic acid sequences then are purified and separated, such as on an agarose gel via electrophoresis. Optionally, once the region is purified it can be validated by standard DNA sequencing methodology and may be introduced into a vector. Any of a number of vectors may be used, which generally comprise markers known to those skilled in the art, and standard methodologies are routinely employed for such introduction. Commonly used vector systems are pSMART (Lucigen, Middleton, Wis.), pET *E. COLi* EXPRESSION SYSTEM (Stratagene, La Jolla, Calif.), pSC-B StrataClone Vector (Stratagene, La Jolla, Calif.), pRANGER-BTB vectors (Lucigen, Middleton, Wis.), and TOPO vector (Invitrogen Corp, Carlsbad, Calif., USA). Similarly, the vector then is introduced into any of a number of host cells. Commonly used host cells are *E. cloni* 100 (Lucigen, Middleton, Wis.), *E. cloni* 10GF' (Lucigen, Middleton, Wis.), StrataClone Competent cells (Stratagene, La Jolla, Calif.), *E. coli* BL21, *E. coli* BW25113, and *E. coli* K12 MG1655. Some of these vectors possess promoters, such as inducible promoters, adjacent the region into which the sequence of interest is inserted (such as into a multiple cloning site), while other vectors, such as pSMART vectors (Lucigen, Middleton, Wis.), are provided without promoters and with dephosphorylated blunt ends. The culturing of such plasmid-laden cells permits plasmid replication and thus replication of the segment of interest, which often corresponds to expression of the segment of interest.

Various vector systems comprise a selectable marker, such as an expressible gene encoding a protein needed for growth or survival under defined conditions. Common selectable markers contained on backbone vector sequences include genes that encode for one or more proteins required for antibiotic resistance as well as genes required to complement auxotrophic deficiencies or supply critical nutrients not present or available in a particular culture media. Vectors also comprise a replication system suitable for a host cell of interest.

The plasmids containing the segment of interest can then be isolated by routine methods and are available for introduction into other microorganism host cells of interest. Various methods of introduction are known in the art and can include vector introduction or genomic integration. In various alternative embodiments the DNA segment of interest may be separated from other plasmid DNA if the former will be introduced into a host cell of interest by means other than such plasmid.

While steps of the above general prophetic example involve use of plasmids, other vectors known in the art may be used instead. These include cosmids, viruses (e.g., bacteriophage, animal viruses, plant viruses), and artificial chromosomes (e.g., yeast artificial chromosomes (YAC) and bacteria artificial chromosomes (BAC)).

Host cells into which the segment of interest is introduced may be evaluated for performance as to a particular enzymatic step, and/or tolerance or bio-production of a chemical compound of interest. Selections of better performing genetically modified host cells may be made, selecting for overall performance, tolerance, or production or accumulation of the chemical of interest.

It is noted that this procedure may incorporate a nucleic acid sequence for a single gene (or other nucleic acid sequence segment of interest), or multiple genes (under control of separate promoters or a single promoter), and the procedure may be repeated to create the desired heterologous nucleic acid sequences in expression vectors, which are then supplied to a selected microorganism so as to have, for example, a desired complement of enzymatic conversion step functionality for any of the herein-disclosed metabolic pathways. However, it is noted that although many approaches rely on expression via transcription of all or part of the sequence of interest, and then translation of the transcribed mRNA to yield a polypeptide such as an enzyme, certain sequences of interest may exert an effect by means other than such expression.

The specific laboratory methods used for the above approaches are well-known in the art and may be found in various references known to those skilled in the art, such as Sambrook and Russell, Molecular Cloning: A Laboratory Manual, Third Edition 2001 (volumes 1-3), Cold Spring Harbor Laboratory Press, Cold Spring Harbor, N.Y. (hereinafter, Sambrook and Russell, 2001).

As an alternative to the above, other genetic modifications may also be practiced, such as a deletion of a nucleic acid sequence of the host cell's genome. One non-limiting method to achieve this is by use of Red/ET recombination, known to those of ordinary skill in the art and described in U.S. Pat. Nos. 6,355,412 and 6,509,156, issued to Stewart et al. and incorporated by reference herein for its teachings of this method. Material and kits for such method are available from Gene Bridges (Gene Bridges GmbH, Dresden, Germany, www.genebridges.com), and the method may proceed by following the manufacturer's instructions. Targeted deletion of genomic DNA may be practiced to alter a host cell's metabolism so as to reduce or eliminate production of undesired metabolic products, such as gene deletions for particular genes shown in FIG. 4. This may be used in combination with other genetic modifications such as described above in this general example.

The above-described approaches and compositions may be combined with other approaches and compositions that are directed to providing, or to improving, a desired property (e.g. productivity improvements in a microorganism). Various bioproduction pathways, and methods of incorporating them into a microorganism, are known in the art and also are described in other patent applications having a common co-inventor with the present patent application. Any of such may be combined with any of the above-described approaches and combinations.

Example 3

Mutational Development of Selected Polynucleotides (Prophetic)

A selected gene sequence is subjected to a mutation development protocol, starting by constructing a mutant library of a native or previously evolved and/or codon-optimized polynucleotide by use of an error-inducing PCR site-directed mutagenesis method.

A polynucleotide exhibiting enzymatic activity of the selected gene (which may be any disclosed herein, e.g., a decarboxylase or mmsB) will be cloned into an appropriate expression system for *E. coli*. This sequence may be codon optimized Cloning of a codon-optimized polynucleotide and its adequate expression of the will be accomplished via gene synthesis supplied from a commercial supplier using standard techniques. The gene will be synthesized with an eight amino acid C-terminal tag to enable affinity based protein purification. Once obtained using standard methodology, the gene will be cloned into an expression system using standard techniques.

The plasmid containing the above-described polynucleotide will be mutated by standard methods resulting in a large library of mutants ($>10^6$). The mutant sequences will be excised from these plasmids and again cloned into an expression vector, generating a final library of greater than $10^6$ clones for subsequent screening. These numbers ensure a greater than 99% probability that the library will contain a mutation in every amino acid encoded by sequence. It is acknowledged that each method of creating a mutational library has its own biases, including transformation into mutator strains of *E. coli*, error prone PCR, and in addition more site directed mutagenesis. In some embodiments, various methods may be considered and possibly several explored in parallel.

One such method is the use of the XL1-Red mutator strain, which is deficient in several repair mechanisms necessary for accurate DNA replication and generates mutations in plasmids at a rate 5,000 times that of the wild-type mutation rate, may be employed using appropriate materials following a manufacturer's instructions (See Stratagene QuikChange Mutagenesis Kit, Stratagene, La Jolla, Calif. USA). This technique or other techniques known to those skilled in the art, may be employed and then a population of such mutants, e.g., in a library, is evaluated, such as by a screening or selection method, to identify clones having a suitable or favorable mutation.

With the successful construction of a mutant library, it will be possible to screen this library for increased activity. The screening process will be designed to screen the entire library of greater than $10^6$ mutants. This is done by screening methods suited to the particular enzymatic reaction.

Example 4

Cloning of Oxaloacetate Alpha-Decarboxylase Candidate Enzymes

Candidate oxaloacetate alpha-decarboxylase genes were synthesized using codons optimized for expression in *E. coli* and sub-cloned into expression vectors to provide protein for oxaloacetate alpha-decarboxylase assays. For gene synthesis, the protein sequences for pyruvate decarboxylase (pdc) from *Zymomonas mobilis* (SEQ ID NO:035), 2-oxoglutarate decarboxylase (oad) from *Leuconostoc mesenteroides* (SEQ ID NO:036), and alpha-ketoglutarate decarboxylase (kgd) from *Mycobacterium tuberculosis* (SEQ ID NO:037) were used to create codon optimized genes for expression in *E. coli* by the service provided by DNA 2.0 (Menlo Park, Calif. USA). Additionally, the protein coding regions of the codon optimized PDC and OAD genes were augmented with six histidines and five histidines, respectively. These additional amino acids provide a C-terminal histidine-tag for protein purification via immobilized metal-affinity chromatography. These plasmids were designated pJ201:pdc (SEQ ID NO:038), pJ251:oad (SEQ ID NO:039), and pJ206:kgd (SEQ ID NO:040), respectively.

The pdc and oad genes were individually sub-cloned into a pTrc-HisB expression vector obtained from Invitrogen (SEQ ID NO:041)(Carlsbad, Calif.). Sub-cloning for pdc gene was accomplished as follows: First, the expression vector was subjected to enzymatic restriction digestion with the restriction enzymes NcoI and NheI. Restriction enzymes were obtained from New England BioLabs (Ipswich, Mass. USA), and used according to manufacturer's instructions. The digestion mixtures were separated by agarose gel electrophoresis, and visualized under UV transillumination as described in the Common Methods Section. Agarose gel slices containing the DNA piece corresponding to the cut vector product were cut from the gel and the DNA recovered with a standard gel extraction protocol and components from Qiagen according to manufacturer's instructions. The gene inserts were amplified by polymerase chain reactions, cut with restriction enzymes, purified, and ligated to the cut vector. For the pdc gene containing insert, a polymerase chain reaction was performed with the forward primer being GGGATATCAT GAGCTATACC GTTGG (SEQ ID NO:042), and the reverse primer being GAAATAGTTC TCTAGAGAAG CTTC (SEQ ID NO:043) and the pJ201:pdc plasmid was used as template. These primers provide a BspHI site at the start codon and an XbaI site after the stop codon. This PCR product was prepared for restriction digest using a PCR purification kit from Qiagen Corporation (Valencia, Calif., USA) using the manufacturer's instructions. The PCR product was prepared by restriction digest with BspHI and XbaI obtained from New England BioLabs (Ipswich, Mass. USA), and used according to manufacturer's instructions. After digestion, mixtures were separated by agarose gel electrophoresis, and visualized under UV transillumination as described in the Common Methods Section. An agarose gel slice containing the DNA piece corresponding to the amplified pdc gene fusion was cut from the gel and the DNA recovered with a standard gel extraction protocol and components from Qiagen according to manufacturer's instructions. The recovered product and the prepared vector backbone were ligated together with T4 DNA ligase obtained from New England BioLabs (Ipswich, Mass. USA) according to manufacturer's instructions. Ligation mixtures were transformed into chemically competent 100 cells (Lucigen, Middleton, Wis.) according to the manufacturer's instructions. Colonies possibly containing the new plasmid were cultured, and their DNA was isolated using a standard miniprep protocol and components from Qiagen (Valencia, Calif. USA) according to the manufacturer's instruction. Isolated plasmids were checked by restriction digests and confirmed by sequencing. The sequenced-verified isolated plasmids produced with this procedure were designated pTrc:pdc-his (SEQ ID NO:044).

Sub-cloning for oad gene was accomplished as follows: First, the expression vector was subjected to enzymatic restriction digestion with the restriction enzymes NcoI and NheI. Restriction enzymes were obtained from New England BioLabs (Ipswich, Mass. USA), and used according to manufacturer's instructions. The digestion mixtures were separated by agarose gel electrophoresis, and visualized under UV transillumination as described in the Common Methods Section. Agarose gel slices containing the DNA piece corresponding to the cut vector product were cut from the gel and the DNA recovered with a standard gel extraction protocol and components from Qiagen according to manufacturer's instructions. The gene inserts were amplified by polymerase chain reactions, cut with restriction enzymes, purified, and ligated to the cut vector. For the oad gene containing insert, a polymerase chain reaction was performed with the forward primer being GGAGAATTACCATGGCGGATACCCTG (SEQ ID NO:045), and the reverse primer being GGGAATCTAG ACTAATGATG ATGGTGG (SEQ ID NO:046), and the pJ251:oad plasmid was used as template. These primers provide an NcoI site and the start codon and an XbaI site after the stop codon. This PCR product was prepared for restriction digest purified using a PCR purification kit from Qiagen Corporation (Valencia, Calif., USA) using the manufacturer's instructions. The PCR product was prepared by restriction digest with NcoI and XbaI obtained from New England BioLabs (Ipswich, Mass. USA), and used according to manufacturer's instructions. After digestion, mixtures were separated by agarose gel electrophoresis, and visualized under UV transillumination as described in the Common Methods Section. An agarose gel slice containing the DNA piece corresponding to the amplified pdc gene fusion was cut from the gel and the DNA recovered with a standard gel extraction protocol and components from Qiagen according to manufacturer's instructions. The recovered product and the prepared vector backbone were ligated together with T4 DNA ligase obtained from New England BioLabs (Ipswich, Mass. USA) according to manufacturer's instructions. Ligations were transformed into chemically competent 100 cells from Lucigen according to the manufacturer's instructions. Colonies possibly containing the new plasmid were cultured, and their DNA was isolated using a standard miniprep protocol and components from Qiagen (Valencia, Calif. USA) according to the manufacturer's instruction. Isolated plasmids were checked by restriction digests and confirmed by sequencing. The sequenced-verified isolated plasmids produced with this procedure were designated pTrc:oad-his (SEQ ID NO:047).

The kgd gene was sub-cloned into a pKK223:cterm-His expression vector. Sub-cloning for kdg gene was accomplished as follows: First, the pKK223:c-term-His expression vector (SEQ ID NO:050) was subjected to enzymatic restriction digestion with the restriction enzymes NcoI and HindIII. Restriction enzymes were obtained from New England BioLabs (Ipswich, Mass. USA), and used according to manufacturer's instructions. The digestion mixtures were separated by agarose gel electrophoresis, and visualized under UV transillumination as described in the Common Methods Section. Agarose gel slices containing the DNA piece corresponding to the cut vector product were cut from the gel and the DNA recovered with a standard gel extraction protocol and components from Qiagen according to manufacturer's instructions. The gene inserts were amplified by polymerase chain reactions, cut with restriction enzymes, purified, and ligated to the cut vector. For the kgd gene containing insert, a polymerase chain reaction was performed with the forward primer being AGGTTCCCA TGGTGACTCA GGACCCG (SEQ ID NO:048), and the reverse primer being GTAAGCT-TAG TGGTGATGGT GATGACCGAA CGCTTCGTCC (SEQ ID NO:049), and the pJ206:kgd plasmid was used as template. These primers provide an NcoI site and the start codon, and penta-histidine coding sequence for affinity purification of protein followed by a stop codon as well as a HindIII site. This PCR product was prepared for restriction digest purified using a PCR purification kit from Qiagen Corpoaration (Valencia, Calif., USA) using the manufacturer's instructions. The PCR product was prepared by restriction digest with NcoI and HindIII obtained from New England BioLabs (Ipswich, Mass. USA), and used according to manufacturer's instructions. After digestion, mixtures were separated by agarose gel electrophoresis, and visualized under UV transillumination as described in the Common Methods Section. An agarose gel slice containing the DNA piece corresponding to the amplified pdc gene fusion was cut from the gel and the DNA recovered with a standard gel extraction protocol and components from Qiagen according to manufacturer's instructions. The recovered product and the prepared vector backbone were ligated together with T4 DNA ligase obtained from New England BioLabs (Ipswich, Mass. USA) according to manufacturer's instructions. Ligations were transformed into chemically competent 100 cells from Lucigen according to the manufacturer's instructions. Colonies possibly containing the new plasmid were cultured, and their DNA was isolated using a standard miniprep protocol and components from Qiagen (Valencia, Calif. USA) according to the manufacturer's instruction. Isolated plasmids were checked by restriction digests and confirmed by sequencing. The sequenced-verified isolated plasmids produced with this procedure were designated pKK223:kgd-his (SEQ ID NO:053).

Example 5

Preparation and Evaluation of Over-Expressed Oxaloacetate Alpha-Decarboxylase Candidate Enzymes and Selected Mutant Enzymes In order to evaluate candidate enzymes for native oxaloacetate alpha-decarboxylase function, each of the protein was purified. Plasmids containing each of the genes were individually transformed into electro-competent BW25113 cells. For each enzyme that was tested, starter cultures from single colonies were grown overnight at 37° C. with 250 rpm agitation in 20 mL of LB media with 200 ug/mL ampicillin selection. The next morning, these cultures were used to inoculate a 1 L of TB media with 200 ug/mL ampicillin selection. Cultures were grown at 37° C. with 250 rpm agitation. Protein induction was initiated when the optical density of the culture measured at 600 nm reached between 0.5 and 0.7—(about 4 to 6 hr) with addition of IPTG to a final concentration of 1 mM. The cultures allowed to grow overnight at 30° C. The cells were harvested by centrifugation (6000×g for 15 minutes) and kept frozen at −70° C. until purification.

Purification was performed as follows: Cells were thawed on ice and then resuspended in 40 mL of Buffer A (25 mM Trizma base pH 8.0, 500 mM NaCl, and 1 mM Imidazole) supplemented with lysozyme (Sigma-Aldrich, St. Louis Mo.), Dnase I (Sigma-Aldrich, St. Louis Mo.), and Complete EDTA-free protease inhibitor cocktail (EMD, Gibbstown N.J.). Resuspend cells were incubated on ice for at least 5 minutes or until the culture showed signs of lysis. To completely lyse the cells, the suspension was sonicated (85% power on a Branson probe tip sonicator) with five 10 second burst intervened by resting on ice for at least a minute. The cell lysate was diluted to 50 mL with Buffer A and clarified by centrifugation at 10000×g for 15 minutes.

Proteins were purified from the lysate as follows: The clarified lysate was subjected to affinity purification with a nickel-charged fast flow column (Pharmacia). Clarified cell lysates was loaded on to the column at 1 mL per minute. The column was then washed with at least 50 column volumes of Buffer A until the flow through had an absorption at 260 nm equal to that of Buffer A. The protein was eluted with Elution Buffer (25 mM Trizma base pH 8.0, 100 mM NaCl, and 300 mM Imidazole) at 1 mL per minute and collected in 1.0 mL fractions. Fractions containing protein were identified using the BioRad Total Protein Assay method. Fractions showing protein were combined and concentrated by centrifugation using a Amicon ultra concentration unit (10 kDa cutoff) (Millipore, Milford Mass.). Concentrated proteins were further purified to remove imidazole using a pre-equilibrated (25 mM Trizma base pH 8.0, 100 mM NaCl) PD Miditrap G25 column (GE Lifesciences, Piscataway N.J.) according the manufacturer's instructions. Proteins were concentrated a final time, glycerol was added to about 10% volume, protein aliquots were snap frozen on dry ice, and the proteins were stored at −70° C. until use. Final protein concentrations were measured using Bio-Rad Total Protein Assay (BioRad, Hercules Calif.)

The purification of each candidate protein was confirmed by SDS-PAGE and by SDS-PAGE followed by visualization via western blot analysis. Protein samples were prepared for SDS-PAGE by dilution in 100 uL of SDS sample buffer (Tris-Cl pH6.8, SDS, glycerol, β-mercaptoethanol, Bromophenol blue), boiled for 5 minutes and spun at 17,000 G for 5 minutes. A portion of the sample was loaded on a 10% pre-cast SDS-PAGE gel (BioRad Ready Gel Tris-HCl Gel-161-1101). Electrophoresis was carried out using a BioRad Mini-Protean II system according to manufacturer's instructions. SDS gels were either stained with Coomassie Stain or transferred to nitrocellulose membrane using the same Bio-Rad Mini-Protean II wet transfer system according to manufacturer's specifications for western blot visualization. Membranes were blocked for 1 hour at room temperature using PBST (NaCl, KCl, $Na_2HPO_4$, $KH_2PO_4$, Tween 20)+5% w/v nonfat dry milk Blots were then probed with a rabbit polyclonal anti-6×HIS-HRP antibody (AbCam Ab1187, 1:5000 dilution) in PBST+5% w/v nonfat dry milk for 1 hour at room temperature, washed 4 times in PBST for 5 minutes, and followed by developing with TMB substrate (Promega TMB Stabilized Substrate for HRP, cat#W4121). Protein expression was assessed by the presence or absence of bands at the expected molecular weight for each proteins of interest. The presence of each enzyme was confirmed in this manner (FIG. 8).

Example 6

Evaluation of Native Oxaloacetate Alpha-Decarboxylase Function Via a Spectrophotometric Assay to Determine the Specific Activities of the Native Candidate Enzymes A coupled assay was developed in order to biochemically assess the oxaloacetate alpha-decarboxylase activity of the candidate enzymes. The coupled assay used exogenously-added purified E. coli YdfG protein, which converts malonate semialdehyde to 3-HP with the concomitant conversion of NADPH to $NADP^+$ (FIG. 5). As the reduced form, NADPH, has a strong absorbance peak at 340 nm and the oxidized form does not, it is possible to monitor the progress of these coupled reactions via a spectrophotometric assay. 3-HP is also detectable by standard analytical methods, for example HPLC and GS-MS.

Assays were performed as 200 microliter reactions in a 96-well plate format using a Molecular Dynamics Spectra-Max 384 microplate reader with SoftmaxPro software (Molecular Dynamics, Sunnyvale Calif.) to quantitate the rate of change in the 340 nm absorbance. All assays were conducted at 37° C., and the instrument was allowed to mix the plate for 1 second prior to each measurements. The progress of each reaction was monitored for 20 minutes during which measurements were made every 20 seconds. Reaction conditions consisted of 50 mM PIPES pH 6.8 (unless otherwise stated), 2 mM thymidine pyrophosphate, 10 mM dithiothreitol, 4 mM magnesium chloride, 1 mM NADPH (EMD Bioscience), 0.075 mg/mL purified YdfG (Molecular Throughput), and 5 mM oxaloacetate (unless otherwise stated). All chemicals were obtained from Sigma-Aldrich (St. Louis, Mo.) unless otherwise stated. Reactions were initiated with the addition of 10 microliters of concentrated purified protein to each reaction well. In addition, a negative control was performed with each experimental set to control for the rate of background NADPH oxidation. Once the reaction time course was read and the slopes of each well were calculated, the specific activities over the negative control of each candidate protein were calculated. All values reported are the average specific activities measured in triplicate. The following table shows the native specific activities of PDC and OAD determined by this method at varying oxaloacetate concentrations.

| | Specific Activities as Measured by the Spectrophotometric Assay at pH 6.8 | | | |
|---|---|---|---|---|
| [OAA] (mM) | average PDC Specific activity (units/mg) | standard deviation | Average OAD Specific activity (units/mg) | standard deviation |
| 10 | 0.0076 | 0.0024 | 0.0144 | 0.0012 |
| 5 | 0.003 | 0.0001 | 0.006 | 0.0003 |
| 2.5 m | 0.0025 | 0.0003 | 0.003 | 0.0007 |
| 1 | 0.0015 | 0.0002 | 0.0017 | 0.0009 |
| 0.5 | 0.002 | 0.0002 | 0 | 0.0004 |
| 0.1 | 0.0004 | 0.0003 | 0.0014 | 0.001 |

Activity of KGD was not measured by the spectrophotometric assay. These reactions were subjected to GC-MS analysis to confirm that 3-HP was produced, and that the candidate oxaloacetate alpha-decarboxylase enzymes were able to convert oxaloacetate to malonate semialdehyde. These results are shown in the following table. 3-HP was produced by PDC, OAD, and KGD in the presence of 5 mM oxaloacetate. These results show that these enzymes possess low levels of native oxaloacetate alpha-decarboxylase function.

| Production of 3HP from spectrophotometric assay samples | | |
|---|---|---|
| Enzyme | Beginning [OAA] | Final [3HP] (g/L) |
| Pdc (pH 6.0) | 5 mM | 0.041 +/− 0.003 |
| Oad2 (pH 6.8) | 5 mM | 0.004 +/− 0.001 |
| Kgd (pH 6.8) | 5 mM | 0.004 +/− 0.001 |

Example 7

Confirmation of Oxaloacetate Alpha-Decarboxylase Enzyme Activity—Using GC-MS—

Conformation of 3-HP production as well as assessment of the pH dependence of each candidate enzyme was performed as described above, except that coupled reactions with YdfG were evaluated for 3-HP production by GC-MS. Reaction conditions consisted of 50 mM PIPES pH 6.8, 2 mM thymidine pyrophosphate, 10 mM dithiothreitol, 4 mM magnesium chloride, 1 mM NADPH (EMD Bioscience), 0.075 mg/mL purified YdfG (Molecular Throughput), and 5 mM oxaloacetate (unless otherwise stated). All chemicals were obtained from Sigma-Aldrich unless otherwise stated. Reactions were performed at 0.6 mL volumes in triplicate and were initiated with the addition of 600 micrograms of purified protein. In addition, a negative control lacking protein was also performed with each set. Reactions were allowed to proceed at 37° C. for at least 12 hours.

The following method is used for GC-MS analysis of 3-HP. Soluble monomeric 3-HP is quantified using GC-MS after a single exaction with ethyl acetate from a reaction sample. Once the 3-HP has been extracted into the ethyl acetate, the active hydrogens on the 3-HP are replaced with trimethylsilyl groups using N,O-Bis-(Trimethylsilyl) trifluoroacetamide to make the compound volatile for GC analysis. A standard curve of known 3-HP concentrations is prepared at the beginning of the run and a known quantity of ketohexanoic acid (1 g/L) is added to both the standards and the samples to act as an internal standard for Quantitation, with tropic acid as an additional internal standard. The 3-HP content of individual samples is then assayed by examining the ratio of the ketohexanoic acid ion (m/z=247) to the 3-HP ion (219) and compared to the standard curve. 3-HP is quantified using a 3HP standard curve at the beginning of the run and the data are analyzed using HP Chemstation. The GC-MS system consists of a Hewlett Packard model 5890 GC and Hewlett Packard model 5972 MS. The column is Supelco SPB-1 (60 m×0.32 mm×0.25 µm film thickness). The capillary coating is a non-polar methylsilicone. The carrier gas is helium at a flow rate of 1 mL/min. The 3-HP as derivatized is separated from other components in the ethyl acetate extract using either of two similar temperature regimes. In a first temperature gradient regime, the column temperature starts with 40° C. for 1 minute, then is raised at a rate of 10° C./minute to 235° C., and then is raised at a rate of 50° C./minute to 300° C. In a second temperature regime, which was demonstrated to process samples more quickly, the column temperature starts with 70° C. which is held for 1 mM, followed by a ramp-up of 10° C./minute to 235° C. which is followed by a ramp-up of 50° C./minute to 300° C. FIG. 9 shows the detected amount of each candidate enzyme at pH 5.5, pH 6.0, and pH 6.8. PDC showed optimal activity at pH 5.5 while OAD and KGD showed optimal activity at pH 6.8.

Example 8

Variants with Increased Oxaloacetate Alpha-Decarboxylase Activity

Three variants derived from the oad gene were identified that had an increase in oxaloacetate alpha-decarboxylase activity when evaluated in the spectrophotometric assay. Results are provided in the following table. The variants had 1.6 fold, 2.2 fold, and 2.8 fold increases in oxaloacetate alpha-decarboxylase specific activity, respectively. The variants carried the following changes relative to the parent oad gene: N45T, R249L, D302G, V418A, and L476Q; T479N; and: R394C, D434G, and T511A, respectively, where the first amino acid is the one found in the parent sequence at the specified site, and the second amino acid is the one found at that site in the variant (using single-letter codes for the amino acid). It is known in the art that various combinations of any and all of these mutations may be used to produce enzymes with increased oxaloacetate alpha-decarboxylase activity over the parental OAD enzyme. As is also known in the art, substitutions of other amino acids at these sites could also increase oxaloacetate alpha-decarboxylase specific activity relative to that of the parental enzyme.

| Enzymes | Mutations | Average Specific Activity (units/mg) | Standard Deviation | Fold Increase |
|---|---|---|---|---|
| Native Oad | None | 0.0078 | 0.0008 | — |
| Mutant Oad 1 | N45T, R249L, D302G, V418A, and L476Q | 0.0121 | 0.0001 | 1.6 |
| Mutant Oad 2 | T479N | 0.0173 | 0.0009 | 2.2 |
| Mutant Oad 3 | R394C, D434G, and T511A | 0.0222 | 0.0012 | 2.8 |

The following are non-limiting general prophetic examples directed to practicing the present invention in other microorganism species.

General Prophetic Example 9

Improvement of 3-HP Tolerance and/or Bio-Production in *Rhodococcus erythropolis*

A series of *E. coli-Rhodococcus* shuttle vectors are available for expression in *R. erythropolis*, including, but not limited to, pRhBR17 and pDA71 (Kostichka et al., Appl. Microbiol. Biotechnol. 62:61-68 (2003)). Additionally, a series of promoters are available for heterologous gene expression in *R. erythropolis* (see for example Nakashima et al., Appl. Environ. Microbiol. 70:5557-5568 (2004), and Tao et al., Appl. Microbiol. Biotechnol. 2005, DOI 10.1007/s00253-005-0064). Targeted gene disruption of chromosomal genes in *R. erythropolis* may be created using the method described by Tao et al., supra, and Brans et al. (Appl. Environ. Microbiol. 66: 2029-2036 (2000)). These published resources are incorporated by reference for their respective indicated teachings and compositions.

The nucleic acid sequences required for providing an increase in 3-HP tolerance, as described herein, optionally with nucleic acid sequences to provide and/or improve a 3-HP biosynthesis pathway, are cloned initially in pDA71 or pRhBR71 and transformed into *E. coli*. The vectors are then transformed into *R. erythropolis* by electroporation, as described by Kostichka et al., supra. The recombinants are grown in synthetic medium containing glucose and the tolerance to and/or bio-production of 3-HP are followed using methods known in the art or described herein.

General Prophetic Example 10

Improvement of 3-HP Tolerance and/or Bio-Production in *B. licheniformis*

Most of the plasmids and shuttle vectors that replicate in *B. subtilis* are used to transform *B. licheniformis* by either protoplast transformation or electroporation. The nucleic acid sequences required for improvement of 3-HP tolerance, and/or for 3-HP biosynthesis are isolated from various sources, codon optimized as appropriate, and cloned in plasmids pBE20 or pBE60 derivatives (Nagarajan et al., Gene 114:121-126 (1992)). Methods to transform *B. licheniformis* are known in the art (for example see Fleming et al. Appl. Environ. Microbiol., 61(11):3775-3780 (1995)). These published resources are incorporated by reference for their respective indicated teachings and compositions.

The plasmids constructed for expression in *B. subtilis* are transformed into *B. licheniformis* to produce a recombinant microorganism that then demonstrates improved 3-HP tolerance, and, optionally, 3-HP bio-production.

General Prophetic Example 11

Improvement of 3-HP Tolerance and/or Bio-Production in *Paenibacillus macerans*

Plasmids are constructed as described herein for expression in *B. subtilis* and used to transform *Paenibacillus macerans* by protoplast transformation to produce a recombinant microorganism that demonstrates improved 3-HP tolerance, and, optionally, 3-HP bio-production.

General Prophetic Example 12

Expression of 3-HP Tolerance and/or Bio-Production in *Alcaligenes* (*Ralstonia*) *eutrophus* (currently referred to as *Cupriavidus necator*)

Methods for gene expression and creation of mutations in *Alcaligenes eutrophus* are known in the art (see for example Taghavi et al., Appl. Environ. Microbiol., 60(10):3585-3591 (1994)). This published resource is incorporated by reference for its indicated teachings and compositions. Any of the nucleic acid sequences identified to improve 3-HP tolerance, and/or for 3-HP biosynthesis are isolated from various sources, codon optimized as appropriate, and cloned in any of the broad host range vectors described herein, and electroporated to generate recombinant microorganisms that demonstrate improved 3-HP tolerance, and, optionally, 3-HP bio-production. The poly(hydroxybutyrate) pathway in *Alcaligenes* has been described in detail, a variety of genetic techniques to modify the *Alcaligenes* eutrophus genome is known, and those tools can be applied for engineering a 3-HP toleragenic or, optionally, a 3-HP-gena-toleragenic recombinant microorganism.

General Prophetic Example 13

Improvement of 3-HP Tolerance and/or Bio-Production in *Pseudomonas putida*

Methods for gene expression in *Pseudomonas putida* are known in the art (see for example Ben-Bassat et al., U.S. Pat. No. 6,586,229, which is incorporated herein by reference for these teachings). Any of the nucleic acid sequences identified to improve 3-HP tolerance, and/or for 3-HP biosynthesis are isolated from various sources, codon optimized as appropriate, and cloned in any of the broad host range vectors described herein, and electroporated to generate recombinant microorganisms that demonstrate improved 3-HP tolerance, and, optionally, 3-HP biosynthetic production. For example, these nucleic acid sequences are inserted into pUCP18 and this ligated DNA are electroporated into electrocompetent *Pseudomonas putida* KT2440 cells to generate recombinant *P. putida* microorganisms that exhibit increased 3-HP tolerance and optionally also comprise 3-HP biosynthesis pathways comprised at least in part of introduced nucleic acid sequences.

General Prophetic Example 14

Improvement of 3-HP Tolerance and/or Bio-Production in *Lactobacillus plantarum*

The *Lactobacillus* genus belongs to the Lactobacillales family and many plasmids and vectors used in the transformation of *Bacillus subtilis* and *Streptococcus* are used for *Lactobacillus*. Non-limiting examples of suitable vectors include pAM.beta.1 and derivatives thereof (Renault et al., Gene 183:175-182 (1996); and O'Sullivan et al., Gene 137: 227-231 (1993)); pMBB1 and pHW800, a derivative of pMBB1 (Wyckoff et al. Appl. Environ. Microbiol. 62:1481-1486 (1996)); pMG1, a conjugative plasmid (Tanimoto et al., J. Bacteriol. 184:5800-5804 (2002)); pNZ9520 (Kleerebezem et al., Appl. Environ. Microbiol. 63:4581-4584 (1997)); pAM401 (Fujimoto et al., Appl. Environ. Microbiol. 67:1262-1267 (2001)); and pAT392 (Arthur et al., Antimicrob. Agents Chemother. 38:1899-1903 (1994)). Several plasmids from *Lactobacillus plantarum* have also been reported (e.g., van Kranenburg R, Golic N, Bongers R, Leer R J, de Vos W M, Siezen R J, Kleerebezem M. Appl. Environ. Microbiol. 2005 March; 71(3): 1223-1230).

General Prophetic Example 15

Improvement of 3-HP Tolerance and/or Bio-Production in *Enterococcus faecium*, *Enterococcus gallinarium*, and *Enterococcus faecalis*

The *Enterococcus* genus belongs to the Lactobacillales family and many plasmids and vectors used in the transformation of *Lactobacillus, Bacillus subtilis*, and *Streptococcus* are used for *Enterococcus*. Non-limiting examples of suitable vectors include pAM.beta.1 and derivatives thereof (Renault et al., Gene 183:175-182 (1996); and O'Sullivan et al., Gene 137:227-231 (1993)); pMBB1 and pHW800, a derivative of pMBB1 (Wyckoff et al. Appl. Environ. Microbiol. 62:1481-1486 (1996)); pMG1, a conjugative plasmid (Tanimoto et al., J. Bacteriol. 184:5800-5804 (2002)); pNZ9520 (Kleerebezem et al., Appl. Environ. Microbiol. 63:4581-4584 (1997)); pAM401 (Fujimoto et al., Appl. Environ. Microbiol. 67:1262-1267 (2001)); and pAT392 (Arthur et al., Antimicrob. Agents Chemother. 38:1899-1903 (1994)). Expression vectors for *E. faecalis* using the nisA gene from *Lactococcus* may also be used (Eichenbaum et al., Appl. Environ. Microbiol. 64:2763-2769 (1998). Additionally, vectors for gene replacement in the *E. faecium* chromosome are used (Nallaapareddy et al., Appl. Environ. Microbiol. 72:334-345 (2006)).

For each of the General Prophetic Examples 65-71, the following 3-HP bio-production comparison may be incorporated thereto: Using analytical methods for 3-HP such as are described in Subsection III of Common Methods Section, 3-HP is obtained in a measurable quantity at the conclusion of a respective bio-production event conducted with the respective recombinant microorganism (see types of bio-production events, incorporated by reference into each respective General Prophetic Example). That measurable quantity is substantially greater than a quantity of 3-HP produced in a control bio-production event using a suitable respective control microorganism lacking the functional 3-HP pathway so provided in the respective General Prophetic Example. Tolerance improvements also may be assessed by any recognized comparative measurement technique, such as by using a MIC protocol provided in the Common Methods Section.

Common Methods Section

All methods in this Section are provided for incorporation into the Examples where so referenced.

Subsection I. Microorganism Species and Strains, Cultures, and Growth Media

Bacterial species, that may be utilized as needed, are as follows:

*Acinetobacter calcoaceticus* (DSMZ #1139) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of the resuspended *A. calcoaceticus* culture are made into BHI and are allowed to grow for aerobically for 48 hours at 37° C. at 250 rpm until saturated.

*Bacillus subtilis* is a gift from the Gill lab (University of Colorado at Boulder) and is obtained as an actively growing culture. Serial dilutions of the actively growing *B. subtilis* culture are made into Luria Broth (RPI Corp, Mt. Prospect, Ill., USA) and are allowed to grow for aerobically for 24 hours at 37° C. at 250 rpm until saturated.

*Chlorobium limicola* (DSMZ #245) is obtained from the German Collection of Microorganisms and Cell Cultures (Braunschweig, Germany) as a vacuum dried culture. Cultures are then resuspended using Pfennig's Medium I and II (#28 and 29) as described per DSMZ instructions. *C. limicola* is grown at 25° C. under constant vortexing.

*Citrobacter braakii* (DSMZ #30040) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of the resuspended *C. braakii* culture are made into BHI and are allowed to grow for aerobically for 48 hours at 30° C. at 250 rpm until saturated.

*Clostridium acetobutylicum* (DSMZ #792) is obtained from the German Collection of Microorganisms and Cell Cultures (Braunschweig, Germany) as a vacuum dried culture. Cultures are then resuspended in *Clostridium acetobutylicum* medium (#411) as described per DSMZ instructions. *C. acetobutylicum* is grown anaerobically at 37° C. at 250 rpm until saturated.

*Clostridium aminobutyricum* (DSMZ #2634) is obtained from the German Collection of Microorganisms and Cell Cultures (Braunschweig, Germany) as a vacuum dried culture. Cultures are then resuspended in *Clostridium aminobutyricum* medium (#286) as described per DSMZ instructions. *C. aminobutyricum* is grown anaerobically at 37° C. at 250 rpm until saturated.

*Clostridium kluyveri* (DSMZ #555) is obtained from the German Collection of Microorganisms and Cell Cultures (Braunschweig, Germany) as an actively growing culture. Serial dilutions of *C. kluyveri* culture are made into *Clostridium kluyveri* medium (#286) as described per DSMZ instructions. *C. kluyveri* is grown anaerobically at 37° C. at 250 rpm until saturated.

*Cupriavidus metallidurans* (DMSZ #2839) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of the resuspended *C. metallidurans* culture are made into BHI and are allowed to grow for aerobically for 48 hours at 30° C. at 250 rpm until saturated.

*Cupriavidus necator* (DSMZ #428) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of the resuspended *C. necator* culture are made into BHI and are allowed to grow for aerobically for 48 hours at 30° C. at 250 rpm until saturated. As noted elsewhere, previous names for this species are *Alcaligenes eutrophus* and *Ralstonia eutrophus*.

*Desulfovibrio fructosovorans* (DSMZ #3604) is obtained from the German Collection of Microorganisms and Cell Cultures (Braunschweig, Germany) as a vacuum dried culture. Cultures are then resuspended in *Desulfovibrio fructosovorans* medium (#63) as described per DSMZ instructions. *D. fructosovorans* is grown anaerobically at 37° C. at 250 rpm until saturated.

*Escherichia coli* Crooks (DSMZ #1576) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of the resuspended *E. coli* Crooks culture are made into BHI and are allowed to grow for aerobically for 48 hours at 37° C. at 250 rpm until saturated.

*Escherichia coli* K12 is a gift from the Gill lab (University of Colorado at Boulder) and is obtained as an actively growing culture. Serial dilutions of the actively growing *E. coli* K12 culture are made into Luria Broth (RPI Corp, Mt. Prospect, Ill., USA) and are allowed to grow for aerobically for 24 hours at 37° C. at 250 rpm until saturated.

*Halobacterium salinarum* (DSMZ #1576) is obtained from the German Collection of Microorganisms and Cell Cultures (Braunschweig, Germany) as a vacuum dried culture. Cultures are then resuspended in *Halobacterium* medium (#97) as described per DSMZ instructions. *H. salinarum* is grown aerobically at 37° C. at 250 rpm until saturated.

*Lactobacillus delbrueckii* (#4335) is obtained from WYEAST USA (Odell, Oreg., USA) as an actively growing culture. Serial dilutions of the actively growing *L. delbrueckii* culture are made into Brain Heart Infusion (BHI) broth (RPI Corp, Mt. Prospect, Ill., USA) and are allowed to grow for aerobically for 24 hours at 30° C. at 250 rpm until saturated.

*Metallosphaera sedula* (DSMZ #5348) is obtained from the German Collection of Microorganisms and Cell Cultures (Braunschweig, Germany) as an actively growing culture. Serial dilutions of *M. sedula* culture are made into *Metallosphaera* medium (#485) as described per DSMZ instructions. *M. sedula* is grown aerobically at 65° C. at 250 rpm until saturated.

*Propionibacterium freudenreichii* subsp. *shermanii* (DSMZ #4902) is obtained from the German Collection of Microorganisms and Cell Cultures (Braunschweig, Germany) as a vacuum dried culture. Cultures are then resuspended in PYG-medium (#104) as described per DSMZ instructions. *P. freudenreichii* subsp. *shermanii* is grown anaerobically at 30° C. at 250 rpm until saturated.

*Pseudomonas putida* is a gift from the Gill lab (University of Colorado at Boulder) and is obtained as an actively growing culture. Serial dilutions of the actively growing *P. putida* culture are made into Luria Broth (RPI Corp, Mt. Prospect, Ill., USA) and are allowed to grow for aerobically for 24 hours at 37° C. at 250 rpm until saturated.

*Streptococcus mutans* (DSMZ #6178) is obtained from the German Collection of Microorganisms and Cell Cultures (Braunschweig, Germany) as a vacuum dried culture. Cultures are then resuspended in Luria Broth (RPI Corp, Mt. Prospect, Ill., USA). *S. mutans* is grown aerobically at 37° C. at 250 rpm until saturated.

Subsection II: Gel Preparation, DNA Separation, Extraction, Ligation, and Transformation Methods:

Molecular biology grade agarose (RPI Corp, Mt. Prospect, Ill., USA) is added to 1×TAE to make a 1% Agarose in TAE. To obtain 50×TAE add the following to 900 ml distilled $H_2O$: 242 g Tris base (RPI Corp, Mt. Prospect, Ill., USA), 57.1 ml Glacial Acetic Acid (Sigma-Aldrich, St. Louis, Mo., USA), 18.6 g EDTA (Fisher Scientific, Pittsburgh, Pa. USA), and adjust volume to 1 L with additional distilled water. To obtain 1×TAE, add 20 mL of 50×TAE to 980 mL of distilled water. The agarose-TAE solution is then heated until boiling occurred and the agarose is fully dissolved. The solution is allowed to cool to 50° C. before 10 mg/mL ethidium bromide (Acros Organics, Morris Plains, N.J., USA) is added at a concentration of 5 ul per 100 mL of 1% agarose solution. Once the ethidium bromide is added, the solution is briefly mixed and poured into a gel casting tray with the appropriate number of combs (Idea Scientific Co., Minneapolis, Minn., USA) per sample analysis. DNA samples are then mixed accordingly with 5×TAE loading buffer. 5×TAE loading buffer consists of 5×TAE (diluted from 50×TAE as described herein), 20% glycerol (Acros Organics, Morris Plains, N.J., USA), 0.125% Bromophenol Blue (Alfa Aesar, Ward Hill, Mass., USA), and adjust volume to 50 mL with distilled water. Loaded gels are then run in gel rigs (Idea Scientific Co., Minneapolis, Minn., USA) filled with 1×TAE at a constant voltage of 125 volts for 25-30 minutes. At this point, the gels are removed from the gel boxes with voltage and visualized under a UV transilluminator (FOTODYNE Inc., Hartland, Wis., USA).

The DNA isolated through gel extraction is then extracted using the QIAquick Gel Extraction Kit following manufacturer's instructions (Qiagen (Valencia Calif. USA)). Similar methods are known to those skilled in the art.

The thus-extracted DNA then may be ligated into pSMART (Lucigen Corp, Middleton, Wis., USA), StrataClone (Stratagene, La Jolla, Calif., USA) or pCR2.1-TOPO TA (Invitrogen Corp, Carlsbad, Calif., USA) according to manufacturer's instructions. These methods are described in the next subsection of Common Methods.

Ligation Methods:

For ligations into pSMART vectors:

Gel extracted DNA is blunted using PCRTerminator (Lucigen Corp, Middleton, Wis., USA) according to manufacturer's instructions. Then 500 ng of DNA is added to 2.5 uL 4× CloneSmart vector premix, 1 ul CloneSmart DNA ligase (Lucigen Corp, Middleton, Wis., USA) and distilled water is added for a total volume of 10 ul. The reaction is then allowed to sit at room temperature for 30 minutes and then heat inactivated at 70° C. for 15 minutes and then placed on ice. *E. cloni* 10G Chemically Competent cells (Lucigen Corp, Middleton, Wis., USA) are thawed for 20 minutes on ice. 40 ul of chemically competent cells are placed into a microcentrifuge tube and 1 ul of heat inactivated CloneSmart Ligation is added to the tube. The whole reaction is stirred briefly with a pipette tip. The ligation and cells are incubated on ice for 30 minutes and then the cells are heat shocked for 45 seconds at 42° C. and then put back onto ice for 2 minutes. 960 ul of room temperature Recovery media (Lucigen Corp, Middleton, Wis., USA) and places into microcentrifuge tubes. Shake tubes at 250 rpm for 1 hour at 37° C. Plate 100 ul of transformed cells on Luria Broth plates (RPI Corp, Mt. Prospect, Ill., USA) plus appropriate antibiotics depending on the pSMART vector used. Incubate plates overnight at 37° C.

General Transformation and Related Culture Methodologies:

Chemically competent transformation protocols are carried out according to the manufacturer's instructions or according to the literature contained in *Molecular Cloning* (Sambrook and Russell, 2001). Generally, plasmid DNA or ligation products are chilled on ice for 5 to 30 min. in solution with chemically competent cells. Chemically competent cells are a widely used product in the field of biotechnology and are available from multiple vendors, such as those indicated in this Subsection. Following the chilling period cells generally are heat-shocked for 30 seconds at 42° C. without shaking, re-chilled and combined with 250 microliters of rich media, such as S.O.C. Cells are then incubated at 37° C. while shaking at 250 rpm for 1 hour. Finally, the cells are screened for successful transformations by plating on media containing the appropriate antibiotics.

Alternatively, selected cells may be transformed by electroporation methods such as are known to those skilled in the art.

The choice of an *E. coli* host strain for plasmid transformation is determined by considering factors such as plasmid stability, plasmid compatibility, plasmid screening methods and protein expression. Strain backgrounds can be changed by simply purifying plasmid DNA as described herein and transforming the plasmid into a desired or otherwise appropriate *E. coli* host strain such as determined by experimental necessities, such as any commonly used cloning strain (e.g., DH5α, Top10F', *E. cloni* 10G, etc.).

Plasmid DNA was prepared using the commercial miniprep kit from Qiagen (Valencia, Calif. USA) according to manufacturer's instructions.

Subsection IIIa. 3-HP Preparation

A 3-HP stock solution was prepared as follows. A vial of β-propriolactone (Sigma-Aldrich, St. Louis, Mo., USA) was opened under a fume hood and the entire bottle contents was transferred to a new container sequentially using a 25-mL glass pipette. The vial was rinsed with 50 mL of HPLC grade water and this rinse was poured into the new container. Two additional rinses were performed and added to the new container. Additional HPLC grade water was added to the new container to reach a ratio of 50 mL water per 5 mL propriolactone. The new container was capped tightly and allowed to remain in the fume hood at room temperature for 72 hours. After 72 hours the contents were transferred to centrifuge tubes and centrifuged for 10 minutes at 4,000 rpm. Then the solution was filtered to remove particulates and, as needed, concentrated by use of a rotary evaporator at room temperature. Assay for concentration was conducted, and dilution to make a standard concentration stock solution was made as needed.

Subsection IIIb. HPLC, GC/MS and Other Analytical Methods for 3-HP Detection (Analysis of Cultures for 3-HP Production)

For HPLC analysis of 3-HP, the Waters chromatography system (Milford, Mass.) consisted of the following: 600S Controller, 616 Pump, 717 Plus Autosampler, 486 Tunable UV Detector, and an in-line mobile phase Degasser. In addition, an Eppendorf external column heater is used and the data are collected using an SRI (Torrance, Calif.) analog-to-digital converter linked to a standard desk top computer. Data are analyzed using the SRI Peak Simple software. A Coregel 64H ion exclusion column (Transgenomic, Inc., San Jose, Calif.) is employed. The column resin is a sulfonated polystyrene divinyl benzene with a particle size of 10 μm and column dimensions are 300×7.8 mm. The mobile phase consisted of sulfuric acid (Fisher Scientific, Pittsburgh, Pa. USA) diluted with deionized (18 MΩcm) water to a concentration of 0.02 N and vacuum filtered through a 0.2 μm nylon filter. The flow rate of the mobile phase is 0.6 mL/min. The UV detector is operated at a wavelength of 210 nm and the column is heated to 60° C. The same equipment and method as described herein is used for 3-HP analyses for relevant prophetic examples.

The following method is used for GC-MS analysis of 3-HP. Soluble monomeric 3-HP is quantified using GC-MS after a single extraction of the fermentation media with ethyl acetate. Once the 3-HP has been extracted into the ethyl acetate, the active hydrogens on the 3-HP are replaced with trimethylsilyl groups using N,O-Bis-(Trimethylsilyl) trifluoroacetamide to make the compound volatile for GC analysis. A standard curve of known 3-HP concentrations is prepared at the beginning of the run and a known quantity of ketohexanoic acid (1 g/L) is added to both the standards and the samples to act as an internal standard for Quantitation, with tropic acid as an additional internal standard. The 3-HP content of individual samples is then assayed by examining the ratio of the ketohexanoic acid ion (m/z=247) to the 3-HP ion (219) and compared to the standard curve. 3-HP is quantified using a 3HP standard curve at the beginning of the run and the data are analyzed using HP Chemstation. The GC-MS system consists of a Hewlett Packard model 5890 GC and Hewlett Packard model 5972 MS. The column is Supelco SPB-1 (60 m×0.32 mm×0.25 μm film thickness). The capillary coating is a non-polar methylsilicone. The carrier gas is helium at a flow rate of 1 mL/min. The 3-HP as derivatized is separated from other components in the ethyl acetate extract using either of two similar temperature regimes. In a first temperature gradient regime, the column temperature starts with 40° C. for 1 minute, then is raised at a rate of 10° C./minute to 235° C., and then is raised at a rate of 50° C./minute to 300° C. In a second temperature regime, which was demonstrated to process samples more quickly, the column temperature starts with 70° C. which is held for 1 min, followed by a ramp-up of 10° C./minute to 235° C. which is followed by a ramp-up of 50° C./minute to 300° C.

The embodiments, variations, sequences, and figures described herein should provide an indication of the utility and versatility of the present invention. Other embodiments that do not provide all of the features and advantages set forth herein may also be utilized, without departing from the spirit and scope of the present invention. Such modifications and variations are considered to be within the scope of the invention.

TABLE 1

| Protein Function | E.C. Classification | Gene Name in E. coli | SEQ ID NO. of E. coli gene | SEQ ID NO. of Expressed Enzyme |
|---|---|---|---|---|
| Glucose transport | N/A | galP | 003 | 004 |
| Phosphoenol-pyruvate carboxykinase | 4.1.1.49 | pckA | 007 | 008 |
| Phosphoenolpy-ruvate carboxylase | 4.1.1.49 | ppc | 009 | 010 |

TABLE 2

| Protein Function | E.C. Classification | Gene Name in E. coli | SEQ ID NO. of E. coli gene | SEQ ID NO. of Expressed Enzyme |
|---|---|---|---|---|
| Pyruvate dehydrogenase E1p | 1.2.4.1 | aceE | 011 | 012 |
| lipoate acetyltransferase/ dihydrolipoamide acetyltransferase | 2.3.1.12 | aceF | 013 | 014 |
| Pyruvate dehydrogenase E3 (lipoamide dehydrogenase) | 1.8.1.4 | lpd | 015 | 016 |
| Lactate dehydrogenase | 1.1.1.28 | ldhA | 017 | 018 |
| Pyruvate formate lyase (B "inactive") | 2.3.1.- | pflB | 019 | 020 |
| Pyruvate oxidase | 1.2.2.2 | poxB | 021 | 022 |
| Phosphate acetyltransferase | 2.3.1.8 | Pta | 023 | 024 |
| Heat stable, histidyl phosphorylatable protein (of PTS) | N/A | ptsH (HPr) | 025 | 026 |
| Phosphoryl transfer protein (of PTS) | N/A | ptsI | 027 | 028 |
| Polypeptide chain (of PTS) | N/A | Crr | 029 | 030 |
| Pyruvate kinase I | 2.7.1.40 | pykA | 031 | 032 |
| Pyruvate kinase II | 2.7.1.40 | pykF | 033 | 034 |

What is claimed is:
1. A genetically modified microorganism comprising:
   i) a heterologous nucleic acid sequence encoding a 3 hydroxypropionate dehydrogenase;
   ii) a heterologous nucleic acid sequence encoding a cyanase or a carbonic anhydrase; and
   iii) a heterologous nucleic acid sequence encoding an NADPH-dependent transhydrogenase or an acetyl-CoA carboxylase.

2. The genetically modified microorganism of claim 1, wherein the 3-hydroxypropionate dehydrogenase is a native or mutated form of a mmsB protein or a native or mutated form of a ydfG protein.

3. The genetically modified microorganism of claim 1, wherein said genetically modified microorganism comprises a heterologous nucleic acid sequence encoding an NADPH-dependent transhydrogenase.

4. The genetically modified microorganism of claim 1, further comprising a modification of a gene to increase the NADPH/NADP$^+$ ratio, wherein the modification is selected from the group consisting of: increasing activity of pgi, increasing activity of pntAB, gapA:gapN substitution or replacement, and disrupting sthA.

5. The genetically modified microorganism of claim 1, wherein said genetically modified microorganism comprises a heterologous nucleic acid sequence encoding a cyanase or a carbonic anhydrase that increases intracellular bicarbonate levels.

6. The genetically modified microorganism of claim 1, wherein said genetically modified microorganism comprises a heterologous nucleic acid sequence encoding an acetyl-CoA carboxylase pathway.

7. The genetically modified microorganism of claim 1, wherein said genetically modified microorganism is selected from the group consisting of: *Escherichia coli*, *Cupriavidus necator*, *Oligotropha carboxidovorans*, and *Pseudomonas putida*.

8. The genetically modified microorganism of claim 1, wherein said genetically modified microorganism is an *Escherichia coli*.

9. The genetically modified microorganism of claim 1, wherein said genetically modified microorganism is a gram-positive bacterium.

10. The genetically modified microorganism of claim 1, wherein said genetically modified microorganism is selected from the group consisting of: *Clostridium, Rhodococcus, Bacillus, Lactobacillus, Enterococcus, Paenibacillus, Arthrobacter, Corynebacterium,* and *Brevibacterium*.

11. The genetically modified microorganism of claim 1, wherein said genetically modified microorganism is selected from the group consisting of: *Bacillus licheniformis, Paenibacillus macerans, Rhodococcus erythropolis, Lactobacillus plantarum, Enterococcus faecium, Enterococcus gallinarium, Enterococcus faecalis,* and *Bacillus subtilis*.

12. The genetically modified microorganism of claim 1, wherein said genetically modified microorganism is a fungus.

13. The genetically modified microorganism of claim 1, wherein said genetically modified microorganism is a yeast.

14. The genetically modified microorganism of claim 13, wherein said yeast is selected from the group consisting of: *Pichia, Candida, Hansenula,* and *Saccharomyces*.

15. The genetically modified microorganism of claim 1, wherein said genetically modified microorganism is selected from the group consisting of: *Zymomonas, Escherichia, Pseudomonas, Alcaligenes, Salmonella, Shigella, Burkholderia, Oligotropha,* and *Klebsiella*.

16. The genetically modified microorganism of claim 1, further comprising at least one heterologous nucleic acid sequence encoding an oxaloacetate alpha-decarboxylase.

17. The genetically modified microorganism of claim 16, additionally comprising at least one heterologous nucleic acid sequence encoding a phosphoenolpyruvate carboxykinase or a phosphoenol pyruvate carboxylase.

18. The genetically modified microorganism of claim 17, further comprising at least one genetic modification to reduce enzymatic activity of a protein selected from the group consisting of: lactate dehydrogenase, pyruvate formate lyase, phosphate acetyltransferase, heat stable, histidyl phosphorylatable protein, phosphoryl transfer protein, polypeptide chain, pyruvate kinase I, and pyruvate kinase II.

19. The genetically modified microorganism of claim 16, wherein the oxaloacetate alpha-decarboxylase is selected from the group consisting of: SEQ ID NOs: 54, 55, and 56.

20. A genetically modified microorganism comprising:
   i) a heterologous nucleic acid sequence encoding an enzyme selected from the group consisting of:
      a native or mutated form of a mmsB protein, and a native or mutated form of a ydfG protein,
   ii) a genetic modification to decrease or eliminate an enzymatic activity selected from the group consisting of: lactate dehydrogenase, phosphate acetyltransferase, and pyruvate-formate lyase;
   iii) a heterologous nucleic acid sequence encoding an acetyl-CoA carboxylase; and
   iv) a heterologous nucleic acid sequence encoding a cyanase.

21. The genetically modified microorganism of claim 20, wherein the lactate dehydrogenase is encoded by a nucleic acid sequence having at least 90% sequence identity to SEQ ID NO:19 or has an amino acid sequence having at least 90% sequence identity to SEQ ID NO: 20.

22. The genetically modified microorganism of claim 20, wherein the phosphate acetyltransferase is encoded by a nucleic acid sequence having at least 90% sequence identity to SEQ ID NOs: 25 or has an amino acid sequence having at least 90% sequence identity to SEQ ID NO: 26.

23. The genetically modified microorganism of claim 20, wherein the pyruvate-formate lyase is encoded by a nucleic acid sequence having at least 90% sequence identity to SEQ ID NOs: 21 or has an amino acid sequence having at least 90% sequence identity to SEQ ID NO: 22.

24. The genetically modified microorganism of claim 20, wherein said genetically modified microorganism comprises a heterologous nucleic acid sequence encoding an acetyl-CoA carboxylase.

25. A genetically modified microorganism comprising:
   i) a heterologous nucleic acid sequence encoding a 3-hydroxypropionate dehydrogenase; and
   ii) a heterologous nucleic acid sequence encoding a cyanase or a carbonic anhydrase.

26. The genetically modified microorganism of claim 25, further comprising:
   iii) a heterologous nucleic acid sequence encoding an acetyl-CoA carboxylase.

* * * * *

SEQUENCE LISTING

```
<160> NUMBER OF SEQ ID NOS: 68

<210> SEQ ID NO 1
<211> LENGTH: 452
<212> TYPE: PRT
<213> ORGANISM: Bacillus cereus

<400> SEQUENCE: 1

Met Met Met Met Lys Thr Lys Gln Thr Asp Glu Leu Leu Ala Lys Asp
1               5                   10                  15

Glu Gln Tyr Val Trp His Gly Met Arg Pro Phe Ser Pro Asn Ser Thr
            20                  25                  30

Met Val Gly Ala Lys Ala Glu Gly Cys Trp Val Glu Asp Ile Gln Gly
        35                  40                  45
```

-continued

Lys Arg Tyr Leu Asp Gly Met Ser Gly Leu Trp Cys Val Asn Ser Gly
 50                  55                  60

Tyr Gly Arg Lys Glu Leu Ala Glu Ala Tyr Lys Gln Leu Gln Thr
 65                  70                  75                  80

Leu Ser Tyr Phe Pro Met Ser Gln Ser His Glu Pro Ala Ile Lys Leu
                     85                  90                  95

Ala Glu Lys Leu Asn Glu Trp Leu Gly Gly Glu Tyr Val Ile Phe Phe
             100                 105                 110

Ser Asn Ser Gly Ser Glu Ala Asn Glu Thr Ala Phe Lys Ile Ala Arg
             115                 120                 125

Gln Tyr Tyr Ala Gln Lys Gly Glu Pro His Arg Tyr Lys Phe Met Ser
 130                 135                 140

Arg Tyr Arg Gly Tyr His Gly Asn Thr Met Ala Thr Met Ala Ala Thr
145                 150                 155                 160

Gly Gln Ala Gln Arg Arg Tyr Gln Tyr Glu Pro Phe Ala Ser Gly Phe
                 165                 170                 175

Leu His Val Thr Pro Pro Asp Cys Tyr Arg Met Pro Glu Ile Glu Gly
             180                 185                 190

Gln His Ile Tyr Asp Val Glu Cys Val Lys Glu Val Asp Arg Val Met
             195                 200                 205

Thr Trp Glu Leu Ser Glu Thr Ile Ala Ala Phe Ile Met Glu Pro Ile
210                 215                 220

Ile Thr Gly Gly Gly Ile Leu Met Pro Pro Gln Asp Tyr Met Lys Ala
225                 230                 235                 240

Val His Glu Met Cys Gln Lys His Gly Ala Leu Leu Ile Ser Asp Glu
                 245                 250                 255

Val Ile Cys Gly Phe Gly Arg Thr Gly Lys Ala Phe Gly Phe Met Asn
             260                 265                 270

Tyr Asp Val Lys Pro Asp Ile Ile Thr Met Ala Lys Gly Ile Thr Ser
             275                 280                 285

Ala Tyr Leu Pro Leu Ser Ala Thr Ala Val Lys Lys Glu Ile Tyr Glu
290                 295                 300

Ala Phe Lys Gly Lys Gly Glu Tyr Glu Phe Phe Arg His Ile Asn Thr
305                 310                 315                 320

Phe Gly Gly Asn Pro Ala Ala Cys Ala Leu Ala Leu Lys Asn Leu Glu
                 325                 330                 335

Ile Met Glu Asn Glu Asn Leu Ile Glu Arg Ser Ala Gln Met Gly Ser
             340                 345                 350

Leu Leu Leu Glu Gln Leu Lys Asp Glu Ile Gly Glu His Pro Leu Val
             355                 360                 365

Gly Asn Ile Arg Gly Lys Gly Leu Leu Val Gly Ile Glu Leu Val Asn
370                 375                 380

Asp Lys Glu Thr Lys Glu Pro Ile Asp Asn Asp Lys Ile Ala Ser Val
385                 390                 395                 400

Val Asn Ala Cys Lys Glu Lys Gly Leu Ile Ile Gly Arg Asn Gly Met
                 405                 410                 415

Thr Thr Ala Gly Tyr Asn Asn Val Leu Thr Leu Ala Pro Pro Leu Val
             420                 425                 430

Ile Ser Ser Glu Glu Ile Ala Phe Val Val Gly Thr Leu Lys Thr Ala
             435                 440                 445

Met Glu Arg Ile
450

<210> SEQ ID NO 2
<211> LENGTH: 1371
<212> TYPE: DNA
<213> ORGANISM: Artificial Sequence
<220> FEATURE:
<223> OTHER INFORMATION: Description of Artificial Sequence: Codon-optimized (for E. Coli) synthetic polynucleotide

<400> SEQUENCE: 2

| | | | | | |
|---|---|---|---|---|---|
| tgatgatgat | gaaaaccaag | cagacggatg | agctgctggc | gaaggacgaa | cagtatgtgt | 60 |
| ggcatggcat | gcgcccgttt | agcccgaatt | ccactatggt | tggtgcaaaa | gcagaaggtt | 120 |
| gctgggtcga | ggacattcag | ggcaagcgtt | atctggatgg | catgagcggt | ctgtggtgcg | 180 |
| tgaattcggg | ttatggccgt | aaagagttgg | cggaggcggc | gtacaagcag | ctgcaaaccc | 240 |
| tgagctattt | cccgatgtct | cagagccacg | aaccggcgat | caaactggcg | gagaaactga | 300 |
| atgaatggtt | gggtggtgaa | tatgtgatct | ttttcagcaa | ttccggtagc | gaggcaaacg | 360 |
| aaacggcctt | caagattgcg | cgccaatact | acgcgcaaaa | aggcgaaccg | catcgttaca | 420 |
| agttcatgtc | tcgttaccgc | ggctatcacg | gcaataccat | ggccaccatg | gccgccaccg | 480 |
| gtcaagcgca | acgccgttac | caatacgagc | cgtttgcttc | tggttttctg | catgttacgc | 540 |
| ctccggattg | ttaccgcatg | ccggaaatcg | aaggccagca | catctatgac | gtcgaatgcg | 600 |
| tgaaagaagt | ggatcgtgtg | atgacctggg | aactgtccga | aaccatcgca | gccttcatca | 660 |
| tggagccgat | tatcacgggc | ggtggtattc | tgatgccacc | gcaggactac | atgaaggcag | 720 |
| ttcacgagat | gtgccagaag | cacggcgctc | tgctgattag | cgacgaagtc | atctgcggtt | 780 |
| tcggccgtac | gggtaaggcg | tttggttttca | tgaactacga | tgttaaaccg | gacatcatta | 840 |
| cgatggcgaa | aggtattacg | agcgcatatc | tgcctctgag | cgcgactgcg | gttaagaaag | 900 |
| agatctacga | agccttcaag | ggtaagggtg | agtatgaatt | ctttcgtcac | atcaataccct | 960 |
| ttggtggtaa | tccagccgcg | tgtgcattgg | cactgaaaaa | cttggagatt | atggagaatg | 1020 |
| aaaacctgat | tgaacgcagc | gcccaaatgg | gtagcctgct | gctggagcag | ctgaaggatg | 1080 |
| agatcggcga | gcacccgctg | gttggtaaca | tccgcggcaa | gggcctgctg | gtcggcatcg | 1140 |
| agctggtcaa | cgacaaagaa | accaaagaac | cgatcgataa | tgacaagatt | gctagcgtcg | 1200 |
| tgaatgcttg | taaagagaag | ggtctgatta | tcggtcgtaa | cggcatgacc | accgcgggtt | 1260 |
| acaacaacgt | tctgaccttg | gcaccgccgc | tggtgatcag | ctccgaagag | attgcgtttg | 1320 |
| tggttggtac | gctgaaaacc | gcaatggagc | gtattcacca | tcatcatcac | t | 1371 |

<210> SEQ ID NO 3
<211> LENGTH: 298
<212> TYPE: PRT
<213> ORGANISM: Pseudomonas aeruginosa

<400> SEQUENCE: 3

Met Thr Asp Ile Ala Phe Leu Gly Leu Gly Asn Met Gly Gly Pro Met
1               5                   10                  15

Ala Ala Asn Leu Leu Lys Ala Gly His Arg Val Asn Val Phe Asp Leu
            20                  25                  30

Gln Pro Lys Ala Val Leu Gly Leu Val Glu Gln Gly Ala Gln Gly Ala
        35                  40                  45

Asp Ser Ala Leu Gln Cys Cys Glu Gly Ala Glu Val Val Ile Ser Met
    50                  55                  60

Leu Pro Ala Gly Gln His Val Glu Ser Leu Tyr Leu Gly Asp Asp Gly
65                  70                  75                  80

```
Leu Leu Ala Arg Val Ala Gly Lys Pro Leu Ile Asp Cys Ser Thr
             85                  90                  95

Ile Ala Pro Glu Thr Ala Arg Lys Val Ala Glu Ala Ala Ala Lys
        100                 105                 110

Gly Leu Thr Leu Leu Asp Ala Pro Val Ser Gly Gly Val Gly Gly Ala
        115                 120                 125

Arg Ala Gly Thr Leu Ser Phe Ile Val Gly Gly Pro Ala Glu Gly Phe
        130                 135                 140

Ala Arg Ala Arg Pro Val Leu Glu Asn Met Gly Arg Asn Ile Phe His
145                 150                 155                 160

Ala Gly Asp His Gly Ala Gly Gln Val Ala Lys Ile Cys Asn Asn Met
                165                 170                 175

Leu Leu Gly Ile Leu Met Ala Gly Thr Ala Glu Ala Leu Ala Leu Gly
                180                 185                 190

Val Lys Asn Gly Leu Asp Pro Ala Val Leu Ser Glu Val Met Lys Gln
            195                 200                 205

Ser Ser Gly Gly Asn Trp Ala Leu Asn Leu Tyr Asn Pro Trp Pro Gly
    210                 215                 220

Val Met Pro Gln Ala Pro Ala Ser Asn Gly Tyr Ala Gly Gly Phe Gln
225                 230                 235                 240

Val Arg Leu Met Asn Lys Asp Leu Gly Leu Ala Leu Ala Asn Ala Gln
                245                 250                 255

Ala Val Gln Ala Ser Thr Pro Leu Gly Ala Leu Ala Arg Asn Leu Phe
                260                 265                 270

Ser Leu His Ala Gln Ala Asp Ala Glu His Glu Gly Leu Asp Phe Ser
            275                 280                 285

Ser Ile Gln Lys Leu Tyr Arg Gly Lys Asp
    290                 295

<210> SEQ ID NO 4
<211> LENGTH: 895
<212> TYPE: DNA
<213> ORGANISM: Pseudomonas aeruginosa

<400> SEQUENCE: 4
atgaccgaca ttgcgtttct gggtctgggc aatatgggcg gtccgatggc cgcgaacctg      60
ctgaaagccg ccaccgtgt gaatgtgttc gacctgcaac aaaaagcggt cctgggcttg     120
gttgagcaag gcgcgcaggg cgcagactct gctctgcaat gttgtgaggg tgcggaggtc     180
gtgatttcta tgctgccagc aggccagcat gtggaaagcc tgtacctggg cgatgatggt     240
ctgctggcac gcgtggcggg caagcctttg ctgattgact gtagcaccat cgcaccggaa     300
acggcgcgta aggtggcgga ggcagccgca gcaaagggcc tgacgctgct ggatgccccg     360
gtttcgggcg gtgtcggtgg tgcccgtgca ggtacgctgt cgtttatcgt gggtggtccg     420
gcggagggtt ttgcgcgtgc gcgtccggtt ctggagaata tgggtcgcaa cattttccac     480
gcgggtgatc acggcgctgg tcaggtggcg aaaatctgta acaacatgct gctgggtatc     540
ttgatggcgg gcaccgccga agccttggcg ctgggcgtca aaaacggtct ggacccggca     600
gtgctgtccg aagtgatgaa acagagcagc ggtggtaact gggcgctgaa tctgtacaat     660
ccgtggccgg gtgtgatgcc gcaggcccca gcctctaatg gctacgcagg cggcttccaa     720
gtgcgcctga tgaacaaaga cctgggcctg gcgctggcga atgcgcaagc ggtccaagcg     780
agcaccccgc tgggcgcact ggcccgtaac ctgtttagcc tgcacgctca gccgacgcc     840
gagcacgaag gtctggactt cagctctatt caaaaactgt atcgcggtaa ggatt         895
```

<210> SEQ ID NO 5
<211> LENGTH: 1392
<212> TYPE: DNA
<213> ORGANISM: Escherichia coli

<400> SEQUENCE: 5

| | |
|---|---:|
| cctgacgcta aaaacaggg gcggtcaaac aaggcaatga cgttttcgt ctgcttcctt | 60 |
| gccgctctgg cgggattact ctttggcctg gatatcggtg taattgctgg cgcactgccg | 120 |
| tttattgcag atgaattcca gattacttcg cacacgcaag aatgggtcgt aagctccatg | 180 |
| atgttcggtg cggcagtcgg tgcggtgggc agcggctggc tctcctttaa actcgggcgc | 240 |
| aaaaagagcc tgatgatcgg cgcaattttg tttgttgccg gttcgctgtt ctctgcggct | 300 |
| gcgccaaacg ttgaagtact gattctttcc cgcgttctac tggggctggc ggtgggtgtg | 360 |
| gcctcttata ccgcaccgct gtacctctct gaaattgcgc cggaaaaaat tcgtggcagt | 420 |
| atgatctcga tgtatcagtt gatgatcact atcgggatcc tcggtgctta tctttctgat | 480 |
| accgccttca gctacaccgg tgcatggcgc tggatgctgg gtgtgattat catcccggca | 540 |
| attttgctgc tgattggtgt cttcttcctg ccagacagcc cacgttggtt tgccgccaaa | 600 |
| cgccgttttg ttgatgccga acgcgtgctg ctacgcctgc gtgacaccag cgcggaagcg | 660 |
| aaacgcgaac tggatgaaat ccgtgaaagt ttgcaggtta acagagtgg ctgggcgctg | 720 |
| tttaaagaga cagcaactt ccgccgcgcg tgttccttg gcgtactgtt gcaggtaatg | 780 |
| cagcaattca ccgggatgaa cgtcatcatg tattacgcgc cgaaaatctt cgaactggcg | 840 |
| ggttatacca acactaccga gcaaatgtgg gggaccgtga ttgtcggcct gaccaacgta | 900 |
| cttgccacct ttatcgcaat cggccttgtt gaccgctggg gacgtaaacc aacgctaacg | 960 |
| ctgggcttcc tggtgatggc tgctggcatg ggcgtactcg gtacaatgat gcatatcggt | 1020 |
| attcactctc cgtcggcgca gtatttcgcc atcgccatgc tgctgatgtt tattgtcggt | 1080 |
| tttgccatga gtgccggtcc gctgatttgg gtactgtgct ccgaaattca gccgctgaaa | 1140 |
| ggccgcgatt ttggcatcac ctgctccact gccaccaact ggattgccaa catgatcgtt | 1200 |
| ggcgcaacgt tcctgaccat gctcaacacg ctgggtaacg ccaacacctt ctgggtgtat | 1260 |
| gcggctctga acgtactgtt tatcctgctg acattgtggc tggtaccgga accaaacac | 1320 |
| gtttcgctgg aacatattga acgtaatctg atgaaaggtc gtaaactgcg cgaaataggc | 1380 |
| gctcacgatt aa | 1392 |

<210> SEQ ID NO 6
<211> LENGTH: 464
<212> TYPE: PRT
<213> ORGANISM: Escherichia coli

<400> SEQUENCE: 6

Met Pro Asp Ala Lys Lys Gln Gly Arg Ser Asn Lys Ala Met Thr Phe
1               5                   10                  15

Phe Val Cys Phe Leu Ala Ala Leu Ala Gly Leu Leu Phe Gly Leu Asp
            20                  25                  30

Ile Gly Val Ile Ala Gly Ala Leu Pro Phe Ile Ala Asp Glu Phe Gln
        35                  40                  45

Ile Thr Ser His Thr Gln Glu Trp Val Val Ser Met Met Phe Gly
    50                  55                  60

Ala Ala Val Gly Ala Val Gly Ser Gly Trp Leu Ser Phe Lys Leu Gly
65                  70                  75                  80

Arg Lys Lys Ser Leu Met Ile Gly Ala Ile Leu Phe Val Ala Gly Ser
                85                  90                  95

Leu Phe Ser Ala Ala Pro Asn Val Glu Val Leu Ile Leu Ser Arg
            100                 105                 110

Val Leu Leu Gly Leu Ala Val Gly Val Ala Ser Tyr Thr Ala Pro Leu
        115                 120                 125

Tyr Leu Ser Glu Ile Ala Pro Glu Lys Ile Arg Gly Ser Met Ile Ser
130                 135                 140

Met Tyr Gln Leu Met Ile Thr Ile Gly Ile Leu Gly Ala Tyr Leu Ser
145                 150                 155                 160

Asp Thr Ala Phe Ser Tyr Thr Gly Ala Trp Arg Trp Met Leu Gly Val
                165                 170                 175

Ile Ile Ile Pro Ala Ile Leu Leu Ile Gly Val Phe Phe Leu Pro
            180                 185                 190

Asp Ser Pro Arg Trp Phe Ala Ala Lys Arg Arg Phe Val Asp Ala Glu
        195                 200                 205

Arg Val Leu Leu Arg Leu Arg Asp Thr Ser Ala Glu Ala Lys Arg Glu
210                 215                 220

Leu Asp Glu Ile Arg Glu Ser Leu Gln Val Lys Gln Ser Gly Trp Ala
225                 230                 235                 240

Leu Phe Lys Glu Asn Ser Asn Phe Arg Arg Ala Val Phe Leu Gly Val
                245                 250                 255

Leu Leu Gln Val Met Gln Gln Phe Thr Gly Met Asn Val Ile Met Tyr
            260                 265                 270

Tyr Ala Pro Lys Ile Phe Glu Leu Ala Gly Tyr Thr Asn Thr Thr Glu
        275                 280                 285

Gln Met Trp Gly Thr Val Ile Val Gly Leu Thr Asn Val Leu Ala Thr
290                 295                 300

Phe Ile Ala Ile Gly Leu Val Asp Arg Trp Gly Arg Lys Pro Thr Leu
305                 310                 315                 320

Thr Leu Gly Phe Leu Val Met Ala Ala Gly Met Gly Val Leu Gly Thr
                325                 330                 335

Met Met His Ile Gly Ile His Ser Pro Ser Ala Gln Tyr Phe Ala Ile
            340                 345                 350

Ala Met Leu Leu Met Phe Ile Val Gly Phe Ala Met Ser Ala Gly Pro
        355                 360                 365

Leu Ile Trp Val Leu Cys Ser Glu Ile Gln Pro Leu Lys Gly Arg Asp
370                 375                 380

Phe Gly Ile Thr Cys Ser Thr Ala Thr Asn Trp Ile Ala Asn Met Ile
385                 390                 395                 400

Val Gly Ala Thr Phe Leu Thr Met Leu Asn Thr Leu Gly Asn Ala Asn
                405                 410                 415

Thr Phe Trp Val Tyr Ala Ala Leu Asn Val Leu Phe Ile Leu Leu Thr
            420                 425                 430

Leu Trp Leu Val Pro Glu Thr Lys His Val Ser Leu Glu His Ile Glu
        435                 440                 445

Arg Asn Leu Met Lys Gly Arg Lys Leu Arg Glu Ile Gly Ala His Asp
450                 455                 460

<210> SEQ ID NO 7
<211> LENGTH: 1620
<212> TYPE: DNA
<213> ORGANISM: Escherichia coli

<400> SEQUENCE: 7

```
cgcgttaaca atggtttgac cccgcaagaa ctcgaggctt atggtatcag tgacgtacat    60
gatatcgttt acaacccaag ctacgacctg ctgtatcagg aagagctcga tccgagcctg   120
acaggttatg agcgcgggt gttaactaat ctgggtgccg ttgccgtcga taccgggatc   180
ttcaccggtc gttcaccaaa agataagtat atcgtccgtg acgataccac tcgcgatact   240
ttctggtggg cagacaaagg caaggtaag aacgacaaca aacctctctc tccgaaacc    300
tggcagcatc tgaaaggcct ggtgaccagg cagctttccg gcaaacgtct gttcgttgtc   360
gacgctttct gtggtgcgaa cccggatact cgtctttccg tccgtttcat caccgaagtg   420
gcctggcagg cgcattttgt caaaaacatg tttattcgcc cgagcgatga agaactggca   480
ggtttcaaac cagactttat cgttatgaac ggcgcgaagt gcactaaccc gcagtggaaa   540
gaacagggtc tcaactccga aaacttcgtg gcgtttaacc tgaccgagcg catgcagctg   600
attggcggca cctggtacgg cggcgaaatg aagaaaggga tgttctcgat gatgaactac   660
ctgctgccgc tgaaaggtat cgcttctatg cactgctccg ccaacgttgg tgagaaaggc   720
gatgttgcgg tgttcttcgg cctttccggc accggtaaaa ccacccttc caccgacccg   780
aaacgtcgcc tgattggcga tgacgaacac ggctgggacg atgacggcgt gtttaacttc   840
gaaggcggct gctacgcaaa aactatcaag ctgtcgaaag aagcggaacc tgaaatctac   900
aacgctatcc gtcgtgatgc gttgctggaa acgtcaccg tgcgtgaaga tggcactatc   960
gactttgatg atggttcaaa aaccgagaac acccgcgttt cttatccgat ctatcacatc  1020
gataacattg ttaagccggt ttccaaagcg gccacgcga ctaaggttat cttcctgact  1080
gctgatgctt tcggcgtgtt gccgccggtt tctcgcctga ctgccgatca aacccagtat  1140
cacttcctct ctggcttcac cgccaaactg gccggtactg agcgtggcat caccgaaccg  1200
acgccaacct tctccgcttg cttcggcgcg gcattcctgt cgctgcaccc gactcagtac  1260
gcagaagtgc tggtgaaacg tatgcaggcg gcgggcgcgc aggcttatct ggttaacact  1320
ggctggaacg gcactggcaa acgtatctcg attaaagata cccgcgccat tatcgacgcc  1380
atcctcaacg gttcgctgga taatgcagaa accttcactc tgccgatgtt taacctggcg  1440
atcccaaccg aactgccggg cgtagacacg aagattctcg atccgcgtaa cacctacgct  1500
tctccggaac agtggcagga aaaagccgaa accctggcga aactgtttat cgacaacttc  1560
gataaataca ccgacacccc tgcgggtgcc gcgctggtag cggctggtcc gaaactgtaa  1620
```

<210> SEQ ID NO 8
<211> LENGTH: 540
<212> TYPE: PRT
<213> ORGANISM: Escherichia coli

<400> SEQUENCE: 8

```
Met Arg Val Asn Asn Gly Leu Thr Pro Gln Glu Leu Glu Ala Tyr Gly
1               5                   10                  15

Ile Ser Asp Val His Asp Ile Val Tyr Asn Pro Ser Tyr Asp Leu Leu
                20                  25                  30

Tyr Gln Glu Glu Leu Asp Pro Ser Leu Thr Gly Tyr Glu Arg Gly Val
            35                  40                  45

Leu Thr Asn Leu Gly Ala Val Ala Val Asp Thr Gly Ile Phe Thr Gly
        50                  55                  60

Arg Ser Pro Lys Asp Lys Tyr Ile Val Arg Asp Asp Thr Thr Arg Asp
65                  70                  75                  80
```

-continued

Thr Phe Trp Trp Ala Asp Lys Gly Lys Gly Lys Asn Asp Asn Lys Pro
                    85                  90                  95

Leu Ser Pro Glu Thr Trp Gln His Leu Lys Gly Leu Val Thr Arg Gln
            100                 105                 110

Leu Ser Gly Lys Arg Leu Phe Val Val Asp Ala Phe Cys Gly Ala Asn
        115                 120                 125

Pro Asp Thr Arg Leu Ser Val Arg Phe Ile Thr Glu Val Ala Trp Gln
    130                 135                 140

Ala His Phe Val Lys Asn Met Phe Ile Arg Pro Ser Asp Glu Glu Leu
145                 150                 155                 160

Ala Gly Phe Lys Pro Asp Phe Ile Val Met Asn Gly Ala Lys Cys Thr
                165                 170                 175

Asn Pro Gln Trp Lys Glu Gln Gly Leu Asn Ser Glu Asn Phe Val Ala
            180                 185                 190

Phe Asn Leu Thr Glu Arg Met Gln Leu Ile Gly Gly Thr Trp Tyr Gly
        195                 200                 205

Gly Glu Met Lys Lys Gly Met Phe Ser Met Met Asn Tyr Leu Leu Pro
    210                 215                 220

Leu Lys Gly Ile Ala Ser Met His Cys Ser Ala Asn Val Gly Glu Lys
225                 230                 235                 240

Gly Asp Val Ala Val Phe Phe Gly Leu Ser Gly Thr Gly Lys Thr Thr
                245                 250                 255

Leu Ser Thr Asp Pro Lys Arg Arg Leu Ile Gly Asp Asp Glu His Gly
            260                 265                 270

Trp Asp Asp Asp Gly Val Phe Asn Phe Glu Gly Gly Cys Tyr Ala Lys
        275                 280                 285

Thr Ile Lys Leu Ser Lys Glu Ala Glu Pro Glu Ile Tyr Asn Ala Ile
    290                 295                 300

Arg Arg Asp Ala Leu Leu Glu Asn Val Thr Val Arg Glu Asp Gly Thr
305                 310                 315                 320

Ile Asp Phe Asp Asp Gly Ser Lys Thr Glu Asn Thr Arg Val Ser Tyr
                325                 330                 335

Pro Ile Tyr His Ile Asp Asn Ile Val Lys Pro Val Ser Lys Ala Gly
            340                 345                 350

His Ala Thr Lys Val Ile Phe Leu Thr Ala Asp Ala Phe Gly Val Leu
        355                 360                 365

Pro Pro Val Ser Arg Leu Thr Ala Asp Gln Thr Gln Tyr His Phe Leu
    370                 375                 380

Ser Gly Phe Thr Ala Lys Leu Ala Gly Thr Glu Arg Gly Ile Thr Glu
385                 390                 395                 400

Pro Thr Pro Thr Phe Ser Ala Cys Phe Gly Ala Ala Phe Leu Ser Leu
                405                 410                 415

His Pro Thr Gln Tyr Ala Glu Val Leu Val Lys Arg Met Gln Ala Ala
            420                 425                 430

Gly Ala Gln Ala Tyr Leu Val Asn Thr Gly Trp Asn Gly Thr Gly Lys
        435                 440                 445

Arg Ile Ser Ile Lys Asp Thr Arg Ala Ile Asp Ala Ile Leu Asn
    450                 455                 460

Gly Ser Leu Asp Asn Ala Glu Thr Phe Thr Leu Pro Met Phe Asn Leu
465                 470                 475                 480

Ala Ile Pro Thr Glu Leu Pro Gly Val Asp Thr Lys Ile Leu Asp Pro
                485                 490                 495

Arg Asn Thr Tyr Ala Ser Pro Glu Gln Trp Gln Glu Lys Ala Glu Thr

```
                500            505             510
        Leu Ala Lys Leu Phe Ile Asp Asn Phe Asp Lys Tyr Thr Asp Thr Pro
                515             520             525

Ala Gly Ala Ala Leu Val Ala Ala Gly Pro Lys Leu
                530             535             540

<210> SEQ ID NO 9
<211> LENGTH: 2647
<212> TYPE: DNA
<213> ORGANISM: Escherichia coli

<400> SEQUENCE: 9
aacgaacaat attccgcatt gcgtagtaat gtcagtatgc tcggcaaagt gctgggagaa      60
accatcaagg atgcgttggg agaacacatt cttgaacgcg tagaaactat ccgtaagttg     120
tcgaaatctt cacgcgctgg caatgatgct aaccgccagg agttgctcac caccttacaa     180
aatttgtcga acgacgagct gctgcccgtt gcgcgtgcgt ttagtcagtt cctgaacctg     240
gccaacaccg ccgagcaata ccacagcatt tcgccgaaag gcgaagctgc cagcaacccg     300
gaagtgatcg cccgcaccct gcgtaaactg aaaaaccagc cggaactgag cgaagacacc     360
atcaaaaaag cagtggaatc gctgtcgctg gaactggtcc tcacggctca cccaaccgaa     420
attacccgtc gtacactgat ccacaaaatg gtggaagtga acgcctgttt aaaacagctc     480
gataacaaag atatcgctga ctacgaacac aaccagctga tgcgtcgcct cgccagttg      540 atcgcccagt catggcatac cgatgaaatc cgtaagctgc gtccaagccc ggtagatgaa     600
gccaaatggg gctttgccgt agtggaaaac agcctgtggc aaggcgtacc aaattacctg     660
cgcgaactga cgaacaact ggaagagaac ctcggctaca aactgcccgt cgaatttgtt      720
ccggtccgtt ttacttcgtg gatgggcggc gaccgcgacg gcaacccgaa cgtcactgcc     780
gatatcaccc gccacgtcct gctactcagc cgctggaaag ccaccgattt gttcctgaaa     840
gatattcagg tgctggtttc tgaactgtcg atggttgaag cgacccctga actgctggcg     900
ctggttggcg aagaaggtgc cgcagaaccg tatcgctatc tgatgaaaaa cctgcgttct     960
cgcctgatgg cgacacaggc atggctggaa gcgcgcctga aggcgaaga actgccaaaa    1020 ccagaaggcc tgctgacaca aaacgaagaa ctgtgggaac cgctctacgc ttgctaccag    1080
tcacttcagg cgtgtggcat gggtattatc gccaacggcg atctgctcga caccctgcgc    1140
cgcgtgaaat gtttcggcgt accgctggtc cgtattgata tccgtcagga gagcacgcgt    1200
cataccgaag cgctgggcga gctgacccgc tacctcggta tcggcgacta cgaaagctgg    1260
tcagaggccg acaaacaggc gttcctgatc gcgaactga actccaaacg tccgcttctg     1320
ccgcgcaact ggcaaccaag cgccgaaacg cgcgaagtgc tcgatacctg ccaggtgatt    1380
gccgaagcac gcaaggctc cattgccgcc tacgtgatct cgatggcgaa aacgccgtcc    1440
gacgtactgg ctgtccacct gctgctgaaa gaagcgggta tcgggtttgc gatgccggtt    1500
gctccgctgt ttgaaaccct cgatgatctg aacaacgcca acgatgtcat gacccagctg    1560
ctcaatattg actggtatcg tggcctgatt cagggcaaac agatggtgat gattggctat    1620
tccgactcag caaagatgc gggagtgatg gcagcttcct gggcgcaata tcaggcacag    1680
gatgcattaa tcaaaacctg cgaaaaagcg ggtattgagc tgacgttgtt ccacggtcgc    1740
ggcggttcca ttggtcgcgg cggcgcacct gctcatgcgg cgctgctgtc acaaccgcca    1800
ggaagcctga aggcggcct gcgcgtaacc gaacagggcg agatgatccg ctttaaatat    1860
ggtctgccag aaatcaccgt cagcagcctg tcgctttata ccggggcgat tctggaagcc    1920
```

-continued

```
aacctgctgc caccgccgga gccgaaagag agctggcgtc gcattatgga tgaactgtca   1980
gtcatctcct gcgatgtcta ccgcggctac gtacgtgaaa acaaagattt tgtgccttac   2040
ttccgctccg ctacgccgga caagaactg gcaaactgc cgttgggttc acgtccggcg    2100
aaacgtcgcc caaccggcgg cgtcgagtca ctacgcgcca ttccgtggat cttcgcctgg   2160
acgcaaaacc gtctgatgct ccccgcctgg ctgggtgcag gtacggcgct gcaaaaagtg   2220
gtcgaagacg gcaaacagag cgagctggag gctatgtgcc gcgattggcc attcttctcg   2280
acgcgtctcg gcatgctgga tggtcttc gccaaagcag acctgtggct ggcggaatac    2340
tatgaccaac gcctggtaga caaagcactg tggccgttag gtaaagagtt acgcaacctg   2400
caagaagaag acatcaaagt ggtgctggcg attgccaacg attcccatct gatggccgat   2460
ctgccgtgga ttgcagagtc tattcagcta cggaatattt acaccgaccc gctgaacgta   2520
ttgcaggccg agttgctgca ccgctcccgc caggcagaaa agaaggcca ggaaccggat    2580 cctcgcgtcg aacaagcgtt aatggtcact attgccggga ttgcggcagg tatgcgtaat   2640
accggct                                                              2647
```

<210> SEQ ID NO 10
<211> LENGTH: 883
<212> TYPE: PRT
<213> ORGANISM: Escherichia coli

<400> SEQUENCE: 10

```
Met Asn Glu Gln Tyr Ser Ala Leu Arg Ser Asn Val Ser Met Leu Gly
1               5                  10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240
```

```
Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
                260                 265                 270

Trp Lys Ala Thr Asp Leu Phe Leu Lys Asp Ile Gln Val Leu Val Ser
                275                 280                 285

Glu Leu Ser Met Val Glu Ala Thr Pro Glu Leu Leu Ala Leu Val Gly
                290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
                340                 345                 350

Trp Glu Pro Leu Tyr Ala Cys Tyr Gln Ser Leu Gln Ala Cys Gly Met
                355                 360                 365

Gly Ile Ile Ala Asn Gly Asp Leu Leu Asp Thr Leu Arg Arg Val Lys
370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
                420                 425                 430

Glu Leu Asn Ser Lys Arg Pro Leu Pro Arg Asn Trp Gln Pro Ser
                435                 440                 445

Ala Glu Thr Arg Glu Val Leu Asp Thr Cys Gln Val Ile Ala Glu Ala
450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
                500                 505                 510

Asn Ala Asn Asp Val Met Thr Gln Leu Leu Asn Ile Asp Trp Tyr Arg
                515                 520                 525

Gly Leu Ile Gln Gly Lys Gln Met Val Met Ile Gly Tyr Ser Asp Ser
530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575

Leu Phe His Gly Arg Gly Gly Ser Ile Gly Arg Gly Gly Ala Pro Ala
                580                 585                 590

His Ala Ala Leu Leu Ser Gln Pro Pro Gly Ser Leu Lys Gly Gly Leu
                595                 600                 605

Arg Val Thr Glu Gln Gly Glu Met Ile Arg Phe Lys Tyr Gly Leu Pro
                610                 615                 620

Glu Ile Thr Val Ser Ser Leu Ser Leu Tyr Thr Gly Ala Ile Leu Glu
625                 630                 635                 640

Ala Asn Leu Leu Pro Pro Glu Pro Lys Glu Ser Trp Arg Arg Ile
                645                 650                 655
```

```
Met Asp Glu Leu Ser Val Ile Ser Cys Asp Val Tyr Arg Gly Tyr Val
            660                 665                 670

Arg Glu Asn Lys Asp Phe Val Pro Tyr Phe Arg Ser Ala Thr Pro Glu
        675                 680                 685

Gln Glu Leu Gly Lys Leu Pro Leu Gly Ser Arg Pro Ala Lys Arg Arg
    690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
                725                 730                 735

Ala Leu Gln Lys Val Val Glu Asp Gly Lys Gln Ser Glu Leu Glu Ala
            740                 745                 750

Met Cys Arg Asp Trp Pro Phe Phe Ser Thr Arg Leu Gly Met Leu Glu
        755                 760                 765

Met Val Phe Ala Lys Ala Asp Leu Trp Leu Ala Glu Tyr Tyr Asp Gln
    770                 775                 780

Arg Leu Val Asp Lys Ala Leu Trp Pro Leu Gly Lys Glu Leu Arg Asn
785                 790                 795                 800

Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
        835                 840                 845

Arg Ser Arg Gln Ala Lys Glu Gly Gln Pro Asp Pro Arg Val
    850                 855                 860

Glu Gln Ala Leu Met Val Thr Ile Ala Gly Ile Ala Ala Gly Met Arg
865                 870                 875                 880

Asn Thr Gly

<210> SEQ ID NO 11
<211> LENGTH: 2661
<212> TYPE: DNA
<213> ORGANISM: Escherichia coli

<400> SEQUENCE: 11
tcagaacgtt tcccaaatga cgtggatccg atcgaaactc gcgactggct ccaggcgatc      60
gaatcggtca tccgtgaaga aggtgttgag cgtgctcagt atctgatcga ccaactgctt     120
gctgaagccc gcaaaggcgg tgtaaacgta gccgcaggca aggtatcag caactacatc      180 aacaccatcc ccgttgaaga caaccggag tatccgggta atctggaact ggaacgccgt      240
attcgttcag ctatccgctg gaacgccatc atgacggtgc tgcgtgcgtc gaaaaaagac      300
ctcgaactgg gcggccatat ggcgtccttc cagtcttccg caaccattta tgatgtgtgc      360
tttaaccact tcttccgtgc acgcaacgag caggatggcg cgacctggt ttacttccag       420 ggccacatct ccccgggcgt gtacgctcgt gctttcctgg aaggtcgtct gactcaggag      480
cagctggata acttccgtca ggaagttcac ggcaatggcc tctcttccta ccgcacccg       540 aaactgatgc cggaattctg gcagttcccg accgtatcta tgggtctggg tccgattggt      600
gctatttacc aggctaaatt cctgaaatat ctggaacacc gtggcctgaa agatacctct      660
aaacaaaccg tttacgcgtt cctcggtgac ggtgaaatgg acgaaccgga atccaaaggt      720
gcgatcacca tcgctacccg tgaaaaactg gataacctgg tcttcgttat caactgtaac      780
ctgcagcgtc ttgacggccc ggtcaccggt aacggcaaga tcatcaacga actggaaggc      840
```

```
atcttcgaag gtgctggctg gaacgtgatc aaagtgatgt ggggtagccg ttgggatgaa      900
ctgctgcgta aggataccag cggtaaactg atccagctga tgaacgaaac cgttgacggc      960
gactaccaga ccttcaaatc gaaagatggt gcgtacgttc gtgaacactt cttcggtaaa     1020
tatcctgaaa ccgcagcact ggttgcagac tggactgacg agcagatctg ggcactgaac     1080
cgtggtggtc acgatccgaa gaaaatctac gctgcattca agaaagcgca ggaaaccaaa     1140
ggcaaagcga cagtaatcct tgctcatacc attaaaggtt acggcatggg cgacgcggct     1200
gaaggtaaaa acatcgcgca ccaggttaag aaaatgaaca tggacggtgt gcgtcatatc     1260
cgcgaccgtt tcaatgtgcc ggtgtctgat gcagatatcg aaaaactgcc gtacatcacc     1320
ttcccggaag gttctgaaga gcatacctat ctgcacgctc agcgtcagaa actgcacggt     1380
tatctgccaa gccgtcagcc gaacttcacc gagaagcttg agctgccgag cctgcaagac     1440
ttcggcgcgc tgttggaaga gcagagcaaa gagatctcta ccactatcgc tttcgttcgt     1500
gctctgaacg tgatgctgaa gaacaagtcg atcaaagatc gtctggtacc gatcatcgcc     1560
gacgaagcgc gtacttcgg tatggaaggt ctgttccgtc agattggtat ttacagcccg     1620
aacggtcagc agtacacccc gcaggaccgc gagcaggttg cttactataa agaagacgag     1680
aaaggtcaga ttctgcagga agggatcaac gagctgggcg caggttgttc ctggctggca     1740
gcggcgacct cttacagcac caacaatctg ccgatgatcc cgttctacat ctattactcg     1800
atgttcggct tccagcgtat tggcgatctg tgctgggcgg ctggcgacca gcaagcgcgt     1860
ggcttcctga tcggcggtac ttccggtcgt accaccctga acggcgaagg tctgcagcac     1920
gaagatggtc acagccacat tcagtcgctg actatcccga actgtatctc ttacgacccg     1980
gcttacgctt acgaagttgc tgtcatcatg catgacggtc tggagcgtat gtacggtgaa     2040
aaacaagaga acgtttacta ctacatcact acgctgaacg aaaactacca catgccggca     2100
atgccggaag gtgctgagga aggtatccgt aaaggtatct acaaactcga actattgaa     2160 ggtagcaaag gtaaagttca gctgctcggc tccggttcta tcctgcgtca cgtccgtgaa     2220
gcagctgaga tcctggcgaa agattacggc gtaggttctg acgtttatag cgtgacctcc     2280
ttcaccgagc tggcgcgtga tggtcaggat tgtgaacgct ggaacatgct gcacccgctg     2340
gaaactccgc gcgttccgta tatcgctcag gtgatgaacg acgctccggc agtggcatct     2400
accgactata tgaaactgtt cgctgagcag gtccgtactt acgtaccggc tgacgactac     2460
cgcgtactgg gtactgatgg cttcggtcgt tccgacagcc gtgagaacct gcgtcaccac     2520
ttcgaagttg atgcttctta tgtcgtggtt gcggcgctgg gcgaactggc taaacgtggc     2580
gaaatcgata gaaagtggt tgctgacgca atcgccaaat tcaacatcga tgcagataaa     2640
gttaacccgc gtctggcgta a                                               2661
```

<210> SEQ ID NO 12
<211> LENGTH: 887
<212> TYPE: PRT
<213> ORGANISM: Escherichia coli

<400> SEQUENCE: 12

```
Met Ser Glu Arg Phe Pro Asn Asp Val Asp Pro Ile Glu Thr Arg Asp
1               5                   10                  15

Trp Leu Gln Ala Ile Glu Ser Val Ile Arg Glu Glu Gly Val Glu Arg
            20                  25                  30

Ala Gln Tyr Leu Ile Asp Gln Leu Leu Ala Glu Ala Arg Lys Gly Gly
        35                  40                  45
```

```
Val Asn Val Ala Ala Gly Thr Gly Ile Ser Asn Tyr Ile Asn Thr Ile
     50                  55                  60

Pro Val Glu Glu Gln Pro Glu Tyr Pro Gly Asn Leu Glu Leu Glu Arg
 65                  70                  75                  80

Arg Ile Arg Ser Ala Ile Arg Trp Asn Ala Ile Met Thr Val Leu Arg
                 85                  90                  95

Ala Ser Lys Lys Asp Leu Glu Leu Gly Gly His Met Ala Ser Phe Gln
            100                 105                 110

Ser Ser Ala Thr Ile Tyr Asp Val Cys Phe Asn His Phe Arg Ala
            115                 120                 125

Arg Asn Glu Gln Asp Gly Gly Asp Leu Val Tyr Phe Gln Gly His Ile
        130                 135                 140

Ser Pro Gly Val Tyr Ala Arg Ala Phe Leu Glu Gly Arg Leu Thr Gln
145                 150                 155                 160

Glu Gln Leu Asp Asn Phe Arg Gln Glu Val His Gly Asn Gly Leu Ser
                165                 170                 175

Ser Tyr Pro His Pro Lys Leu Met Pro Glu Phe Trp Gln Phe Pro Thr
                180                 185                 190

Val Ser Met Gly Leu Gly Pro Ile Gly Ala Ile Tyr Gln Ala Lys Phe
            195                 200                 205

Leu Lys Tyr Leu Glu His Arg Gly Leu Lys Asp Thr Ser Lys Gln Thr
            210                 215                 220

Val Tyr Ala Phe Leu Gly Asp Gly Glu Met Asp Glu Pro Glu Ser Lys
225                 230                 235                 240

Gly Ala Ile Thr Ile Ala Thr Arg Glu Lys Leu Asp Asn Leu Val Phe
                245                 250                 255

Val Ile Asn Cys Asn Leu Gln Arg Leu Asp Gly Pro Val Thr Gly Asn
            260                 265                 270

Gly Lys Ile Ile Asn Glu Leu Glu Gly Ile Phe Glu Gly Ala Gly Trp
            275                 280                 285

Asn Val Ile Lys Val Met Trp Gly Ser Arg Trp Asp Glu Leu Leu Arg
        290                 295                 300

Lys Asp Thr Ser Gly Lys Leu Ile Gln Leu Met Asn Glu Thr Val Asp
305                 310                 315                 320

Gly Asp Tyr Gln Thr Phe Lys Ser Lys Asp Gly Ala Tyr Val Arg Glu
                325                 330                 335

His Phe Phe Gly Lys Tyr Pro Glu Thr Ala Ala Leu Val Ala Asp Trp
            340                 345                 350

Thr Asp Glu Gln Ile Trp Ala Leu Asn Arg Gly Gly His Asp Pro Lys
            355                 360                 365

Lys Ile Tyr Ala Ala Phe Lys Lys Ala Gln Glu Thr Lys Gly Lys Ala
        370                 375                 380

Thr Val Ile Leu Ala His Thr Ile Lys Gly Tyr Gly Met Gly Asp Ala
385                 390                 395                 400

Ala Glu Gly Lys Asn Ile Ala His Gln Val Lys Lys Met Asn Met Asp
                405                 410                 415

Gly Val Arg His Ile Arg Asp Arg Phe Asn Val Pro Val Ser Asp Ala
            420                 425                 430

Asp Ile Glu Lys Leu Pro Tyr Ile Thr Phe Pro Glu Gly Ser Glu Glu
            435                 440                 445

His Thr Tyr Leu His Ala Gln Arg Gln Lys Leu His Gly Tyr Leu Pro
        450                 455                 460
```

```
Ser Arg Gln Pro Asn Phe Thr Glu Lys Leu Glu Leu Pro Ser Leu Gln
465                 470                 475                 480

Asp Phe Gly Ala Leu Leu Glu Glu Gln Ser Lys Glu Ile Ser Thr Thr
                485                 490                 495

Ile Ala Phe Val Arg Ala Leu Asn Val Met Leu Lys Asn Lys Ser Ile
                500                 505                 510

Lys Asp Arg Leu Val Pro Ile Ile Ala Asp Glu Ala Arg Thr Phe Gly
                515                 520                 525

Met Glu Gly Leu Phe Arg Gln Ile Gly Ile Tyr Ser Pro Asn Gly Gln
    530                 535                 540

Gln Tyr Thr Pro Gln Asp Arg Glu Gln Val Ala Tyr Lys Glu Asp
545                 550                 555                 560

Glu Lys Gly Gln Ile Leu Gln Glu Gly Ile Asn Glu Leu Gly Ala Gly
                565                 570                 575

Cys Ser Trp Leu Ala Ala Thr Ser Tyr Ser Thr Asn Asn Leu Pro
                580                 585                 590

Met Ile Pro Phe Tyr Ile Tyr Tyr Ser Met Phe Gly Phe Gln Arg Ile
            595                 600                 605

Gly Asp Leu Cys Trp Ala Ala Gly Asp Gln Gln Ala Arg Gly Phe Leu
            610                 615                 620

Ile Gly Gly Thr Ser Gly Arg Thr Thr Leu Asn Gly Glu Gly Leu Gln
625                 630                 635                 640

His Glu Asp Gly His Ser His Ile Gln Ser Leu Thr Ile Pro Asn Cys
                645                 650                 655

Ile Ser Tyr Asp Pro Ala Tyr Ala Tyr Glu Val Ala Val Ile Met His
                660                 665                 670

Asp Gly Leu Glu Arg Met Tyr Gly Glu Lys Gln Glu Asn Val Tyr Tyr
                675                 680                 685

Tyr Ile Thr Thr Leu Asn Glu Asn Tyr His Met Pro Ala Met Pro Glu
                690                 695                 700

Gly Ala Glu Glu Gly Ile Arg Lys Gly Ile Tyr Lys Leu Glu Thr Ile
705                 710                 715                 720

Glu Gly Ser Lys Gly Lys Val Gln Leu Leu Gly Ser Gly Ser Ile Leu
                725                 730                 735

Arg His Val Arg Glu Ala Ala Glu Ile Leu Ala Lys Asp Tyr Gly Val
                740                 745                 750

Gly Ser Asp Val Tyr Ser Val Thr Ser Phe Thr Glu Leu Ala Arg Asp
            755                 760                 765

Gly Gln Asp Cys Glu Arg Trp Asn Met Leu His Pro Leu Glu Thr Pro
            770                 775                 780

Arg Val Pro Tyr Ile Ala Gln Val Met Asn Asp Ala Pro Ala Val Ala
785                 790                 795                 800

Ser Thr Asp Tyr Met Lys Leu Phe Ala Glu Gln Val Arg Thr Tyr Val
                805                 810                 815

Pro Ala Asp Asp Tyr Arg Val Leu Gly Thr Asp Gly Phe Gly Arg Ser
            820                 825                 830

Asp Ser Arg Glu Asn Leu Arg His His Phe Glu Val Asp Ala Ser Tyr
            835                 840                 845

Val Val Val Ala Ala Leu Gly Glu Leu Ala Lys Arg Gly Glu Ile Asp
                850                 855                 860

Lys Lys Val Val Ala Asp Ala Ile Ala Lys Phe Asn Ile Asp Ala Asp
865                 870                 875                 880

Lys Val Asn Pro Arg Leu Ala
```

885

<210> SEQ ID NO 13
<211> LENGTH: 1887
<212> TYPE: DNA
<213> ORGANISM: Escherichia coli

<400> SEQUENCE: 13

| | | | | | |
|---|---|---|---|---|---|
| gctatcgaaa | tcaaagtacc | ggacatcggg | gctgatgaag | ttgaaatcac | cgagatcctg | 60 |
| gtcaaagtgg | gcgacaaagt | tgaagccgaa | cagtcgctga | tcaccgtaga | aggcgacaaa | 120 |
| gcctctatgg | aagttccgtc | tccgcaggcg | ggtatcgtta | agagatcaa | agtctctgtt | 180 |
| ggcgataaaa | cccagaccgg | cgcactgatt | atgattttcg | attccgccga | cggtgcagca | 240 |
| gacgctgcac | ctgctcaggc | agaagagaag | aaagaagcag | ctccggcagc | agcaccagcg | 300 |
| gctgcggcgg | caaaagacgt | taacgttccg | gatatcggca | gcgacgaagt | tgaagtgacc | 360 |
| gaaatcctgg | tgaaagttgg | cgataaagtt | gaagctgaac | agtcgctgat | caccgtagaa | 420 |
| ggcgacaagg | cttctatgga | agttccggct | ccgtttgctg | gcaccgtgaa | agagatcaaa | 480 |
| gtgaacgtgg | gtgacaaagt | gtctaccggc | tcgctgatta | tggtcttcga | agtcgcgggt | 540 |
| gaagcaggcg | cggcagctcc | ggccgctaaa | caggaagcag | ctccggcagc | ggcccctgca | 600 |
| ccagcggctg | gcgtgaaaga | agttaacgtt | ccggatatcg | gcggtgacga | agttgaagtg | 660 |
| actgaagtga | tggtgaaagt | gggcgacaaa | gttgccgctg | aacagtcact | gatcaccgta | 720 |
| gaaggcgaca | agcttctat | ggaagttccg | gcgccgtttg | caggcgtcgt | gaaggaactg | 780 |
| aaagtcaacg | ttggcgataa | agtgaaaact | ggctcgctga | ttatgatctt | cgaagttgaa | 840 |
| ggcgcagcgc | ctgcggcagc | tcctgcgaaa | caggaagcgg | cagcgccggc | accggcagca | 900 |
| aaagctgaag | ccccggcagc | agcaccagct | gcgaaagcgg | aaggcaaatc | tgaatttgct | 960 |
| gaaaacgacg | cttatgttca | cgcgactccg | ctgatccgcc | gtctggcacg | cgagtttggt | 1020 |
| gttaaccttg | cgaaagtgaa | gggcactggc | cgtaaaggtc | gtatcctgcg | cgaagacgtt | 1080 |
| caggcttacg | tgaaagaagc | tatcaaacgt | gcagaagcag | ctccggcagc | gactggcggt | 1140 |
| ggtatccctg | gcatgctgcc | gtggccgaag | gtggacttca | gcaagtttgg | tgaaatcgaa | 1200 |
| gaagtggaac | tgggccgcat | ccagaaaatc | tctggtgcga | acctgagccg | taactgggta | 1260 |
| atgatcccgc | atgttactca | cttcgacaaa | accgatatca | ccgagttgga | agcgttccgt | 1320 |
| aaacagcaga | acgaagaagc | ggcgaaacgt | aagctggatg | tgaagatcac | cccggttgtc | 1380 |
| ttcatcatga | aagccgttgc | tgcagctctt | gagcagatgc | ctcgcttcaa | tagttcgctg | 1440 |
| tcggaagacg | gtcagcgtct | gaccctgaag | aaatacatca | acatcggtgt | ggcggtggat | 1500 |
| accccgaacg | gtctggttgt | tccggtattc | aaagacgtca | caagaaagg | catcatcgag | 1560 |
| ctgtctcgcg | agctgatgac | tatttctaag | aaagcgcgtg | acggtaagct | gactgcgggc | 1620 |
| gaaatgcagg | gcggttgctt | caccatctcc | agcatcggcg | gcctgggtac | tacccacttc | 1680 |
| gcgccgattg | tgaacgcgcc | ggaagtggct | atcctcggcg | tttccaagtc | cgcgatggag | 1740 |
| ccggtgtgga | atggtaaaga | gttcgtgccg | cgtctgatgc | tgccgatttc | tctctccttc | 1800 |
| gaccaccgcg | tgatcgacgg | tgctgatggt | gcccgtttca | ttaccatcat | taacaacacg | 1860 |
| ctgtctgaca | ttcgccgtct | ggtgatg | | | | 1887 |

<210> SEQ ID NO 14
<211> LENGTH: 630
<212> TYPE: PRT
<213> ORGANISM: Escherichia coli

<400> SEQUENCE: 14

```
Met Ala Ile Glu Ile Lys Val Pro Asp Ile Gly Ala Asp Glu Val Glu
1               5                   10                  15

Ile Thr Glu Ile Leu Val Lys Val Gly Asp Lys Val Glu Ala Glu Gln
            20                  25                  30

Ser Leu Ile Thr Val Glu Gly Asp Lys Ala Ser Met Glu Val Pro Ser
        35                  40                  45

Pro Gln Ala Gly Ile Val Lys Glu Ile Lys Val Ser Val Gly Asp Lys
    50                  55                  60

Thr Gln Thr Gly Ala Leu Ile Met Ile Phe Asp Ser Ala Asp Gly Ala
65                  70                  75                  80

Ala Asp Ala Ala Pro Ala Gln Ala Glu Glu Lys Lys Glu Ala Ala Pro
                85                  90                  95

Ala Ala Ala Pro Ala Ala Ala Ala Lys Asp Val Asn Val Pro Asp
                100                 105                 110

Ile Gly Ser Asp Glu Val Glu Val Thr Glu Ile Leu Val Lys Val Gly
            115                 120                 125

Asp Lys Val Glu Ala Glu Gln Ser Leu Ile Thr Val Glu Gly Asp Lys
130                 135                 140

Ala Ser Met Glu Val Pro Ala Pro Phe Ala Gly Thr Val Lys Glu Ile
145                 150                 155                 160

Lys Val Asn Val Gly Asp Lys Val Ser Thr Gly Ser Leu Ile Met Val
                165                 170                 175

Phe Glu Val Ala Gly Glu Ala Gly Ala Ala Pro Ala Ala Lys Gln
            180                 185                 190

Glu Ala Ala Pro Ala Ala Ala Pro Ala Pro Ala Ala Gly Val Lys Glu
            195                 200                 205

Val Asn Val Pro Asp Ile Gly Gly Asp Glu Val Glu Val Thr Glu Val
            210                 215                 220

Met Val Lys Val Gly Asp Lys Val Ala Ala Glu Gln Ser Leu Ile Thr
225                 230                 235                 240

Val Glu Gly Asp Lys Ala Ser Met Glu Val Pro Ala Pro Phe Ala Gly
                245                 250                 255

Val Val Lys Glu Leu Lys Val Asn Val Gly Asp Lys Val Lys Thr Gly
                260                 265                 270

Ser Leu Ile Met Ile Phe Glu Val Glu Gly Ala Ala Pro Ala Ala Ala
            275                 280                 285

Pro Ala Lys Gln Glu Ala Ala Pro Ala Pro Ala Ala Lys Ala Glu
            290                 295                 300

Ala Pro Ala Ala Ala Pro Ala Ala Lys Ala Glu Gly Lys Ser Glu Phe
305                 310                 315                 320

Ala Glu Asn Asp Ala Tyr Val His Ala Thr Pro Leu Ile Arg Arg Leu
                325                 330                 335

Ala Arg Glu Phe Gly Val Asn Leu Ala Lys Val Lys Gly Thr Gly Arg
            340                 345                 350

Lys Gly Arg Ile Leu Arg Glu Asp Val Gln Ala Tyr Val Lys Glu Ala
            355                 360                 365

Ile Lys Arg Ala Glu Ala Ala Pro Ala Ala Thr Gly Gly Gly Ile Pro
            370                 375                 380

Gly Met Leu Pro Trp Pro Lys Val Asp Phe Ser Lys Phe Gly Glu Ile
385                 390                 395                 400

Glu Glu Val Glu Leu Gly Arg Ile Gln Lys Ile Ser Gly Ala Asn Leu
```

|     | 405 |     |     |     |     | 410 |     |     |     |     | 415 |     |     |
|-----|-----|-----|-----|-----|-----|-----|-----|-----|-----|-----|-----|-----|-----|

Ser Arg Asn Trp Val Met Ile Pro His Val Thr His Phe Asp Lys Thr
            420                 425                 430

Asp Ile Thr Glu Leu Glu Ala Phe Arg Lys Gln Gln Asn Glu Glu Ala
            435                 440                 445

Ala Lys Arg Lys Leu Asp Val Lys Ile Thr Pro Val Val Phe Ile Met
450                 455                 460

Lys Ala Val Ala Ala Leu Glu Gln Met Pro Arg Phe Asn Ser Ser
465                 470                 475                 480

Leu Ser Glu Asp Gly Gln Arg Leu Thr Leu Lys Lys Tyr Ile Asn Ile
                485                 490                 495

Gly Val Ala Val Asp Thr Pro Asn Gly Leu Val Val Pro Val Phe Lys
            500                 505                 510

Asp Val Asn Lys Lys Gly Ile Ile Glu Leu Ser Arg Glu Leu Met Thr
            515                 520                 525

Ile Ser Lys Lys Ala Arg Asp Gly Lys Leu Thr Ala Gly Glu Met Gln
            530                 535                 540

Gly Gly Cys Phe Thr Ile Ser Ser Ile Gly Gly Leu Gly Thr Thr His
545                 550                 555                 560

Phe Ala Pro Ile Val Asn Ala Pro Glu Val Ala Ile Leu Gly Val Ser
                565                 570                 575

Lys Ser Ala Met Glu Pro Val Trp Asn Gly Lys Glu Phe Val Pro Arg
            580                 585                 590

Leu Met Leu Pro Ile Ser Leu Ser Phe Asp His Arg Val Ile Asp Gly
                595                 600                 605

Ala Asp Gly Ala Arg Phe Ile Thr Ile Ile Asn Asn Thr Leu Ser Asp
            610                 615                 620

Ile Arg Arg Leu Val Met
625                 630

<210> SEQ ID NO 15
<211> LENGTH: 1422
<212> TYPE: DNA
<213> ORGANISM: Escherichia coli

<400> SEQUENCE: 15
agtactgaaa tcaaaactca ggtcgtggta cttggggcag gccccgcagg ttactccgct      60
gccttccgtt gcgctgattt aggtctggaa accgtaatcg tagaacgtta caacacccct     120
ggcggtgttt gcctgaacgt cggctgtatc ccttctaaag cactgctgca cgtagcaaaa     180
gttatcgaag aagccaaagc gctggctgaa cacggtatcg tcttcggcga accgaaaacc     240
gatatcgaca gattcgtac ctggaaagag aaagtgatca atcagctgac cggtggtctg     300
gctggtatgg cgaaaggccg caaagtcaaa gtggtcaacg gtctgggtaa attcaccggg     360
gctaacaccc tggaagttga aggtgagaac ggcaaaaccg tgatcaactt cgacaacgcg     420
atcattgcag cgggttctcg cccgatccaa ctgccgttta tccgcatga agatccgcgt     480 atctgggact ccactgacgc gctggaactg aaagaagtac agaacgcct gctggtaatg     540 ggtggcggta tcatcggtct ggaaatgggc accgtttacc acgcgctggg ttcacagatt     600
gacgtggttg aaatgttcga ccaggttatc ccggcagctg acaaagacat cgttaaagtc     660
ttcaccaagc gtatcagcaa gaaattcaac ctgatgctgg aaccaaagt taccgccgtt     720 gaagcgaaag aagacggcat ttatgtgacg atggaaggca aaaagagcac cgctgaaccg     780
cagcgttacg acgccgtgct ggtagcgatt ggtcgtgtgc cgaacggtaa aaacctcgac     840

```
gcaggcaaag caggcgtgga agttgacgac cgtggtttca tccgcgttga caaacagctg    900
cgtaccaacg taccgcacat ctttgctatc ggcgatatcg tcggtcaacc gatgctggca    960
cacaaaggtg ttcacgaagg tcacgttgcc gctgaagtta cgccggtaa gaaacactac    1020 ttcgatccga agttatccc gtccatcgcc tataccgaac agaagttgc atgggtgggt    1080 ctgactgaga agaagcgaa agagaaaggc atcagctatg aaaccgccac cttcccgtgg    1140
gctgcttctg tcgtgctat cgcttccgac tgcgcagacg gtatgaccaa gctgattttc    1200
gacaaagaat ctcaccgtgt gatcggtggt gcgattgtcg gtactaacgg cggcgagctg    1260
ctgggtgaaa tcggcctggc aatcgaaatg ggttgtgatg ctgaagacat cgcactgacc    1320
atccacgcgc acccgactct gcacgagtct gtgggcctgg cggcagaagt gttcgaaggt    1380
agcattaccg acctgccgaa cccgaaagcg aagaagaagt aa    1422

<210> SEQ ID NO 16
<211> LENGTH: 474
<212> TYPE: PRT
<213> ORGANISM: Escherichia coli

<400> SEQUENCE: 16

Met Ser Thr Glu Ile Lys Thr Gln Val Val Leu Gly Ala Gly Pro
1               5                   10                  15

Ala Gly Tyr Ser Ala Ala Phe Arg Cys Ala Asp Leu Gly Leu Glu Thr
                20                  25                  30

Val Ile Val Glu Arg Tyr Asn Thr Leu Gly Gly Val Cys Leu Asn Val
            35                  40                  45

Gly Cys Ile Pro Ser Lys Ala Leu Leu His Val Ala Lys Val Ile Glu
        50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Val Glu Met Phe Asp
        195                 200                 205

Gln Val Ile Pro Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270
```

```
Arg Val Pro Asn Gly Lys Asn Leu Asp Ala Gly Lys Ala Gly Val Glu
            275                 280                 285

Val Asp Asp Arg Gly Phe Ile Arg Val Asp Lys Gln Leu Arg Thr Asn
        290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 17
<211> LENGTH: 987
<212> TYPE: DNA
<213> ORGANISM: Escherichia coli

<400> SEQUENCE: 17
aaactcgccg tttatagcac aaaacagtac gacaagaagt acctgcaaca ggtgaacgag      60
tcctttggct ttgagctgga attttttgac tttctgctga cggaaaaaac cgctaaaact     120
gccaatggct gcgaagcggt atgtattttc gtaaacgatg acggcagccg cccggtgctg     180
gaagagctga aaagcacgg cgttaaatat atcgccctgc gctgtgccgg tttcaataac     240
gtcgaccttg acgcgcaaa gaactggggc tgaaagtag tccgtgttcc agcctatgat     300
ccagaggccg ttgctgaaca cgccatcggt atgatgatga cgctgaaccg ccgtattcac     360
cgcgcgtatc agcgtacccg tgatgctaac ttctctctgg aaggtctgac cggctttact     420
atgtatggca aaacggcagg cgttatcggt accggtaaaa tcggtgtggc gatgctgcgc     480
attctgaaag gttttggtat gcgtctgctg gcgttcgatc cgtatccaag tgcagcggcg     540
ctggaactcg gtgtggagta tgtcgatctg ccaaccctgt tctctgaatc agacgttatc     600
tctctgcact gcccgctgac accggaaaac tatcatctgt gaacgaagc cgccttcgaa     660 cagatgaaaa atggcgtgat gatcgtcaat accagtcgcg gtgcattgat tgattctcag     720
gcagcaattg aagcgctgaa aaatcagaaa attggttcgt gggtatgga cgtgtatgag     780 aacgaacgcg atctattctt tgaagataaa tccaacgacg tgatccagga tgacgtattc     840
cgtcgcctgt ctgcctgcca caacgtgctg tttaccgggc accaggcatt cctgacagca     900
gaagctctga ccagtatttc tcagactacg ctgcaaaact taagcaatct ggaaaaaggc     960
```
gaaacctgcc cgaacgaact ggtttaa 987

<210> SEQ ID NO 18
<211> LENGTH: 329
<212> TYPE: PRT
<213> ORGANISM: Escherichia coli

<400> SEQUENCE: 18

Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
            20                  25                  30

Leu Leu Thr Glu Lys Thr Ala Lys Thr Ala Asn Gly Cys Glu Ala Val
        35                  40                  45

Cys Ile Phe Val Asn Asp Gly Ser Arg Pro Val Leu Glu Glu Leu
    50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
        115                 120                 125

Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Glu Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Val Phe Arg Arg Leu Ser Ala Cys His
        275                 280                 285

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325

<210> SEQ ID NO 19
<211> LENGTH: 2277
<212> TYPE: DNA
<213> ORGANISM: Escherichia coli

<400> SEQUENCE: 19

```
tccgagctta atgaaaagtt agccacagcc tgggaaggtt ttaccaaagg tgactggcag      60
aatgaagtaa acgtccgtga cttcattcag aaaaactaca ctccgtacga gggtgacgag     120
tccttcctgg ctggcgctac tgaagcgacc accaccctgt gggacaaagt aatggaaggc     180
gttaaactgg aaaaccgcac tcacgcgcca gttgactttg acaccgctgt tgcttccacc     240
atcacctctc acgacgctgg ctacatcaac aagcagcttg agaaaatcgt tggtctgcag     300
actgaagctc cgctgaaacg tgctcttatc ccgttcggtg tatcaaaat gatcgaaggt      360
tcctgcaaag cgtacaaccg cgaactggat ccgatgatca aaaaaatctt cactgaatac     420
cgtaaaactc acaaccaggg cgtgttcgac gtttacactc cggacatcct gcgttgccgt     480
aaatctggtt ttctgaccgg tctgccagat gcatatggcc gtggccgtat catcggtgac     540
taccgtcgcg ttgcgctgta cggtatcgac tacctgatga agacaaaact ggcacagttc     600
acttctctgc aggctgatct ggaaaacggc gtaaacctgg aacagactat ccgtctgcgc     660
gaagaaatcg ctgaacagca ccgcgctctg gtcagatga agaaatggc tgcgaaatac       720
ggctacgaca tctctggtcc ggctaccaac gctcaggaag ctatccagtg gacttacttc     780
ggctacctgg ctgctgttaa gtctcagaac ggtgctgcaa tgtccttcgg tcgtacctcc     840
accttcctgg atgtgtacat cgaacgtgac ctgaaagctg gcaagatcac cgaacaagaa     900
gcgcaggaaa tggttgacca cctggtcatg aaactgcgta tggttcgctt cctgcgtact     960
ccggaatacg atgaactgtt ctctggcgac ccgatctggg caaccgaatc tatcggtggt    1020
atgggcctcg acggtcgtac cctggttacc aaaaacagct tccgtttcct gaacaccctg    1080
tacaccatgg gtccgtctcc ggaaccgaac atgaccattc tgtggtctga aaaactgccg    1140
ctgaacttca agaaattcgc cgctaaagtg tccatcgaca cctcttctct gcagtatgag    1200
aacgatgacc tgatgcgtcc ggacttcaac aacgatgact acgctattgc ttgctgcgta    1260
agcccgatga tcgttggtaa acaaatgcag ttcttcggtg cgcgtgcaaa cctggcgaaa    1320
accatgctgt acgcaatcaa cggcggcgtt gacgaaaaac tgaaaatgca ggttggtccg    1380
aagtctgaac cgatcaaagg cgatgtcctg aactatgatg aagtgatgga gcgcatggat    1440
cacttcatgg actggctggc taaacagtac atcactgcac tgaacatcat ccactacatg    1500
cacgacaagt acagctacga agcctctctg atggcgctgc acgaccgtga cgttatccgc    1560
accatggcgt gtggtatcgc tggtctgtcc gttgctgctg actccctgtc tgcaatcaaa    1620
tatgcgaaag ttaaaccgat tcgtgacgaa acggtctgg ctatcgactt cgaaatcgaa     1680
ggcgaatacc cgcagtttgg taacaatgat ccgcgtgtag atgacctggc tgttgacctg    1740
gtagaacgtt tcatgaagaa aattcagaaa ctgcacacct accgtgacgc tatcccgact    1800
cagtctgttc tgaccatcac ttctaacgtt gtgtatggta agaaaacggg taacaccccca   1860
gacggtcgtc gtgctggcgc gccgttcgga ccgggtgcta cccgatgca cggtcgtgac     1920
cagaaaggtg cagtagcctc tctgacttcc gttgctaaac tgccgtttgc ttacgctaaa    1980
gatggtatct cctacacctt ctctatcgtt ccgaacgcac tgggtaaaga cgacgaagtt    2040
cgtaagacca acctggctgg tctgatggat ggttacttcc accacgaagc atccatcgaa    2100
ggtggtcagc acctgaacgt taacgtgatg aaccgtgaaa tgctgctcga cgcgatggaa    2160
aacccggaaa atatccgca gctgaccatc cgtgtatctg gctacgcagt acgtttcaac    2220
tcgctgacta agaacagca gcaggacgtt attactcgta ccttcactca atctatg        2277
```

<210> SEQ ID NO 20
<211> LENGTH: 760
<212> TYPE: PRT
<213> ORGANISM: Escherichia coli

<400> SEQUENCE: 20

```
Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
        35                  40                  45

Glu Ala Thr Thr Thr Leu Trp Asp Lys Val Met Glu Gly Val Lys Leu
    50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Leu Ala Gln Phe Thr Ser Leu Gln Ala Asp Leu
        195                 200                 205

Glu Asn Gly Val Asn Leu Glu Gln Thr Ile Arg Leu Arg Glu Glu Ile
    210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
        355                 360                 365

Glu Pro Asn Met Thr Ile Leu Trp Ser Glu Lys Leu Pro Leu Asn Phe
    370                 375                 380
```

```
Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Tyr Ala
            405                 410                 415

Ile Ala Cys Cys Val Ser Pro Met Ile Val Gly Lys Gln Met Gln Phe
                420                 425                 430

Phe Gly Ala Arg Ala Asn Leu Ala Lys Thr Met Leu Tyr Ala Ile Asn
            435                 440                 445

Gly Gly Val Asp Glu Lys Leu Lys Met Gln Val Gly Pro Lys Ser Glu
            450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
                500                 505                 510

Ala Leu His Asp Arg Asp Val Ile Arg Thr Met Ala Cys Gly Ile Ala
            515                 520                 525

Gly Leu Ser Val Ala Ala Asp Ser Leu Ser Ala Ile Lys Tyr Ala Lys
530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
            580                 585                 590

His Thr Tyr Arg Asp Ala Ile Pro Thr Gln Ser Val Leu Thr Ile Thr
            595                 600                 605

Ser Asn Val Val Tyr Gly Lys Lys Thr Gly Asn Thr Pro Asp Gly Arg
610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
            645                 650                 655

Phe Ala Tyr Ala Lys Asp Gly Ile Ser Tyr Thr Phe Ser Ile Val Pro
            660                 665                 670

Asn Ala Leu Gly Lys Asp Asp Glu Val Arg Lys Thr Asn Leu Ala Gly
            675                 680                 685

Leu Met Asp Gly Tyr Phe His His Glu Ala Ser Ile Glu Gly Gly Gln
            690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Ser Met
755                 760

<210> SEQ ID NO 21
<211> LENGTH: 1716
<212> TYPE: DNA
<213> ORGANISM: Escherichia coli
```

<400> SEQUENCE: 21

```
aaacaaacgg ttgcagctta tatcgccaaa acactcgaat cggcaggggt gaaacgcatc      60
tggggagtca caggcgactc tctgaacggt cttagtgaca gtcttaatcg catgggcacc     120
atcgagtgga tgtccacccg ccacgaagaa gtggcggcct ttgccgctgg cgctgaagca     180
caacttagcg gagaactggc ggtctgcgcc ggatcgtgcg gccccggcaa cctgcactta     240
atcaacggcc tgttcgattg ccaccgcaat cacgttccgg tactgccgat tgccgctcat     300
attccctcca gcgaaattgg cagcggctat ttccaggaaa cccacccaca agagctattc     360
cgcgaatgta gtcactattg cgagctggtt tccagcccgg agcagatccc acaagtactg     420
gcgattgcca tgcgcaaagc ggtgcttaac cgtggcgttt cggttgtcgt gttaccaggc     480
gacgtggcgt taaacctgc gccagaaggg gcaaccatgc actggtatca tgcgccacaa     540
ccagtcgtga cgccggaaga agaagagtta cgcaaactgg cgcaactgct gcgttattcc     600
agcaatatcg ccctgatgtg tggcagcggc tgcgcggggg cgcataaaga gttagttgag     660
tttgccggga aaattaaagc gcctattgtt catgccctgc gcggtaaaga acatgtcgaa     720
tacgataatc cgtatgatgt tggaatgacc gggttaatcg gcttctcgtc aggttttccat    780
accatgatga acgccgacac gttagtgcta ctcggcacga aatttcccta ccgcgccttc     840
tacccgaccg atgccaaaat cattcagatt gatatcaacc cagccagcat cggcgctcac     900
agcaaggtgg atatggcact ggtcggcgat atcaagtcga ctctgcgtgc attgcttcca     960
ttggtggaag aaaaagccga tcgcaagttt ctggataaag cgctggaaga ttaccgcgac    1020
gcccgcaaag ggctggacga tttagctaaa ccgagcgaga agccattca cccgcaatat     1080
ctggcgcagc aaaattagtca ttttgccgcc gatgacgcta ttttcacctg tgacgttggt    1140
acgccaacgg tgtgggcggc acgttatcta aaaatgaacg gcaagcgtcg cctgttaggt    1200
tcgtttaacc acggttcgat ggctaacgcc atgccgcagg cgctgggtgc gcaggcgaca    1260
gagccagaac gtcaggtggt cgccatgtgc ggcgatggcg ttttagcat gttgatgggc     1320
gatttcctct cagtagtgca gatgaaactg ccagtgaaaa ttgtcgtctt aacaacagc     1380
gtgctgggct ttgtggcgat ggagatgaaa gctggtggct atttgactga cggcaccgaa    1440
ctacacgaca caaactttgc ccgcattgcc gaagcgtgcg gcattacggg tatccgtgta    1500
gaaaaagcgt ctgaagttga tgaagccctg caacgcgcct tctccatcga cggtccggtg    1560
ttggtggatg tggtggtcgc caaagaagag ttagccattc caccgcagat caaactcgaa    1620
caggccaaag gtttcagcct gtatatgctg cgcgcaatca tcagcggacg cggtgatgaa    1680
gtgatcgaac tggcgaaaac aaactggcta aggtaa                              1716
```

<210> SEQ ID NO 22
<211> LENGTH: 572
<212> TYPE: PRT
<213> ORGANISM: Escherichia coli

<400> SEQUENCE: 22

```
Met Lys Gln Thr Val Ala Ala Tyr Ile Ala Lys Thr Leu Glu Ser Ala
1               5                   10                  15

Gly Val Lys Arg Ile Trp Gly Val Thr Gly Asp Ser Leu Asn Gly Leu
            20                  25                  30

Ser Asp Ser Leu Asn Arg Met Gly Thr Ile Glu Trp Met Ser Thr Arg
        35                  40                  45

His Glu Glu Val Ala Ala Phe Ala Ala Gly Ala Glu Ala Gln Leu Ser
    50                  55                  60
```

```
Gly Glu Leu Ala Val Cys Ala Gly Ser Cys Gly Pro Gly Asn Leu His
 65                  70                  75                  80

Leu Ile Asn Gly Leu Phe Asp Cys His Arg Asn His Val Pro Val Leu
                 85                  90                  95

Ala Ile Ala Ala His Ile Pro Ser Ser Glu Ile Gly Ser Gly Tyr Phe
            100                 105                 110

Gln Glu Thr His Pro Gln Glu Leu Phe Arg Glu Cys Ser His Tyr Cys
            115                 120                 125

Glu Leu Val Ser Ser Pro Glu Gln Ile Pro Gln Val Leu Ala Ile Ala
            130                 135                 140

Met Arg Lys Ala Val Leu Asn Arg Gly Val Ser Val Val Leu Pro
145                 150                 155                 160

Gly Asp Val Ala Leu Lys Pro Ala Pro Glu Gly Ala Thr Met His Trp
                165                 170                 175

Tyr His Ala Pro Gln Pro Val Val Thr Pro Glu Glu Glu Leu Arg
                180                 185                 190

Lys Leu Ala Gln Leu Leu Arg Tyr Ser Ser Asn Ile Ala Leu Met Cys
                195                 200                 205

Gly Ser Gly Cys Ala Gly Ala His Lys Glu Leu Val Glu Phe Ala Gly
210                 215                 220

Lys Ile Lys Ala Pro Ile Val His Ala Leu Arg Gly Lys Glu His Val
225                 230                 235                 240

Glu Tyr Asp Asn Pro Tyr Asp Val Gly Met Thr Gly Leu Ile Gly Phe
                245                 250                 255

Ser Ser Gly Phe His Thr Met Met Asn Ala Asp Thr Leu Val Leu Leu
                260                 265                 270

Gly Thr Gln Phe Pro Tyr Arg Ala Phe Tyr Pro Thr Asp Ala Lys Ile
                275                 280                 285

Ile Gln Ile Asp Ile Asn Pro Ala Ser Ile Gly Ala His Ser Lys Val
            290                 295                 300

Asp Met Ala Leu Val Gly Asp Ile Lys Ser Thr Leu Arg Ala Leu Leu
305                 310                 315                 320

Pro Leu Val Glu Glu Lys Ala Asp Arg Lys Phe Leu Asp Lys Ala Leu
                325                 330                 335

Glu Asp Tyr Arg Asp Ala Arg Lys Gly Leu Asp Asp Leu Ala Lys Pro
                340                 345                 350

Ser Glu Lys Ala Ile His Pro Gln Tyr Leu Ala Gln Gln Ile Ser His
            355                 360                 365

Phe Ala Ala Asp Asp Ala Ile Phe Thr Cys Asp Val Gly Thr Pro Thr
            370                 375                 380

Val Trp Ala Ala Arg Tyr Leu Lys Met Asn Gly Lys Arg Arg Leu Leu
385                 390                 395                 400

Gly Ser Phe Asn His Gly Ser Met Ala Asn Ala Met Pro Gln Ala Leu
                405                 410                 415

Gly Ala Gln Ala Thr Glu Pro Glu Arg Gln Val Val Ala Met Cys Gly
            420                 425                 430

Asp Gly Gly Phe Ser Met Leu Met Gly Asp Phe Leu Ser Val Val Gln
            435                 440                 445

Met Lys Leu Pro Val Lys Ile Val Phe Asn Asn Ser Val Leu Gly
            450                 455                 460

Phe Val Ala Met Glu Met Lys Ala Gly Gly Tyr Leu Thr Asp Gly Thr
465                 470                 475                 480
```

```
Glu Leu His Asp Thr Asn Phe Ala Arg Ile Ala Glu Ala Cys Gly Ile
                485                 490                 495

Thr Gly Ile Arg Val Glu Lys Ala Ser Glu Val Asp Glu Ala Leu Gln
        500                 505                 510

Arg Ala Phe Ser Ile Asp Gly Pro Val Leu Val Asp Val Val Ala
        515                 520                 525

Lys Glu Glu Leu Ala Ile Pro Pro Gln Ile Lys Leu Glu Gln Ala Lys
        530                 535                 540

Gly Phe Ser Leu Tyr Met Leu Arg Ala Ile Ile Ser Gly Arg Gly Asp
545                 550                 555                 560

Glu Val Ile Glu Leu Ala Lys Thr Asn Trp Leu Arg
                565                 570
```

<210> SEQ ID NO 23
<211> LENGTH: 2142
<212> TYPE: DNA
<213> ORGANISM: Escherichia coli

<400> SEQUENCE: 23

```
tcccgtatta ttatgctgat ccctaccgga accagcgtcg gtctgaccag cgtcagcctt     60
ggcgtgatcc gtgcaatgga acgcaaaggc gttcgtctga gcgttttcaa acctatcgct    120
cagccgcgta ccggtggcga tgcgcccgat cagactacga ctatcgtgcg tgcgaactct    180
tccaccacga cggccgctga accgctgaaa atgagctacg ttgaaggtct gctttccagc    240
aatcagaaag atgtgctgat ggaagagatc gtcgcaaact accacgctaa caccaaagac    300
gctgaagtcg ttctggttga aggtctggtc ccgacacgta agcaccagtt tgcccagtct    360
ctgaactacg aaatcgctaa aacgctgaat gcggaaatcg tcttcgttat gtctcagggc    420
actgacaccc cggaacagct gaaagagcgt atcgaactga cccgcaacag cttcggcggt    480
gccaaaaaca ccaacatcac cggcgttatc gttaacaaac tgaacgcacc ggttgatgaa    540
cagggtcgta ctcgcccgga tctgtccgag atttcgacg actcttccaa agctaaagta    600
aacaatgttg atccggcgaa gctgcaagaa tccagcccgc tgccggttct cggcgctgtg    660
ccgtggagct ttgacctgat cgcgactcgt gcgatcgata tggctcgcca cctgaatgcg    720
accatcatca cgaaggcga catcaatact cgccgcgtta atccgtcac tttctgcgca    780
cgcagcattc cgcacatgct ggagcacttc cgtgccggtt ctctgctggt gacttccgca    840
gaccgtcctg acgtgctggt ggccgcttgc ctggcagcca tgaacggcgt agaaatcggt    900
gccctgctgc tgactggcgg ttacgaaatg gacgcgcgca tttctaaaact gtgcgaacgt    960
gctttcgcta ccggcctgcc ggtatttatg gtgaacacca cacctggca gacctctctg   1020
agcctgcaga gcttcaacct ggaagttccg gttgacgatc acgaacgtat cgagaaagtt   1080
caggaatacg ttgctaacta catcaacgct gactggatcg aatctctgac tgccacttct   1140
gagcgcagcc gtcgtctgtc tccgcctgcg ttccgttatc agctgactga acttgcgcgc   1200
aaagcgggca acgtatcgt actgccggaa ggtgacgaac gcgtaccgt taaagcagcc   1260
gctatctgtg ctgaacgtgg tatcgcaact tgcgtactgc tgggtaatcc ggcagagatc   1320
aaccgtgttg cagcgtctca gggtgtagaa ctgggtgcag ggattgaaat cgttgatcca   1380
gaagtggttc gcgaaagcta tgttggtcgt ctggtcgaac tgcgtaagaa caaaggcatg   1440
accgaaaccg ttgcccgcga acagctgaaa gacaacgtgg tgctcggtac gctgatgctg   1500
gaacaggatg aagttgatgg tctggttttcc ggtgctgttc acactaccgc aaacaccatc   1560
cgtccgccgc tgcagctgat caaaactgca ccgggcagct ccctggtatc ttccgtgttc   1620
```

-continued

```
ttcatgctgc tgccggaaca ggtttacgtt tacggtgact gtgcgatcaa cccggatccg    1680
accgctgaac agctggcaga aatcgcgatt cagtccgctg attccgctgc ggccttcggt    1740
atcgaaccgc gcgttgctat gctctcctac tccaccggta cttctggtgc aggtagcgac    1800
gtagaaaaag ttcgcgaagc aactcgtctg gcgcaggaaa acgtcctga cctgatgatc     1860 gacggtccgc tgcagtacga cgctgcggta atggctgacg ttgcgaaatc caaagcgccg    1920
aactctccgg ttgcaggtcg cgctaccgtg ttcatcttcc cggatctgaa caccggtaac    1980
accacctaca aagcggtaca gcgttctgcc gacctgatct ccatcgggcc gatgctgcag    2040
ggtatgcgca agccggttaa cgacctgtcc cgtggcgcac tggttgacga tatcgtctac    2100
accatcgcgc tgactgcgat tcagtctgca cagcagcagt aa                       2142
```

<210> SEQ ID NO 24
<211> LENGTH: 714
<212> TYPE: PRT
<213> ORGANISM: Escherichia coli

<400> SEQUENCE: 24

```
Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
                20                  25                  30

Arg Leu Ser Val Phe Lys Pro Ile Ala Gln Pro Arg Thr Gly Gly Asp
            35                  40                  45

Ala Pro Asp Gln Thr Thr Thr Ile Val Arg Ala Asn Ser Ser Thr Thr
        50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
    210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
```

```
            275                 280                 285
Ala Ala Cys Leu Ala Ala Met Asn Gly Val Glu Ile Gly Ala Leu Leu
290                 295                 300
Leu Thr Gly Gly Tyr Glu Met Asp Ala Arg Ile Ser Lys Leu Cys Glu
305                 310                 315                 320
Arg Ala Phe Ala Thr Gly Leu Pro Val Phe Met Val Asn Thr Asn Thr
                325                 330                 335
Trp Gln Thr Ser Leu Ser Leu Gln Ser Phe Asn Leu Glu Val Pro Val
                340                 345                 350
Asp Asp His Glu Arg Ile Glu Lys Val Gln Glu Tyr Val Ala Asn Tyr
                355                 360                 365
Ile Asn Ala Asp Trp Ile Glu Ser Leu Thr Ala Thr Ser Glu Arg Ser
                370                 375                 380
Arg Arg Leu Ser Pro Pro Ala Phe Arg Tyr Gln Leu Thr Glu Leu Ala
385                 390                 395                 400
Arg Lys Ala Gly Lys Arg Ile Val Leu Pro Glu Gly Asp Glu Pro Arg
                405                 410                 415
Thr Val Lys Ala Ala Ile Cys Ala Glu Arg Gly Ile Ala Thr Cys
                420                 425                 430
Val Leu Leu Gly Asn Pro Ala Glu Ile Asn Arg Val Ala Ala Ser Gln
                435                 440                 445
Gly Val Glu Leu Gly Ala Gly Ile Glu Ile Val Asp Pro Glu Val Val
450                 455                 460
Arg Glu Ser Tyr Val Gly Arg Leu Val Glu Leu Arg Lys Asn Lys Gly
465                 470                 475                 480
Met Thr Glu Thr Val Ala Arg Glu Gln Leu Glu Asp Asn Val Val Leu
                485                 490                 495
Gly Thr Leu Met Leu Glu Gln Asp Glu Val Asp Gly Leu Val Ser Gly
                500                 505                 510
Ala Val His Thr Thr Ala Asn Thr Ile Arg Pro Pro Leu Gln Leu Ile
                515                 520                 525
Lys Thr Ala Pro Gly Ser Ser Leu Val Ser Ser Val Phe Phe Met Leu
530                 535                 540
Leu Pro Glu Gln Val Tyr Val Tyr Gly Asp Cys Ala Ile Asn Pro Asp
545                 550                 555                 560
Pro Thr Ala Glu Gln Leu Ala Glu Ile Ala Ile Gln Ser Ala Asp Ser
                565                 570                 575
Ala Ala Ala Phe Gly Ile Glu Pro Arg Val Ala Met Leu Ser Tyr Ser
                580                 585                 590
Thr Gly Thr Ser Gly Ala Gly Ser Asp Val Glu Lys Val Arg Glu Ala
                595                 600                 605
Thr Arg Leu Ala Gln Glu Lys Arg Pro Asp Leu Met Ile Asp Gly Pro
                610                 615                 620
Leu Gln Tyr Asp Ala Ala Val Met Ala Asp Val Ala Lys Ser Lys Ala
625                 630                 635                 640
Pro Asn Ser Pro Val Ala Gly Arg Ala Thr Val Phe Ile Phe Pro Asp
                645                 650                 655
Leu Asn Thr Gly Asn Thr Thr Tyr Lys Ala Val Gln Arg Ser Ala Asp
                660                 665                 670
Leu Ile Ser Ile Gly Pro Met Leu Gln Gly Met Arg Lys Pro Val Asn
                675                 680                 685
Asp Leu Ser Arg Gly Ala Leu Val Asp Asp Ile Val Tyr Thr Ile Ala
                690                 695                 700
```

Leu Thr Ala Ile Gln Ser Ala Gln Gln Gln
705                 710

<210> SEQ ID NO 25
<211> LENGTH: 255
<212> TYPE: DNA
<213> ORGANISM: Escherichia coli

<400> SEQUENCE: 25

| ttccagcaag aagttaccat taccgctccg aacggtctgc acacccgccc tgctgcccag | 60 |
| tttgtaaaag aagctaaggg cttcacttct gaaattactg tgacttccaa cggcaaaagc | 120 |
| gccagcgcga aaagcctgtt taaactgcag actctgggcc tgactcaagg taccgttgtg | 180 |
| actatctccg cagaaggcga agacgagcag aaagcggttg aacatctggt taaactgatg | 240 |
| gcggaactcg agtaa | 255 |

<210> SEQ ID NO 26
<211> LENGTH: 85
<212> TYPE: PRT
<213> ORGANISM: Escherichia coli

<400> SEQUENCE: 26

Met Phe Gln Gln Glu Val Thr Ile Thr Ala Pro Asn Gly Leu His Thr
1               5                   10                  15

Arg Pro Ala Ala Gln Phe Val Lys Glu Ala Lys Gly Phe Thr Ser Glu
                20                  25                  30

Ile Thr Val Thr Ser Asn Gly Lys Ser Ala Ser Ala Lys Ser Leu Phe
            35                  40                  45

Lys Leu Gln Thr Leu Gly Leu Thr Gln Gly Thr Val Val Thr Ile Ser
        50                  55                  60

Ala Glu Gly Glu Asp Glu Gln Lys Ala Val Glu His Leu Val Lys Leu
65                  70                  75                  80

Met Ala Glu Leu Glu
                85

<210> SEQ ID NO 27
<211> LENGTH: 1725
<212> TYPE: DNA
<213> ORGANISM: Escherichia coli

<400> SEQUENCE: 27

| atttcaggca ttttagcatc cccgggtatc gctttcggta aagctctgct tctgaaagaa | 60 |
| gacgaaattg tcattgaccg gaaaaaaatt tctgccgacc aggttgatca ggaagttgaa | 120 |
| cgttttctga gcggtcgtgc caaggcatca gcccagctgg aaacgatcaa acgaaaagct | 180 |
| ggtgaaacgt tcggtgaaga aaagaagcc atctttgaag gcatattat gctgctcgaa | 240 |
| gatgaggagc tggagcagga atcatagcc ctgattaaag ataagcacat gacagctgac | 300 |
| gcagctgctc atgaagttat cgaaggtcag gcttctgccc tggaagagct ggatgatgaa | 360 |
| tacctgaaag aacgtgcggc tgacgtacgt gatatcggta agcgcctgct gcgcaacatc | 420 |
| ctgggcctga gattatcga cctgagcgcc attcaggatg aagtcattct ggttgccgct | 480 |
| gacctgacgc cgtccgaaac cgcacagctg aacctgaaga aggtgctggg tttcatcacc | 540 |
| gacgcgggtg gccgtacttc ccacacctct atcatggcgc gttctctgga actacctgct | 600 |
| atcgtgggta ccggtagcgt cacctctcag gtgaaaaatg acgactatct gattctggat | 660 |
| gccgtaaata atcaggttta cgtcaatcca accaacgaag ttattgataa aatgcgcgct | 720 |

-continued

```
gttcaggagc aagtggcttc tgaaaaagca gagcttgcta aactgaaaga tctgccagct      780
attacgctgg acggtcacca ggtagaagta tgcgctaaca ttggtacggt tcgtgacgtt      840
gaaggtgcag agcgtaacgg cgctgaaggc gttggtctgt atcgtactga gttcctgttc      900
atggaccgcg acgcactgcc cactgaagaa gaacagtttg ctgcttacaa agcagtggct      960
gaagcgtgtg gctcgcaagc ggttatcgtt cgtaccatgg acatcggcgg cgacaaagag     1020
ctgccataca tgaacttccc gaaagaagag aacccgttcc tcggctggcg cgctatccgt     1080
atcgcgatgg atcgtagaga gatcctgcgc gatcagctcc gcgctatcct gcgtgcctcg     1140
gctttcggta aattgcgcat tatgttcccg atgatcatct ctgttgaaga agtgcgtgca     1200
ctgcgcaaag agatcgaaat ctacaaacag gaactgcgcg acgaaggtaa agcgtttgac     1260
gagtcaattg aaatcggcgt aatggtggaa acaccggctg ccgcaacaat tgcacgtcat     1320
ttagccaaag aagttgattt ctttagtatc ggcaccaatg atttaacgca gtacactctg     1380
gcagttgacc gtggtaatga tatgatttca cacctttacc agccaatgtc accgtccgtg     1440
ctgaacttga tcaagcaagt tattgatgct tctcatgctg aaggcaaatg gactggcatg     1500
tgtggtgagc ttgctggcga tgaacgtgct acacttctgt tgctggggat gggtctggac     1560
gaattctcta tgagcgccat ttctatcccg cgcattaaga agattatccg taacacgaac     1620
ttcgaagatg cgaaggtgtt agcagagcag gctcttgctc aaccgacaac ggacgagtta     1680
atgacgctgg ttaacaagtt cattgaagaa aaaacaatct gctaa                    1725
```

<210> SEQ ID NO 28
<211> LENGTH: 575
<212> TYPE: PRT
<213> ORGANISM: Escherichia coli

<400> SEQUENCE: 28

```
Met Ile Ser Gly Ile Leu Ala Ser Pro Gly Ile Ala Phe Gly Lys Ala
1               5                   10                  15

Leu Leu Leu Lys Glu Asp Glu Ile Val Ile Asp Arg Lys Lys Ile Ser
            20                  25                  30

Ala Asp Gln Val Asp Gln Glu Val Glu Arg Phe Leu Ser Gly Arg Ala
        35                  40                  45

Lys Ala Ser Ala Gln Leu Glu Thr Ile Lys Thr Lys Ala Gly Glu Thr
    50                  55                  60

Phe Gly Glu Glu Lys Glu Ala Ile Phe Glu Gly His Ile Met Leu Leu
65                  70                  75                  80

Glu Asp Glu Glu Leu Glu Gln Glu Ile Ile Ala Leu Ile Lys Asp Lys
                85                  90                  95

His Met Thr Ala Asp Ala Ala His Glu Val Ile Glu Gly Gln Ala
            100                 105                 110

Ser Ala Leu Glu Glu Leu Asp Asp Glu Tyr Leu Lys Glu Arg Ala Ala
        115                 120                 125

Asp Val Arg Asp Ile Gly Lys Arg Leu Leu Arg Asn Ile Leu Gly Leu
    130                 135                 140

Lys Ile Ile Asp Leu Ser Ala Ile Gln Asp Glu Val Ile Leu Val Ala
145                 150                 155                 160

Ala Asp Leu Thr Pro Ser Glu Thr Ala Gln Leu Asn Leu Lys Lys Val
                165                 170                 175

Leu Gly Phe Ile Thr Asp Ala Gly Gly Arg Thr Ser His Thr Ser Ile
            180                 185                 190
```

```
Met Ala Arg Ser Leu Glu Leu Pro Ala Ile Val Gly Thr Gly Ser Val
            195                 200                 205

Thr Ser Gln Val Lys Asn Asp Asp Tyr Leu Ile Leu Asp Ala Val Asn
210                 215                 220

Asn Gln Val Tyr Val Asn Pro Thr Asn Glu Val Ile Asp Lys Met Arg
225                 230                 235                 240

Ala Val Gln Glu Gln Val Ala Ser Glu Lys Ala Leu Ala Lys Leu
                245                 250                 255

Lys Asp Leu Pro Ala Ile Thr Leu Asp Gly His Gln Val Glu Val Cys
            260                 265                 270

Ala Asn Ile Gly Thr Val Arg Asp Val Glu Gly Ala Glu Arg Asn Gly
            275                 280                 285

Ala Glu Gly Val Gly Leu Tyr Arg Thr Glu Phe Leu Phe Met Asp Arg
            290                 295                 300

Asp Ala Leu Pro Thr Glu Glu Gln Phe Ala Ala Tyr Lys Ala Val
305                 310                 315                 320

Ala Glu Ala Cys Gly Ser Gln Ala Val Ile Val Arg Thr Met Asp Ile
                325                 330                 335

Gly Gly Asp Lys Glu Leu Pro Tyr Met Asn Phe Pro Lys Glu Glu Asn
            340                 345                 350

Pro Phe Leu Gly Trp Arg Ala Ile Arg Ile Ala Met Asp Arg Arg Glu
            355                 360                 365

Ile Leu Arg Asp Gln Leu Arg Ala Ile Leu Arg Ala Ser Ala Phe Gly
            370                 375                 380

Lys Leu Arg Ile Met Phe Pro Met Ile Ile Ser Val Glu Glu Val Arg
385                 390                 395                 400

Ala Leu Arg Lys Glu Ile Glu Ile Tyr Lys Gln Glu Leu Arg Asp Glu
                405                 410                 415

Gly Lys Ala Phe Asp Glu Ser Ile Glu Ile Gly Val Met Val Glu Thr
            420                 425                 430

Pro Ala Ala Ala Thr Ile Ala Arg His Leu Ala Lys Glu Val Asp Phe
            435                 440                 445

Phe Ser Ile Gly Thr Asn Asp Leu Thr Gln Tyr Thr Leu Ala Val Asp
450                 455                 460

Arg Gly Asn Asp Met Ile Ser His Leu Tyr Gln Pro Met Ser Pro Ser
465                 470                 475                 480

Val Leu Asn Leu Ile Lys Gln Val Ile Asp Ala Ser His Ala Glu Gly
                485                 490                 495

Lys Trp Thr Gly Met Cys Gly Glu Leu Ala Gly Asp Glu Arg Ala Thr
            500                 505                 510

Leu Leu Leu Leu Gly Met Gly Leu Asp Glu Phe Ser Met Ser Ala Ile
            515                 520                 525

Ser Ile Pro Arg Ile Lys Lys Ile Ile Arg Asn Thr Asn Phe Glu Asp
530                 535                 540

Ala Lys Val Leu Ala Glu Gln Ala Leu Ala Gln Pro Thr Thr Asp Glu
545                 550                 555                 560

Leu Met Thr Leu Val Asn Lys Phe Ile Glu Glu Lys Thr Ile Cys
                565                 570                 575

<210> SEQ ID NO 29
<211> LENGTH: 507
<212> TYPE: DNA
<213> ORGANISM: Escherichia coli

<400> SEQUENCE: 29
```

-continued

```
ggtttgttcg ataaactgaa atctctggtt ccgacgaca agaaggatac cggaactatt      60
gagatcattg ctccgctctc tggcgagatc gtcaatatcg aagacgtgcc ggatgtcgtt     120
tttgcggaaa aaatcgttgg tgatggtatt gctatcaaac caacgggtaa caaaatggtc     180
gcgccagtag acggcaccat tggtaaaatc tttgaaacca ccacgcatt ctctatcgaa      240 tctgatagcg gcgttgaact gttcgtccac ttcggtatcg acaccgttga actgaaaggc     300
gaaggcttca gcgtattgc tgaagaaggt cagcgcgtga agttggcga tactgtcatt      360 gaatttgatc tgccgctgct ggaagagaaa gccaagtcta ccctgactcc ggttgttatc     420
tccaacatgg acgaaatcaa agaactgatc aaactgtccg gtagcgtaac cgtgggtgaa     480
accccggtta tccgcatcaa gaagtaa                                        507
```

<210> SEQ ID NO 30
<211> LENGTH: 169
<212> TYPE: PRT
<213> ORGANISM: Escherichia coli

<400> SEQUENCE: 30

```
Met Gly Leu Phe Asp Lys Leu Lys Ser Leu Val Ser Asp Lys Lys
1               5                   10                  15

Asp Thr Gly Thr Ile Glu Ile Ile Ala Pro Leu Ser Gly Glu Ile Val
                20                  25                  30

Asn Ile Glu Asp Val Pro Asp Val Phe Ala Glu Lys Ile Val Gly
            35                  40                  45

Asp Gly Ile Ala Ile Lys Pro Thr Gly Asn Lys Met Val Ala Pro Val
        50                  55                  60

Asp Gly Thr Ile Gly Lys Ile Phe Glu Thr Asn His Ala Phe Ser Ile
65                  70                  75                  80

Glu Ser Asp Ser Gly Val Glu Leu Phe Val His Phe Gly Ile Asp Thr
                85                  90                  95

Val Glu Leu Lys Gly Glu Gly Phe Lys Arg Ile Ala Glu Glu Gly Gln
            100                 105                 110

Arg Val Lys Val Gly Asp Thr Val Ile Glu Phe Asp Leu Pro Leu Leu
        115                 120                 125

Glu Glu Lys Ala Lys Ser Thr Leu Thr Pro Val Val Ile Ser Asn Met
    130                 135                 140

Asp Glu Ile Lys Glu Leu Ile Lys Leu Ser Gly Ser Val Thr Val Gly
145                 150                 155                 160

Glu Thr Pro Val Ile Arg Ile Lys Lys
                165
```

<210> SEQ ID NO 31
<211> LENGTH: 1443
<212> TYPE: DNA
<213> ORGANISM: Escherichia coli

<400> SEQUENCE: 31

```
atgtccagaa ggcttcgcag aacaaaaatc gttaccacgt taggcccagc aacagatcgc      60
gataataatc ttgaaaaagt tatcgcggcg ggtgccaacg ttgtacgtat gaacttttct     120
cacggctcgc tgaagatca aaatgcgc gcggataaag ttcgtgagat tgccgcaaaa       180
ctggggcgtc atgtggctat tctgggtgac ctccaggggc ccaaaatccg tgtatccacc     240 tttaagaag gcaagttttt cctcaatatt ggggataaat tcctgctcga cgccaacctg     300
ggtaaaggtg aaggcgacaa agaaaaagtc ggtatcgact acaaaggcct gcctgctgac     360
```

-continued

```
gtcgtgcctg gtgacatcct gctgctggac gatggtcgcg tccagttaaa agtactggaa    420
gttcagggca tgaaagtgtt caccgaagtc accgtcggtg tcccctctc caacaataaa    480
ggtatcaaca aacttggcgg cggtttgtcg gctgaagcgc tgaccgaaaa agacaaagca    540
gacattaaga ctgcggcgtt gattggcgta gattacctgg ctgtctcctt cccacgctgt    600
ggcgaagatc tgaactatgc ccgtcgcctg gcacgcgatg caggatgtga tgcgaaaatt    660
gttgccaagg ttgaacgtgc ggaagccgtt tgcagccagg atgcaatgga tgacatcatc    720
ctcgcctctg acgtggtaat ggttgcacgt ggcgacctcg tgtggaaat tggcgacccg     780
gaactggtcg gcattcagaa agcgttgatc cgtcgtgcgc gtcagctaaa ccgagcggta    840
atcacggcga cccagatgat ggagtcaatg attactaacc cgatgccgac gcgtgcagaa    900
gtcatggacg tagcaaacgc cgttctggat ggtactgacg ctgtgatgct gtctgcagaa    960
actgccgctg gcagtatcc gtcagaaacc gttgcagcca tggcgcgcgt ttgcctgggt    1020
gcggaaaaaa tcccgagcat caacgtttct aaacaccgtc tggacgttca gttcgacaat    1080
gtggaagaag ctattgccat gtcagcaatg tacgcagcta ccacctgaa aggcgttacg     1140
gcgatcatca ccatgaccga tcgggtcgt accgcgctga tgacctcccg tatcagctct    1200
ggtctgccaa ttttcgccat gtcgcgccat gaacgtacgc tgaacctgac tgctctctat    1260
cgtggcgtta cgccggtgca ctttgatagc gctaatgacg gcgtagcagc tgccagcgaa    1320
gcggttaatc tgctgcgcga taaaggttac ttgatgtctg gtgacctggt gattgtcacc    1380
cagggcgacg tgatgagtac cgtgggttct actaatacca cgcgtatttt aacggtagag    1440
taa                                                                   1443
```

<210> SEQ ID NO 32
<211> LENGTH: 480
<212> TYPE: PRT
<213> ORGANISM: Escherichia coli

<400> SEQUENCE: 32

```
Met Ser Arg Arg Leu Arg Arg Thr Lys Ile Val Thr Thr Leu Gly Pro
  1               5                  10                  15

Ala Thr Asp Arg Asp Asn Asn Leu Glu Lys Val Ile Ala Ala Gly Ala
                 20                  25                  30

Asn Val Val Arg Met Asn Phe Ser His Gly Ser Pro Glu Asp His Lys
             35                  40                  45

Met Arg Ala Asp Lys Val Arg Glu Ile Ala Ala Lys Leu Gly Arg His
         50                  55                  60

Val Ala Ile Leu Gly Asp Leu Gln Gly Pro Lys Ile Arg Val Ser Thr
 65                  70                  75                  80

Phe Lys Glu Gly Lys Val Phe Leu Asn Ile Gly Asp Lys Phe Leu Leu
                 85                  90                  95

Asp Ala Asn Leu Gly Lys Gly Glu Gly Asp Lys Glu Lys Val Gly Ile
                100                 105                 110

Asp Tyr Lys Gly Leu Pro Ala Asp Val Val Pro Gly Asp Ile Leu Leu
            115                 120                 125

Leu Asp Asp Gly Arg Val Gln Leu Lys Val Leu Glu Val Gln Gly Met
        130                 135                 140

Lys Val Phe Thr Glu Val Thr Val Gly Gly Pro Leu Ser Asn Asn Lys
145                 150                 155                 160

Gly Ile Asn Lys Leu Gly Gly Gly Leu Ser Ala Glu Ala Leu Thr Glu
                165                 170                 175
```

Lys Asp Lys Ala Asp Ile Lys Thr Ala Ala Leu Ile Gly Val Asp Tyr
            180                 185                 190

Leu Ala Val Ser Phe Pro Arg Cys Gly Glu Asp Leu Asn Tyr Ala Arg
        195                 200                 205

Arg Leu Ala Arg Asp Ala Gly Cys Asp Ala Lys Ile Val Ala Lys Val
    210                 215                 220

Glu Arg Ala Glu Ala Val Cys Ser Gln Asp Ala Met Asp Asp Ile Ile
225                 230                 235                 240

Leu Ala Ser Asp Val Val Met Val Ala Arg Gly Asp Leu Gly Val Glu
            245                 250                 255

Ile Gly Asp Pro Glu Leu Val Gly Ile Gln Lys Ala Leu Ile Arg Arg
        260                 265                 270

Ala Arg Gln Leu Asn Arg Ala Val Ile Thr Ala Thr Gln Met Met Glu
    275                 280                 285

Ser Met Ile Thr Asn Pro Met Pro Thr Arg Ala Glu Val Met Asp Val
290                 295                 300

Ala Asn Ala Val Leu Asp Gly Thr Asp Ala Val Met Leu Ser Ala Glu
305                 310                 315                 320

Thr Ala Ala Gly Gln Tyr Pro Ser Glu Thr Val Ala Ala Met Ala Arg
            325                 330                 335

Val Cys Leu Gly Ala Glu Lys Ile Pro Ser Ile Asn Val Ser Lys His
        340                 345                 350

Arg Leu Asp Val Gln Phe Asp Asn Val Glu Glu Ala Ile Ala Met Ser
    355                 360                 365

Ala Met Tyr Ala Ala Asn His Leu Lys Gly Val Thr Ala Ile Ile Thr
370                 375                 380

Met Thr Glu Ser Gly Arg Thr Ala Leu Met Thr Ser Arg Ile Ser Ser
385                 390                 395                 400

Gly Leu Pro Ile Phe Ala Met Ser Arg His Glu Arg Thr Leu Asn Leu
            405                 410                 415

Thr Ala Leu Tyr Arg Gly Val Thr Pro Val His Phe Asp Ser Ala Asn
        420                 425                 430

Asp Gly Val Ala Ala Ser Glu Ala Val Asn Leu Leu Arg Asp Lys
    435                 440                 445

Gly Tyr Leu Met Ser Gly Asp Leu Val Ile Val Thr Gln Gly Asp Val
    450                 455                 460

Met Ser Thr Val Gly Ser Thr Asn Thr Thr Arg Ile Leu Thr Val Glu
465                 470                 475                 480

<210> SEQ ID NO 33
<211> LENGTH: 1410
<212> TYPE: DNA
<213> ORGANISM: Escherichia coli

<400> SEQUENCE: 33
aaaaagacca aaattgtttg caccatcgga ccgaaaaccg aatctgaaga gatgttagct      60
aaaatgctgg acgctggcat gaacgttatg cgtctgaact tctctcatgg tgactatgca     120
gaacacggtc agcgcattca gaatctgcgc aacgtgatga gcaaaactgg taaaaccgcc     180
gctatcctgc ttgataccaa aggtccggaa atccgcacca tgaaactgga aggcggtaac     240
gacgtttctc tgaaagctgg tcagaccttt actttcacca ctgataaatc tgttatcggc     300
aacagcgaaa tggttgcggt aacgtatgaa ggtttccacta ctgacctgtc tgttggcaac     360
accgtactgg ttgacgatgg tctgatcggt atggaagtta ccgccattga aggtaacaaa     420

```
gttatctgta aagtgctgaa caacggtgac ctgggcgaaa acaaaggtgt gaacctgcct    480
ggcgttttca ttgctctgcc agcactggct gaaaaagaca acaggacct gatctttggt    540
tgcgaacaag gcgtagactt tgttgctgct tcctttattc gtaagcgttc tgacgttatc    600
gaaatccgtg agcacctgaa agcgcacggc ggcgaaaaca tccacatcat ctccaaaatc    660
gaaaaccagg aaggcctcaa caacttcgac gaaatcctcg aagcctctga cggcatcatg    720
gttgcgcgtg cgacctggg tgtagaaatc ccggtagaag aagttatctt cgcccagaag    780
atgatgatcg aaaaatgtat ccgtgcacgt aaagtcgtta tcactgcgac ccagatgctg    840
gattccatga tcaaaaaccc acgcccgact cgcgcagaag ccggtgacgt tgcaaacgcc    900
atcctcgacg gtactgacgc agtgatgctg tctggtgaat ccgcaaaagg taaatacccg    960
ctggaagcgg tttctatcat ggcgaccatc tgcgaacgta ccgaccgcgt gatgaacagc   1020
cgtctcgagt tcaacaatga caaccgtaaa ctgcgcatta ccgaagcggt atgccgtggt   1080
gccgttgaaa ctgctgaaaa actggatgct ccgctgatcg tggttgctac tcagggcggt   1140
aaatctgctc gcgcagtacg taaatacttc ccggatgcca ccatcctggc actgaccacc   1200
aacgaaaaaa cggctcatca gttggtactg agcaaaggcg ttgtgccgca gcttgttaaa   1260
gagatcactt ctactgatga tttctaccgt ctgggtaaag aactggctct gcagagcggt   1320
ctggcacaca aaggtgacgt tgtagttatg gtttctggtg cactggtacc gagcggcact   1380
actaacaccg catctgttca cgtcctgtaa                                    1410
```

<210> SEQ ID NO 34
<211> LENGTH: 470
<212> TYPE: PRT
<213> ORGANISM: Escherichia coli

<400> SEQUENCE: 34

```
Met Lys Lys Thr Lys Ile Val Cys Thr Ile Gly Pro Lys Thr Glu Ser
1               5                   10                  15

Glu Glu Met Leu Ala Lys Met Leu Asp Ala Gly Met Asn Val Met Arg
            20                  25                  30

Leu Asn Phe Ser His Gly Asp Tyr Ala Glu His Gly Gln Arg Ile Gln
        35                  40                  45

Asn Leu Arg Asn Val Met Ser Lys Thr Gly Lys Thr Ala Ala Ile Leu
    50                  55                  60

Leu Asp Thr Lys Gly Pro Glu Ile Arg Thr Met Lys Leu Glu Gly Gly
65                  70                  75                  80

Asn Asp Val Ser Leu Lys Ala Gly Gln Thr Phe Thr Phe Thr Thr Asp
                85                  90                  95

Lys Ser Val Ile Gly Asn Ser Glu Met Val Ala Val Thr Tyr Glu Gly
            100                 105                 110

Phe Thr Thr Asp Leu Ser Val Gly Asn Thr Val Leu Val Asp Asp Gly
        115                 120                 125

Leu Ile Gly Met Glu Val Thr Ala Ile Glu Gly Asn Lys Val Ile Cys
    130                 135                 140

Lys Val Leu Asn Asn Gly Asp Leu Gly Glu Asn Lys Gly Val Asn Leu
145                 150                 155                 160

Pro Gly Val Ser Ile Ala Leu Pro Ala Leu Ala Glu Lys Asp Lys Gln
                165                 170                 175

Asp Leu Ile Phe Gly Cys Glu Gln Gly Val Asp Phe Val Ala Ala Ser
            180                 185                 190
```

```
Phe Ile Arg Lys Arg Ser Asp Val Ile Glu Ile Arg Glu His Leu Lys
            195                 200                 205

Ala His Gly Gly Glu Asn Ile His Ile Ser Lys Ile Glu Asn Gln
    210                 215                 220

Glu Gly Leu Asn Asn Phe Asp Glu Ile Leu Glu Ala Ser Asp Gly Ile
225                 230                 235                 240

Met Val Ala Arg Gly Asp Leu Gly Val Glu Ile Pro Val Glu Glu Val
                245                 250                 255

Ile Phe Ala Gln Lys Met Met Ile Glu Lys Cys Ile Arg Ala Arg Lys
            260                 265                 270

Val Val Ile Thr Ala Thr Gln Met Leu Asp Ser Met Ile Lys Asn Pro
        275                 280                 285

Arg Pro Thr Arg Ala Glu Ala Gly Asp Val Ala Asn Ala Ile Leu Asp
    290                 295                 300

Gly Thr Asp Ala Val Met Leu Ser Gly Glu Ser Ala Lys Gly Lys Tyr
305                 310                 315                 320

Pro Leu Glu Ala Val Ser Ile Met Ala Thr Ile Cys Glu Arg Thr Asp
                325                 330                 335

Arg Val Met Asn Ser Arg Leu Glu Phe Asn Asn Asp Asn Arg Lys Leu
            340                 345                 350

Arg Ile Thr Glu Ala Val Cys Arg Gly Ala Val Glu Thr Ala Glu Lys
        355                 360                 365

Leu Asp Ala Pro Leu Ile Val Val Ala Thr Gln Gly Gly Lys Ser Ala
    370                 375                 380

Arg Ala Val Arg Lys Tyr Phe Pro Asp Ala Thr Ile Leu Ala Leu Thr
385                 390                 395                 400

Thr Asn Glu Lys Thr Ala His Gln Leu Val Leu Ser Lys Gly Val Val
                405                 410                 415

Pro Gln Leu Val Lys Glu Ile Thr Ser Thr Asp Asp Phe Tyr Arg Leu
            420                 425                 430

Gly Lys Glu Leu Ala Leu Gln Ser Gly Leu Ala His Lys Gly Asp Val
        435                 440                 445

Val Val Met Val Ser Gly Ala Leu Val Pro Ser Gly Thr Thr Asn Thr
    450                 455                 460

Ala Ser Val His Val Leu
465                 470

<210> SEQ ID NO 35
<211> LENGTH: 569
<212> TYPE: PRT
<213> ORGANISM: Zymomonasmobilis

<400> SEQUENCE: 35

Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95
```

```
Ile Ser Gly Ala Pro Asn Asn Asp His Ala Ala Gly His Val Leu
            100                 105                 110

His His Ala Leu Gly Lys Thr Asp Tyr His Tyr Gln Leu Glu Met Ala
            115                 120                 125

Lys Asn Ile Thr Ala Ala Glu Ala Ile Tyr Thr Pro Glu Ala
130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
                180                 185                 190

Ala Ser Leu Asn Ala Ala Val Glu Glu Thr Leu Lys Phe Ile Ala Asn
                195                 200                 205

Arg Asp Lys Val Ala Val Leu Val Gly Ser Lys Leu Arg Ala Ala Gly
            210                 215                 220

Ala Glu Glu Ala Ala Val Lys Phe Ala Asp Ala Leu Gly Gly Ala Val
225                 230                 235                 240

Ala Thr Met Ala Ala Ala Lys Ser Phe Phe Pro Glu Glu Asn Pro His
                245                 250                 255

Tyr Ile Gly Thr Ser Trp Gly Glu Val Ser Tyr Pro Gly Val Glu Lys
            260                 265                 270

Thr Met Lys Glu Ala Asp Ala Val Ile Ala Leu Ala Pro Val Phe Asn
            275                 280                 285

Asp Tyr Ser Thr Thr Gly Trp Thr Asp Ile Pro Asp Pro Lys Lys Leu
            290                 295                 300

Val Leu Ala Glu Pro Arg Ser Val Val Asn Gly Ile Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ala Leu Asp Phe Phe Lys Ser Leu Asn Ala Gly Glu
                340                 345                 350

Leu Lys Lys Ala Ala Pro Ala Asp Pro Ser Ala Pro Leu Val Asn Ala
                355                 360                 365

Glu Ile Ala Arg Gln Val Glu Ala Leu Leu Thr Pro Asn Thr Thr Val
370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
                405                 410                 415

Trp Ser Val Pro Ala Ala Phe Gly Tyr Ala Val Gly Ala Pro Glu Arg
                420                 425                 430

Arg Asn Ile Leu Met Val Gly Asp Gly Ser Phe Gln Leu Thr Ala Gln
            435                 440                 445

Glu Val Ala Gln Met Val Arg Leu Lys Leu Pro Val Ile Ile Phe Leu
            450                 455                 460

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
                485                 490                 495

Asn Gly Asn Gly Gly Tyr Asp Ser Gly Ala Gly Lys Gly Leu Lys Ala
            500                 505                 510
```

-continued

```
Lys Thr Gly Gly Glu Leu Ala Glu Ala Ile Lys Val Ala Leu Ala Asn
            515                 520                 525

Thr Asp Gly Pro Thr Leu Ile Glu Cys Phe Ile Gly Arg Glu Asp Cys
    530                 535                 540

Thr Glu Glu Leu Val Lys Trp Gly Lys Arg Val Ala Ala Ala Asn Ser
545                 550                 555                 560

Arg Lys Pro Val Asn Lys Leu Leu Gly
                565

<210> SEQ ID NO 36
<211> LENGTH: 541
<212> TYPE: PRT
<213> ORGANISM: Leuconostoc mesenteroides

<400> SEQUENCE: 36

Met Thr Asp Thr Leu Thr Phe Asn Thr Lys His Leu Leu Glu Ala Leu
1               5                  10                  15

Phe Glu Ser Gly Ile Arg His Phe Ile Val Ser Pro Gly Ser Arg Ser
            20                  25                  30

Thr Pro Ile Ala Leu Leu Ala Glu Tyr Ala Glu Gln Asn Asn Glu
        35                  40                  45

Ile Lys Leu Phe Val Asp Val Asp Glu Arg Ser Ala Gly Phe Phe Ala
    50                  55                  60

Leu Gly Ile Ala Lys Thr Leu Leu Glu Pro Val Val Leu Leu Gly Thr
65                  70                  75                  80

Ser Gly Thr Ala Ile Ala Glu Tyr Met Pro Ala Val Ala Glu Ala Tyr
                85                  90                  95

Ala Ala Asn Ile Pro Leu Val Val Leu Ser Thr Asp Arg Pro Gln Glu
            100                 105                 110

Leu Gln Phe Asn Gly Ala Pro Gln Thr Ile Pro Gln Ser Asn Leu Phe
        115                 120                 125

Gly Gln Leu Thr Lys Gln Ala Val Leu Ile Arg Leu Gln Asp Met His
    130                 135                 140

Ser Asp Val Thr Glu Tyr Ile Asp Phe Ile Val Gln Lys Val Val Asn
145                 150                 155                 160

Leu Ser Ile Thr Ala Pro Arg Gly Pro Ile Gln Ile Asn Leu Pro Leu
                165                 170                 175

Arg Lys Pro Leu Met Pro Val Leu Asp Arg Gln Asp Glu Val His Val
            180                 185                 190

Gln Arg Val Val Phe Asp Lys Gln Ser Val Gln Tyr Arg Leu Pro Pro
        195                 200                 205

Ile Thr Ala Lys Arg Leu Leu Ile Leu Ala Gly Pro Asn Val Leu Asn
    210                 215                 220

Ser Tyr Asp Asp Ser Leu Lys Lys Phe Ala Ile Lys Asn Asn Val Pro
225                 230                 235                 240

Val Ile Ala Asp Val Leu Ser Gln Ser Arg His Thr Tyr Thr Ile His
                245                 250                 255

Gly Ile Asp Val Leu Leu Gln Ala His Lys Ile Asn Ala Asp Leu Lys
            260                 265                 270

Pro Asp Leu Val Val Arg Phe Gly Lys Thr Pro Val Ser Ala Arg Val
        275                 280                 285

Leu Gln Trp Leu Lys Glu Glu Asn Ile Leu Thr Trp His Val Asp Glu
    290                 295                 300

Asp Ala Gly Val Asp His Thr Arg His Ile Val Arg Ala Ile Lys Met
305                 310                 315                 320
```

-continued

```
Ala Pro His Asp Phe Leu Glu Ser Met His Leu Thr Leu Ser Lys Asn
            325                 330                 335

Gln Ile Asp Phe Asn Gln Lys Trp Leu Ser Leu Pro Lys Val Ile Lys
        340                 345                 350

Thr Arg Asn Glu Met Asn Ile Ile Thr Ala Leu Asp Asp Ala Val Pro
    355                 360                 365

Asp Asp Thr His Ile Phe Val Ala Asn Ser Met Pro Ile Arg Asp Met
370                 375                 380

Asp Asn Phe Phe Thr Gly Asn His Thr Gln Arg Ile Tyr Ala Asn Arg
385                 390                 395                 400

Gly Ala Asn Gly Ile Asp Gly Val Ile Ser Ser Ala Leu Gly Met Ser
                405                 410                 415

Ala Val Val Lys Gln Arg Ser Val Leu Leu Thr Gly Asp Leu Thr Leu
            420                 425                 430

Phe His Asp Met Asn Gly Leu Met Met Ala Lys Asn Tyr Gln Leu Pro
        435                 440                 445

Leu Asp Ile Ile Val Ile Asn Asn Asn Gly Gly Ile Phe Ser Phe
    450                 455                 460

Leu Pro Gln Ala Gly Ala Pro Lys Tyr Phe Glu Gln Leu Phe Gly Thr
465                 470                 475                 480

Pro Leu Asn Ile Asp Ile Lys Lys Ile Ala Asp Leu Tyr Tyr Ile Asp
                485                 490                 495

Tyr His Gln Leu Asn Val Pro Glu Ala Leu Ser Gln Ile Leu Gln Thr
            500                 505                 510

Pro Ser Lys Thr Thr Arg Leu Ile Glu Tyr Lys Ser Asp His Gln Arg
        515                 520                 525

Asn Arg Asp Asp His Arg Glu Val Leu Glu Met Leu Lys
    530                 535                 540

<210> SEQ ID NO 37
<211> LENGTH: 1242
<212> TYPE: PRT
<213> ORGANISM: Mycobacterium tuberculosis

<400> SEQUENCE: 37

Met Asn Leu Arg Gly Thr Ala Ala Arg Arg His Arg Ala Thr Gly
1               5                   10                  15

Asp Thr Leu Asp Ala Arg Gln Leu Val Arg Gln Leu Arg Gln Leu
            20                  25                  30

Gln Thr Glu Thr Arg Pro Gly Ala Leu Val Arg Trp Phe Leu Leu Asp
        35                  40                  45

Pro Lys Glu Leu Phe Asp Ile Phe Val Thr Ile Gln Gly Phe Thr Gln
    50                  55                  60

Thr Thr Arg Gln Arg Arg Gln Leu Leu Gln Thr His Asn Cys Gln
65              70                  75                  80

Ile Ile Thr Val Val Phe Arg Leu Ala Cys Arg Gln Phe Ile Ile Gln
                85                  90                  95

Leu Thr Gly Gly Gln Gln Asn Thr Ala Asn Phe Ile Ala Val Ala Asp
            100                 105                 110

Thr Ile Leu Val Gly Arg Phe Leu Gln Asp Ala Thr Glu Phe Asn Leu
        115                 120                 125

Gly Lys Ile Leu Asn Leu Arg Asn Arg Leu Val Ala Gln His Gly
    130                 135                 140

Phe Arg Gly Lys His Asp Gln Arg Thr Leu Asp Ala Val Gln Arg Val
```

```
            145                 150                 155                 160
        Ala Ala Gln Gln Val Lys Val Ile Gly Arg Gly Ala Arg His Arg Asp
                        165                 170                 175
        Arg His Ala Thr Leu Ser Pro Gln Leu Gln Lys Ala Leu Asn Ala Arg
                        180                 185                 190
        Arg Arg Val Val Arg Ala Leu Thr Leu Val Ala Val Trp Gln Gln Gln
                        195                 200                 205
        Asn Asn Val Gly Gln Leu Thr Pro Phe Arg Phe Ala Arg Ala Asp Glu
                        210                 215                 220
        Leu Val Asn Asp Arg Leu Gly Thr Ile Asn Lys Val Ala Glu Leu Arg
        225                 230                 235                 240
        Leu Pro Gln His Asn Arg Val Trp Ile Ala Asn Gly Ile Thr Val Leu
                        245                 250                 255
        Lys Thr His Ser Arg Val Phe Arg Gln Arg Ile Ile Asn Gln Glu
                        260                 265                 270
        Leu Thr Thr Gly Arg Ala Ala Val Ala Val Ser Arg Gln Gln Leu Gln
                        275                 280                 285
        Arg Gly Glu Leu Leu Ala Gly Val Thr Val Asp Gln His Arg Met Thr
                        290                 295                 300
        Leu Ala Lys Gly Ala Thr Thr Arg Val Leu Thr Ala Gln Thr Asp Gln
        305                 310                 315                 320
        Leu Ala Leu Ser Asn Gln Ala Ala Gln Arg Gln Gln Leu Thr Lys Arg
                        325                 330                 335
        Pro Val Asn Leu Thr Leu Ile Arg His Leu Thr Thr Leu Phe Gln His
                        340                 345                 350
        Arg Leu Asn Ala Arg Val Cys Arg Glu Thr Val Arg Gln Arg Gln Glu
                        355                 360                 365
        Gly Ile Thr Asp Thr Cys Gln Gln Gly Phe Val Asn Ser Gly Arg Gln
                        370                 375                 380
        Ala Arg Trp Asp His Leu Val Arg Leu Asp Ala Leu Arg Arg Leu Asp
        385                 390                 395                 400
        Ala Val Leu Leu Gln Phe Ala His Phe Val Glu His Thr Leu Gln Leu
                        405                 410                 415
        Ala Leu Val Ile Ala Gln Arg Ile Leu Arg Leu Phe His Ala Asp Val
                        420                 425                 430
        Ala Thr Thr Asp Gln Ser Leu Gly Val Gly Phe Thr Gly Ala Thr Leu
                        435                 440                 445
        Gly Val His Asp Val Ile Asp Ile Arg Ile Gly His Arg Trp Ile Val
                        450                 455                 460
        Thr Leu Ile Met Thr Thr Thr Ile Ala Gln His Val Asn Asn Asn
        465                 470                 475                 480
        Val Leu Phe Lys Ala Leu Ala Glu Val Asn Cys Gln Thr Arg Asn Pro
                        485                 490                 495
        Asp Thr Arg Phe Trp Ile Val Ala Val His Val Glu Asp Trp Arg Thr
                        500                 505                 510
        Asp His Leu Arg His Ile Arg Ala Val Leu Ala Arg Thr Arg Val Phe
                        515                 520                 525
        Arg Ser Gly Gly Glu Ala Asp Leu Val Val His Asn Asp Val Asn Arg
                        530                 535                 540
        Thr Thr His Thr Ile Ala Arg Gln Ile Cys Gln Ile Gln Arg Leu Arg
        545                 550                 555                 560
        Asn Asn Ala Leu Thr Arg Glu Gly Arg Ile Thr Val Gln His Gln Arg
                        565                 570                 575
```

```
Asn Asp Gly Glu Cys Thr Leu Ala Val Gly Val Asn Gly Thr Val Val
            580                 585                 590

Gln Gln Val Leu Leu Arg Thr His Gln Thr Phe Gln His Trp Ile Asp
        595                 600                 605

Arg Phe Gln Met Gly Arg Ile Cys Arg Gln Gly Asn Leu Asn Ile Val
    610                 615                 620

Ile Ala Lys His Leu Gln Ile Gln Thr Arg Arg Thr Gln Val Val Leu
625                 630                 635                 640

Asp Ile Ala Gly Thr Val Ser Leu Gly Arg Val Gln Ile Ala Phe Lys
                645                 650                 655

Leu Arg Lys Asp Leu Arg Ile Arg Phe Ala His Asp Val Arg Gln Asp
            660                 665                 670

Ile Gln Ala Thr Thr Val Arg His Ala Asn Asp His Phe Ile Gln Thr
        675                 680                 685

Met Leu Gly Thr Leu Val Asn Arg Arg Val His His Trp Asn Asn Arg
    690                 695                 700

Phe Arg Thr Leu Gln Ala Lys Thr Leu Leu Ala His Ile Leu Gly Leu
705                 710                 715                 720

Gln Glu Gly Phe Lys Arg Leu Arg Cys Val Gln Phe Arg Gln Asp Val
                725                 730                 735

Leu Leu Leu Ser Asn Gly Arg Phe Asp Val Leu Arg Leu Asp Thr Leu
            740                 745                 750

Leu Gln Pro Leu Leu Leu Phe Arg Val Gln Asn Val Arg Val Leu Asn
        755                 760                 765

Thr Asp Val Thr Ala Val Arg Val Ala Gln Gln Thr Gln His Val Thr
770                 775                 780

Gln Leu Phe Val Leu Ser Thr Arg Glu Thr Val Asn Leu Lys Asp Ala
785                 790                 795                 800

Val Gln Val Pro Gln Ser Gln Ala Met Arg Gln His Leu Gln Ile Arg
                805                 810                 815

Met Arg Thr Lys Ala Arg Leu Ile Gln Ala Gln Arg Val Gly Val Arg
            820                 825                 830

His Gln Met Ala Ala Val Ala Ile Gly Arg Asp Gln Val His His Thr
        835                 840                 845

Cys Val Leu Val Asn Asp Arg Val Arg Ile Ile Gly Ala Pro Thr His
    850                 855                 860

Trp Gln Val Arg Asp Ala Gln Leu Ala Glu Asp Leu Ile Pro Glu Ala
865                 870                 875                 880

Ile Arg Gln Gln Gln Phe Met Asn Gly Thr Gln Glu Val Thr Ala Phe
                885                 890                 895

Arg Thr Leu Asn Asp Thr Val Val Gly Arg Ser Gln Gly Asn Gln
            900                 905                 910

Phe Ala Asn Thr Gln Leu Ser Asp Ala Phe Leu Gly Arg Ala Leu Glu
        915                 920                 925

Leu Arg Arg Ile Phe His Arg Thr Asp Thr Asp Ser Thr Leu Thr
    930                 935                 940

Trp His Gln Ala Trp His Arg Val His Arg Ala Asn Arg Ala Arg Ile
945                 950                 955                 960

Arg Gln Arg Asn Arg Asn Ala Ser Glu Val Leu Gly Gly Gln Phe Thr
                965                 970                 975

Ile Thr Ser Thr Thr Asp Asp Val Leu Val Arg Gly Asn Glu Leu Arg
            980                 985                 990
```

| | | | | | | | | | | | |
|---|---|---|---|---|---|---|---|---|---|---|---|
|Glu|Ala|His|Arg|Leu|Ala|Thr|Phe|Asp|Thr|Gly|His His Gln Arg Ala|
| | |995| | | |1000| | | |1005| |

Leu Ala Ile Phe Thr Leu Gln Val Asn Ser Gln Thr Gln Ile Gly
   1010                        1015                      1020

Val Arg Arg Ser Asn Arg Arg Arg Leu Thr Val His Leu Arg Val
   1025                        1030                      1035

Val Ala Ile His Ile Arg Glu Leu Leu Asn Arg Leu Asn Gln Ser
   1040                        1045                      1050

Ile Thr Gln Gln Met Gly Lys Ala Asp Phe Thr Thr Arg Ala
   1055                        1060                      1065

Phe Gln Leu Ile Ile Asp His Asp Thr Ile Ile Asp Gln Gln Phe
   1070                        1075                      1080

Arg Trp His Ser Thr His Arg Gly Arg Arg Arg His Phe Gln Arg
   1085                        1090                      1095

Arg Ala His Val Leu His Asp Ser Ser Arg Arg Thr Thr Gln Asp
   1100                        1105                      1110

Ser Asn Phe Ile Ala Phe Gly Trp Arg Arg His Arg Gly Leu Gly
   1115                        1120                      1125

Gly Gln Ser Arg His Asp Thr Val Ala Arg Cys Gly Arg Val Gly
   1130                        1135                      1140

Arg Phe Arg Arg Arg Leu Arg Ser Arg Arg Cys Arg Thr Leu Ser
   1145                        1150                      1155

Asp Gln Arg Ala Gly His Thr Ser Arg Leu Ser Ser Arg Leu Gly
   1160                        1165                      1170

Ser Arg Leu Arg Ala Ile Val His Gln Lys Leu Met Pro Ala Trp
   1175                        1180                      1185

Val Asn Gly Arg Arg Ile Ile Thr Lys Phe Thr Ile His Thr Asn
   1190                        1195                      1200

Thr Arg Arg Val Leu Ser His His Gly Tyr Ile Ser Phe Leu Lys
   1205                        1210                      1215

Asn Ser Ile Ser Gln Arg Gln Gly Arg His Lys Ile Tyr Ser Lys
   1220                        1225                      1230

Cys Ile Ile Asn Thr Asp Asn Ile Leu
   1235                        1240

<210> SEQ ID NO 38
<211> LENGTH: 4412
<212> TYPE: DNA
<213> ORGANISM: Artificial Sequence
<220> FEATURE:
<223> OTHER INFORMATION: Description of Artificial Sequence: Synthetic
     plasmid pJ201:pdc

<400> SEQUENCE: 38

```
tagaaaaact catcgagcat caaatgaaac tgcaatttat tcatatcagg attatcaata      60
ccatattttt gaaaagccg tttctgtaat gaaggagaaa actcaccgag gcagttccat     120
aggatggcaa gatcctggta tcggtctgcg attccgactc gtccaacatc aatacaacct    180
attaatttcc cctcgtcaaa ataaggttaa tcaagtgaga atcaccatg agtgacgact      240 gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgttttttccg gggatcgcag tggtgagtaa ccatgcatca    540
```

```
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttaggggggtg tcgcccttcg ctgaacatat gagctatacc   1200
gttggcacct atctggcaga acgcctggtg cagatcggcc tgaaacacca cttcgcggtg   1260
gcgggtgact acaacctggt gctgctggac aacttgctgt tgaacaagaa tatggaacag   1320
gtgtactgct gtaatgagct gaattgtggc ttcagcgcgg agggttacgc ccgggccaaa   1380
ggtgcagccg cagcggttgt gacctatagc gttggcgcgc tgagcgcatt tgatgcgatt   1440
ggtggtgcgt acgctgagaa tttgccggtc atcctgatca gcggcgcacc gaacaacaac   1500
gaccatgctg cgggccacgt gctgcatcac gcgctgggta agaccgacta tcattatcag   1560
ttggagatgg cgaagaatat cacggccgct gcggaagcta tctatacgcc ggaagaggct   1620
cctgcaaaaa tcgatcacgt tatcaaaacc gcactgcgtg agaagaagcc agtgtacctg   1680
gagattgcct gcaacattgc gtctatgccg tgcgcagcac cgggtcctgc gagcgcgttg   1740
tttaacgatg aggccagcga cgaagcgagc ctgaacgcgg ctgttgaaga aacgctgaaa   1800
ttcattgcaa atcgtgataa ggttgctgtc ctggttggca gcaagctgcg tgccgcaggc   1860
gcggaagaag cagcggtgaa gttcgcagat gccctgggtg gcgcggtcgc aaccatggct   1920
gccgcaaaat ctttctttcc ggaagagaat ccacactata tcggcactag ctggggtgag   1980
gtgtcttatc cgggcgtcga gaaaaccatg aaagaagcgg atgcggtgat cgccctggct   2040
ccggttttca cgattacag caccactggc tggacggata ttccggaccc gaaaaagctg   2100
gtgctggcgg agccgcgtag cgtggtggtc aatggtatcc gttttccgtc cgtccatctg   2160
aaggactacc tgacccgcct ggcgcagaag gttagcaaga aaacgggtgc gctggatttc   2220
ttcaaatcgc tgaatgcagg tgaactgaaa aaggcagccc cagcagatcc gtccgcaccg   2280
ctggtgaatg cggagatcgc gcgtcaagtc gaagctctgc tgacgccgaa cacgaccgtt   2340
atcgcggaga cgggtgacag ctggtttaac gcgcaacgta tgaagttgcc gaatggtgct   2400
cgagttgagt acgagatgca atggggccac attggctggt ccgtgcctgc agcctttggt   2460
tacgccgttg gtgccccgga gcgtcgcaac attctgatgg tgggtgacgg tagctttcaa   2520
ctgaccgccc aagaggtcgc tcagatggtc cgcctgaaac tgcctgtcat cattttcctg   2580
atcaataact acggttacac gatcgaggtt atgatccatg atggcccgta caacaacatt   2640
aagaattggg actacgcggg tttgatggag gttttcaatg gcaacggtgg ttatgactcc   2700
ggtgcgggta aggtctgaa agcaaagacg ggtggcgagc tcgcagaggc gattaaggtt   2760
gcgctggcga ataccgacgg cccgaccttg attgagtgtt tcattggtcg cgaggattgc   2820
accgaagaac tggtcaaatg gggcaagcgc gtcgcagccg cgaattcccg taaaccggtt   2880
```

-continued

| | |
|---|---|
| aataagcttc tcggccatca ccatcaccat cactagaagc ttctctagag aactatttcc | 2940 |
| gtcaatcgag ttcgtaccta agggcgacac aaaatttatt ctaaatgcat aataaatact | 3000 |
| gataacatct tatagtttgt attatatttt gtattatcgt tgacatgtat aattttgata | 3060 |
| tcaaaaactg attttcoctt tattattttc gagatttatt tcttaattc tctttaacaa | 3120 |
| actagaaata ttgtatatac aaaaaatcat aaataataga tgaatagttt aattataggt | 3180 |
| gttcatcaat cgaaaaagca acgtatctta tttaaagtgc gttgctttt tctcatttat | 3240 |
| aaggttaaat aattctcata tatcaagcaa agtgacaggc gcccttaaat attctgacaa | 3300 |
| atgctctttc cctaaactcc ccccataaaa aaacccgccg aagcgggttt ttacgttatt | 3360 |
| tgcggattaa cgattactcg ttatcagaac cgcccagggg gcccgagctt aagactggcc | 3420 |
| gtcgttttac aacacagaaa gagtttgtag aaacgcaaaa aggccatccg tcaggggcct | 3480 |
| tctgcttagt ttgatgcctg gcagttccct actctcgcct tccgcttcct cgctcactga | 3540 |
| ctcgctgcgc tcggtcgttc ggctgcggcg agcggtatca gctcactcaa aggcggtaat | 3600 |
| acggttatcc acagaatcag gggataacgc aggaaagaac atgtgagcaa aaggccagca | 3660 |
| aaaggccagg aaccgtaaaa aggccgcgtt gctggcgttt ttccataggc tccgccccc | 3720 |
| tgacgagcat cacaaaaatc gacgctcaag tcagaggtgg cgaaacccga caggactata | 3780 |
| aagataccag gcgtttcccc ctggaagctc cctcgtgcgc tctcctgttc cgaccctgcc | 3840 |
| gcttaccgga tacctgtccg cctttctccc ttcgggaagc gtggcgcttt ctcatagctc | 3900 |
| acgctgtagg tatctcagtt cggtgtaggt cgttcgctcc aagctgggct gtgtgcacga | 3960 |
| accccccgtt cagcccgacc gctgcgcctt atccggtaac tatcgtcttg agtccaaccc | 4020 |
| ggtaagacac gacttatcgc cactggcagc agccactggt aacaggatta gcagagcgag | 4080 |
| gtatgtaggc ggtgctacag agttcttgaa gtggtgggct aactacggct acactagaag | 4140 |
| aacagtattt ggtatctgcg ctctgctgaa gccagttacc ttcggaaaaa gagttggtag | 4200 |
| ctcttgatcc ggcaaacaaa ccaccgctgg tagcggtggt ttttttgttt gcaagcagca | 4260 |
| gattacgcgc agaaaaaaag gatctcaaga agatcctttg atcttttcta cggggtctga | 4320 |
| cgctcagtgg aacgacgcgc gcgtaactca cgttaaggga ttttggtcat gagcttgcgc | 4380 |
| cgtcccgtca gtcagcgta atgctctgct tt | 4412 |

<210> SEQ ID NO 39
<211> LENGTH: 4418
<212> TYPE: DNA
<213> ORGANISM: Artificial Sequence
<220> FEATURE:
<223> OTHER INFORMATION: Description of Artificial Sequence: Synthetic
      plasmid pJ251:oad

<400> SEQUENCE: 39

| | |
|---|---|
| gcttttagaa aaactcatcg agcatcaaat gaaactgcaa tttattcata tcaggattat | 60 |
| caataccata ttttgaaaa agccgtttct gtaatgaagg agaaaactca ccgaggcagt | 120 |
| tccataggat ggcaagatcc tggtatcggt ctgcgattcc gactcgtcca acatcaatac | 180 |
| aacctattaa tttcccctcg tcaaaaataa ggttatcaag tgagaaatca ccatgagtga | 240 |
| cgactgaatc cggtgagaat ggcaaaagtt tatgcatttc tttccagact tgttcaacag | 300 |
| gccagccatt acgctcgtca tcaaaatcac tcgcatcaac caaaccgtta ttcattcgtg | 360 |
| attgcgcctg agcgaggcga aatacgcgat cgctgttaaa aggacaatta caaacaggaa | 420 |
| tcgagtgcaa ccggcgcagg aacactgcca gcgcatcaac aatattttca cctgaatcag | 480 |

```
gatattcttc taatacctgg aacgctgttt ttccggggat cgcagtggtg agtaaccatg    540
catcatcagg agtacggata aaatgcttga tggtcggaag tggcataaat tccgtcagcc    600
agtttagtct gaccatctca tctgtaacat cattggcaac gctacctttg ccatgtttca    660
gaaacaactc tggcgcatcg ggcttcccat acaagcgata gattgtcgca cctgattgcc    720
cgacattatc gcgagcccat ttatacccat ataaatcagc atccatgttg gaatttaatc    780
gcggcctcga cgtttcccgt tgaatatggc tcatattctt cctttttcaa tattattgaa    840
gcatttatca gggttattgt ctcatgagcg gatacatatt tgaatgtatt tagaaaaata    900
aacaaatagg ggtcagtgtt acaaccaatt aaccaattct gaacattatc gcgagcccat    960
ttatacctga atatggctca taacacccct tgtttgcctg gcggcagtag cgcggtggtc   1020
ccacctgacc ccatgccgaa ctcagaagtg aaacgccgta gcgccgatgg tagtgtgggg   1080
actccccatg cgagagtagg gaactgccag gcatcaaata aaacgaaagg ctcagtcgaa   1140
agactgggcc tttcgcccgg gctaattagg gggtgtcgcc cttattcgac tctataggga   1200
agttcctatt ctctagaaag tataggaact tctgaagggg ggtttcgccc ggggacagct   1260
gtcggtttga ataaatgaca aaaagcaaag cctttgtgcc gatgaatctc tatactgttt   1320
cacagacctg ctgccctgcg gggcggccat cttcctttat tcgcttataa gcgtggagaa   1380
ttaaaatgac ggatacccctg accttcaaca ccaaacattt gttggaagcg ctgtttgaaa   1440
gcggtattcg tcacttcatt gtttctccgg gttctcgtag cacccgatt gcactgctgc    1500 tggcagaata cgcagagcag aataacgaga tcaagctgtt cgttgacgtg gatgagcgca   1560
gcgcgggttt cttcgcactg gcatcgcgaa aacgttgct ggagccggtt gttttgctgg    1620
gtacctcggg taccgccatc gctgaataca tgcctgcggt ggcggaagcc tatgcggcga   1680
atatcccgct ggtcgtgttg agcaccgatc gtccacagga attgcagttc aacggcgcac   1740
cgcaaactat tccgcaaagc aacctgttcg gtcaactgac gaaacaggca gtcctgattc   1800
gcctgcaaga catgcacagc gatgtgaccg agtacatcga cttatcgtt cagaaggtcg    1860 ttaatctgtc cattaccgcg cctcgtggcc cgattcagat caacctgccg ctgcgcaaac   1920
cgctgatgcc ggtcctggat cgtcaagacg aggtgcacgt tcagcgtgtc gtgtttgaca   1980
aacaaagcgt gcaatatcgc ttgccgccga ttacggcgaa acgcctgctg atcctggcag   2040
gtccgaatgt cctgaatagc tacgatgata gcctgaagaa gtttgcgatc aaaaacaatg   2100
ttccagttat cgcggatgtt ctgtcccaaa gccgccacac gtataccatt cacggtattg   2160
acgttctgct gcaagcccac aagatcaacg ccgacctgaa accggatctg gtggttcgtt   2220
ttggcaagac gccggttagc gcgcgtgtcc tgcaatggct gaaagaagag aacattctga   2280
cctggcacgt ggacgaggac gcaggcgtgg atcacacccg tcatatcgtc cgtgccatca   2340
agatggcgcc tcatgatttt ctggaatcca tgcatctgac gttgagcaaa accagattg    2400 acttcaacca gaagtggctg tctctgccga aagtgatcaa aactcgtaac gagatgaata   2460
tcatcaccgc attggacgac gcggtcccgg atgcactca catcttcgtg gcgaacagca    2520
tgccgattcg tgacatggac aactttttca cgggtaatca cacccagcgc atttacgcta   2580
atcgtggtgc aaatggtatt gatggcgtga ttagctccgc cctgggcatg agcgcggtcg   2640
tcaagcaacg ttcggtcctg ctgacggtg acctgacgct gtttcatgac atgaacggtc    2700
tgatgatggc gaagaattac cagctgccgc tggacatcat tgtgattaac aacaatggcg   2760
gtggcatttt cagcttcttg ccacaagccg gtgctccgaa gtactttgag cagctgttcg   2820
gtaccccgct gaacattgac atcaaaaaga ttgctgacct gtattacatc gattaccatc   2880
```

```
agttgaatgt gccggaggcc ctgagccaga tcctgcagac gccgagcaaa accacccgcc    2940
tgatcgagta taagtccgat caccagcgta accgtgacga tcatcgcgaa gtgctggaga    3000
tgctgaaaca ccaccatcat cattagcacg tgaaaatgaa gggaagttcc tatactttct    3060
agagaatagg aacttctata gggagtcgaa taagggcgac acaaaaggta ttctaaatgc    3120
ataataaata ctgataacat cttatagttt gtattatatt ttgtattatc gttgacatgt    3180
ataattttga tatcaaaaac tgattttccc tttattattt tcgagattta ttttcttaat    3240
tctctttaac aaactagaaa tattgtatat acaaaaaatc ataaataata gatgaatagt    3300
ttaattatag gtgttcatca atcgaaaaag caacgtatct tatttaaagt gcgttgcttt    3360
tttctcattt ataaggttaa ataattctca tatatcaagc aaagtgacag gcgcccttaa    3420
atattctgac aaatgctctt tccctaaact cccccataa aaaacccgc cgaagcgggt    3480 ttttacgtta tttgcggatt aacgattact cgttatcaga accgcccagg atgcctggca    3540
gttccctact ctcgccgctg cgctcggtcg ttcggctgcg ggacctcagc gctagcggag    3600
tgtatactgg cttactatgt tggcactgat gagggtgtca gtgaagtgct tcatgtggca    3660
ggagaaaaaa ggctgcaccg gtgcgtcagc agaatatgtg atacaggata tattccgctt    3720
cctcgctcac tgactcgcta cgctcggtcg ttcgactgcg gcgagcggaa atggcttacg    3780
aacggggcgg agatttcctg gaagatgcca ggaagatact aacagggaa gtgagagggc    3840 cgcggcaaag ccgttttcc ataggctccg ccccctgac aagcatcacg aaatctgacg    3900
ctcaaatcag tggtggcgaa acccgacagg actataaaga taccaggcgt ttccccctgg    3960
cggctccctc gtgcgctctc ctgttcctgc ctttcggttt accggtgtca ttccgctgtt    4020
atggccgcgt ttgtctcatt ccacgcctga cactcagttc cgggtaggca gttcgctcca    4080
agctggactg tatgcacgaa ccccccgttc agtccgaccg ctgcgcctta tccggtaact    4140
atcgtcttga gtccaacccg gaaagacatg caaaagcacc actggcagca gccactggta    4200
attgatttag aggagttagt cttgaagtca tgcgccggtt aaggctaaac tgaaaggaca    4260
agttttggtg actgcgctcc tccaagccag ttacctcggt tcaaagagtt ggtagctcag    4320
agaaccttcg aaaaaccgcc ctgcaaggcg gttttttcgt tttcagagca agagattacg    4380
cgcagaccaa aacgatctca agaagatcat cttattaa                           4418
```

<210> SEQ ID NO 40
<211> LENGTH: 8621
<212> TYPE: DNA
<213> ORGANISM: Artificial Sequence
<220> FEATURE:
<223> OTHER INFORMATION: Description of Artificial Sequence: Synthetic plasmid pJ206:kgd

<400> SEQUENCE: 40

```
ggtggcggta cttgggtcga tatcaaagtg catcacttct tcccgtatgc ccaactttgt      60
atagagagcc actgcgggat cgtcaccgta atctgcttgc acgtagatca cataagcacc     120
aagcgcgttg gcctcatgct tgaggagatt gatgagcgcg gtggcaatgc cctgcctccg     180
gtgctcgccg gagactgcga gatcatagat atagatctca ctacgcggct gctcaaactt     240
gggcagaacg taagccgcga gagcgccaac aaccgcttct tggtcgaagg cagcaagcgc     300
gatgaatgtc ttactacgga gcaagttccc gaggtaatcg gagtccggct gatgttggga     360
gtaggtggct acgtcaccga actcacgacc gaaaagatca agagcagccc gcatggattt     420
gacttggtca gggccgagcc tacatgtgcg aatgatgccc atacttgagc cacctaactt     480
```

```
tgttttaggg cgactgccct gctgcgtaac atcgttgctg ctccataaca tcaaacatcg    540
acccacggcg taacgcgctt gctgcttgga tgcccgaggc atagactgta caaaaaaaca    600
gtcataacaa gccatgaaaa ccgccactgc gccgttacca ccgctgcgtt cggtcaaggt    660
tctggaccag ttgcgtgagc gcattttttt ttcctcctcg gcgtttacgc cccgccctgc    720
cactcatcgc agtactgttg taattcatta agcattctgc cgacatggaa gccatcacag    780
acggcatgat gaacctgaat cgccagcggc atcagcacct tgtcgccttg cgtataatat    840
ttgcccatag tgaaaacggg ggcgaagaag ttgtccatat tggccacgtt aaatcaaaa     900 ctggtgaaac tcacccaggg attggcgctg acgaaaaaca tattctcaat aaacccttta    960
gggaaatagg ccaggttttc accgtaacac gccacatctt gcgaatatat gtgtagaaac   1020
tgccggaaat cgtcgtggta ttcactccag agcgatgaaa acgtttcagt ttgctcatgg   1080
aaaacggtgt aacaagggtg aacactatcc catatcacca gctcaccgtc tttcattgcc   1140
atacggaact ccggatgagc attcatcagg cgggcaagaa tgtgaataaa ggccggataa   1200
aacttgtgct tattttcctt tacggtcttt aaaaaggccg taatatccag ctgaacggtc   1260
tggttatagg tacattgagc aactgactga atgcctcaa  aatgttcttt acgatgccat   1320
tgggatatat caacggtggt atatccagtg atttttttct ccattttttt ttcctccttt   1380
agaaaaactc atcgagcatc aaatgaaact gcaatttatt catatcagga ttatcaatac   1440 catattttg  aaaagccgt ttctgtaatg aaggagaaaa ctcaccgagg cagttccata   1500
ggatggcaag atcctggtat cggtctgcga ttccgactcg tccaacatca atacaaccta   1560
ttaatttccc ctcgtcaaaa ataaggttat caagtgagaa atcaccatga gtgacgactg   1620
aatccggtga gaatggcaaa agtttatgca tttctttcca gacttgttca acaggccagc   1680
cattacgctc gtcatcaaaa tcactcgcat caaccaaacc gttattcatt cgtgattgcg   1740
cctgagcgag gcgaaatacg cgatcgctgt taaaaggaca attacaaaca ggaatcgagt   1800
gcaaccggcg caggaacact gccagcgcat caacaatatt tcacctgaa  tcaggatatt   1860 cttctaatac ctggaacgct gtttttccgg ggatcgcagt ggtgagtaac catgcatcat   1920
caggagtacg gataaaatgc ttgatggtcg gaagtggcat aaattccgtc agccagttta   1980
gtctgaccat ctcatctgta acatcattgg caacgctacc tttgccatgt ttcagaaaca   2040
actctggcgc atcgggcttc ccatacaagc gatagattgt cgcacctgat tgcccgacat   2100
tatcgcgagc ccatttatac ccatataaat cagcatccat gttggaattt aatcgcggcc   2160
tcgacgtttc ccgttgaata tggctcattt ttttttcctc ctttaccaat gcttaatcag   2220
tgaggcacct atctcagcga tctgtctatt tcgttcatcc atagttgcct gactccccgt   2280
cgtgtagata actacgatac gggagggctt accatctggc cccagcgctg cgatgatacc   2340
gcgagaacca cgctcaccgg ctccggattt atcagcaata aaccagccag ccggaagggc   2400
cgagcgcaga agtggtcctg caactttatc cgcctccatc cagtctatta attgttgccg   2460
ggaagctaga gtaagtagtt cgccagttaa tagtttgcgc aacgttgttg ccatcgctac   2520
aggcatcgtg gtgtcacgct cgtcgtttgg tatggcttca ttcagctccg gttcccaacg   2580
atcaaggcga gttacatgat cccccatgtt gtgcaaaaaa gcggttagct ccttcggtcc   2640
tccgatcgtt gtcagaagta agttggccgc agtgttatca ctcatggtta tggcagcact   2700
gcataattct cttactgtca tgccatccgt aagatgcttt tctgtgactg gtgagtactc   2760
aaccaagtca ttctgagaat agtgtatgcg gcgaccgagt tgctcttgcc cggcgtcaat   2820
```

```
acgggataat accgcgccac atagcagaac tttaaaagtg ctcatcattg gaaaacgttc    2880
ttcggggcga aaactctcaa ggatcttacc gctgttgaga tccagttcga tgtaacccac    2940
tcgtgcaccc aactgatctt cagcatcttt tactttcacc agcgtttctg ggtgagcaaa    3000
aacaggaagg caaaatgccg caaaaaaggg aataagggcg acacggaaat gttgaatact    3060
catattcttc cttttcaat attattgaag catttatcag ggttattgtc tcatgagcgg     3120
atacatattt gaatgtattt agaaaaataa acaaatagg gtcagtgtta caaccaatta     3180
accaattctg aacattatcg cgagcccatt tatacctgaa tatggctcat aacacccctt    3240
gtttgcctgg cggcagtagc gcggtggtcc cacctgaccc catgccgaac tcagaagtga    3300
aacgccgtag cgccgatggt agtgtgggga ctccccatgc gagagtaggg aactgccagg    3360
catcaaataa aacgaaaggc tcagtcgaaa gactgggcct ttcgcccggg ctaattgagg    3420
ggtgtcgccc ttttgacgga tatcaagctt ctattaaccg aacgcttcgt ccaagatttc    3480
ttgctgctcc acggcatgaa ccttcgagga accgctgctc ggcgcagaca tcgcgcgacg    3540
ggagatacgc ttgatgcccg ccaacttgtc cggcagcaac tccggcaact ccaaaccgaa    3600
acgcggccag gcgccctggt tcgctggttc ctcctggacc caaaagaact ctttgacatt    3660
ttcgtaacga tccagggttt cacgcagacg acgacgcggc aacggcgcca gttgctccag    3720
acgcacaatt gccagatcat tacggttgtc tttcgccttg cgtgccgcca attcataata    3780
caacttaccg gaggtcaaca gaatacggct aactttattg cggtcgccga taccatcctc    3840
gtaggtcggt tcctccagga cgctacggaa tttaatctcg gtaaaatcct taatctccga    3900
aaccgccgcc ttgtggcgca gcatggattt cggggtaaac acgatcaacg gacgttggat    3960
gccgtccaac gcgtggcggc gcagcaagtg aaagtaattg gacggggtgc tcggcatcgc    4020
gatcgtcatg ctaccctcag cccacagctg caaaaagcgc tcaatgcgcg ccgacgtgtg    4080
gtccgggccc tgaccctcgt ggccgtgtgg cagcaacaga caacgttgg acagctgacc      4140 ccatttcgct tcgcccgagc tgatgaactc gtcaatgatc gactgggcac cattaacaaa    4200
gtcgccgaat tgcgcctccc acagcacaac cgcgtctgga ttgccaacgg tataaccgta    4260
ctcaaaaccc acagccgcgt attccgacaa cggcgaatca taaaccagga acttaccacc    4320
ggtcgggctg ccgtcgctgt tagtcgccag cagctgcagc ggggtgaact cctcgccggt    4380
gtgacggtcg atcagcacag aatgacgctg gctaaaggtg ccacgacgag agtcttgacc    4440
gctcagacgg accagcttgc cctcagcaac caggctgccc agcgccagca actcaccaaa    4500
cgcccagtca atcttaccct catacgccat ctcacgacgc ttttccagca ccggctgaac    4560
gcgcgggtgt gccgtgaaac cgttaggcag cgccaggaag gcatcaccga tacgtgccag    4620
cagggatttg tcaacagcgg tcgccaggcc cgctgggatc atttggtccg actcgacgct    4680
ctccgacggt tggacgccgt gcttctccag ttcgcgcact tcgttgaaca cacgctccag    4740
ttggccctgg taatcgcgca gcgcatcctc cgcctctttc atgctgatgt cgccacgacc    4800
gatcagagcc tcggtgtagg atttacgggc gccacgcttg gtgtccacga cgtcatagac    4860
atacggattg gtcatagatg gatcgtcacc ctcattatga ccacgacgac gatagcacag    4920
catgtcaata acaacgtcct tttaaagcg ttggcggaag tcaactgcca aacgcgcaac    4980
ccagacacac gcttctggat cgtcgccgtt cacgtggaag attggcgcac cgatcatctt    5040
cgccacatcc gtgcagtact cgctcgaacg agagtattcc ggagcggtgg tgaagccgat    5100
ttggttgttc acaatgatgt gaatcgtacc acccacacga tagccaggca gatttgccag    5160
attcagcgtc tccgcaacaa cgccttgacc cgcgaaggcc gcatcaccgt gcagcatcaa    5220
```

```
cggaacgacg gagaatgcac gttggccgtc ggagtcaatg gaaccgtggt ccagcaggtc   5280
ttgcttcgca cgcaccaaac cttccagcac tggatcgacc gcttccaaat gggacggatt   5340
tgccgtcagg gaaacctgaa tatcgttatc gccaaacatt tgcagataca gacccgtcgc   5400
acccaggtgg tacttgacat cgccggaacc gtgagcctgg gacgggttca gattgccttc   5460
aaactccgta agatttgcg aatacggttt gcccacgatg ttcgccagga cattcaagcg    5520
accacggtgc ggcatgccaa tgaccacttc atccaaacca tgctcggcac attggtcaat   5580
cgccgcgtcc atcattggaa taacagattc cgcaccctcc aggctaaaac gcttttggcc   5640
cacatacttg gtttgcagga aggtttcaaa cgcctccgct gcgttcagtt tcgacaagat   5700
gtacttttgt tgagcaacgg tcggtttgac gtgcttcgtc tcgacacgct gctccagcca   5760
ctccttttgt tccgggtcca gaatgtgcgc gtactcaaca ccgatgtgac ggcagtacgc   5820
gtcgcgcagc aaacccagca cgtcacgcag ctttttgtat tgagcacccg cgaaaccgtc   5880
aaccttaaag acgcggtcca ggtcccacag agtcaggcca tgcgtcaaca cctccaaatc   5940
cggatgcgaa cgaaagcgcg ccttatccaa gcgcaacggg tcggtgtccg ccatcagatg   6000
gccgcggttg cgataggccg cgatcaggtt catcacacgt gcgttcttgt caacgatcga   6060
gtccggatta tcggtgctcc aacgcactgg caggtacggg atgctcagct cgcggaagac   6120
ctcatcccag aagccatcag acaacagcag ttcatgaatg gtacgcagga agtcaccgct   6180
ttccgcacct tgaatgatac ggtggtcgta ggtagaagtc agggtaatca gtttgccaat   6240
acccagctca gcgatgcgtt cctcggacgc gccttggaac tccgccggat attccatcgc   6300
accgacaccg atgatagcac cttgacctgg catcaggcgt ggcacagagt gcaccgtgcc   6360
aatcgtgccc ggattcgtca gcgaaatcgt aacgccagcg aagtcctcgg tggtcagttt   6420
accatcacga gcacgacgga cgatgtcctc gtacgcggta acgaactgcg cgaagcgcat   6480
cgtctcgcaa cgtttgatac cggccaccac cagagagcgc ttgccatctt taccttgcag   6540
gtcaatagcc agacccagat tggtgtgcgc aggagtaacc gccgtcggct taccgtccac   6600
ctccgtgtag tggcgattca tattcgggaa cttcttaacc gcctgaacca gagcataacc   6660
cagcaaatgg gtaaagctga ttttaccacc acgcgtgcgt ttcaactgat tattgatcac   6720
gatacgatta tcgatcaaca atttcgctgg cacagcacgc accgaggtcg ccgtaggcac   6780
ttccagcgac gcgctcatgt tcttcacgac agcagccgcc gcaccacgca ggacagcaac   6840
ttcatcgcct tcggctggcg gaggcaccgc ggtcttggcg gccagagccg ccacgacacc   6900
gttgcccgct gcgccgtgt cggccggttt cggcggcgct gcggagccg ccgctgccgc     6960 acgctcagcg accaaagggc tggtcacacg agtcggctca gcagccggtt gggaagtcgg   7020
ctccgggcta tagtccacca gaaactcatg ccagcttggg tcaacggaag acggatcatc   7080
acgaaattta cgatacatac caacacgaga cgggtcctga gtcaccatgg atatatctcc   7140
ttcttaaaga attcgatatc tcagcgacaa gggcgacaca aaattattc taaatgcata    7200 ataaatactg ataacatctt atagtttgta ttatattttg tattatcgtt gacatgtata   7260
attttgatat caaaaactga ttttcccttt attatttttcg agatttattt tcttaattct  7320
ctttaacaaa ctagaaatat tgtatataca aaaaatcata aataatagat gaatagttta   7380
attataggtg ttcatcaatc gaaaaagcaa cgtatcttat ttaaagtgcg ttgcttttttt  7440 ctcatttata aggttaaaata attctctatat atcaagcaaa gtgacaggcg ccccttaaata 7500 ttctgacaaa tgctctttcc ctaaactccc cccataaaaa aacccgccga agcgggtttt   7560
```

-continued

```
tacgttattt gcggattaac gattactcgt tatcagaacc gcccagggggg cccgagctta    7620 agactggccg tcgttttaca acacagaaag agtttgtaga aacgcaaaaa ggccatccgt    7680
caggggcctt ctgcttagtt tgatgcctgg cagttcccta ctctcgcctt ccgcttcctc    7740
gctcactgac tcgctgcgct cggtcgttcg gctgcggcga cggtatcag ctcactcaaa    7800 ggcggtaata cggttatcca cagaatcagg ggataacgca ggaaagaaca tgtgagcaaa    7860
aggccagcaa aaggccagga accgtaaaaa ggccgcgttg ctggcgtttt tccataggct    7920 ccgccccccct gacgagcatc acaaaaatcg acgctcaagt cagaggtggc gaaacccgac    7980
aggactataa agataccagg cgtttccccc tggaagctcc ctcgtgcgct ctcctgttcc    8040
gaccctgccg cttaccggat acctgtccgc ctttctccct tcgggaagcg tggcgctttc    8100
tcatagctca cgctgtaggt atctcagttc ggtgtaggtc gttcgctcca agctgggctg    8160
tgtgcacgaa ccccccgttc agcccgaccg ctgcgcctta tccggtaact atcgtcttga    8220
gtccaacccg gtaagacacg acttatcgcc actggcagca gccactggta acaggattag    8280
cagagcgagg tatgtaggcg gtgctacaga gttcttgaag tggtgggcta actacggcta    8340
cactagaaga acagtatttg gtatctgcgc tctgctgaag ccagttacct tcggaaaaag    8400
agttggtagc tcttgatccg gcaaacaaac caccgctggt agcggtggtt ttttgtttg    8460 caagcagcag attacgcgca gaaaaaaagg atctcaagaa gatcctttga tcttttctac    8520
ggggtctgac gctcagtgga acgacgcgcg cgtaactcac gttaagggat tttggtcatg    8580
agcttgcgcc gtcccgtcaa gtcagcgtaa tgctctgctt a                         8621
```

<210> SEQ ID NO 41
<211> LENGTH: 4401
<212> TYPE: DNA
<213> ORGANISM: Artificial Sequence
<220> FEATURE:
<223> OTHER INFORMATION: Description of Artificial Sequence: Synthetic plasmid pTrc-HisB

<400> SEQUENCE: 41

```
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc   120
gcactcccgt tctggataat gttttttgcg ccgacatcat aacggttctg gcaaatattc   180
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
caatttatca gacaatctgt gtgggcactc gaccggaatt atcgattaac tttattatta   360
aaaattaaag aggtatatat taatgtatcg attaaataag gaggaataaa ccatggggggg   420 ttctcatcat catcatcatc atggtatggc tagcatgact ggtggacagc aaatgggtcg   480
ggatctgtac gacgatgacg ataaggatcc gagctcgaga tctgcagctg gtaccatatg   540
ggaattcgaa gcttggctgt tttggcggat gagagaagat tttcagcctg atacagatta   600
aatcagaacg cagaagcggt ctgataaaac agaatttgcc tggcggcagt agcgcggtgg   660
tcccacctga ccccatgccg aactcagaag tgaaacgccg tagcgccgat ggtagtgtgg   720
ggtctcccca tgcgagagta gggaactgcc aggcatcaaa taaaacgaaa ggctcagtcg   780
aaagactggg cctttcgttt tatctgttgt ttgtcggtga acgctctcct gagtaggaca   840
aatccgccgg gagcggattt gaacgttgcg aagcaacggc ccggagggtg cgggcagga   900 cgcccgccat aaactgccag gcatcaaatt aagcagaagg ccatcctgac ggatggcctt   960
```

-continued

```
tttgcgtttc tacaaactct ttttgtttat tttctaaat acattcaaat atgtatccgc   1020
tcatgagaca ataaccctga taaatgcttc aataatattg aaaaaggaag agtatgagta   1080
ttcaacattt ccgtgtcgcc cttattccct tttttgcggc attttgcctt cctgttttg    1140
ctcacccaga aacgctggtg aaagtaaaag atgctgaaga tcagttgggt gcacgagtgg   1200
gttacatcga actggatctc aacagcggta agatccttga gagttttcgc cccgaagaac   1260
gttttccaat gatgagcact tttaaagttc tgctatgtgg cgcggtatta tcccgtgttg   1320
acgccgggca agagcaactc ggtcgccgca tacactattc tcagaatgac ttggttgagt   1380
actcaccagt cacagaaaag catcttacgg atggcatgac agtaagagaa ttatgcagtg   1440
ctgccataac catgagtgat aacactgcgg ccaacttact tctgacaacg atcggaggac   1500
cgaaggagct aaccgctttt ttgcacaaca tgggggatca tgtaactcgc cttgatcgtt   1560
gggaaccgga gctgaatgaa gccataccaa acgacgagcg tgacaccacg atgcctgtag   1620
caatggcaac aacgttgcgc aaactattaa ctggcgaact acttactcta gcttcccggc   1680
aacaattaat agactggatg gaggcggata aagttgcagg accacttctg cgctcggccc   1740
ttccggctgg ctggtttatt gctgataaat ctggagccgg tgagcgtggg tctcgcggta   1800
tcattgcagc actggggcca gatggtaagc cctcccgtat cgtagttatc tacacgacgg   1860
ggagtcaggc aactatggat gaacgaaata gacagatcgc tgagataggt gcctcactga   1920
ttaagcattg gtaactgtca gaccaagttt actcatatat actttagatt gatttaaaac   1980
ttcattttta atttaaaagg atctaggtga agatccttt tgataatctc atgaccaaaa    2040
tcccttaacg tgagttttcg ttccactgag cgtcagaccc cgtagaaaag atcaaaggat   2100
cttcttgaga tccttttttt ctgcgcgtaa tctgctgctt gcaaacaaaa aaaccaccgc   2160
taccagcggt ggtttgtttg ccggatcaag agctaccaac tctttttccg aaggtaactg   2220
gcttcagcag agcgcagata ccaaatactg tccttctagt gtagccgtag ttaggccacc   2280
acttcaagaa ctctgtagca ccgcctacat acctcgctct gctaatcctg ttaccagtgg   2340
ctgctgccag tggcgataag tcgtgtctta ccgggttgga ctcaagacga tagttaccgg   2400
ataaggcgca gcggtcgggc tgaacggggg gttcgtgcac acagcccagc ttggagcgaa   2460
cgacctacac cgaactgaga tacctacagc gtgagctatg agaaagcgcc acgcttcccg   2520
aagggagaaa ggcggacagg tatccggtaa gcggcagggt cggaacagga gagcgcacga   2580
gggagcttcc agggggaaac gcctggtatc tttatagtcc tgtcgggttt cgccacctct   2640
gacttgagcg tcgatttttg tgatgctcgt caggggggcg gagcctatgg aaaaacgcca   2700
gcaacgcggc ctttttacgg ttcctggcct tttgctggcc ttttgctcac atgttctttc   2760
ctgcgttatc ccctgattct gtggataacc gtattaccgc ctttgagtga gctgataccg   2820
ctcgccgcag ccgaacgacc gagcgcagcg agtcagtgag cgaggaagcg gaagagcgcc   2880
tgatgcggta ttttctcctt acgcatctgt gcggtatttc acaccgcata tggtgcactc   2940
tcagtacaat ctgctctgat gccgcatagt taagccagta tacactccgc tatcgctacg   3000
tgactgggtc atggctgcgc cccgacaccc gccaacaccc gctgacgcgc cctgacgggc   3060
ttgtctgctc ccggcatccg cttacagaca agctgtgacc gtctccggga gctgcatgtg   3120
tcagaggttt tcaccgtcat caccgaaacg cgcgaggcag cagatcaatt cgcgcgcgaa   3180
ggcgaagcgg catgcattta cgttgacacc atcgaatggc gcaaaacctt tcgcggtatg   3240
gcatgatagc gcccggaaga gagtcaattc agggtggtga atgtgaaacc agtaacgtta   3300
tacgatgtcg cagagtatgc cggtgtctct tatcagaccg tttcccgcgt ggtgaaccag   3360
```

-continued

```
gccagccacg tttctgcgaa aacgcgggaa aaagtggaag cggcgatggc ggagctgaat    3420
tacattccca accgcgtggc acaacaactg gcgggcaaac agtcgttgct gattggcgtt    3480
gccacctcca gtctggccct gcacgcgccg tcgcaaattg tcgcggcgat taaatctcgc    3540
gccgatcaac tgggtgccag cgtggtggtg tcgatggtag aacgaagcgg cgtcgaagcc    3600
tgtaaagcgg cggtgcacaa tcttctcgcg caacgcgtca gtgggctgat cattaactat    3660
ccgctggatg accaggatgc cattgctgtg gaagctgcct gcactaatgt tccggcgtta    3720
tttcttgatg tctctgacca gacacccatc aacagtatta ttttctccca tgaagacggt    3780
acgcgactgg gcgtggagca tctggtcgca ttgggtcacc agcaaatcgc gctgttagcg    3840
ggcccattaa gttctgtctc ggcgcgtctg cgtctggctg gctggcataa atatctcact    3900
cgcaatcaaa ttcagccgat agcggaacgg gaaggcgact ggagtgccat gtccggtttt    3960
caacaaacca tgcaaatgct gaatgagggc atcgttccca ctgcgatgct ggttgccaac    4020
gatcagatgg cgctgggcgc aatgcgcgcc attaccgagt ccgggctgcg cgttggtgcg    4080
gatatctcgg tagtgggata cgacgatacc gaagacagct catgttatat cccgccgtca    4140
accaccatca acaggatttt cgcctgctg gggcaaacca gcgtggaccg cttgctgcaa    4200
ctctctcagg gccaggcggt gaagggcaat cagctgttgc ccgtctcact ggtgaaaaga    4260
aaaaccaccc tggcgcccaa tacgcaaacc gcctctcccc gcgcgttggc cgattcatta    4320
atgcagctgg cacgacaggt ttcccgactg gaaagcgggc agtgagcgca acgcaattaa    4380
tgtgagttag cgcgaattga g                                             4401
```

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gggatatcat gagctatacc gttgg                                           25

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gaaatagttc tctagagaag cttc                                            24

<210> SEQ ID NO 44
<211> LENGTH: 6123
<212> TYPE: DNA
<213> ORGANISM: Artificial Sequence
<220> FEATURE:
<223> OTHER INFORMATION: Description of Artificial Sequence: Synthetic
      plasmid pTrc:pdc-his

<400> SEQUENCE: 44

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
```

```
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgagcta    420
taccgttggc acctatctgg cagaacgcct ggtgcagatc ggcctgaaac accacttcgc    480
ggtggcgggt gactacaacc tggtgctgct ggacaacttg ctgttgaaca agaatatgga    540
acaggtgtac tgctgtaatg agctgaattg tggcttcagc gcggagggtt acgcccgggc    600
caaaggtgca gccgcagcgg ttgtgaccta tagcgttggc gcgctgagcg catttgatgc    660
gattggtggt gcgtacgctg agaatttgcc ggtcatcctg atcagcggcg caccgaacaa    720
caacgaccat gctgcgggcc acgtgctgca tcacgcgctg gtaagaccg actatcatta     780 tcagttggag atggcgaaga atatcacggc cgctgcggaa gctatctata cgccggaaga    840
ggctcctgca aaaatcgatc acgttatcaa aaccgcactg cgtgagaaga gccagtgta    900 cctggagatt gcctgcaaca ttgcgtctat gccgtgcgca gcaccgggtc ctgcgagcgc    960
gttgtttaac gatgaggcca gcgacgaagc gagcctgaac gcggctgttg aagaaacgct    1020
gaaattcatt gcaaatcgtg ataaggttgc tgtcctggtt ggcagcaagc tgcgtgccgc    1080
aggcgcggaa gaagcagcgg tgaagttcgc agatgccctg ggtggcgcgg tcgcaaccat    1140
ggctgccgca aaatctttct ttccggaaga gaatccacac tatatcggca ctagctgggg    1200
tgaggtgtct tatccgggcg tcgagaaaac catgaaagaa gcggatgcgg tgatcgccct    1260
ggctccggtt ttcaacgatt acagcaccac tggctggacg gatattccgg acccgaaaaa    1320
gctggtgctg gcggagccgc gtagcgtggt ggtcaatggt atccgttttc cgtccgtcca    1380
tctgaaggac tacctgaccc gcctggcgca gaaggttagc aagaaaacgg gtgcgctgga    1440
tttcttcaaa tcgctgaatg caggtgaact gaaaaaggca gccccagcag atccgtccgc    1500
accgctggtg aatgcggaga tcgcgcgtca agtcgaagct ctgctgacgc cgaacacgac    1560
cgttatcgcg gagacgggtg acagctggtt taacgcgcaa cgtatgaagt tgccgaatgg    1620
tgctcgagtt gagtacgaga tgcaatgggg ccacattggc tggtccgtgc ctgcagcctt    1680
tggttacgcc gttggtgccc cggagcgtcg caacattctg atggtgggtg acggtagctt    1740
tcaactgacc gcccaagagg tcgctcagat ggtccgcctg aaactgcctg tcatcatttt    1800
cctgatcaat aactacggtt acacgatcga ggttatgatc catgatggcc cgtacaacaa    1860
cattaagaat tgggactacg cgggtttgat ggaggttttc aatggcaacg gtggttatga    1920
ctccggtgcg ggtaaaggtc tgaaagcaaa gacgggtggc gagctcgcag aggcgattaa    1980
ggttgcgctg gcgaataccg acggcccgac cttgattgag tgtttcattg gtcgcgagga    2040
ttgcaccgaa gaactggtca atggggcaa gcgcgtcgca gccgcgaatt cccgtaaacc    2100
ggttaataag cttctcggcc atcaccatca ccatcactag aagcttctct aggtatggct    2160
agcatgactg gtggacagca aatgggtcgg gatctgtacg acgatgacga taaggatcga    2220 tgggatccg agctcgagat ctgcagctgg taccatatgg gaattcgaag cttggctgtt    2280
ttggcggatg agagaagatt ttcagcctga tacagattaa atcagaacgc agaagcggtc    2340
tgataaaaca gaatttgcct ggcggcagta gcgcggtggt cccacctgac cccatgccga    2400
actcagaagt gaaacgccgt agcgccgatg gtagtgtggg gtctccccat gcgagagtag    2460
ggaactgcca ggcatcaaat aaaacgaaag gctcagtcga aagactgggc ctttcgtttt    2520
```

```
atctgttgtt tgtcggtgaa cgctctcctg agtaggacaa atccgccggg agcggatttg    2580
aacgttgcga agcaacggcc cggagggtgg cgggcaggac gcccgccata aactgccagg    2640
catcaaatta agcagaaggc catcctgacg gatggccttt ttgcgtttct acaaactctt    2700
tttgtttatt tttctaaata cattcaaata tgtatccgct catgagacaa taaccctgat    2760
aaatgcttca ataatattga aaaggaaga gtatgagtat tcaacatttc cgtgtcgccc    2820
ttattccctt ttttgcggca ttttgccttc ctgttttttgc tcacccagaa acgctggtga    2880
aagtaaaaga tgctgaagat cagttgggtg cacgagtggg ttacatcgaa ctggatctca    2940
acagcggtaa gatccttgag agttttcgcc ccgaagaacg ttttccaatg atgagcactt    3000
ttaaagttct gctatgtggc gcggtattat cccgtgttga cgccgggcaa gagcaactcg    3060
gtcgccgcat acactattct cagaatgact tggttgagta ctcaccagtc acagaaaagc    3120
atcttacgga tggcatgaca gtaagagaat tatgcagtgc tgccataacc atgagtgata    3180
acactgcggc caacttactt ctgacaacga tcggaggacc gaaggagcta accgcttttt    3240
tgcacaacat gggggatcat gtaactcgcc ttgatcgttg gaaccggag ctgaatgaag    3300
ccataccaaa cgacgagcgt gacaccacga tgcctgtagc aatggcaaca acgttgcgca    3360
aactattaac tggcgaacta cttactctag cttcccggca acaattaata gactggatgg    3420
aggcggataa agttgcagga ccacttctgc gctcggccct tccggctggc tggtttattg    3480
ctgataaatc tggagccggt gagcgtgggt ctcgcggtat cattgcagca ctggggccag    3540
atggtaagcc ctcccgtatc gtagttatct acacgacggg gagtcaggca actatggatg    3600
aacgaaatag acagatcgct gagataggtg cctcactgat taagcattgg taactgtcag    3660
accaagttta ctcatatata ctttagattg atttaaaact tcattttttaa tttaaaagga    3720
tctaggtgaa gatcctttt gataatctca tgaccaaaat cccttaacgt gagttttcgt    3780
tccactgagc gtcagacccc gtagaaaaga tcaaaggatc ttcttgagat cctttttttc    3840
tgcgcgtaat ctgctgcttg caaacaaaaa aaccaccgct accagcggtg gtttgtttgc    3900
cggatcaaga gctaccaact ctttttccga aggtaactgg cttcagcaga gcgcagatac    3960
caaatactgt ccttctagtg tagccgtagt taggccacca cttcaagaac tctgtagcac    4020
cgcctacata cctcgctctg ctaatcctgt taccagtggc tgctgccagt ggcgataagt    4080
cgtgtcttac cgggttggac tcaagacgat agttaccgga taaggcgcag cggtcgggct    4140
gaacgggggg ttcgtgcaca cagcccagct tggagcgaac gacctacacc gaactgagat    4200
acctacagcg tgagctatga gaaagcgcca cgcttcccga agggagaaag gcggacaggt    4260
atccggtaag cggcagggtc ggaacaggag agcgcacgag ggagcttcca gggggaaacg    4320
cctggtatct ttatagtcct gtcgggtttc gccacctctg acttgagcgt cgatttttgt    4380
gatgctcgtc aggggggcgg agcctatgga aaaacgccag caacgcggcc ttttacggt    4440
tcctggcctt ttgctggcct tttgctcaca tgttctttcc tgcgttatcc cctgattctg    4500
tggataaccg tattaccgcc tttgagtgag ctgataccgc tcgccgcagc cgaacgaccg    4560
agcgcagcga gtcagtgagc gaggaagcgg aagagcgcct gatgcggtat tttctcctta    4620
cgcatctgtg cggtatttca caccgcatat ggtgcactct cagtacaatc tgctctgatg    4680
ccgcatagtt aagccagtat acactccgct atcgctacgt gactgggtca tggctgcgcc    4740
ccgacacccg ccaacacccg ctgacgcgcc ctgacgggct tgtctgctcc cggcatccgc    4800
ttacagacaa gctgtgaccg tctccgggag ctgcatgtgt cagaggtttt caccgtcatc    4860
accgaaacgc gcgaggcagc agatcaattc gcgcgcgaag gcgaagcggc atgcatttac    4920
```

-continued

```
gttgacacca tcgaatggcg caaaaccttt cgcggtatgg catgatagcg cccggaagag    4980
agtcaattca gggtggtgaa tgtgaaacca gtaacgttat acgatgtcgc agagtatgcc    5040
ggtgtctctt atcagaccgt ttcccgcgtg gtgaaccagg ccagccacgt ttctgcgaaa    5100
acgcgggaaa aagtggaagc ggcgatggcg gagctgaatt acattcccaa ccgcgtggca    5160
caacaactgg cgggcaaaca gtcgttgctg attggcgttg ccacctccag tctggccctg    5220
cacgcgccgt cgcaaattgt cgcggcgatt aaatctcgcg ccgatcaact gggtgccagc    5280
gtggtggtgt cgatggtaga acgaagcggc gtcgaagcct gtaaagcggc ggtgcacaat    5340
cttctcgcgc aacgcgtcag tgggctgatc attaactatc cgctggatga ccaggatgcc    5400
attgctgtgg aagctgcctg cactaatgtt ccggcgttat ttcttgatgt ctctgaccag    5460
acacccatca acagtattat tttctcccat gaagacggta cgcgactggg cgtggagcat    5520
ctggtcgcat tgggtcacca gcaaatcgcg ctgttagcgg cccattaag ttctgtctcg     5580 gcgcgtctgc gtctggctgg ctggcataaa tatctcactc gcaatcaaat tcagccgata    5640
gcggaacggg aaggcgactg gagtgccatg tccggttttc aacaaaccat gcaaatgctg    5700
aatgagggca tcgttcccac tgcgatgctg gttgccaacg atcagatggc gctgggcgca    5760
atgcgcgcca ttaccgagtc cgggctgcgc gttggtgcgg atatctcggt agtgggatac    5820
gacgataccg aagacagctc atgttatatc ccgccgtcaa ccaccatcaa acaggatttt    5880
cgcctgctgg ggcaaaccag cgtggaccgc ttgctgcaac tctctcaggg ccaggcggtg    5940
aagggcaatc agctgttgcc cgtctcactg gtgaaaagaa aaaccaccct ggcgcccaat    6000
acgcaaaccg cctctccccg cgcgttggcc gattcattaa tgcagctggc acgacaggtt    6060
tcccgactgg aaagcgggca gtgagcgcaa cgcaattaat gtgagttagc gcgaattgat    6120
ctg                                                                   6123
```

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggagaattac catggcggat accctg                                           26

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gggaatctag actaatgatg atggtgg                                          27

<210> SEQ ID NO 47
<211> LENGTH: 5787
<212> TYPE: DNA
<213> ORGANISM: Artificial Sequence
<220> FEATURE:
<223> OTHER INFORMATION: Description of Artificial Sequence: Synthetic
      plasmid pTrc:oad-his

<400> SEQUENCE: 47

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagaccatgg cggataccct gaccttcaac accaaacatt     300
tgttggaagc gctgtttgaa agcggtattc gtcacttcat tgtttctccg ggttctcgta     360 gcacccgat tgcactgctg ctggcagaat acgcagagca gaataacgag atcaagctgt      420
tcgttgacgt ggatgagcgc agcgcgggtt tcttcgcact gggcatcgcg aaaacgttgc     480
tggagccggt tgttttgctg ggtacctcgg gtaccgccat cgctgaatac atgcctgcgg     540
tggcggaagc ctatgcggcg aatatcccgc tggtcgtgtt gagcaccgat cgtccacagg     600
aattgcagtt caacggcgca ccgcaaacta ttccgcaaag caacctgttc ggtcaactga     660
cgaaacagga gtcctgatt cgcctgcaag acatgcacag cgatgtgacc gagtacatcg       720
actttatcgt tcagaaggtc gttaatctgt ccattaccgc gcctcgtggc ccgattcaga     780
tcaacctgcc gctgcgcaaa ccgctgatgc cggtcctgga tcgtcaagac gaggtgcacg     840
ttcagcgtgt cgtgtttgac aaacaaagcg tgcaatatcg cttgccgccg attacggcga     900
aacgcctgct gatcctggca ggtccgaatg tcctgaatag ctacgatgat agcctgaaga     960
agtttgcgat caaaaacaat gttccagtta tcgcggatgt tctgtcccaa agccgccaca    1020
cgtataccat tcacggtatt gacgttctgc tgcaagccca caagatcaac gccgacctga    1080
aaccggatct ggtggttcgt tttggcaaga cgccggttag cgcgcgtgtc ctgcaatggc    1140
tgaaagaaga gaacattctg acctggcacg tggacgagga cgcaggcgtg gatcacaccc    1200
gtcatatcgt ccgtgccatc aagatggcgc ctcatgattt tctggaatcc atgcatctga    1260
cgttgagcaa aaaccagatt gacttcaacc agaagtggct gtctctgccg aaagtgatca    1320
aaactcgtaa cgagatgaat atcatcaccg cattggacga cgcggtcccg gatgacactc    1380
acatcttcgt ggcgaacagc atgccgattc gtgacatgga caacttttc acgggtaatc     1440 acacccagcg catttacgct aatcgtggtg caaatggtat tgatggcgtg attagctccg    1500
ccctgggcat gagcgcggtc gtcaagcaac gttcggtcct gctgacgggt gacctgacgc    1560
tgtttcatga catgaacggt ctgatgatgg cgaagaatta ccagctgccg ctggacatca    1620
ttgtgattaa caacaatggc ggtggcattt tcagcttctt gccacaagcc ggtgctccga    1680
agtactttga gcagctgttc ggtaccccgc tgaacattga catcaaaaag attgctgacc    1740
tgtattacat cgattaccat cagttgaatg tgccggaggc cctgagccag atcctgcaga    1800
cgccgagcaa aaccacccgc ctgatcgagt ataagtccga tcaccagcgt aaccgtgacg    1860
atcatcgcga agtgctggag atgctgaaac accaccatca tcattagtct agagtcgacc    1920
tgcaggcatg caagcttggc tgttttggcg gatgagagaa gattttcagc ctgatacaga    1980
ttaaatcaga acgcagaagc ggtctgataa aacagaattt gcctggcggc agtagcgcgg    2040
tggtcccacc tgacccccatg ccgaactcag aagtgaaacg ccgtagcgcc gatggtagtg    2100
tggggtctcc ccatgcgaga gtagggaact gccaggcatc aaataaaacg aaaggctcag    2160
tcgaaagact gggcctttcg ttttatctgt tgtttgtcgg tgaacgctct cctgagtagg    2220
acaaatccgc cgggagcgga tttgaacgtt gcgaagcaac ggcccggagg gtggcgggca    2280
ggacgcccgc cataaactgc caggcatcaa attaagcaga aggccatcct gacggatggc    2340
```

```
cttttttgcgt ttctacaaac tcttttttgtt tattttttcta aatacattca aatatgtatc    2400
cgctcatgag acaataaccc tgataaatgc ttcaataata ttgaaaaagg aagagtatga    2460
gtattcaaca tttccgtgtc gcccttattc ccttttttgc ggcattttgc cttcctgttt    2520
ttgctcaccc agaaacgctg gtgaaagtaa aagatgctga agatcagttg ggtgcacgag    2580
tgggttacat cgaactggat ctcaacagcg gtaagatcct tgagagtttt cgccccgaag    2640
aacgttttcc aatgatgagc acttttaaag ttctgctatg tggcgcggta ttatcccgtg    2700
ttgacgccgg gcaagagcaa ctcggtcgcc gcatacacta ttctcagaat gacttggttg    2760
agtactcacc agtcacagaa aagcatctta cggatggcat gacagtaaga gaattatgca    2820
gtgctgccat aaccatgagt gataacactg cggccaactt acttctgaca acgatcggag    2880
gaccgaagga gctaaccgct tttttgcaca catgggggga tcatgtaact cgccttgatc    2940
gttgggaacc ggagctgaat gaagccatac caaacgacga gcgtgacacc acgatgccta    3000
cagcaatggc aacaacgttg cgcaaactat taactggcga actacttact ctagcttccc    3060
ggcaacaatt aatagactgg atggaggcgg ataaagttgc aggaccactt ctgcgctcgg    3120
cccttccggc tggctggttt attgctgata atctggagc cggtgagcgt gggtctcgcg    3180
gtatcattgc agcactgggg ccagatggta agccctcccg tatcgtagtt atctacacga    3240
cggggagtca ggcaactatg gatgaacgaa atagacagat cgctgagata ggtgcctcac    3300
tgattaagca ttggtaactg tcagaccaag tttactcata tactttttag attgatttaa    3360
aacttcattt ttaatttaaa aggatctagg tgaagatcct ttttgataat ctcatgacca    3420
aaatccctta acgtgagttt tcgttccact gagcgtcaga ccccgtagaa aagatcaaag    3480
gatcttcttg agatcctttt tttctgcgcg taatctgctg cttgcaaaca aaaaaaccac    3540
cgctaccagc ggtggtttgt ttgccggatc aagagctacc aactctttt ccgaaggtaa    3600 ctggcttcag cagagcgcag ataccaaata ctgtccttct agtgtagccg tagttaggcc    3660
accacttcaa gaactctgta gcaccgccta catacctcgc tctgctaatc ctgttaccag    3720
tggctgctgc cagtggcgat aagtcgtgtc ttaccgggtt ggactcaaga cgatagttac    3780
cggataaggc gcagcggtcg ggctgaacgg ggggttcgtg cacacagccc agcttggagc    3840
gaacgaccta caccgaactg agatacctac agcgtgagct atgagaaagc gccacgcttc    3900
ccgaagggag aaaggcggac aggtatccgg taagcggcag ggtcggaaca ggagagcgca    3960
cgagggagct tccaggggga aacgcctggt atctttatag tcctgtcggg tttcgccacc    4020
tctgacttga gcgtcgattt ttgtgatgct cgtcaggggg gcggagccta tggaaaaacg    4080
ccagcaacgc ggcctttta cggttcctgg ccttttgctg gccttttgct cacatgttct    4140
ttcctgcgtt atccctgat tctgtggata accgtattac cgcctttgag tgagctgata    4200
ccgctcgccg cagccgaacg accgagcgca gcgagtcagt gagcgaggaa gcggaagagc    4260
gcctgatgcg gtattttctc cttacgcatc tgtgcggtat ttcacaccgc atatggtgca    4320
ctctcagtac aatctgctct gatgccgcat agttaagcca gtatacactc cgctatcgct    4380
acgtgactgg gtcatggctg cgccccgaca cccgccaaca cccgctgacg cgccctgacg    4440
ggcttgtctg ctcccggcat ccgcttacag acaagctgtg accgtctccg ggagctgcat    4500
gtgtcagagg ttttcaccgt catcaccgaa acgcgcgagg cagcagatca attcgcgcgc    4560
gaaggcgaag cggcatgcat ttacgttgac accatcgaat ggtgcaaaac ctttcgcggt    4620
atggcatgat agcgcccgga agagagtcaa ttcagggtgg tgaatgtgaa accagtaacg    4680
ttatacgatg tcgcagagta tgccggtgtc tcttatcaga ccgtttcccg cgtggtgaac    4740
```

```
caggccagcc acgtttctgc gaaaacgcgg gaaaaagtgg aagcggcgat ggcggagctg      4800
aattacattc ccaaccgcgt ggcacaacaa ctggcgggca aacagtcgtt gctgattggc      4860
gttgccacct ccagtctggc cctgcacgcg ccgtcgcaaa ttgtcgcggc gattaaatct      4920
cgcgccgatc aactgggtgc cagcgtggtg gtgtcgatgg tagaacgaag cggcgtcgaa      4980
gcctgtaaag cggcggtgca caatcttctc gcgcaacgcg tcagtgggct gatcattaac      5040
tatccgctgg atgaccagga tgccattgct gtggaagctg cctgcactaa tgttccggcg      5100
ttatttcttg atgtctctga ccagacaccc atcaacagta ttattttctc ccatgaagac      5160
ggtacgcgac tggcgtgga gcatctggtc gcattgggtc accagcaaat cgcgctgtta       5220
gcgggcccat taagttctgt ctcggcgcgt ctgcgtctgg ctggctggca taaatatctc      5280
actcgcaatc aaattcagcc gatagcggaa cgggaaggcg actggagtgc catgtccggt      5340
tttcaacaaa ccatgcaaat gctgaatgag ggcatcgttc ccactgcgat gctggttgcc      5400
aacgatcaga tggcgctggg cgcaatgcgc gccattaccg agtccgggct gcgcgttggt      5460
gcggatatct cggtagtggg atacgacgat accgaagaca gctcatgtta tcccgccg        5520 tcaaccacca tcaaacagga ttttcgcctg ctggggcaaa ccagcgtgga ccgcttgctg      5580
caactctctc agggccaggc ggtgaagggc aatcagctgt tgcccgtctc actggtgaaa      5640
agaaaaacca ccctggcgcc caatacgcaa accgcctctc ccgcgcgtt ggccgattca       5700 ttaatgcagc tggcacgaca ggtttcccga ctggaaagcg ggcagtgagc gcaacgcaat      5760
taatgtgagt tagcgcgaat tgatctg                                          5787

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aggttcccat ggtgactcag gacccg                                           26

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtaagcttag tggtgatggt gatgaccgaa cgcttcgtcc                            40

<210> SEQ ID NO 50
<211> LENGTH: 4614
<212> TYPE: DNA
<213> ORGANISM: Artificial Sequence
<220> FEATURE:
<223> OTHER INFORMATION: Description of Artificial Sequence: Synthetic
      plasmid pKK223:cterm-His

<400> SEQUENCE: 50
ttgacaatta atcatcggct cgtataatgt gtggaattgt gagcggataa caatttcaca      60
caggaaacag aaccatggga cataacggat ctagatctca ccatcaccac cattagtcga     120
cctgcagcca agcttggctg ttttggcgga tgagagaaga ttttcagcct gatacagatt     180
```

```
aaatcagaac gcagaagcgg tctgataaaa cagaatttgc ctggcggcag tagcgcggtg      240
gtcccacctg accccatgcc gaactcagaa gtgaaacgcc gtagcgccga tggtagtgtg      300
gggtctcccc atgcgagagt agggaactgc caggcatcaa ataaaacgaa aggctcagtc      360
gaaagactgg gcctttcgtt ttatctgttg tttgtcggtg aacgctctcc tgagtaggac      420
aaatccgccg ggagcggatt tgaacgttgc gaagcaacgg cccggagggt ggcgggcagg      480
acgcccgcca taaactgcca ggcatcaaat taagcagaag gccatcctga cggatggcct      540
ttttgcgttt ctacaaactc ttttgtttat ttttctaaat acattcaaat atgtatccgc      600
tcatgagaca ataaccctga taaatgcttc aataatattg aaaaaggaag agtatgagta      660
ttcaacattt ccgtgtcgcc cttattccct tttttgcggc attttgcctt cctgtttttg      720
ctcacccaga aacgctggtg aaagtaaaag atgctgaaga tcagttgggt gcacgagtgg      780
gttacatcga actggatctc aacagcggta agatccttga gttttcgc cccgaagaac        840 gttttccaat gatgagcact tttaaagttc tgctatgtgg cgcggtatta tcccgtgttg      900
acgccgggca agagcaactc ggtcgccgca tacactattc tcagaatgac ttggttgagt      960
actcaccagt cacagaaaag catcttacgg atggcatgac agtaagagaa ttatgcagtg     1020
ctgccataac catgagtgat aacactgcgg ccaacttact tctgacaacg atcggaggac     1080
cgaaggagct aaccgctttt ttgcacaaca tgggggatca tgtaactcgc cttgatcgtt     1140
gggaaccgga gctgaatgaa gccataccaa acgacgagcg tgacaccacg atgctgtagc     1200
aatggcaaca acgttgcgca aactattaac tggcgaacta cttactctag cttcccggca     1260
acaattaata gactggatgg aggcggataa agttgcagga ccacttctgc gctcggccct     1320
tccggctggc tggtttattg ctgataaatc tggagccggt gagcgtgggt ctcgcggtat     1380
cattgcagca ctggggccag atggtaagcc ctcccgtatc gtagttatct acacgacggg     1440
gagtcaggca actatggatg aacgaaatag acagatcgct gagataggtg cctcactgat     1500
taagcattgg taactgtcag accaagttta ctcatatata ctttagattg atttaaaact     1560 tcattttaa tttaaaagga tctaggtgaa gatccttttt gataatctca tgaccaaaat      1620
cccttaacgt gagttttcgt tccactgagc gtcagacccc gtagaaaaga tcaaaggatc     1680
ttcttgagat cctttttttc tgcgcgtaat ctgctgcttg caaacaaaaa aaccaccgct     1740
accagcggtg gtttgtttgc cggatcaaga gctaccaact cttttttccga aggtaactgg     1800 cttcagcaga gcgcagatac caaatactgt ccttctagtg tagccgtagt taggccacca     1860
cttcaagaac tctgtagcac cgcctacata cctcgctctg ctaatcctgt taccagtggc     1920
tgctgccagt ggcgataagt cgtgtcttac cgggttggac tcaagacgat agttaccgga     1980
taaggcgcag cggtcgggct gaacggggggg ttcgtgcaca cagcccagct tggagcgaac     2040
gacctacacc gaactgagat acctacagcg tgagcattga gaaagcgcca cgcttcccga     2100
agggagaaag gcggacaggt atccggtaag cggcagggtc ggaacaggag agcgcacgag     2160
ggagcttcca gggggaaacg cctggtatct ttatagtcct gtcgggtttc gccacctctg     2220
acttgagcgt cgatttttgt gatgctcgtc agggggggcgg agcctatgga aaaacgccag     2280
caacgcggcc ttttttacggt tcctggcctt ttgctggcct tttgctcaca tgttctttcc     2340
tgcgttatcc cctgattctg tggataaccg tattaccgcc tttgagtgag ctgataccgc     2400
tcgccgcagc cgaacgaccg agcgcagcga gtcagtgagc gaggaagcgg aagagcgcct     2460
gatgcggtat tttctcctta cgcatctgtg cggtatttca caccgcatat ggtgcactct     2520
```

```
cagtacaatc tgctctgatg ccgcatagtt aagccagtat acactccgct atcgctacgt    2580
gactgggtca tggctgcgcc ccgacacccg ccaacacccg ctgacgcgcc ctgacgggct    2640
tgtctgctcc cggcatccgc ttacagacaa gctgtgaccg tctccgggag ctgcatgtgt    2700
cagaggtttt caccgtcatc accgaaacgc gcgaggcagc tgcggtaaag ctcatcagcg    2760
tggtcgtgaa gcgattcaca gatgtctgcc tgttcatccg cgtccagctc gttgagtttc    2820
tccagaagcg ttaatgtctg gcttctgata aagcgggcca tgttaagggc ggttttttcc    2880
tgtttggtca ctgatgcctc cgtgtaaggg ggatttctgt tcatgggggt aatgataccg    2940
atgaaacgag agaggatgct cacgatacgg gttactgatg atgaacatgc ccggttactg    3000
gaacgttgtg agggtaaaca actggcggta tggatgcggc gggaccagag aaaaatcact    3060
cagggtcaat gccagcgctt cgttaataca gatgtaggtg ttccacaggg tagccagcag    3120
catcctgcga tgcagatccg gaacataatg gtgcagggcg ctgacttccg cgtttccaga    3180
ctttacgaaa cacggaaacc gaagaccatt catgttgttg ctcaggtcgc agacgttttg    3240
cagcagcagt cgcttcacgt tcgctcgcgt atcggtgatt cattctgcta accagtaagg    3300
caaccccgcc agcctagccg ggtcctcaac gacaggagca cgatcatgcg cacccgtggc    3360
caggacccaa cgctgcccga gatgcgccgc gtgcggctgc tggagatggc ggacgcgatg    3420
gatatgttct gccaagggtt ggtttgcgca ttcacagttc tccgcaagaa ttgattggct    3480
ccaattcttg gagtggtgaa tccgttagcg aggtgccgcc ggcttccatt caggtcgagg    3540
tggcccggct ccatgcaccg cgacgcaacg cggggaggca gacaaggtat agggcggcgc    3600
ctacaatcca tgccaacccg ttccatgtgc tcgccgaggc ggcataaatc gccgtgacga    3660
tcagcggtcc agtgatcgaa gttaggctgg taagagccgc gagcgatcct tgaagctgtc    3720
cctgatggtc gtcatctacc tgcctggaca gcatggcctg caacgcgggc atcccgatgc    3780
cgccggaagc gagaagaatc ataatgggga aggccatcca gcctcgcgtc gcgaacgcca    3840
gcaagacgta gcccagcgcg tcggccgcca tgccggcgat aatggcctgc ttctcgccga    3900
aacgtttggt ggcgggacca gtgacgaagg cttgagcgag ggcgtgcaag attccgaata    3960
ccgcaagcga caggccgatc atcgtcgcgc tccagcgaaa gcggtcctcg ccgaaaatga    4020
cccagagcgc tgccggcacc tgtcctacga gttgcatgat aaagaagaca gtcataagtg    4080
cggcgacgat agtcatgccc cgcgcccacc ggaaggagct gactgggttg aaggctctca    4140
agggcatcgg tcgacgctct cccttatgcg actcctgcat taggaagcag cccagtagta    4200
ggttgaggcc gttgagcacc gccgccgcaa ggaatggtgc atgcaaggag atggcgccca    4260
acagtccccc ggccacgggg cctgccacca tacccacgcc gaaacaagcg ctcatgagcc    4320
cgaagtggcg agcccgatct tccccatcgg tgatgtcggc gatataggcg ccagcaaccg    4380
cacctgtggc gccggtgatg ccggccacga tgcgtccggc gtagaggatc cgggcttatc    4440
gactgcacgg tgcaccaatg cttctggcgt caggcagcca tcggaagctg tggtatggct    4500
gtgcaggtcg taaatcactg cataattcgt gtcgctcaag gcgcactccc gttctggata    4560
atgttttttg cgccgacatc ataacggttc tggcaaatat tctgaaatga gctg         4614
```

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
aggttcccat ggtgactcag gacccg                                              26

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gtaagcttag tggtgatggt gatgaccgaa cgcttcgtcc                               40

<210> SEQ ID NO 53
<211> LENGTH: 8241
<212> TYPE: DNA
<213> ORGANISM: Artificial Sequence
<220> FEATURE:
<223> OTHER INFORMATION: Description of Artificial Sequence: Synthetic
      plasmid pKK223:kgd-his
<220> FEATURE:
<221> NAME/KEY: modified_base
<222> LOCATION: (1425)..(1425)
<223> OTHER INFORMATION: a, c, t, g, unknown or other

<400> SEQUENCE: 53
atggatcgta aatttcgtga tgatccgtct tccgttgacc caagctggca tgagtttctg        60
gtggactata gcccggagcc gacttcccaa ccggctgctg agccgactcg tgtgaccagc       120
cctttggtcg ctgagcgtgc ggcagcggcg gctccgcaag cgccgccgaa accggccgac       180
acggccgcag cgggcaacgg tgtcgtggcg gctctggccg ccaagaccgc ggtgcctccg       240
ccagccgaag cgatgaagt tgctgtcctg cgtggtgcgg cggctgctgt cgtgaagaac        300
atgagcgcgt cgctggaagt gcctacggcg acctcggtgc gtgctgtgcc agcgaaattg      360
ttgatcgata atcgtatcgt gatcaataat cagttgaaac gcacgcgtgg tggtaaaatc      420
agctttaccc atttgctggg ttatgctctg gttcaggcgg ttaagaagtt cccgaatatg      480
aatcgccact acacggaggt ggacggtaag ccgacggcgg ttactcctgc gcacaccaat      540
ctgggtctgg ctattgacct gcaaggtaaa gatggcaagc gctctctggt ggtggccggt      600
atcaaacgtt gcgagacgat gcgcttcgcg cagttcgtta ccgcgtacga ggacatcgtc      660
cgtcgtgctc gtgatggtaa actgaccacc gaggacttcg ctggcgttac gatttcgctg      720
acgaatccgg gcacgattgg cacggtgcac tctgtgccac gcctgatgcc aggtcaaggt      780
gctatcatcg gtgtcggtgc gatggaatat ccggcggagt tccaaggcgc gtccgaggaa      840
cgcatcgctg agctgggtat tggcaaactg attaccctga cttctaccta cgaccaccgt      900
atcattcaag gtgcggaaag cggtgacttc ctgcgtacca ttcatgaact gctgttgtct      960
gatggcttct gggatgaggt cttccgcgag ctgagcatcc cgtacctgcc agtgcgttgg     1020
agcaccgata tccggactc gatcgttgac aagaacgcac gtgtgatgaa cctgatcgcg      1080
gcctatcgca accgcggcca tctgatggcg gacaccgacc cgttgcgctt ggataaggcg      1140
cgctttcgtt cgcatccgga tttggaggtg ttgacgcatg gcctgactct gtgggaccty      1200
gaccgcgtct ttaaggttga cggtttcgcg ggtgctcaat acaaaaagct gcgtgacgtg      1260
ctgggtttgc tgcgcgacgc gtactgccgt cacatcggtg ttgagtacgc gcacattctg      1320
gacccggaac aaaaggagtg gctggagcag cgtgtcgaga cgaagcacgt caaaccgacc      1380
gttgctcaac aaaagtacat cttgtcgaaa ctgaacgcag cggangcgtt tgaaaccttc      1440

```
ctgcaaacca agtatgtggg ccaaaagcgt tttagcctgg agggtgcgga atctgttatt    1500
ccaatgatgg acgcggcgat tgaccaatgt gccgagcatg gtttggatga agtggtcatt    1560
ggcatgccgc accgtggtcg cttgaatgtc ctggcgaaca tcgtgggcaa accgtattcg    1620
caaatcttta cggagtttga aggcaatctg aacccgtccc aggctcacgg ttccggcgat    1680
gtcaagtacc acctgggtgc gacgggtctg tatctgcaaa tgtttggcga taacgatatt    1740
caggtttccc tgacggcaaa tccgtcccat ttggaagcgg tcgatccagt gctgaaggt    1800
ttggtgcgtg cgaagcaaga cctgctggac cacggttcca ttgactccga cggccaacgt    1860
gcattctccg tcgttccgtt gatgctgcac ggtgatgcgg ccttcgcggg tcaaggcgtt    1920
gttgcggaga cgctgaatct ggcaaatctg cctggctatc gtgtgggtgg tacgattcac    1980
atcattgtga acaaccaaat cggcttcacc accgctccgg aatactctcg ttcgagcgag    2040
tactgcacgg atgtggcgaa gatgatcggt gcgccaatct tccacgtgaa cggcgacgat    2100
ccagaagcgt gtgtctgggt tgcgcgtttg gcagttgact ccgccaacg ctttaaaaag    2160
gacgttgtta ttgacatgct gtgctatcgt cgtcgtggtc ataatgaggg tgacgatcca    2220
tctatgacca atccgtatgt ctatgacgtc gtggacacca agcgtggcgc ccgtaaatcc    2280
tacaccgagg ctctgatcgg tcgtggcgac atcagcatga agaggcgga ggatgcgctg    2340
cgcgattacc agggccaact ggagcgtgtg ttcaacgaag tgcgcgaact ggagaagcac    2400
ggcgtccaac cgtcggagag cgtcgagtcg gaccaaatga tcccagcggg cctggcgacc    2460
gctgttgaca aatccctgct ggcacgtatc ggtgatgcct tcctggcgct gcctaacggt    2520
ttcacggcac acccgcgcgt tcagccggtg ctggaaaagc gtcgtgagat ggcgtatgag    2580
ggtaagattg actgggcgtt tggtgagttg ctggcgctgg gcagcctggt tgctgagggc    2640
aagctggtcc gtctgagcgg tcaagactct cgtcgtggca cctttagcca gcgtcattct    2700
gtgctgatcg accgtcacac cggcgaggag ttcaccccgc tgcagctgct ggcgactaac    2760
agcgacggca gcccgaccgg tggtaagttc ctggtttatg attcgccgtt gtcggaatac    2820
gcggctgtgg gttttgagta cggttatacc gttggcaatc cagacgcggt tgtgctgtgg    2880
gaggcgcaat tcggcgactt tgttaatggt gcccagtcga tcattgacga gttcatcagc    2940
tcgggcgaag cgaaatgggg tcagctgtcc aacgttgttc tgttgctgcc acacggccac    3000
gagggtcagg gcccggacca cacgtcggcg cgcattgagc gcttttttgca gctgtgggct    3060
gagggtagca tgacgatcgc gatgccgagc accccgtcca attactttca cttgctgcgc    3120
cgccacgcgt tggacggcat ccaacgtccg ttgatcgtgt ttaccccgaa atccatgctg    3180
cgccacaagg cggcggtttc ggagattaag gattttaccg agattaaatt ccgtagcgtc    3240
ctggaggaac cgacctacga ggatggtatc ggcgaccgca ataaagttag ccgtattctg    3300
ttgacctccg gtaagttgta ttatgaattg gcggcacgca aggcgaaaga caaccgtaat    3360
gatctggcaa ttgtgcgtct ggagcaactg gcgccgttgc cgcgtcgtcg tctgcgtgaa    3420
accctggatc gttacgaaaa atgtcaaagag ttcttttggg tccaggagga accagcgaac    3480
cagggcgcct ggccgcgttt cggtttggag ttgccggagt tgctgccgga caagttggcg    3540
ggcatcaagc gtatctcccg tcgcgcgatg tctgcgccga gcagcggttc ctcgaaggtt    3600
catgccgtgg agcagcaaga aatcttggac gaagcgttcg gatctagatc tcaccatcac    3660
caccattagt cgacctgcag ccaagcttgg ctgttttggc ggatgagaga agattttcag    3720
cctgatacag attaaatcag aacgcagaag cggtctgata aaacagaatt tgcctggcgg    3780
cagtagcgcg gtggtcccac ctgaccccat gccgaactca gaagtgaaac gccgtagcgc    3840
```

```
cgatggtagt gtggggtctc cccatgcgag agtagggaac tgccaggcat caaataaaac    3900
gaaaggctca gtcgaaagac tgggcctttc gttttatctg ttgtttgtcg gtgaacgctc    3960
tcctgagtag gacaaatccg ccgggagcgg atttgaacgt tgcgaagcaa cggcccggag    4020
ggtggcgggc aggacgcccg ccataaactg ccaggcatca aattaagcag aaggccatcc    4080
tgacggatgg cctttttgcg tttctacaaa ctcttttgtt tattttttcta aatacattca    4140 aatatgtatc cgctcatgag acaataaccc tgataaatgc ttcaataata ttgaaaaagg    4200
aagagtatga gtattcaaca tttccgtgtc gcccttattc ccttttttgc ggcattttgc    4260
cttcctgttt ttgctcaccc agaaacgctg gtgaaagtaa aagatgctga agatcagttg    4320
ggtgcacgag tgggttacat cgaactggat ctcaacagcg gtaagatcct tgagagtttt    4380
cgccccgaag aacgttttcc aatgatgagc acttttaaag ttctgctatg tggcgcggta    4440
ttatcccgtg ttgacgccgg gcaagagcaa ctcggtcgcc gcatacacta ttctcagaat    4500
gacttggttg agtactcacc agtcacagaa aagcatctta cggatggcat gacagtaaga    4560
gaattatgca gtgctgccat aaccatgagt gataacactg cggccaactt acttctgaca    4620
acgatcggag gaccgaagga gctaaccgct tttttgcaca acatggggga tcatgtaact    4680
cgccttgatc gttgggaacc ggagctgaat gaagccatac caaacgacga gcgtgacacc    4740
acgatgctgt agcaatggca acaacgttgc gcaaactatt aactggcgaa ctacttactc    4800
tagcttcccg gcaacaatta atagactgga tggaggcgga taaagttgca ggaccacttc    4860
tgcgctcggc ccttccggct ggctggttta ttgctgataa atctggagcc ggtgagcgtg    4920
ggtctcgcgg tatcattgca gcactggggc cagatggtaa gccctcccgt atcgtagtta    4980
tctacacgac ggggagtcag gcaactatgg atgaacgaaa tagacagatc gctgagatag    5040
gtgcctcact gattaagcat tggtaactgt cagaccaagt ttactcatat atactttaga    5100
ttgatttaaa acttcatttt taatttaaaa ggatctaggt gaagatcctt tttgataatc    5160
tcatgaccaa aatcccttaa cgtgagtttt cgttccactg agcgtcagac cccgtagaaa    5220
agatcaaagg atcttcttga gatcctttt ttctgcgcgt aatctgctgc ttgcaaacaa    5280
aaaaaccacc gctaccagcg gtggtttgtt tgccggatca agagctacca actctttttc    5340
cgaaggtaac tggcttcagc agagcgcaga taccaaatac tgtccttcta gtgtagccgt    5400
agttaggcca ccacttcaag aactctgtag caccgcctac atacctcgct ctgctaatcc    5460
tgttaccagt ggctgctgcc agtggcgata agtcgtgtct taccgggttg gactcaagac    5520
gatagttacc ggataaggcg cagcggtcgg gctgaacggg gggttcgtgc acacagccca    5580
gcttggagcg aacgacctac accgaactga gatacctaca gcgtgagcat tgagaaagcg    5640
ccacgcttcc cgaagggaga aaggcggaca ggtatccggt aagcggcagg gtcggaacag    5700
gagagcgcac gagggagctt ccagggggaa acgcctggta tctttatagt cctgtcgggt    5760
ttcgccacct ctgacttgag cgtcgatttt tgtgatgctc gtcagggggg cggagcctat    5820
ggaaaaacgc cagcaacgcg gcctttttac ggttcctggc cttttgctgg ccttttgctc    5880
acatgttctt tcctgcgtta tcccctgatt ctgtggataa ccgtattacc gcctttgagt    5940
gagctgatac cgctcgccgc agccgaacga ccgagcgcag cgagtcagtg agcgaggaag    6000
cggaagagcg cctgatgcgg tattttctcc ttacgcatct gtgcggtatt tcacaccgca    6060
tatggtgcac tctcagtaca atctgctctg atgccgcata gttaagccag tatacactcc    6120
gctatcgcta cgtgactggg tcatggctgc gccccgacac ccgccaacac ccgctgacgc    6180
gccctgacgg gcttgtctgc tcccggcatc cgcttacaga caagctgtga ccgtctccgg    6240
```

-continued

```
gagctgcatg tgtcagaggt tttcaccgtc atcaccgaaa cgcgcgaggc agctgcggta      6300
aagctcatca gcgtggtcgt gaagcgattc acagatgtct gcctgttcat ccgcgtccag      6360
ctcgttgagt ttctccagaa gcgttaatgt ctggcttctg ataaagcggg ccatgttaag      6420
ggcggttttt tcctgtttgg tcactgatgc ctccgtgtaa gggggatttc tgttcatggg      6480
ggtaatgata ccgatgaaac gagagaggat gctcacgata cgggttactg atgatgaaca      6540
tgcccggtta ctgaacgttg tgagggtaa caactggcg gtatggatgc ggcgggacca       6600 gagaaaatc actcagggtc aatgccagcg cttcgttaat acagatgtag gtgttccaca       6660
gggtagccag cagcatcctg cgatgcagat ccggaacata atggtgcagg cgctgactt       6720 ccgcgtttcc agactttacg aaacacggaa accgaagacc attcatgttg ttgctcaggt      6780
cgcagacgtt ttgcagcagc agtcgcttca cgttcgctcg cgtatcggtg attcattctg      6840
ctaaccagta aggcaacccc gccagcctag ccgggtcctc aacgacagga gcacgatcat      6900
gcgcacccgt ggccaggacc caacgctgcc cgagatgcgc cgcgtgcggc tgctggagat      6960
ggcggacgcg atggatatgt tctgccaagg gttggtttgc gcattcacag ttctccgcaa      7020
gaattgattg gctccaattc ttggagtggt gaatccgtta gcgaggtgcc gccggcttcc      7080
attcaggtcg aggtggcccg gctccatgca ccgcgacgca acgcggggag cagacaagg      7140 tatagggcgg cgcctacaat ccatgccaac ccgttccatg tgctcgccga ggcggcataa      7200
atcgccgtga cgatcagcgg tccagtgatc gaagttaggc tggtaagagc gcgagcgat      7260 ccttgaagct gtccctgatg gtcgtcatct acctgcctgg acagcatggc ctgcaacgcg      7320
ggcatcccga tgccgccgga agcgagaaga atcataatgg ggaaggccat ccagcctcgc      7380
gtcgcgaacg ccagcaagac gtagcccagc gcgtcggccg ccatgccggc gataatggcc      7440
tgcttctcgc cgaaacgttt ggtggcggga ccagtgacga aggcttgagc gagggcgtgc      7500
aagattccga ataccgcaag cgacaggccg atcatcgtcg cgctccagcg aaagcggtcc      7560
tcgccgaaaa tgacccagag cgctgccggc acctgtccta cgagttgcat gataaagaag      7620
acagtcataa gtgcggcgac gatagtcatg ccccgcgccc accggaagga gctgactggg      7680
ttgaaggctc tcaagggcat cggtcgacgc tctcccttat gcgactcctg cattaggaag      7740
cagcccagta gtaggttgag gccgttgagc accgccgccg caaggaatgg tgcatgcaag      7800
gagatggcgc ccaacagtcc cccggccacg gggcctgcca ccatacccac gccgaaacaa      7860
gcgctcatga gcccgaagtg gcgagcccga tcttccccat cggtgatgtc ggcgatatag      7920
gcgccagcaa ccgcacctgt ggcgccggtg atgccggcca cgatgcgtcc ggcgtagagg      7980
atccgggctt atcgactgca cggtgcacca atgcttctgg cgtcaggcag ccatcggaag      8040
ctgtggtatg gctgtgcagg tcgtaaatca ctgcataatt cgtgtcgctc aaggcgcact      8100
cccgttctgg ataatgtttt ttgcgccgac atcataacgg ttctggcaaa tattctgaaa      8160
tgagctgttg acaattaatc atcggctcgt ataatgtgtg gaattgtgag cggataacaa      8220
tttcacacag gaaacagaac c                                                8241
```

<210> SEQ ID NO 54
<211> LENGTH: 541
<212> TYPE: PRT
<213> ORGANISM: Leuconostoc mesenteroides

<400> SEQUENCE: 54

Met Thr Asp Thr Leu Thr Phe Asn Thr Lys His Leu Leu Glu Ala Leu
1               5                   10                  15

```
Phe Glu Ser Gly Ile Arg His Phe Ile Val Ser Pro Gly Arg Ser
             20                  25                  30
Thr Pro Ile Ala Leu Leu Ala Glu Tyr Ala Glu Gln Thr Asn Glu
         35                  40                  45
Ile Lys Leu Phe Val Asp Val Asp Glu Arg Ser Ala Gly Phe Phe Ala
 50                  55                  60
Leu Gly Ile Ala Lys Thr Leu Leu Glu Pro Val Val Leu Leu Gly Thr
 65                  70                  75                  80
Ser Gly Thr Ala Ile Ala Glu Tyr Met Pro Ala Val Ala Glu Ala Tyr
                 85                  90                  95
Ala Ala Asn Ile Pro Leu Val Val Leu Ser Thr Asp Arg Pro Gln Glu
                100                 105                 110
Leu Gln Phe Asn Gly Ala Pro Gln Thr Ile Pro Gln Ser Asn Leu Phe
            115                 120                 125
Gly Gln Leu Thr Lys Gln Ala Val Leu Ile Arg Leu Gln Asp Met His
        130                 135                 140
Ser Asp Val Thr Glu Tyr Ile Asp Phe Ile Val Gln Lys Val Val Asn
145                 150                 155                 160
Leu Ser Ile Thr Ala Pro Arg Gly Pro Ile Gln Ile Asn Leu Pro Leu
                165                 170                 175
Arg Lys Pro Leu Met Pro Val Leu Asp Arg Gln Asp Glu Val His Val
            180                 185                 190
Gln Arg Val Val Phe Asp Lys Gln Ser Val Gln Tyr Arg Leu Pro Pro
        195                 200                 205
Ile Thr Ala Lys Arg Leu Leu Ile Leu Ala Gly Pro Asn Val Leu Asn
210                 215                 220
Ser Tyr Asp Asp Ser Leu Lys Lys Phe Ala Ile Lys Asn Asn Val Pro
225                 230                 235                 240
Val Ile Ala Asp Val Leu Ser Gln Ser Leu His Thr Tyr Thr Ile His
                245                 250                 255
Gly Ile Asp Val Leu Leu Gln Ala His Lys Ile Asn Ala Asp Leu Lys
            260                 265                 270
Pro Asp Leu Val Val Arg Phe Gly Lys Thr Pro Val Ser Ala Arg Val
        275                 280                 285
Leu Gln Trp Leu Lys Glu Glu Asn Ile Leu Thr Trp His Val Gly Glu
290                 295                 300
Asp Ala Gly Val Asp His Thr Arg His Ile Val Arg Ala Ile Lys Met
305                 310                 315                 320
Ala Pro His Asp Phe Leu Glu Ser Met His Leu Thr Leu Ser Lys Asn
                325                 330                 335
Gln Ile Asp Phe Asn Gln Lys Trp Leu Ser Leu Pro Lys Val Ile Lys
            340                 345                 350
Thr Arg Asn Glu Met Asn Ile Ile Thr Ala Leu Asp Asp Ala Val Pro
        355                 360                 365
Asp Asp Thr His Ile Phe Val Ala Asn Ser Met Pro Ile Arg Asp Met
370                 375                 380
Asp Asn Phe Phe Thr Gly Asn His Thr Gln Arg Ile Tyr Ala Asn Arg
385                 390                 395                 400
Gly Ala Asn Gly Ile Asp Gly Val Ile Ser Ser Ala Leu Gly Met Ser
                405                 410                 415
Ala Val Ala Lys Gln Arg Ser Val Leu Leu Thr Gly Asp Leu Thr Leu
            420                 425                 430
Phe His Asp Met Asn Gly Leu Met Met Ala Lys Asn Tyr Gln Leu Pro
```

```
                    435                 440                 445
Leu Asp Ile Ile Val Ile Asn Asn Gly Gly Ile Phe Ser Phe
    450                 455                 460

Leu Pro Gln Ala Gly Ala Pro Lys Tyr Phe Glu Gln Phe Gly Thr
465                 470                 475                 480

Pro Leu Asn Ile Asp Ile Lys Lys Ile Ala Asp Leu Tyr Tyr Ile Asp
                    485                 490                 495

Tyr His Gln Leu Asn Val Pro Glu Ala Leu Ser Gln Ile Leu Gln Thr
                500                 505                 510

Pro Ser Lys Thr Thr Arg Leu Ile Glu Tyr Lys Ser Asp His Gln Arg
                515                 520                 525

Asn Arg Asp Asp His Arg Glu Val Leu Glu Met Leu Lys
                530                 535                 540

<210> SEQ ID NO 55
<211> LENGTH: 541
<212> TYPE: PRT
<213> ORGANISM: Leuconostoc mesenteroides

<400> SEQUENCE: 55

Met Thr Asp Thr Leu Thr Phe Asn Thr Lys His Leu Leu Glu Ala Leu
1               5                   10                  15

Phe Glu Ser Gly Ile Arg His Phe Ile Val Ser Pro Gly Ser Arg Ser
                20                  25                  30

Thr Pro Ile Ala Leu Leu Ala Glu Tyr Ala Glu Gln Asn Asn Glu
            35                  40                  45

Ile Lys Leu Phe Val Asp Val Asp Glu Arg Ser Ala Gly Phe Phe Ala
    50                  55                  60

Leu Gly Ile Ala Lys Thr Leu Leu Glu Pro Val Val Leu Leu Gly Thr
65                  70                  75                  80

Ser Gly Thr Ala Ile Ala Glu Tyr Met Pro Ala Val Ala Glu Ala Tyr
                85                  90                  95

Ala Ala Asn Ile Pro Leu Val Val Leu Ser Thr Asp Arg Pro Gln Glu
            100                 105                 110

Leu Gln Phe Asn Gly Ala Pro Gln Thr Ile Pro Gln Ser Asn Leu Phe
        115                 120                 125

Gly Gln Leu Thr Lys Gln Ala Val Leu Ile Arg Leu Gln Asp Met His
    130                 135                 140

Ser Asp Val Thr Glu Tyr Ile Asp Phe Ile Val Gln Lys Val Val Asn
145                 150                 155                 160

Leu Ser Ile Thr Ala Pro Arg Gly Pro Ile Gln Ile Asn Leu Pro Leu
                165                 170                 175

Arg Lys Pro Leu Met Pro Val Leu Asp Arg Gln Asp Glu Val His Val
            180                 185                 190

Gln Arg Val Val Phe Asp Lys Gln Ser Val Gln Tyr Arg Leu Pro Pro
        195                 200                 205

Ile Thr Ala Lys Arg Leu Leu Ile Leu Ala Gly Pro Asn Val Leu Asn
    210                 215                 220

Ser Tyr Asp Asp Ser Leu Lys Lys Phe Ala Ile Lys Asn Asn Val Pro
225                 230                 235                 240

Val Ile Ala Asp Val Leu Ser Gln Ser Arg His Thr Tyr Thr Ile His
                245                 250                 255

Gly Ile Asp Val Leu Leu Gln Ala His Lys Ile Asn Ala Asp Leu Lys
            260                 265                 270
```

```
Pro Asp Leu Val Val Arg Phe Gly Lys Thr Pro Val Ser Ala Arg Val
            275                 280                 285

Leu Gln Trp Leu Lys Glu Glu Asn Ile Leu Thr Trp His Val Asp Glu
290                 295                 300

Asp Ala Gly Val Asp His Thr Arg His Ile Val Arg Ala Ile Lys Met
305                 310                 315                 320

Ala Pro His Asp Phe Leu Glu Ser Met His Leu Thr Leu Ser Lys Asn
                325                 330                 335

Gln Ile Asp Phe Asn Gln Lys Trp Leu Ser Leu Pro Lys Val Ile Lys
            340                 345                 350

Thr Arg Asn Glu Met Asn Ile Ile Thr Ala Leu Asp Asp Ala Val Pro
        355                 360                 365

Asp Asp Thr His Ile Phe Val Ala Asn Ser Met Pro Ile Arg Asp Met
370                 375                 380

Asp Asn Phe Phe Thr Gly Asn His Thr Gln Arg Ile Tyr Ala Asn Arg
385                 390                 395                 400

Gly Ala Asn Gly Ile Asp Gly Val Ile Ser Ser Ala Leu Gly Met Ser
                405                 410                 415

Ala Val Val Lys Gln Arg Ser Val Leu Leu Thr Gly Asp Leu Thr Leu
            420                 425                 430

Phe His Asp Met Asn Gly Leu Met Met Ala Lys Asn Tyr Gln Leu Pro
        435                 440                 445

Leu Asp Ile Ile Val Ile Asn Asn Gly Gly Gly Ile Phe Ser Phe
450                 455                 460

Leu Pro Gln Ala Gly Ala Pro Lys Tyr Phe Glu Gln Leu Phe Gly Asn
465                 470                 475                 480

Pro Leu Asn Ile Asp Ile Lys Lys Ile Ala Asp Leu Tyr Tyr Ile Asp
                485                 490                 495

Tyr His Gln Leu Asn Val Pro Glu Ala Leu Ser Gln Ile Leu Gln Thr
            500                 505                 510

Pro Ser Lys Thr Thr Arg Leu Ile Glu Tyr Lys Ser Asp His Gln Arg
        515                 520                 525

Asn Arg Asp Asp His Arg Glu Val Leu Glu Met Leu Lys
530                 535                 540

<210> SEQ ID NO 56
<211> LENGTH: 541
<212> TYPE: PRT
<213> ORGANISM: Leuconostoc mesenteroides

<400> SEQUENCE: 56

Met Thr Asp Thr Leu Thr Phe Asn Thr Lys His Leu Leu Glu Ala Leu
1               5                   10                  15

Phe Glu Ser Gly Ile Arg His Phe Ile Val Ser Pro Gly Ser Arg Ser
            20                  25                  30

Thr Pro Ile Ala Leu Leu Leu Ala Glu Tyr Ala Glu Gln Asn Asn Glu
        35                  40                  45

Ile Lys Leu Phe Val Asp Val Asp Glu Arg Ser Ala Gly Phe Phe Ala
    50                  55                  60

Leu Gly Ile Ala Lys Thr Leu Leu Glu Pro Val Leu Leu Gly Thr
65                  70                  75                  80

Ser Gly Thr Ala Ile Ala Glu Tyr Met Pro Ala Val Ala Glu Ala Tyr
                85                  90                  95

Ala Ala Asn Ile Pro Leu Val Val Leu Ser Thr Asp Arg Pro Gln Glu
            100                 105                 110
```

```
Leu Gln Phe Asn Gly Ala Pro Gln Thr Ile Pro Gln Ser Asn Leu Phe
            115                 120                 125

Gly Gln Leu Thr Lys Gln Ala Val Leu Ile Arg Leu Gln Asp Met His
    130                 135                 140

Ser Asp Val Thr Glu Tyr Ile Asp Phe Ile Val Gln Lys Val Val Asn
145                 150                 155                 160

Leu Ser Ile Thr Ala Pro Arg Gly Pro Ile Gln Ile Asn Leu Pro Leu
                165                 170                 175

Arg Lys Pro Leu Met Pro Val Leu Asp Arg Gln Asp Glu Val His Val
            180                 185                 190

Gln Arg Val Val Phe Asp Lys Gln Ser Val Gln Tyr Arg Leu Pro Pro
        195                 200                 205

Ile Thr Ala Lys Arg Leu Leu Ile Leu Ala Gly Pro Asn Val Leu Asn
    210                 215                 220

Ser Tyr Asp Asp Ser Leu Lys Lys Phe Ala Ile Lys Asn Asn Val Pro
225                 230                 235                 240

Val Ile Ala Asp Val Leu Ser Gln Ser Arg His Thr Tyr Thr Ile His
                245                 250                 255

Gly Ile Asp Val Leu Leu Gln Ala His Lys Ile Asn Ala Asp Leu Lys
            260                 265                 270

Pro Asp Leu Val Val Arg Phe Gly Lys Thr Pro Val Ser Ala Arg Val
        275                 280                 285

Leu Gln Trp Leu Lys Glu Asn Ile Leu Thr Trp His Val Asp Glu
    290                 295                 300

Asp Ala Gly Val Asp His Thr Arg His Ile Val Arg Ala Ile Lys Met
305                 310                 315                 320

Ala Pro His Asp Phe Leu Glu Ser Met His Leu Thr Leu Ser Lys Asn
                325                 330                 335

Gln Ile Asp Phe Asn Gln Lys Trp Leu Ser Leu Pro Lys Val Ile Lys
            340                 345                 350

Thr Arg Asn Glu Met Asn Ile Ile Thr Ala Leu Asp Asp Ala Val Pro
        355                 360                 365

Asp Asp Thr His Ile Phe Val Ala Asn Ser Met Pro Ile Arg Asp Met
370                 375                 380

Asp Asn Phe Phe Thr Gly Asn His Thr Gln Cys Ile Tyr Ala Asn Arg
385                 390                 395                 400

Gly Ala Asn Gly Ile Asp Gly Val Ile Ser Ser Ala Leu Gly Met Ser
                405                 410                 415

Ala Val Val Lys Gln Arg Ser Val Leu Leu Thr Gly Asp Leu Thr Leu
            420                 425                 430

Phe His Gly Met Asn Gly Leu Met Met Ala Lys Asn Tyr Gln Leu Pro
        435                 440                 445

Leu Asp Ile Ile Val Ile Asn Asn Asn Gly Gly Ile Phe Ser Phe
450                 455                 460

Leu Pro Gln Ala Gly Ala Pro Lys Tyr Phe Glu Gln Leu Phe Gly Thr
465                 470                 475                 480

Pro Leu Asn Ile Asp Ile Lys Lys Ile Ala Asp Leu Tyr Tyr Ile Asp
                485                 490                 495

Tyr His Gln Leu Asn Val Pro Glu Ala Leu Ser Gln Ile Leu Gln Ala
            500                 505                 510

Pro Ser Lys Thr Thr Arg Leu Ile Glu Tyr Lys Ser Asp His Gln Arg
        515                 520                 525
```

```
Asn Arg Asp Asp His Arg Glu Val Leu Glu Met Leu Lys
        530                 535                 540
```

```
<210> SEQ ID NO 57
<211> LENGTH: 219
<212> TYPE: PRT
<213> ORGANISM: Escherichia coli

<400> SEQUENCE: 57

Met Lys Glu Ile Ile Asp Gly Phe Leu Lys Phe Gln Arg Glu Ala Phe
1               5                   10                  15

Pro Lys Arg Glu Ala Leu Phe Lys Gln Leu Ala Thr Gln Gln Ser Pro
            20                  25                  30

Arg Thr Leu Phe Ile Ser Cys Ser Asp Ser Arg Leu Val Pro Glu Leu
        35                  40                  45

Val Thr Gln Arg Glu Pro Gly Asp Leu Phe Val Ile Arg Asn Ala Gly
    50                  55                  60

Asn Ile Val Pro Ser Tyr Gly Pro Glu Pro Gly Gly Val Ser Ala Ser
65                  70                  75                  80

Val Glu Tyr Ala Val Ala Ala Leu Arg Val Ser Asp Ile Val Ile Cys
                85                  90                  95

Gly His Ser Asn Cys Gly Ala Met Thr Ala Ile Ala Ser Cys Gln Cys
            100                 105                 110

Met Asp His Met Pro Ala Val Ser His Trp Leu Arg Tyr Ala Asp Ser
        115                 120                 125

Ala Arg Val Val Asn Glu Ala Arg Pro His Ser Asp Leu Pro Ser Lys
    130                 135                 140

Ala Ala Ala Met Val Arg Glu Asn Val Ile Ala Gln Leu Ala Asn Leu
145                 150                 155                 160

Gln Thr His Pro Ser Val Arg Leu Ala Leu Glu Glu Gly Arg Ile Ala
                165                 170                 175

Leu His Gly Trp Val Tyr Asp Ile Glu Ser Gly Ser Ile Ala Ala Phe
            180                 185                 190

Asp Gly Ala Thr Arg Gln Phe Val Pro Leu Ala Ala Asn Pro Arg Val
        195                 200                 205

Cys Ala Ile Pro Leu Arg Gln Pro Thr Ala Ala
    210                 215
```

```
<210> SEQ ID NO 58
<211> LENGTH: 219
<212> TYPE: PRT
<213> ORGANISM: Psuedomonas fluorescens
<220> FEATURE:
<223> OTHER INFORMATION: Carbonic anhydrase P. fluorescens Pf-5

<400> SEQUENCE: 58

Met Gln Asn Ile Ile Asp Gly Phe Leu Lys Phe Gln Arg Glu Ala Phe
1               5                   10                  15

Pro Gln Arg Ser Glu Leu Phe Lys Gln Leu Ala Ser Thr Gln Asn Pro
            20                  25                  30

Gly Thr Leu Phe Val Thr Cys Ser Asp Ser Arg Val Val Pro Glu Leu
        35                  40                  45

Leu Thr Gln Gln Glu Pro Gly Asp Leu Phe Val Ile Arg Asn Ala Gly
    50                  55                  60

Asn Ile Val Pro Ser Tyr Gly Pro Glu Pro Gly Gly Val Ser Ala Thr
65                  70                  75                  80

Val Glu Tyr Ala Val Ala Val Leu Gly Val Ser Asp Ile Val Ile Cys
```

```
                    85                  90                  95
Gly His Ser Asp Cys Gly Ala Met Thr Ala Ile Ser Thr Cys Lys Cys
            100                 105                 110

Leu Asp His Leu Pro Ala Val Ala Asn Trp Leu Arg His Ala Glu Ser
        115                 120                 125

Ala Lys Val Ile Asn Ala Ala Arg Gln His Ala Ser Pro Ala Glu His
    130                 135                 140

Leu Asp Ala Leu Val Arg Asp Asn Val Ile Ala Gln Leu Ala Asn Leu
145                 150                 155                 160

Lys Thr His Pro Ser Val Ala Leu Ala Leu Glu Gln Gly Arg Leu Asn
                165                 170                 175

Leu His Gly Trp Val Tyr Asp Ile Glu Ser Gly Ala Ile Val Ala Leu
            180                 185                 190

Asp Gly Asn Thr Gln Arg Phe Val Ser Leu Ala Glu Tyr Pro His Thr
        195                 200                 205

Cys Ala Leu Ala Ser Gln Ala Ser Ser Ala Ala
    210                 215

<210> SEQ ID NO 59
<211> LENGTH: 213
<212> TYPE: PRT
<213> ORGANISM: Yersinia ruckeri
<220> FEATURE:
<223> OTHER INFORMATION: Carbonic anhydrase Y. ruckeri ATCC 29473

<400> SEQUENCE: 59

Met Gln Asp Ile Ile Asp Gly Phe Leu Lys Phe Gln Arg Glu Val Phe
1               5                   10                  15

Pro Gln Arg Ser Glu Leu Phe Lys Arg Leu Ala Asp Thr Gln His Pro
            20                  25                  30

Gly Ala Leu Phe Val Thr Cys Ser Asp Ser Arg Val Val Pro Glu Leu
        35                  40                  45

Leu Thr Gln Arg Glu Pro Gly Glu Leu Phe Val Ile Arg Asn Ala Gly
    50                  55                  60

Asn Ile Val Pro Ser Tyr Gly Pro Glu Pro Gly Gly Val Ser Ala Thr
65                  70                  75                  80

Val Glu Tyr Ala Val Ala Val Leu Gly Val Thr Asp Val Val Ile Cys
                85                  90                  95

Gly His Ser Asn Cys Gly Ala Met Ser Ala Ile Ala Glu Cys Gln Cys
            100                 105                 110

Leu Asp His Leu Pro Ala Val Ala Ala Trp Leu Arg His Ala Asp Ser
        115                 120                 125

Ala Lys Leu Val Asn Ala Ala Leu Pro His Ala Ser Pro Lys Asp Arg
    130                 135                 140

Leu Asn Ser Leu Val Arg Glu Asn Val Ile Ala Gln Leu Ala Asn Ile
145                 150                 155                 160

Lys Thr His Pro Ser Val Ala Leu Ala Cys Ala Gln Gly Arg Leu Arg
                165                 170                 175

Leu His Gly Trp Val Tyr Asp Ile Glu Thr Gly Ser Ile Asp Val Leu
            180                 185                 190

Asp Glu Leu Thr Arg Thr Phe Ser Pro Leu Ser Ala Tyr Ser Val Val
        195                 200                 205

Ser Lys Pro Thr Glu
    210
```

<210> SEQ ID NO 60
<211> LENGTH: 219
<212> TYPE: PRT
<213> ORGANISM: Hahella chejuensis
<220> FEATURE:
<223> OTHER INFORMATION: Carbonic anhydrase Hahella chejuensis KCTC 2396

<400> SEQUENCE: 60

Met Lys Asp Ile Ile Glu Gly Phe Leu Lys Phe Gln Arg Glu Ala Phe
1               5                   10                  15

Pro Glu Arg Lys Glu Leu Phe Lys Asp Leu Ala Asn Gln Gln Gln Pro
            20                  25                  30

Arg Thr Leu Phe Ile Ser Cys Ser Asp Ser Arg Leu Val Pro Glu Leu
        35                  40                  45

Val Thr Gln Arg Glu Pro Gly Asp Leu Phe Val Ile Arg Asn Ala Gly
    50                  55                  60

Asn Ile Val Pro Pro Tyr Gly Pro Glu Pro Gly Gly Val Ser Ala Ser
65                  70                  75                  80

Val Glu Tyr Ala Val Ala Ala Leu Arg Val Ala Asp Ile Val Val Cys
                85                  90                  95

Gly His Ser Asn Cys Gly Ala Met Thr Ala Val Ala Thr Cys Gln Cys
            100                 105                 110

Ile Asp His Met Pro Ala Val Ala His Trp Leu Arg Tyr Ala Asp Ser
        115                 120                 125

Ala Lys Val Val Asn Gln Ala Arg Lys His Ala Ser Glu Arg Ala Lys
    130                 135                 140

Ile Glu Asp Met Val Arg Glu Asn Val Ile Ala Gln Leu Ala Asn Leu
145                 150                 155                 160

Gln Thr His Pro Ser Val Arg Leu Ala Leu Gln Glu Gly Arg Leu Thr
                165                 170                 175

Met His Gly Trp Phe Tyr Asp Ile Glu Ser Gly Ile Asp Ala Tyr
            180                 185                 190

Asp Gly Ser Arg His Ala Phe Val Pro Leu Ala Glu His Pro Glu Ala
        195                 200                 205

Arg Ala Ile Pro Gly Lys Leu Ser His Ala Val
    210                 215

<210> SEQ ID NO 61
<211> LENGTH: 219
<212> TYPE: PRT
<213> ORGANISM: Burkholderia cenocepacia
<220> FEATURE:
<223> OTHER INFORMATION: Carbonic anhydrase Burkholderia cenocepacia
      J23152

<400> SEQUENCE: 61

Met Lys Asp Ile Ile Glu Gly Phe Leu Lys Phe Gln Arg Asp Ala Tyr
1               5                   10                  15

Pro Ala Arg Ala Ala Leu Phe Arg Asp Leu Ala Arg Ser Gln Asn Pro
            20                  25                  30

Arg Ala Leu Phe Ile Ser Cys Ser Asp Ser Arg Leu Val Pro Glu Leu
        35                  40                  45

Val Thr Gln Arg Glu Pro Gly Asp Leu Phe Val Ile Arg Asn Ala Gly
    50                  55                  60

Asn Ile Val Pro Ser Tyr Gly Pro Glu Pro Gly Gly Val Ser Ala Ser
65                  70                  75                  80

Val Glu Tyr Ala Val Ala Ala Leu Arg Val Thr Asp Val Val Ile Cys
                85                  90                  95

Gly His Ser Asp Cys Gly Ala Met Thr Ala Ile Ala Thr Cys Gln Cys
            100                 105                 110

Met Asp His Met Pro Ala Val Gly His Trp Leu Arg Tyr Ala Asp Ser
        115                 120                 125

Ala Arg Val Val Asn Glu Ala Arg Thr His Arg Ser Glu Arg Glu Arg
    130                 135                 140

Ile Asp Ser Met Val Arg Glu Asn Val Ala Gln Leu Ala Asn Leu
145                 150                 155                 160

Lys Thr His Pro Ala Val Arg Leu Ala Leu Glu Gly Arg Leu Ala
                165                 170                 175

Leu His Gly Trp Val Tyr Asp Ile Glu Ser Gly Cys Ile Asp Ala Tyr
            180                 185                 190

Asp Gly Ala Thr Gly Arg Phe Val Ser Leu Ala Asp His Pro Gly Val
        195                 200                 205

Arg Ala Thr Pro Ala Thr Leu Pro Val Ala Ala
    210                 215

<210> SEQ ID NO 62
<211> LENGTH: 215
<212> TYPE: PRT
<213> ORGANISM: Yersinia frederiksenii
<220> FEATURE:
<223> OTHER INFORMATION: Carbonic anhydrase Yersinia frederiksenii ATCC
      33461

<400> SEQUENCE: 62

Met Lys Glu Ile Ile Asp Gly Phe Leu Lys Phe Gln Arg Asp Ala Phe
1               5                   10                  15

Pro Glu Arg Ala Glu Leu Phe Arg Ser Leu Ala Thr Gln Gln Ser Pro
            20                  25                  30

Lys Thr Leu Phe Ile Ser Cys Ser Asp Ser Arg Met Val Pro Glu Leu
        35                  40                  45

Val Thr Gln Arg Glu Pro Gly Asp Leu Phe Val Ile Arg Asn Ala Gly
    50                  55                  60

Asn Ile Val Pro Ser Tyr Gly Pro Glu Pro Gly Gly Ile Ser Ala Ser
65                  70                  75                  80

Val Glu Tyr Ala Val Thr Ala Leu Lys Val Thr Asp Ile Val Ile Cys
                85                  90                  95

Gly His Ser Asp Cys Gly Ala Met Thr Ala Ile Ala Lys Cys His Cys
            100                 105                 110

Leu Asp His Met Pro Ala Val Lys His Trp Leu Gln Tyr Ala Asp Ser
        115                 120                 125

Ala Lys Val Val Asn Glu Ser Arg Glu Tyr Lys Asn Ile His Asp Lys
    130                 135                 140

Thr Ile Ser Met Val His Glu Asn Val Val Ala Gln Leu Ala Asn Ile
145                 150                 155                 160

Gln Thr His Pro Ser Val Arg Leu Ala Leu Glu Glu Gly Arg Leu Thr
                165                 170                 175

Ile His Gly Trp Val Tyr Asp Ile Glu Ser Gly Leu Ile Ser Ala Phe
            180                 185                 190

Asp Arg Ala Ser Arg Gln Phe Val Ser Leu Ala Ala Asn Pro Asn Val
        195                 200                 205

Arg Ala Val Pro Ala His Asn
    210                 215

```
<210> SEQ ID NO 63
<211> LENGTH: 219
<212> TYPE: PRT
<213> ORGANISM: Pseudomonas entomophila
<220> FEATURE:
<223> OTHER INFORMATION: Carbonic anhydrase Pseudomonas entomophila L48

<400> SEQUENCE: 63

Met Gln Asp Ile Ile Asp Gly Phe Leu Lys Phe Gln Arg Asp Ala Phe
1               5                   10                  15

Pro Glu Arg Val Lys Leu Phe Lys Asp Leu Ala Thr Gln Gln Ser Pro
            20                  25                  30

Arg Ala Leu Phe Ile Ser Cys Ser Asp Ser Arg Leu Val Pro Glu Leu
        35                  40                  45

Val Thr Gln Arg Glu Pro Gly Asp Leu Phe Val Ile Arg Asn Ala Gly
    50                  55                  60

Asn Ile Val Pro Ser Tyr Gly Pro Glu Pro Gly Gly Val Ser Ala Ser
65                  70                  75                  80

Val Glu Tyr Ala Val Ala Ala Leu Gln Val Ala Asp Ile Val Ile Cys
                85                  90                  95

Gly His Ser Asp Cys Gly Ala Met Thr Ala Ile Ala Thr Cys Lys Cys
            100                 105                 110

Leu Asp His Met Pro Ala Val Ala Gly Trp Leu Arg Tyr Ala Asp Ser
        115                 120                 125

Ala Arg Val Val Asn Glu Ala Arg Gln His Gln Ser Pro His Ala Lys
    130                 135                 140

Val Glu Ala Met Val Arg Glu Asn Val Ile Ala Gln Leu Ala Asn Ile
145                 150                 155                 160

Gln Thr His Pro Ser Val Arg Leu Ala Leu Glu Glu Gly Arg Val Ala
                165                 170                 175

Leu His Gly Trp Ile Tyr Asp Ile Glu Ser Gly Arg Ile Asp Ala Phe
            180                 185                 190

Asp Gly Arg Thr Gly Gln Phe Val Ser Leu Ala Asp Asn Pro Glu Val
        195                 200                 205

Arg Ala Val Ser His Ala Ser Arg His Val Ala
    210                 215

<210> SEQ ID NO 64
<211> LENGTH: 219
<212> TYPE: PRT
<213> ORGANISM: Pseudomonas putida
<220> FEATURE:
<223> OTHER INFORMATION: Carbonate dehydratase Pseudomonas putida W619

<400> SEQUENCE: 64

Met Lys Ala Ile Ile Asp Gly Phe Leu Lys Phe Gln Lys Asn Ala Phe
1               5                   10                  15

Pro Glu Arg Val Lys Leu Phe Lys Asp Leu Ala Asn Gln Gln Ala Pro
            20                  25                  30

Lys Ala Leu Phe Ile Ser Cys Ser Asp Ser Arg Leu Val Pro Glu Leu
        35                  40                  45

Val Thr Gln Arg Glu Pro Gly Asp Leu Phe Val Ile Arg Asn Ala Gly
    50                  55                  60

Asn Ile Val Pro Ser Tyr Gly Pro Glu Pro Gly Gly Val Ser Ala Ser
65                  70                  75                  80

Val Glu Tyr Ala Val Ala Gly Leu Asn Val Ala Asp Ile Val Ile Cys
                85                  90                  95
```

```
Gly His Ser Asp Cys Gly Ala Met Thr Ala Ile Ala Thr Cys Lys Cys
            100                 105                 110

Leu Asp His Met Pro Ala Val Ala Gly Trp Leu Arg Tyr Ala Asp Ser
        115                 120                 125

Ala Lys Val Val Asn Glu Ala Arg His His Val Asp Lys Pro Ser Lys
        130                 135                 140

Val Ala Ser Met Val Arg Glu Asn Val Ile Ala Gln Leu Ala Asn Ile
145                 150                 155                 160

Gln Thr His Pro Ser Val Arg Leu Ala Leu Glu Glu Gly Arg Val Thr
                165                 170                 175

Leu His Gly Trp Ile Tyr Asp Ile Glu Thr Gly Gly Ile Asp Ala Phe
                180                 185                 190

Asp Gly Ser Thr Gly Thr Phe Val Ser Leu Ala Glu Asn Pro Glu Val
            195                 200                 205

His Ala Val Ser Gln Gln Ala Arg His Val Ala
            210                 215
```

<210> SEQ ID NO 65
<211> LENGTH: 217
<212> TYPE: PRT
<213> ORGANISM: Serratia proteamaculans
<220> FEATURE:
<223> OTHER INFORMATION: Carbonate dehydratase Serratia proteamaculans 568

<400> SEQUENCE: 65

```
Met Lys Glu Val Ile Glu Gly Phe Leu Lys Phe Gln Arg Glu Ala Phe
1               5                   10                  15

Val Glu Arg Thr Ala Leu Phe Gln Arg Leu Ala Thr Gln Gln Ser Pro
                20                  25                  30

Arg Thr Leu Phe Ile Ser Cys Ser Asp Ser Arg Leu Val Pro Glu Leu
            35                  40                  45

Ile Thr Gln Arg Glu Pro Gly Asp Leu Phe Val Ile Arg Asn Ala Gly
        50                  55                  60

Asn Ile Val Pro Ser Phe Gly Pro Glu Pro Gly Gly Val Ser Ala Ser
65                  70                  75                  80

Val Glu Tyr Ala Val Ser Ala Leu Gly Val Glu Asp Ile Val Ile Cys
                85                  90                  95

Gly His Ser Asp Cys Gly Ala Met Thr Ala Ile Ala Thr Cys Gln Cys
            100                 105                 110

Leu Gln His Met Pro Thr Val Ala Asn Trp Leu Arg Tyr Ala Asp Ser
        115                 120                 125

Ala Lys Val Val Asn Gln Ala Tyr Gln His Ala Ser Glu Asn Glu Lys
        130                 135                 140

Val Ser Ser Met Val Arg Glu Asn Val Ile Ala Gln Leu Asn Asn Ile
145                 150                 155                 160

Lys Thr His Pro Ser Val Ala Leu Ala Leu Glu Gln Gly Arg Leu Lys
                165                 170                 175

Leu His Gly Trp Val Tyr Asp Ile Ala Ser Gly Gly Ile Glu Ala Leu
                180                 185                 190

Asp Gly Glu Thr Arg Arg Phe Ile Pro Leu Ala Thr Asn Pro Glu Val
            195                 200                 205

Thr Ala Thr Pro Ala Val Ser Arg Phe
        210                 215
```

<210> SEQ ID NO 66
<211> LENGTH: 211
<212> TYPE: PRT
<213> ORGANISM: Erwinia tasmaniensis
<220> FEATURE:
<223> OTHER INFORMATION: Carbonate dehydratase Erwinia tasmaniensis Et1/99

<400> SEQUENCE: 66

```
Met Gln His Ile Val Glu Gly Phe Leu Asn Phe Gln Lys Asp Ile Phe
1               5                   10                  15

Pro Glu Gln Lys Glu Leu Phe Arg Ser Leu Ala Ser Ser Gln Asn Pro
            20                  25                  30

Lys Ala Leu Phe Ile Ser Cys Ser Asp Ser Arg Leu Val Pro Glu Leu
        35                  40                  45

Val Thr Gln Gln Asp Pro Gly Gln Leu Phe Val Ile Arg Asn Ala Gly
    50                  55                  60

Asn Ile Val Pro Ser Phe Gly Pro Glu Pro Gly Val Ser Ala Thr
65                  70                  75                  80

Ile Glu Tyr Ala Val Ala Leu Gly Val Ser Asp Ile Val Ile Cys
                    85                  90                  95

Gly His Ser Asn Cys Gly Ala Met Lys Ala Ile Ala Thr Cys Gln Cys
                100                 105                 110

Leu Ala Pro Met Pro Ala Val Glu His Trp Leu Arg Tyr Ala Asp Ala
            115                 120                 125

Ala Lys Ala Val Val Glu Lys Lys Asn Tyr Asp Thr Glu Glu Asp Lys
        130                 135                 140

Val Asn Ala Met Val Gln Glu Asn Val Ile Ala Gln Leu Asn Asn Ile
145                 150                 155                 160

Lys Thr His Pro Ser Val Ala Val Gly Leu Arg Asn Asn Ala Leu Arg
                165                 170                 175

Leu His Gly Trp Val Tyr Asp Ile Glu Ser Gly Ala Ile Arg Ala Leu
            180                 185                 190

Asp Lys Asp Ser Lys Lys Phe Val Leu Leu Ser Asp Asn Pro Gln Val
        195                 200                 205

His Phe Glu
    210
```

<210> SEQ ID NO 67
<211> LENGTH: 220
<212> TYPE: PRT
<213> ORGANISM: Pseudomonas aeruginosa
<220> FEATURE:
<223> OTHER INFORMATION: Carbonate dehydratase Pseudomonas aeruginosa PA7

<400> SEQUENCE: 67

```
Met Arg Asp Ile Ile Asp Gly Phe Leu Arg Phe Gln Arg Asp Ala Tyr
1               5                   10                  15

Pro Ala Arg Ser Gln Leu Phe Lys Ser Leu Ala Thr Arg Gln Ala Pro
            20                  25                  30

Lys Ala Leu Phe Ile Ala Cys Ser Asp Ser Arg Val Val Pro Glu Leu
        35                  40                  45

Leu Thr Gln Arg Glu Pro Gly Glu Leu Phe Val Ile Arg Asn Ala Gly
    50                  55                  60

Asn Ile Val Pro Gly Tyr Gly Pro Gln Pro Gly Gly Val Ser Ala Ser
65                  70                  75                  80
```

```
Val Glu Tyr Ala Val Ala Val Leu Gly Val Ala Asp Ile Val Val Cys
                85                  90                  95

Gly His Ser Asp Cys Gly Ala Met Gly Ala Ile Ala Ser Cys Ala Cys
            100                 105                 110

Leu Asp His Leu Pro Ala Val Ala Gly Trp Leu Arg His Ala Glu Ala
        115                 120                 125

Ala Arg Ala Met Asn Ser Ala His Glu His Ser Ser Asp Ala Ala Arg
    130                 135                 140

Leu Asp Ala Leu Val Arg His Asn Val Ile Ala Gln Leu Ala Asn Leu
145                 150                 155                 160

Arg Thr His Pro Ser Val Ala Arg Ala Leu Glu Gln Gly Arg Leu Asn
                165                 170                 175

Leu His Gly Trp Val Tyr Asp Ile Glu Ser Gly Arg Ile Asp Ala Leu
            180                 185                 190

Asp Gly Ala Ser Arg Arg Phe Val Ser Leu Ala Glu His Pro Gly Val
        195                 200                 205

Arg Ala Val Gly Gly Glu Pro Gly Gln Ala Val Ala
    210                 215                 220

<210> SEQ ID NO 68
<211> LENGTH: 202
<212> TYPE: PRT
<213> ORGANISM: Streptosporangium roseum
<220> FEATURE:
<223> OTHER INFORMATION: Carbonate dehydratase Streptosporangium roseum
      DSM 43021

<400> SEQUENCE: 68

Met Gln Asp Leu Glu Glu Gly Val Ala Arg Phe Gln Arg Asp Val Phe
1               5                   10                  15

Pro Ala Lys Thr Glu Leu Phe Thr Arg Leu Ala Thr Ala His Gln Pro
            20                  25                  30

Ala Thr Leu Phe Ile Ser Cys Ser Asp Ala Arg Val Val Pro Glu Leu
        35                  40                  45

Ile Thr Gln Ser Glu Pro Gly Glu Leu Phe Val Ile Arg Thr Ala Gly
    50                  55                  60

Asn Leu Val Pro Ala Tyr Ala Pro Gly Ser Ala Asp Gly Val Ala Ala
65                  70                  75                  80

Gly Ile Glu Tyr Ala Val Ala Val Leu Gly Val Ser Asp Ile Val Val
                85                  90                  95

Cys Gly His Ser Gly Cys Gly Ala Met Thr Ala Val Ala Asp Gly Leu
            100                 105                 110

Asp Pro Ala Ala Leu Pro Ala Val Ala Gly Trp Leu Arg His Ala Asp
        115                 120                 125

Ala Ser Arg Ala Arg Val Thr Thr Thr Glu Thr Gly Thr Gly Glu Val
    130                 135                 140

Ala Ala Leu Val Arg Gln Asn Val Leu Thr Gln Leu Ala Asn Leu Ala
145                 150                 155                 160

Thr His Pro Ser Val Ala His Ala Leu Ala Gly Lys Thr Val Thr Leu
                165                 170                 175

His Gly Trp Ile Tyr Asp Ile Gly Thr Gly Thr Val Ala Glu Leu Asp
            180                 185                 190

Ala Thr Gly Arg Pro Ser Ala Leu Ala Val
        195                 200
```